US012618049B2

(12) United States Patent
Valamehr et al.

(10) Patent No.: US 12,618,049 B2
(45) Date of Patent: May 5, 2026

(54) REPROGRAMMING METHODS AND CELL CULTURE PLATFORMS

(71) Applicant: Fate Therapeutics, Inc., San Diego, CA (US)

(72) Inventors: Bahram Valamehr, San Diego, CA (US); Peter Flynn, San Diego, CA (US); Ramzey Abujarour, San Diego, CA (US); Megan Robinson, San Diego, CA (US)

(73) Assignee: FATE THERAPEUTICS, INC., San Diego, CA (US)

( * ) Notice: Subject to any disclaimer, the term of this patent is extended or adjusted under 35 U.S.C. 154(b) by 835 days.

(21) Appl. No.: 17/579,169

(22) Filed: Jan. 19, 2022

(65) Prior Publication Data

US 2022/0228125 A1     Jul. 21, 2022

Related U.S. Application Data

(62) Division of application No. 15/123,217, filed as application No. PCT/US2015/018801 on Mar. 4, 2015, now Pat. No. 11,268,069.

(60) Provisional application No. 61/947,979, filed on Mar. 4, 2014.

(51) Int. Cl.
| | |
|---|---|
| *C12N 5/074* | (2010.01) |
| *C12N 5/073* | (2010.01) |
| *C12N 15/86* | (2006.01) |

(52) U.S. Cl.
CPC ......... *C12N 5/0696* (2013.01); *C12N 5/0603* (2013.01); *C12N 15/86* (2013.01); *C12N 2501/115* (2013.01); *C12N 2501/15* (2013.01); *C12N 2501/235* (2013.01); *C12N 2501/415* (2013.01); *C12N 2501/724* (2013.01); *C12N 2501/727* (2013.01); *C12N 2740/15043* (2013.01)

(58) Field of Classification Search
CPC .................................................... C12N 5/0696
See application file for complete search history.

(56) References Cited

U.S. PATENT DOCUMENTS

| | | |
|---|---|---|
| 4,797,368 A | 1/1989 | Carter et al. |
| 5,010,175 A | 4/1991 | Rutter et al. |
| 5,139,941 A | 8/1992 | Muzyczka et al. |
| 5,288,514 A | 2/1994 | Ellman |
| 5,384,253 A | 1/1995 | Krzyzek et al. |
| 5,478,838 A | 12/1995 | Arita et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |

| | | |
|---|---|---|
| 5,580,859 A | 12/1996 | Felgner et al. |
| 5,589,466 A | 12/1996 | Felgner et al. |
| 5,593,853 A | 1/1997 | Chen et al. |
| 5,656,610 A | 8/1997 | Shuler et al. |
| 5,702,932 A | 12/1997 | Hoy et al. |
| 5,736,524 A | 4/1998 | Huygen et al. |
| 5,780,448 A | 7/1998 | Davis |
| 5,789,215 A | 8/1998 | Berns et al. |
| 5,824,837 A | 10/1998 | Chen et al. |
| 5,843,780 A | 12/1998 | Thomson |
| 5,945,100 A | 8/1999 | Fick |
| 5,981,274 A | 11/1999 | Tyrrell et al. |
| 5,994,136 A | 11/1999 | Naldini et al. |
| 5,994,624 A | 11/1999 | Trolinder et al. |
| 6,013,516 A | 1/2000 | Verma et al. |
| 6,030,943 A | 2/2000 | Crumb et al. |
| 6,200,806 B1 | 3/2001 | Thomson |
| 6,534,476 B2 | 3/2003 | Miyazono et al. |
| 6,692,736 B2 | 2/2004 | Yu et al. |
| 6,696,440 B1 | 2/2004 | Bridges et al. |
| 6,703,420 B1 | 3/2004 | Hobbs, Jr. |
| 6,730,293 B1 | 5/2004 | Rothbard et al. |
| 6,875,608 B1 | 4/2005 | Smith et al. |
| 7,029,913 B2 | 4/2006 | Thomson |
| 7,265,138 B2 | 9/2007 | Doherty et al. |
| 7,585,844 B2 | 9/2009 | Turner et al. |
| 8,044,201 B2 | 10/2011 | Xu et al. |

(Continued)

FOREIGN PATENT DOCUMENTS

| | | |
|---|---|---|
| CN | 101356270 A | 1/2009 |
| CN | 101563449 A | 10/2009 |

(Continued)

OTHER PUBLICATIONS

Aasen et al., "Efficient and rapid generation of induced pluripotent stem cells from human keratinocytes", Nature Biotechnology, 26:1276-1284 (2008).
Abujarour, R. et al. (2013, e-published Jan. 31, 2013). "Optimized surface markers for the prospective isolation of high-quality hiPSCs using flow cytometry selection," Sci Rep 3:1179.
Adcock, "HDAC inhibitors as anti-inflammatory agents", British Journal of Pharmacology, 150(7):829-831 (2007).
Adhikary and Eilers, "Transcriptional regulation and transformation by Myc proteins", Nat Rev Mol Cell Biol., 6(8): 635-645 (2005).
Alessi et al., "Characterization of a 3-phosphoinositide-dependent protein kinase which phosphorylates and activates protein kinase Bα", Current Biology, 7(4): 261-269 (1997).

(Continued)

*Primary Examiner* — Anoop K Singh
*Assistant Examiner* — David A Montanari
(74) *Attorney, Agent, or Firm* — Greenberg Traurig, LLP

(57) ABSTRACT

The invention provides compositions and methods for manufacturing pluripotent cells. In particular, the invention provides improved culture platforms for manufacturing pluripotent cells with ground state pluripotency. In various embodiments, the invention contemplates, in part, a composition comprising: (a) a Wnt pathway agonist; (b) a MEK inhibitor; and (c) a ROCK inhibitor. In certain embodiments, the composition further comprises bFGF or LIF.

15 Claims, 80 Drawing Sheets

Specification includes a Sequence Listing.

(56) References Cited

U.S. PATENT DOCUMENTS

| | | | |
|---|---|---|---|
| 8,222,034 | B2 | 7/2012 | Amit et al. |
| 8,298,825 | B1 | 10/2012 | Hochedlinger et al. |
| 8,524,498 | B2 | 9/2013 | Geijsen et al. |
| 8,603,818 | B1 | 12/2013 | Hochedlinger et al. |
| 8,906,677 | B2 | 12/2014 | Li et al. |
| 9,005,968 | B2 | 4/2015 | Lin et al. |
| 9,068,170 | B2 | 6/2015 | Zhou et al. |
| 9,166,832 | B1 | 10/2015 | Li et al. |
| 9,295,697 | B2 | 3/2016 | Yu |
| 9,394,524 | B2 | 7/2016 | Shi et al. |
| 9,534,205 | B2 | 1/2017 | Shi et al. |
| 9,540,615 | B2 | 1/2017 | Shi et al. |
| 9,732,319 | B2 | 8/2017 | Valamehr et al. |
| 10,844,356 | B2 | 11/2020 | Valamehr et al. |
| 11,268,069 | B2 | 3/2022 | Valamehr et al. |
| 11,441,126 | B2 | 9/2022 | Valamehr et al. |
| 12,351,831 | B2 | 7/2025 | Valamehr et al. |
| 12,415,989 | B2 | 9/2025 | Valamehr et al. |
| 2002/0142457 | A1 | 10/2002 | Umezawa et al. |
| 2003/0087919 | A1 | 5/2003 | Nagarathnam et al. |
| 2003/0125344 | A1 | 7/2003 | Nagarathnam et al. |
| 2003/0204862 | A1 | 10/2003 | Kuehn et al. |
| 2004/0002507 | A1 | 1/2004 | Nagarathnam et al. |
| 2004/0002508 | A1 | 1/2004 | Nagarathnam et al. |
| 2004/0014755 | A1 | 1/2004 | Nagarathnam et al. |
| 2004/0157324 | A1 | 8/2004 | Spradling et al. |
| 2005/0075276 | A1 | 4/2005 | Rudd |
| 2005/0119203 | A1 | 6/2005 | Steinbrecher et al. |
| 2005/0130144 | A1 | 6/2005 | Nakatsuji et al. |
| 2005/0192304 | A1 | 9/2005 | Nagarathnam et al. |
| 2005/0209261 | A1 | 9/2005 | Nagarathnam et al. |
| 2006/0182724 | A1 | 8/2006 | Riordan |
| 2007/0032447 | A1 | 2/2007 | Eilertsen |
| 2007/0128719 | A1 | 6/2007 | Tseng et al. |
| 2007/0134215 | A1 | 6/2007 | Fukuda et al. |
| 2007/0141703 | A1 | 6/2007 | Xu et al. |
| 2007/0149484 | A1 | 6/2007 | Claus et al. |
| 2007/0161107 | A1 | 7/2007 | Mummery et al. |
| 2007/0172946 | A1 | 7/2007 | Smith et al. |
| 2007/0196919 | A1 | 8/2007 | Reh et al. |
| 2007/0254359 | A1 | 11/2007 | Rezania et al. |
| 2007/0259423 | A1 | 11/2007 | Odorico et al. |
| 2007/0264709 | A1 | 11/2007 | Smith et al. |
| 2007/0269412 | A1 | 11/2007 | Kopyov |
| 2007/0281355 | A1 | 12/2007 | Dalton et al. |
| 2007/0298496 | A1 | 12/2007 | Kuo et al. |
| 2008/0004287 | A1 | 1/2008 | Ma et al. |
| 2008/0066197 | A1 | 3/2008 | Ying et al. |
| 2008/0242594 | A1 | 10/2008 | McKay et al. |
| 2008/0268533 | A1 | 10/2008 | Dalton et al. |
| 2009/0068742 | A1 | 3/2009 | Yamanaka |
| 2009/0117439 | A1 | 5/2009 | Fujinami et al. |
| 2009/0203690 | A1 | 8/2009 | Akritopoulou-Zanze et al. |
| 2009/0227032 | A1 | 9/2009 | Yamanaka et al. |
| 2009/0299763 | A1 | 12/2009 | Sakurada |
| 2009/0304646 | A1 | 12/2009 | Sakurada et al. |
| 2010/0009442 | A1 | 1/2010 | Sasai et al. |
| 2010/0093090 | A1 | 4/2010 | Deng et al. |
| 2010/0150889 | A1* | 6/2010 | Townes .................. A61P 35/00 |
| | | | 435/325 |
| 2010/0233804 | A1 | 9/2010 | Zhou et al. |
| 2010/0267141 | A1 | 10/2010 | Shi et al. |
| 2010/0303775 | A1 | 12/2010 | Raya |
| 2011/0033931 | A1 | 2/2011 | Schwartz et al. |
| 2011/0039332 | A1 | 2/2011 | Sakurada et al. |
| 2011/0039338 | A1 | 2/2011 | Yamanaka et al. |
| 2011/0110899 | A1 | 5/2011 | Shi et al. |
| 2011/0306516 | A1 | 12/2011 | Kahler et al. |
| 2012/0009676 | A1 | 1/2012 | Mack |
| 2012/0058562 | A1 | 3/2012 | Thomson et al. |
| 2012/0122212 | A1 | 5/2012 | Grskovic et al. |
| 2012/0128655 | A1* | 5/2012 | Kim .................. C12N 5/0696 |
| | | | 435/377 |
| 2012/0129172 | A1 | 5/2012 | Okano et al. |
| 2012/0196360 | A1 | 8/2012 | Okita et al. |
| 2012/0220034 | A1 | 8/2012 | Ahlfors et al. |
| 2012/0264218 | A1 | 10/2012 | Lin et al. |
| 2013/0011918 | A1 | 1/2013 | West et al. |
| 2013/0273536 | A1 | 10/2013 | Shi et al. |
| 2013/0323833 | A1 | 12/2013 | Zhu et al. |
| 2014/0220681 | A1 | 8/2014 | Valamehr et al. |
| 2014/0369973 | A1 | 12/2014 | Bernstein et al. |
| 2015/0079675 | A1 | 3/2015 | Li et al. |
| 2015/0240214 | A1 | 8/2015 | Lin et al. |
| 2016/0369244 | A1 | 12/2016 | Shi et al. |
| 2017/0073643 | A1 | 3/2017 | Valamehr et al. |
| 2017/0362569 | A1 | 12/2017 | Valamehr et al. |
| 2018/0155717 | A1 | 6/2018 | Valamehr et al. |
| 2019/0218520 | A1 | 7/2019 | Valamehr et al. |
| 2021/0079359 | A1 | 3/2021 | Valamehr et al. |
| 2022/0325249 | A1 | 10/2022 | Valamehr et al. |

FOREIGN PATENT DOCUMENTS

| | | |
|---|---|---|
| CN | 102597221 A | 7/2012 |
| EP | 1970446 A1 | 9/2008 |
| EP | 1992360 A1 | 11/2008 |
| EP | 3 371 314 A1 | 9/2018 |
| GB | 2 436 737 A | 10/2007 |
| GB | 2 450 603 A | 12/2008 |
| JP | 2007-508026 A | 4/2007 |
| JP | 2008-099662 A | 5/2008 |
| JP | 2008-307007 A | 12/2008 |
| JP | 2010-504090 A | 2/2010 |
| JP | 2010-529851 A | 9/2010 |
| JP | 2012-510526 A | 5/2012 |
| JP | 2013-507932 A | 3/2013 |
| JP | 2013-509864 A | 3/2013 |
| JP | 2013-510567 A | 3/2013 |
| WO | WO 1991/019735 A1 | 12/1991 |
| WO | WO 1992/000091 A1 | 1/1992 |
| WO | WO 1993/020242 A1 | 10/1993 |
| WO | WO 1997/000271 A1 | 3/1997 |
| WO | WO 1998/006433 A1 | 2/1998 |
| WO | WO 1999/001426 A1 | 1/1999 |
| WO | WO 2000/078351 A1 | 12/2000 |
| WO | WO 2001/017562 A1 | 3/2001 |
| WO | WO 2002/006213 A2 | 1/2002 |
| WO | WO 2002/076976 A2 | 10/2002 |
| WO | WO 2002/076977 A2 | 10/2002 |
| WO | WO 2002/088346 A2 | 11/2002 |
| WO | WO 2003/059913 A1 | 7/2003 |
| WO | WO 2003/062225 A1 | 7/2003 |
| WO | WO 2003/062227 A1 | 7/2003 |
| WO | WO 2003/077914 A1 | 9/2003 |
| WO | WO 2003/082808 A1 | 10/2003 |
| WO | WO 2003/095628 A2 | 11/2003 |
| WO | WO 2004/039796 A1 | 5/2004 |
| WO | WO 2004/045617 A1 | 6/2004 |
| WO | WO 2005/035506 A1 | 4/2005 |
| WO | WO2005/038010 A2 | 4/2005 |
| WO | WO 2005/051301 A2 | 6/2005 |
| WO | WO 2005/074643 A2 | 8/2005 |
| WO | WO 2005/084158 A2 | 9/2005 |
| WO | WO 2007/016566 A2 | 2/2007 |
| WO | WO 2007/044084 A2 | 4/2007 |
| WO | WO 2007/069666 A1 | 6/2007 |
| WO | WO 2007/085827 A2 | 8/2007 |
| WO | WO 2007/113505 A2 | 10/2007 |
| WO | WO 2007/123667 A2 | 11/2007 |
| WO | WO 2008/006583 A1 | 1/2008 |
| WO | WO 2008/011093 A2 | 1/2008 |
| WO | WO 2008/015418 A2 | 2/2008 |
| WO | WO 2008/035110 A1 | 3/2008 |
| WO | WO 2008/056173 A2 | 5/2008 |
| WO | WO 2008/088882 A2 | 7/2008 |
| WO | WO 2008/089351 A1 | 7/2008 |
| WO | WO 2008/094597 A2 | 8/2008 |
| WO | WO 2008/105630 A1 | 9/2008 |
| WO | WO 2008/108741 A1 | 9/2008 |
| WO | WO 2008/126932 A2 | 10/2008 |
| WO | WO 2008/129554 A1 | 10/2008 |
| WO | WO 2009/006422 A1 | 1/2009 |
| WO | WO 2009/007851 A2 | 1/2009 |

(56) References Cited

FOREIGN PATENT DOCUMENTS

| WO | WO 2009/007852 A2 | 1/2009 | | |
| WO | WO 2009/032194 A1 | 3/2009 | | |
| WO | WO 2009/032456 A2 | 3/2009 | | |
| WO | WO 2009/057831 A1 | 5/2009 | | |
| WO | WO 2009/061442 A1 | 5/2009 | | |
| WO | WO 2009/067756 A1 | 6/2009 | | |
| WO | WO 2009/067757 A1 | 6/2009 | | |
| WO | WO 2009/073523 A2 | 6/2009 | | |
| WO | WO 2009/115295 A1 | 9/2009 | | |
| WO | WO 2009/117439 A1 | 9/2009 | | |
| WO | WO 2010/019569 A1 | 2/2010 | | |
| WO | WO 2010/053472 A1 | 5/2010 | | |
| WO | WO 2010/065721 A1 | 6/2010 | | |
| WO | WO 2010/077955 A1 | 7/2010 | | |
| WO | WO 2010/120785 A2 | 10/2010 | | |
| WO | WO 2011/047300 A1 | 4/2011 | | |
| WO | WO 2011/056971 A2 | 5/2011 | | |
| WO | WO 2011/058558 A2 | 5/2011 | | |
| WO | WO 2011/090221 A1 | 7/2011 | | |
| WO | WO 2011/109695 A1 | 9/2011 | | |
| WO | WO 2011/158852 A1 | 12/2011 | | |
| WO | WO 2011/159692 A1 | 12/2011 | | |
| WO | WO-2012087965 A2 * | 6/2012 | .......... | C12N 5/0606 |
| WO | WO 2013/070852 A2 | 5/2013 | | |
| WO | WO 2013/159103 A1 | 10/2013 | | |
| WO | WO 2013/176197 A1 | 11/2013 | | |
| WO | WO 2015/134652 A1 | 9/2015 | | |
| WO | WO 2017/066634 A1 | 4/2017 | | |

OTHER PUBLICATIONS

Amit et al., "Clonally derived human embryonic stem cell lines maintain pluripotency and proliferative potential for prolonged periods of culture," Developmental Biology, 227:271-278 (2000).

Aoi et al., "Generation of Pluripotent Stem Cells from Adult Mouse Liver and Stomach Cells," Science Express, Feb. 2008 (Corrected Aug. 2008), DOI 10.1126/science.1154884, 8 pages.

Artyomov et al., "A model for genetic and epigenetic regulatory networks identifies rare pathways for transcription factor induced pluripotency", PLoS Computational Biology, 6(5): e1000785, 1-14 (2010).

Barrett et al., "The discovery of the benzhydromate MEK inhibitors CI-1040 and PD 0325901," Bioorganic & Medicinal Chemistry Letters, 18(24):6501-6504 (2008).

Beaujean et al., "Induction of early transcription in one-cell mouse embryos by microinjection of the nonhistone chromosomal protein HMG-I", Developmental Biology, 221(2): 337-354 (2000).

Bedel et al., "Preventing pluripotent cell teratoma in regenerative medicine applied to hematologic disorders," Stem Cells Translational Medicine, 6:382-393 (2017).

Bertrand, "Structural Characterization of the GSK-3β Active Site Using Selective and Non-selective ATP-mimetic Inhibitors", Journal of Molecular Biology, 333(2): 393-407 (2003).

Blelloch et al., "Reprogramming efficiency following somatic cell nuclear transfer is influenced by the differentiation and methylation state of the donor nucleus", Stem Cells, 24(9): 2007-2013 (2006).

Blömer et al., "Highly efficient and sustained gene transfer in adult neurons with a lentivirus vector", Journal of Virology, 71(9):6641-6649 (1997).

Brambrink et al., "Sequential expression of pluripotency markers during direct reprogramming of mouse somatic cells", Cell Stem Cell, 2(2): 151-159 (2008).

Brevini et al., "Embryonic stem cells in domestic animals. No shortcuts to pig embryonic stem cells," Theriogenology, 74:544-550 (2010).

Brons et al., "Derivation of pluripotent epiblast stem cells from mammalian embryos", Nature, 448: 191-195 (2007).

Bru et al., "Rapid induction of pluripotency genes after exposure of human somatic cells to mouse ES cell extracts," Exp. Cell Res., 314:2634-2642 (2008).

Brueckner, et al., "Epigenetic reactivation of tumor suppressor genes by a novel small-molecule inhibitor of human DNA methyltransferases", Cancer Research, 65(14): 6305-6311 (2005).

Buta et al., "Reconsidering pluripotency tests: do we still need teratoma assays?," Stem Cell Research, 11:552-562 (2013).

Byfield et al., "SB-505124 is a selective inhibitor of transforming growth factor-β type I receptors ALK4, ALK5, and ALK7", Molecular Pharmacology, 65(3): 744-752 (2004).

Callahan et al., "Identification of novel inhibitors of the transforming growth factor β1 (TGF-β1) Type 1 receptor (ALK5)", J. Med Chem., 45(5): 999-1001 (2002). (Abstract).

Chahine et al., "Modulation of L-type Ca2+ channels in neonatal rat heart by a novel Ca2+ channel agonist", Canadian Journal of Physiology and Pharmacology, 81(2): 135-141 (2003).

Chambers et al., "Nanog safeguards pluripotency and mediates germline development", Nature, 450: 1230-1234 (2007).

Chang et al., "Transforming growth factor-beta signaling in breast cancer", Frontiers in Bioscience, 12: 4393-4401 (2007).

Chen et al., "High-efficiency transformation of mammalian cells by plasmid DNA", Molecular and Cellular Biology, 7(8): 2745-2752 (1987).

Chen et al., ""Analogous" Organic Synthesis of Small-Compound Libraries: Validation of Combinatorial Chemistry in Small-Molecule Synthesis", J. Amer. Chem. Soc., 116(6): 2661-2662 (1994).

Chen et al., "Reversine increases the plasticity of lineage-committed mammalian cells", PNAS, 104(25): 10482-10487 (2007).

Chen et al., "Self-renewal of embryonic stem cells by a small molecule," PNAS, 103(46): 17266-17271 (2006).

Chin et al., "Induced pluripotent stem cells and embryonic stem cells are distinguished by gene expression signatures," Cell Stem Cell, Jul. 5, 2009, pp. 111-123.

Chin et al., "Inhibition of GSK3β is a common event in neuroprotection by different survival factors", Molecular Brain Research, 137(1-2):193-201 (2005).

Chin et al., "Molecular analyses of human induced pluripotent stem cells and embryonic stem cells," Cell Stem Cell, Aug. 7, 2010, pp. 263-269.

Cho et al., "An unnatural biopolymer", Science, 261(5126): 1303-1305 (1993).

Chou et al., "The growth factor environment defines distinct pluripotent ground states in novel blastocyst-derived stem cells", Cell, 135(3): 449-461 (2008).

Chow, et al., "Measurement of MAP kinase activation by flow cytometry using phospho-specific antibodies to MEK and ERK: Potential for pharmacodynamic monitoring of signal transduction inhibitors", Cytometry (Communications in Clinical Cytometry), 46(2): 72-78 (2001).

Christen et al., "Regeneration and reprogramming compared", BMC Biol, 8: 5, 14 pages (2010).

Claassen et al., "ROCK inhibition enhances the recovery and growth of cryopreserved human embryonic stem cells and human induced pluripotent stem cells", Molecular Reproduction and Development, 76(8): 722-732 (2009).

Collas et al., "On the way to reprogramming cells to pluripotency using cell-free extracts", Reproductive BioMedicine Online, 12(6): 762-770 (2006).

Colman et al., "Induced pluripotent stem cells and the stability of the differentiated state", EMBO Reports, 10(7): 714-721 (2009).

Condorelli, G. et al., "Cardiomyocytes induce endothelial cells to trans-differentiate into cardiac muscle: Implications for myocardium regeneration," PNAS, 98(19): 10733-10738 (2001).

Conti et al., "Niche-independent symmetrical self-renewal of a mammalian tissue stem cell", PLoS Biol., 3(9): e283, 1594-1606 (2005).

Cotten et al., "High-efficiency receptor-mediated delivery of small and large (48 kilobase gene constructs using the endosome-disruption activity of defective or chemically inactivated adenovirus particles", PNAS, 89(13): 6094-6098 (1992).

Cui et al., "Selective inhibition of TGF-β responsive genes by Smad-interacting peptide aptamers from FoxH1, Lef1 and CBP", Oncogene, 24: 3864-3874 (2005).

(56)        References Cited

OTHER PUBLICATIONS

D'Amour et al., "Efficient differentiation of human embryonic stem cells to definitive endoderm", Nat Biotechnol, 23(12): 1534-1541 (2005).

Daheron, L. et al. (Jun. 10, 2012). "Blood—SeV derived fibroblast generated iPSCs," StemBook [Internet]. Cambridge (MA): Harvard Stem Cell Institute 7:48, 7 pages.

Dang et al., "The biology of the mammalian Krüppel-like family of transcription factors", The International Journal of Biochemistry & Cell Biology, 32(11-12): 1103-1121 (2000).

Darenfed, et al., "Molecular characterization of the effects of Y-27632", Cell Motil Cytoskeleton, 64(2): 97-109 (2007).

De Felipe, "Polycistronic viral vectors," Curr. Gene Ther., 2:355-378 (2002).

De Gouville et al., "Inhibition of ALK5 as a new approach to treat liver fibrotic diseases", Drug News Perspective, 19(2): 85-90 (2006).

Debs et al., "Regulation of gene expression in vivo by liposome-mediated delivery of a purified transcription factor", The Journal of Biological Chemistry, 265: 10189-10192 (1990).

Declercq et al., "Zic3 enhances the generation of mouse induced pluripotent stem cells," Stem Cells Development, 22(14):2017-2026 (2013).

Demers et al., "Rat embryonic stem-like (ES-like) cells can contribute to extraembryonic tissues in vivo", Cloning Stem Cells, 9(4): 512-522 (2007).

Dimos et al., "Induced pluripotent stem cells generated from patients with ALS can be differentiated into motor neurons", Science, 321(5893): 1218-1221 (2008).

Djuric et al., "Epigenetics of induced pluripotency, the seven-headed dragon", Stem Cell Research and Therapy, 1(1):3, 7 pages (2010).

Do et al., "Nuclei of embryonic stem cells reprogram somatic cells", Stem Cells, 22(6): 941-949 (2004).

Do, J. T. et al., "Erasure of cellular memory by fusion with pluripotent cells", Stem Cells, 25(4): 1013-1020 (2007).

Dravida, S. et al., "The transdifferentiation potential of limbal fibroblast-like cells," Developmental Brain Research, 160(2): 239-251 (2005).

Dvorak et al., "Expression and potential role of fibroblast growth factor 2 and its receptors in human embryonic stem cells", Stem Cells, 23(8): 1200-1211 (2005).

Efe et al., "Conversion of mouse fibroblasts into cardiomyocytes using a direct reprogramming strategy," Nature Cell Biology, 13(3): 215-222 (2011).

Egler et al., "Histone Deacetylase Inhibition and Blockade of the Glycolytic Pathway Synergistically Induce Glioblastoma Cell Death", Clin. Cancer Res., 14(10): 3132-3140 (2008).

Elliott et al., "Intercellular trafficking and protein delivery by a herpesvirus structural protein", Cell, 88(2): 223-233 (1997).

Emre et al., "The ROCK inhibitor Y-27632 improves recovery of human embryonic stem cells after fluorescence-activated cell sorting with multiple cell surface markers", PLoS One, 5(8): e12148 (2010).

Engel et al., "Allosteric activation of the protein kinase PDK1 with low molecular weight compounds", The EMBO Journal, 25(23): 5469-5480 (2006).

English et al., "Pharmacological inhibitors of MAPK pathways", Trends in Pharmaceutical Sciences, 23(1): 40-45 (2002).

EP Application No. 09721278.1, Extended European Search Report dated Jun. 1, 2011, 11 pages.

EP Application No. 10824189.4, Extended European Search Report dated May 29, 2013, 8 pages.

EP Application No. 11852133.5, Extended European Search Report dated Aug. 13, 2014, 7 pages.

EP Application No. 15177122.7, Extended European Search Report dated Oct. 27, 2015.

Epsztejn-Litman et al., "De novo DNA methylation promoted by G9a prevents reprogramming of embryonically silenced genes", Nature Structural & Molecular Biology, 15(11): 1176-1183, 9 pages (2008).

Ernst et al., "gp130-mediated Signal Transduction in Embryonic Stem Cells Involves Activation of Jak and Ras/Mitogen-activated Protein Kinase Pathways", J. Biol. Chem., 271(47): 30163-30143 (1996).

Esteban et al., "Vitamin C enhances the generation of mouse and human induced pluripotent stem cells", Cell Stem Cell, 6(1): 71-79 (2010). Epub Dec. 31, 2009.

Fang et al., "Tea polyphenol (–)-epigallocatechin-3-gallate inhibits DNA methyltransferase and reactivates methylation-silenced genes in cancer cell lines", Cancer Research, 63: 7563-7570 (2003).

Feldman et al., "G9a-mediated irreversible epigenetic inactivation of Oct-3/4 during early embryogenesis", Nature Cell Biology, 8(2): 188-194 (2006).

Feng et al., "Molecules that Promote or Enhance Reprogramming of Somatic Cells to Induced pluripotent stem cells", Cell Stem Cell, 4(4):301-312 (2009).

Fernandes et al., "A dermal niche for multipotent adult skin-derived precursor cells", Nature Cell Biology, 6: 1082-1093 (2004).

Frame et al., "GSK3 takes centre stage more than 20 years after its discovery", Biochemical Journal, 359(Pt 1): 1-16 (2001).

Frankel et al., "Cellular uptake of the tat protein from human immunodeficiency virus", Cell, 55(6): 1289-1193 (1988).

Franzén et al., "Cloning of a TGFβ type I receptor that forms a heteromeric complex with the TGFβ type II receptor", Cell, 75(4): 681-692 (1993).

Furumai et al., "Potent histone deacetylase inhibitors built from trichostatin A and cyclic tetrapeptide antibiotics including trapoxin", PNAS, 98(1): 87-92 (2001).

Gellibert et al., "Discovery of 4-{4-[3-(Pyridin-2-yl)-1H-pyrazol-4-yl]pyridin-2-yl}-N-(tetrahydro-2H-pyran-4-yl)benzamide (GW788388): A Potent, Selective, and Orally Active Transforming Growth Factor-β Type I Receptor Inhibitor", Journal Medicinal Chemistry, 49(7): 2210-2221 (2006).

Gomez et al., "Derivation of cat embryonic stem-like cells from in vitro-produced blastocysts on homologous and heterologous feeder cells," Theriogenology, 74:498-515 (2010).

Gonzalez et al., "Generation of mouse-induced pluripotent stem cells by transient expression of a single nonviral polycistronic vector", PNAS, 106(22): 8918-8922 (2009).

Gonzalez et al. (Apr. 2011, e-published Feb. 22, 2011). "Methods for making induced pluripotent stem cells: reprogramming a la carte," Nat Rev Genet 12(4):231-242.

Gopal, "Gene transfer method for transient gene expression, stable transformation, and cotransformation of suspension cell cultures", Molecular and Cellular Biology, 5(5):1188-1190 (1985).

Gore, "Combination therapy with DNA methyltransferase inhibitors in hematologic malignancies", Nature Clinical Practice Oncology, 2(Suppl 1): S30-S35 (2005).

Gore et al., "Combined DNA methyltransferase and histone deacetylase inhibition in the treatment of myeloid neoplasms", Cancer Research, 66(12): 6361-6369 (2006).

Gould et al., "Effects of a glycogen synthase kinase-3 inhibitor, lithium, in adenomatous polyposis coli mutant mice", Pharmacological Research, 48(1): 49-53 (2003).

Gould et al., "AR-A014418, a selective GSK-3 inhibitor, produces antidepressant-like effects in the forced swim test", The International Journal of Neuropsychopharmacology, 7(4): 387-390 (2004).

Graf et al., "Forcing cells to change lineages", Nature, 462(7273): 587-594 (2009).

Graham et al., "A new technique for the assay of infectivity of human adenovirus 5 DNA", Virology, 52(2): 456-467 (1973).

Green et al., "Autonomous functional domains of chemically synthesized human immunodeficiency virus tat trans-activator protein", Cell, 55(6): 1179-1188 (1988).

Grunhaus et al., "Association of vaccinia virus-expressed adenovirus E3-19K glycoprotein with class I MHC and its effects on virulence in a murine pneumonia model", Seminar in Virology, 200(2):535-546 (1992).

Gump et al., "TAT transduction: the molecular mechanism and therapeutic prospects", (2007) Trends Mol Med. Oct;I3(10):443-8 (2007).

Guo et al., "Klf4 reverts developmentally programmed restriction of ground state pluripotency", Development, 136: 1063-1069 (2009).

(56) References Cited

OTHER PUBLICATIONS

Hakelien et al., "Transient alteration of cell fate using a nuclear and cytoplasmic extract of an insulinoma cell line," BBRC, 316: 834-841 (2004).

Han et al., "Current concepts in reprogramming somatic cells to pluripotent state", Curr Stem Cell Res Ther, 3: 66-74 (2008).

Han et al., "Induced pluripotent stem cells: emerging techniques for nuclear reprogramming", Antioxidants & Redox Signaling, 15(7): 1799-1820 (2011).

Han et al., "Direct reprogramming of fibroblasts into epiblast stem cells", Nat Cell Biol, 13(1): 66-71 (2011).

Han et al., "HDAC inhibitors TSA and sodium butyrate enhanced the human IL-5 expression by altering histone acetylation status at its promoter region", Immunology Letters, 108(2):143-150 (2007).

Hanna et al, "Treatment of Sickle Cell Anemia Mouse Model with iPS Cells Generated from Autologous Skin," Science, 318: 1920-1922 (2007).

Hanna et al., "Direct cell reprogramming is a stochastic process amenable to acceleration", Nature, 462: 595-601 (2009).

Hanna et al., "Direct reprogramming of terminally differentiated mature B lymphocytes to pluripotency", Cell, 133: 250-264 (2008).

Hanna et al., "Human embryonic stem cells with biological and epigenetic characteristics similar to those of mouse ESCs," Proc. Natl. Acad. Sci. USA, 107(20):9222-9227 (2010).

Hanna et al., "Pluripotency and cellular reprogramming: facts, hypotheses, unresolved issues," Cell, 143:508-525 (2010).

Hay, "An overview of epithelio-mesenchymal transformation", Acta Anat. (Basel) 154: 8-20 (1995).

Hayashi et al., "Dynamic equilibrium and heterogeneity of mouse pluripotent stem cells with distinct functional and epigenetic states", Cell Stem Cell, 3(4): 391-401 (2008).

Heo et al., "EGF stimulates proliferation of mouse embryonic stem cells: involvement of Ca2+ influx and p44/42 MAPKs", Am J Physiol Cell Physiol, 290(1): C123-133 (2006).

Hindie et al., "Structure and allosteric effects of low-molecular-weight activators on the protein kinase PDK1," Nat Chem Biol, 5(10): 758-764 (2009).

Hiraki et al., Culturing human IPS cells under non-feeder conditions alters their basic pluripotent status, Biochemical, 4P-0894 (2010) Abstract only.

Ho et al., "Synthetic Protein Transduction Domains: Enhanced Transduction Potential in Vitro and in Vivo", Cancer Res., 61: 474-477 (2001).

Hochedlinger et al., "Epigenetic reprogramming and induced pluripotency", Development, 136(4): 509-23 (2009).

Hochedlinger, et al., "Ectopic expression of Oct-4 blocks progenitor-cell differentiation and causes dysplasia in epithelial tissues", Cell, 121(3): 465-477 (2005).

Hochedlinger et al., "Nuclear reprogramming and pluripotency," Nature, 441: 1061-1067 (2006).

Hong et al., "Suppression of induced pluripotent stem cell generation by the p53-p21 pathway", Nature, 460: 1132-1135 (2009).

Hou et al., "VEGI-192, a New Isoform of TNFSF15, Specifically Eliminates Tumor Vascular Endothelial Cells and Suppresses Tumor Growth", Clinical Cancer Research, 11: 5595-5602 (2005).

Huangfu et al., "Induction of pluripotent stem cells by defined factors is greatly improved by small-molecule compounds", Nature Biotechnology, 26: 795-797 (2008).

Huangfu et al., "Induction of pluripotent stem cells from primary human fibroblasts with only Oct4 and Sox2", Nature Biotechnology, 26(11): 1269-1275 (2008).

Hudecz et al., "Medium-sized peptides as built in carriers for biologically active compounds," Medicinal Research Reviews, 25(6):679-736 (2005).

Ichida et al., "A small-molecule inhibitor of tgf-Beta signaling replaces sox2 in reprogramming by inducing nanog", Cell Stem Cell, 5(5): 491-503(2009).

Ieda et al., "Direct reprogramming of fibroblasts into functional cardiomyocytes by defined factors", Cell, 142, 375-86 (2010).

Inman et al., "SB-431542 is a potent and specific inhibitor of transforming growth factor-β Superfamily Type I Activin Receptor-Like Kinase (ALK) Receptors ALK4, ALK5, and ALK7", Molecular Pharmacology, 62(1): 65-74 (2002).

Ishizaki et al., "Pharmacological properties of Y-27632, a specific inhibitor of rho-associated kinases", Mol. Pharmacol., 57: 976-983 (2000).

Ivashchenko et al., "Human-induced pluripotent stem cell-derived cardiomyocytes exhibit temporal changes in phenotype," Am. J. Physiol. Heart Circ. Physiol., 305:H913-H922 (2013).

Jean et al., "Pluripotent genes in avian stem cells," Develop. Growth Differ., 55:41-51 (2013).

Jia et al., "A nonviral minicircle vector for deriving human iPS cells", Nat Methods, 7(3): 197-199 (2010).

Joliot et al., "alpha-2,8-Polysialic acid is the neuronal surface receptor of antennapedia homeobox peptide", New Biol., 3(11): 1121-1134 (1991).

Joliot et al., "Antennapedia homeobox peptide regulates neural morphogenesis", Proc. Natl. Acad. Sci. USA, 88(5): 1864-1868 (1991).

Kaji et al., "Virus-free induction of pluripotency and subsequent excision of reprogramming factors", Nature, 458(7239): 771-775 (2009).

Kaminska et al., "TGF beta signalling and its role in tumour pathogenesis", Acta Biochimica Polonica, 52(2): 329-337 (2005).

Kanatsu-Shinohara et al., "Generation of pluripotent stem cells from neonatal mouse testis", Cell, 119(7): 1001-1012 (2004).

Kelly et al., "Drug insight: Histone deacetylase inhibitors—development of the new targeted anticancer agent suberoylanilide hydroxamic acid", Nature Clinical Practice Oncology, 2(3): 150-157 (2005).

Kennedy et al., "Chronic exposure to morphine does not induce dependence at the level of the calcium channel current in human SH-SY5Y cells", Neuroscience, 49(4): 937-44 (1992).

Kitajima, H. et al. (Jun. 11, 2010,e-published May 9, 2010). "Clonal expansion of human pluripotent stem cells on gelatin-coated surface," Biochem Biophys Res Commun 396(4):933-938.

Kim et al. "Pluripotent stem cells induced from adult neural stem cells by reprogramming with two factors", Nature, 454(7204): 646-651 (2008).

Kim et al., "ct4-induced pluripotency in adult neural stem cells", Cell, 136(3): 411-419, (2009).

Kim et al., "Direct reprogramming of human neural stem cells by OCT4," Nature, 461(7264):649-653 (2009).

Kim et al., "Direct reprogramming of mouse fibroblasts to neural progenitors", Proc. Natl. Acad. Sci., USA, 108(9): 7838-7843 (2011).

Kim et al., "Generation of Human Induced Pluripotent Stem Cells by Direct Delivery of Reprogramming Proteins," Cell Stem Cell, 4(6): 472-476 (2009).

Kim et al., Eur J Biochem, "Enzymic properties of recombinant BACE2", Eur. J. Biochem., 269(22): 5668-5677 (2002).

Kim, et al., "Pharmacokinetics and tissue distribution of 3-((5-(6-methylpyridin-2-yl)-4-(quinoxalin-6-yl)-1H-imidazol-2-yl)methyl)benzamide; a novel ALK5 inhibitor and a potential anti-fibrosis drug", Xenobiotica, 38(3): 325-339 (2008).

Klein et al., "The effects of a novel MEK inhibitor PD184161 on MEK-ERK signaling and growth in human liver cancer", Neoplasia, 8: 1-8 (2006).

Krippl et al., "Functions of purified E1A protein microinjected into mammalian cells", Proc. Natl. Acad. Sci. USA, 81(22): 6988-6992 (1984).

Kubicek et al., "Reversal of H3K9me2 by a Small-Molecule Inhibitor for the G9a Histone Methyltransferase," Molecular Cell, 25(3): 473-481 (2007).

Kurosawa, "Application of Rho-associated protein kinase (ROCK) inhibitor to human pluripotent stem cells," J. Bioscience Bioengineering, 114(6):577-581 (2012).

Kuzmenkin et al., "Functional characterization of cardiomyocytes derived from murine induced pluripotent stem cells in vitro", FASEB J., 23(12): 4168-4180 (2009).

(56) References Cited

OTHER PUBLICATIONS

Lafevre, et al., "Recombinant, refolded tetrameric p53 and gonadotropin-releasing hormone-p53 slow proliferation and induce apoptosis in p53-deficient cancer cells", Molecular Cancer Therapeutics, 7(6): 1420-1429 (2008).

Leitch et al., "Naive pluripotency is associated with global DNA hypomethylation," Nature Structural Molecular Biology, 20(3):311-316 (2013).

Leroux et al., "Neurotrophic activity of the Antennapedia homeodomain depends on its specific DNA-binding properties", Proc. Natl. Acad. Sci. USA, 90(19): 9120-9124 (1993).

Levenson, "DNA (cytosine-5) methyltransferase inhibitors: a potential therapeutic agent for schizophrenia", Molecular Pharmacology, 71(3): 635-637 (2007).

Li et al., "Generation of novel rat and human pluripotent stem cells by reprogramming and chemical approaches," Methods in Molecular Biology, 636:293-300 (2010).

Li et al., "Generation of Human-induced Pluripotent Stem Cells in the Absence of Exogenous Sox2", Stem Cells, 27: 2992-3000 (2009).

Li et al., "MEK/ERK signaling contributes to the maintenance of human embryonic stem cell self-renewal", Differentiation, 75(4): 299-307 (2007).

Li et al., "Generation of rat and human induced pluripotent stem cells by combining genetic reprogramming and chemical inhibitors," Cell Stem Cell, 4(1): 16-19 (2009).

Li et al., "Small molecules that modulate embryonic stem cell fate and somatic cell reprogramming," Trends Pharmacal Sci, 31(1): 36-45 (2010).

Liang et al., "Cyclic adenosine 3',5'-monophosphate-dependent activation of mitogen-activated protein kinase in cumulus cells is essential for germinal vesicle breakdown of porcine cumulus-enclosed oocyte", Endocrinology, 146(10): 4437-4444 (2005).

Lim et al., "The pluripotency regulator zic3 is a direct activator of the nanog promoter in ESCs," Stem Cells, 28:1961-1969 (2010).

Lin et al., "A chemical platform for improved induction of human iPSCs", Nat Methods, 6(11): 805-808 (2009).

Lin et al., "A chemical platform for improved induction of human iPSCs", Nat Methods, 6:805-808, Supplemental Information, 7 pages (2009).

Lin et al., "Relationships of human immunodeficiency virus protease with eukaryotic aspartic proteases", Methods Enzymol, 241: 195-224 (1994).

Liu et al., "The calcium channel ligand FPL 64176 enhances L-type but inhibits N-type neuronal calcium currents", Neuropharmacology, 45(2): 281-292 (2003).

Loh et al., "Generation of induced pluripotent stem cells from human blood," Blood, 113(22): 5476-5479 (2009).

Lowry et al., "Generation of human induced pluripotent stem cells from dermal fibroblasts", Proc Natl Acad Sci USA, 105: 2883-2888 (2008).

Lyssiotis et al., "Reprogramming of murine fibroblasts to induced pluripotent stem cells with chemical complementation of Klf4", PNAS, 106: 8912-8917 (2009).

Ma et al., "G9a and Jhdm2a regulate embryonic stem cell fusion-induced reprogramming of adult neural stem cells", Stem Cells, 26(8): 2131-2141 (2008).

Maeda et al., "Endogenous TGF-β signaling suppresses maturation of osteoblastic mesencymal cells," The EMBO Journal, vol. 23, No. 3, Jan. 2004, pp. 552-563.

Maherali et al., "A high-efficiency system for the generation and study of human induced pluripotent stem cells", Cell Stem Cell, 3(3): 340-345 (2008).

Maherali et al., "Guidelines and techniques for the generation of induced pluripotent stem cells", Cell Stem Cell, 3(6): 595-605 (2008).

Maherali et al., "Directly Reprogrammed Fibroblasts Show Global Epigenetic Remodeling and Widespread Tissue Contribution," Cell Stem Cell, 1: 55-70 (2007).

Maherali et al., "Tgfβ Signal Inhibition Cooperates in the Induction of iPSCs and Replaces Sox2 and cMyc," Curr. Biology, 19: 1718-1723 (2009).

Mali et al., "Improved efficiency and pace of generating induced pluripotent stem cells from human adult and fetal fibroblasts", Stem Cells, 26(8): 1998-2005 (2008).

Malik, N. et al. (2013). "A review of the methods for human iPSC derivation," Methods Mol Biol, 997:23-33.

Manning et al., "AKT/PKB signaling: navigating downstream", Cell, 129(7): 1261-1274 (2007).

Marson et al., "Wnt signaling promotes reprogramming of somatic cells to pluripotency", Cell Stem Cell, 3(2): 132-135 (2008).

Martin et al., "Toll-like receptor-mediated cytokine production is differentially regulated by glycogen synthase kinase 3", Nature Immunology, 6(8): 777-784 (2005).

Massagué et al., "Controlling TGF-beta signaling", Genes Dev, 14(6): 627-644 (2000).

Massagué, J. "TGF-beta signal transduction", Annu Rev Biochem, 67: 753-791 (1998).

Mattingly et al., "The mitogen-activated protein kinase/extracellular signal-regulated kinase kinase inhibitor PD184352 (CI-1040) selectively induces apoptosis in malignant schwannoma cell lines", The Journal of Pharmacology and Experimental Therapeutics, 316(1): 456-465 (2006).

Meissner et al., "Direct reprogramming of genetically unmodified fibroblasts into pluripotent stem cells," Nature Biotechnology, 25(10): 1177-1181 (2007).

Mi et al., "Characterization of a class of cationic peptides able to facilitate efficient protein transduction in vitro and in vivo", Mol. Ther., 2(4): 339-347 (2000).

Mikkelsen et al., "Dissecting direct reprogramming through integrative genomic analysis", Nature, 454(7200) :49-55 (2008).

Miller et al., "Radiation resistance in a doxorubicin-resistant human fibrosarcoma cell line", Am. J. Clin. Oncol., 15(3): 216-221 (1992).

Moon et al., "Differentiation of hESCs into mesodermal subtypes: vascular- , hematopoietic- and mesenchymal-lineage cells," Int. J. Stem Cells, 4(1): 24-34 (2011).

Muller et al., "Upping the Ante: Recent Advances in Direct Reprogramming," Mol. Ther., 17: 947-953 (2009).

Munoz et al., "Conventional pluripotency markers are unspecific for bovine embryonic-derived cell-lines," Theriogenology, 69:1159-1164 (2008).

Munster et al., "Phase I/II trial combining the HDAC inhibitor, valproic acid (VPA) and FEC100 (5-fluorouracil, epirubicin and cyclophosphamide) in locally advanced/metastatic breast cancer", Journal of Clinical Oncology, 25(18S):1065 (2007).

Nabel et al., "An inducible transcription factor activates expression of human immunodeficiency virus in T cells", Nature 326(6114):711-713 (1987).

Nagata et al., "Generation of Ground State Human Induced Pluripotent Stem Cells with Kinase Inhibitors", 83th Japanese Association of Biochemistry Annual Meeting, 33th Japanese Association of Molecular Biology Abstract (CD-ROM), Nov. 19, 2010, Abstract No. 4P-0877 (with English Summary).

Nakagawa et al., "Generation of induced pluripotent stem cells without Myc from mouse and human fibroblasts", Nat Biotechnol,26(1): 101-106 (2008).

Nakajima et al., "Effect of Wf-536, a novel ROCK inhibitor, against metastasis of B16 melanoma", Cancer Chemother Pharmacol. 52(4): 319-324 (2003).

Narumiya, et al., "Use and properties of ROCK-specific inhibitor Y-27632", Methods Enzymol., 325: 273-284 (2000).

NCBI Gene "Gene ID: 999 CDH1 cadherin 1 [ *Homo sapiens* (human) ]" available online at https://www.ncbi.nlm.nih.gov/gene/999, accessed Dec. 14, 2020, updated Dec. 13, 2020 (Year: 2020).

Nissenbaum et al., "Global indiscriminate methylation in cell-specific gene promoters following reprogramming into human induced pluripotent stem cells," Stem Cell Reports, 1:509-517 (2013).

Noble et al., "Inhibition of glycogen synthase kinase-3 by lithium correlates with reduced tauopathy and degeneration in vivo", PNAS, 102(9): 6990-6995 (2005).

(56)                References Cited

OTHER PUBLICATIONS

Noggle et al., "A Molecular Basis for Human Embryonic Stem Cell Pluripotency," Stem Cell Reviews and Reports, 1(2): 1550-8943 (2005). DOI: 10.1385/scr:1:2:111.

Ohgushi, "Role of cell-cell adhesion in the survival regulation of human pluripotent stem cells," Experimental Medicine, 30(10):88-94 (2012).

Ohori, M., "Erk inhibitors as a potential new therapy for rheumatoid arthritis", Drug News Perspective, 21(5): 245-250 (2008).

Okada et al., "Effective culture conditions for the induction of pluripotent stem cells", Biochem Biophys Acta, 1800(9): 956-63 (2010).

Okita et al., "Generation of germline-competent induced pluripotent stem cells", Nature, 448(7151): 313-317 (2007).

Okita et al., "Generation of Mouse Induced Pluripotent Stem Cells Without Viral Vectors," Science, 322: 949-953 (2008).

Oliveri et al., "Epigenetic dedifferentiation of somatic cells into pluripotency: cellular alchemy in the age of regenerative medicine?", Regenerative Medicine, 2(5): 795-816 (2007).

Pan et al., "Identification of a nuclear localization signal in OCT4 and generation of a dominant negative mutant by its ablation", J. Biol. Chem., 279(35): 37013-37020 (2004).

Pakzad, M. et al. (Mar. 2010). "Presence of a ROCK inhibitor in extracellular matrix supports more undifferentiated growth of feeder-free human embryonic and induced pluripotent stem cells upon passaging," Stem Cell Rev Rep 6(1):96-107.

Paris et al., "Equine embryos and embryonic stem cells: definining reliable markers of pluripotency," Theriogenology, 74:516-524 (2010).

Park et al., "Reprogramming of human somatic cells to pluripotency with defined factors," Nature, 451(7175):141-146 (2008).

Paskind et al., "Dependence of Moloney murine leukemia virus production on cell growth", Virology, 67(1): 242-248 (1975).

PCT/US2009/037429, International Preliminary Report on Patentability dated Sep. 21, 2010, 7 pages.

PCT/US2009/037429, International Search Report mailed Aug. 12, 2009, 4 pages.

PCT/US2009/037429, Written Opinion mailed Aug. 12, 2009, 6 pages.

PCT/US2010/052896, International Preliminary Report on Patentability dated Apr. 17, 2012, 6 pages.

PCT/US2010/052896, International Search Report mailed Mar. 15, 2011, 4 pages.

PCT/US2010/052896, Written Opinion mailed Mar. 15, 2011, 5 pages.

PCT/US2011/065900, International Preliminary Report on Patentability dated Jun. 25, 2013.

PCT/US2011/065900, International Search Report and Written Opinion mailed Jul. 19, 2012.

PCT/US2015/018801, International Preliminary Report on Patentability, mailed Sep. 6, 2016.

PCT/US2015/018801, International Search Report and Written Opinion mailed May 20, 2015.

Peerani et al., "Niche-mediated control of human embryonic stem cell self-renewal and differentiation", EMBO J., 26(22): 4744-4755 (2007).

Pesce et al., "Differential expression of the Oct-4 transcription factor during mouse germ cell differentiation", Mechanisms of Development, 71: 89-98 (1998).

Planello et al., "Aberrant DNA methylation reprogramming during induced pluripotent stem cell generation is dependent on the choice of reprogramming factors," Cell Regeneration, 3:4 (2014).

Plath et al., "Progress in understanding reprogramming to the induced pluripotent state", Nature Reviews, 12(4): 253-265 (2011).

Plews et al., "Activation of pluripotency genes in human fibroblast cells by a novel mRNA based approach", PLoS One, 5(12): e14397, pp. 1-10 (2010).

Plews et al., "Activation of Pluripotency Genes in Human Fibroblast Cells by a Novel mRNA Based Approach," PLoS One, 5(12): 1-10 (2010).

Potter et al., "Enhancer-dependent expression of human kappa immunoglobulin genes introduced into mouse pre-B lymphocytes by electroporation", Proc. Nat'l Acad. Sci. USA, 81(22): 7161-7165 (1984).

Radcliffe et al., "Multiple gene products from a single vector: 'self-cleaving' 2A peptides," Gene Therapy, 11:1673-1674 (2004).

Riento et al, "Rocks: multifunctional kinases in cell behaviour", Nat. Rev. Mol. Cell. Biol., 4(6): 446-456 (2003).

Rinehart et al., "Multicenter phase II study of the oral MEK inhibitor, CI-1040, in patients with advanced non-small-cell lung, breast, colon, and pancreatic cancer", Journal of Clinical Oncology, 22(22): 4456-4462 (2004).

Roberts et al., "PD98059 Enhanced Insulin, Cytokine, and Growth Factor Activation of Xanthine Oxidoreductase in Epithelial Cells Involves STAT3 and the Glucocoticoid Receptor", Journal of Cellular Biochemistry, 101: 1567-1587 (2007).

Ruhnke et al., "Long-term culture and differentiation of rat embryonic stem cell-like cells into neuronal, glial, endothelial, and hepatic lineages", Stem Cells, 21(4): 428-436 (2003).

Ryan et al., "POU domain family values: flexibility, partnerships, and developmental codes", Genes Dev., 11(10): 1207-1225 (1997).

Saha et al., "TGFbeta/Activin/Nodal pathway in inhibition of human embryonic stem cell differentiation by mechanical strain", Biophys. J., 94(10): 4123-4133 (2008).

Saha et al., "Technical challenges in using human induced pluripotent stem cells to model disease", Cell Stem Cell, 5(6): 584-595 (2009).

Sasaki et al., "The novel and specific Rho-kinase inhibitor (S)-(+)-2-methyl-1-[(4-methyl-5-isoquinoline)sulfonyl]-homopiperazine as a probing molecule for Rho-kinase-involved pathway", Pharmacol. Ther., 93(2-3): 225-232 (2002).

Sato et al., "Molecular signature of human embryonic stem cells and its comparison with the mouse", Dev. Biol., 260(2): 404-413 (2003).

Schenke-Layland et al., "Reprogrammed mouse fibroblasts differentiate into cells of the cardiovascular and hematopoietic lineages", Stem Cell, 26(6): 1537-1546 (2008).

Schermelleh et al., "Trapped in action: direct visualization of DNA methyltransferase activity in living cells", Nature Methods, 2(10): 751-756 (2005).

Schramm et al., "Novel dihydropyridines with positive inotropic action through activation of Ca2+ channels", Nature, 303: 535-537 (1983).

Schugar et al., "Small molecules in stem cell self-renewal and differentiation", Gene Ther, 15(2): 126-135 (2008).

Schulze et al., "Derivation, maintenance, and characterization of rat embryonic stem cells in vitro", Methods Mol Biol, 329: 45-58 (2006).

Seaberg et al., "Clonal identification of multipotent precursors from adult mouse pancreas that generate neural and pancreatic lineages", Nature Biotechnol., 22(9): 1115-1124 (2004).

Sells et al., "Delivery of protein into cells using polycationic liposomes" BioTechniques, 19(1): 72-78 (1995).

Shi "Induction of Pluripotent Stem Cells from Mouse Embryonic Fibroblasts by Oct4 and Klf4 with Small-Molecule Compounds", Cell Stem Cell, 3: 568-574 (2008).

Shi et al., "Dynamic regulation of histone lysine methylation by demethylases", Molecular Cell, 25: 1-14 (2007).

Shi et al., "A Combined Chemical and Genetic Approach for the Generation of Induced Pluripotent Stem Cells", Cell Stem Cell, 2(6): 525-528 (2008).

Shields et al., "Two potent nuclear localization signals in the gut-enriched Krüppel-like factor define a subfamily of closely related Krüppel proteins", J. Biol. Chem., 272: 18504-18507 (1997).

Shimanuki et al., "Modulation of the functional binding sites for TGF-beta on the type II receptor leads to suppression of TGF-beta signaling", Oncogene, 26: 3311-3320 (2007).

Silva et al., "Nanog is the gateway to the pluripotent ground state", Cell, 138(4): 722-737 (2009).

Silva et al., "Promotion of reprogramming to ground state pluripotency by signal inhibition", PLoS Biology, 6(10):253, pp. 2237-2247 (2008).

Singh et al., "A heterogeneous expression pattern for Nanog in embryonic stem cells", Stem Cells, 25(10): 2534-2542 (2007).

(56)            References Cited

OTHER PUBLICATIONS

Soldner et al., "Parkinson's disease patient-derived induced pluripotent stem cells free of viral reprogramming factors", Cell, 136: 964-977 (2009).

Sridharan et al., "Role of the murine reprogramming factors in the induction of pluripotency", Cell, 136(2): 364-377 (2009).

Stacey et al., "Microinjection of transforming ras protein induces c-fos expression", Mol. Cell. Biol., 7: 523-527 (1987).

Stadtfeld et al., "A reprogrammable mouse strain from gene-targeted embryonic stem cells", Nat Methods, 7: 53-55 (2010).

Stadtfeld et al., "Defining molecular cornerstones during fibroblast to iPS cell reprogramming in mouse", Cell Stem Cell, 2: 230-240 (2008).

Stadtfeld et al., "Induced Pluripotent Stem Cells Generated Without Viral Integration," Science, 322: 945-949 (2008).

Stadtfeld et al., "Reprogramming of Pancreatic B Cells into Pluripotent Stem Cells," Curr. Biol., 18(12): 890-894 (2008). doi: 10.1016/j.cub.2008.05.010.

Studier, "Protein production by auto-induction in high density shaking cultures", Protein Expr Purif., 41(1): 207-234 (2005).

Sullivan et al., "Elucidating nuclear reprogramming mechanisms: taking a synergistic approach", Reproductive BioMed. Online, 16(1): 41-50 (2008).

Suzuki et al., "A novel small-molecule inhibitor of transforming growth factor beta type I receptor kinase (SM16) inhibits murine mesothelioma tumor growth in vivo and prevents tumor recurrence after surgical resection", Cancer Research, 67(5): 2351-2359 (2007).

Sylvester et al., "Stem cells: review and update", Arch Surg., 136:93-99, (2004).

Szabo et al., "Direct conversion of human fibroblasts to multilineage blood progenitors", Nature, 468(7323): 521-526 (2010).

Szymczak et al., "Correction of multi-gene deficiency in vivo using a single'self-cleaving' 2A peptide-based retroviral vector," Nature Biotechnology, 22(5): 589-594 (2004).

Tada, et al., "Nuclear reprogramming of somatic cells by in vitro hybridization with ES cells," Curr. Biology, 11: 1553-1558 (2001).

Takahashi et al., "Induction of pluripotent stem cells from fibroblast cultures", Nat Protoc, 2: 3081-3089 (2007).

Takahashi et al., "Induction of Pluripotent Stem Cells from Mouse Embryonic and Adult Fibroblast Cultures by Defined Factors," Cell, 126(4): 663-676 (2006).

Takahashi et al., "Induction of Pluripotent Stem Cells from Adult Human Fobroblasts by Defined Factors", Cell, 131: 861-872 (2007).

Takei, et al., "Bone morphogenetic protein-4 promotes induction of cardiomyocytes from human embryonic stem cells in serum-based embryoid body development," Am J Physiol Heart Circ Physiol, 296(5): H1793-H1803 (2009).

Takeuchi et al., "Directed transdifferentiation of mouse mesoderm to heart tissue by defined factors," Nature, 459(7247): 708-711 (2009).

Taranger et al., "Induction of Dedifferentiation, Genomewide Transcriptional Programming, and Epigenetic Reprogramming by Extracts of Carcinoma and Embryonic Stem Cells," Molecular Biology of the Cell, 16: 5719-5735 (2005).

Tesar et al., "New cell lines from mouse epiblast share defining features with human embryonic stem cells", Nature, 448: 196-199 (2007).

Thiery et al., "Complex networks orchestrate epithelial-mesenchymal transitions", Nat. Rev. Mol. Cell Biol., 7: 131-142 (2006).

Thompson et al., "Recent progress in targeting the Raf/MEK/ERK pathway with inhibitors in cancer drug discovery", Curr. Opin. Pharmacology, 5(4): 350-356 (2005).

Thomson et al. (Jun. 10, 2011). "Pluripotency Factors in Embryonic Stem Cells Regulate Differentiation Into Germ Layers," Cell 145(6):875-889.

Tighe et al., "GSK-3 inhibitors induce chromosome instability", BMC Cell Biol. 8:34 doi//:www.biomedcentral.com/1471-2121/8/34, printout pp. 1-17 (2007).

Tojo et al., "The ALK-5 inhibitor A-83-01 inhibits Smad signaling and epithelia-to-mesenchymal transition by transforming growth factor-β," Cancer Sci, 96(11): 791-800 (2005).

Tosti E., "Calcium ion currents mediating oocyte maturation events", Reprod Biol Endocrinol, 4: 26 (2006).

Toyooka, Yayoi, et al., "Identification and characterization of subpopulations in undifferentiated ES cell culture," Development, 135(5):909-918 (2008).

Tur-Kaspa et al., "Use of electroporation to introduce biologically active foreign genes into primary rat hepatocytes", Mol. Cell Biol., 6: 716-718 (1986).

Ueda et al., "Establishment of rat embryonic stem cells and making of chimera rats", PLoS One, 3: e2800 (2008).

Uehata et al., "Calcium sensitization of smooth muscle mediated by a Rho-associated protein kinase in hypertension", Nature, 389: 990-994 (1997).

Valamehr et al., "Developing defined culture systems for human pluripotent stem cells," Regenerative Medicine, 6(5):623-634 (2011).

Valamehr et al. (2012, e-published Jan. 6, 2012). "A novel platform to enable the high-throughput derivation and characterization of feeder-free human iPSCs," Sci Rep 2:213.

Valamehr et al., "Platform for induction and maintenance of transgene-free hiPSCs resembling ground state pluripotent stem cells," Stem Cell Reports, 2:366-381 (2014).

Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.

Vierbuchen et al., "Direct conversion of fibroblasts to functional neurons by defined factors," Nature, 463(7284): 1035-1042 (2010).

Wadia et al., "Protein transduction technology", Curr. Opin. Biotechnol., 13: 52-56 (2002).

Wagman et al., "Discovery and development of GSK3 inhibitors for the treatment of type 2 diabetes", Current Pharmaceutical Design, 10(10): 1105-1137 (2004).

Wang, J. et al. (Dec. 18, 2014, e-published Oct. 15, 2014). "Primate-specific endogenous retrovirus-driven transcription defines naive-like stem cells," Nature 516(7531):405-409.

Wang et al., "Clinical experience of MEK inhibitors in cancer therapy", Biochimica et Biophysica Acta 1773, pp. 1248-1255 (2007).

Wang et al., "The Immunophilin FKBP12 Functions as a Common Inhibitor of the TGFβ Family Type 1 Receptors", Cell, 86: 435-444 (1996).

Warren et al., "Highly efficient reprogramming to pluripotency and directed differentiation of human cells with synthetic modified mRNA", Cell Stem Cell, 7(5): 618-630 (2010).

Watabe et al., "TGF-β receptor kinase inhibitor enhances growth and integrity of embryonic stem cell-derived endothelial cells", The Journal of Cell Biology, 163(6): 1303-1311 (2003).

Watabe et al., "Roles of TGF-beta family signaling in stem cell renewal and differentiation", Cell Res., 19: 103-115 (2009).

Watanabe et al., "Activation of Akt signaling is sufficient to maintain pluripotency in mouse and primate embryonic stem cells", Oncogene, 25: 2697-2707 (2006).

Watanabe et al., "A Rock inhibitor permits survival of dissociated human embryonic stem cells," Nature Biotechnology, 25(6):681-868 (2007).

Wenlin et al., "Generation of novel rat and human pluripotent stem cells by reprogramming and chemical approaches," Methods in Molecular Biology, 636: 293-300 (2010).

Wernig et al., "c-Myc is Dispensable for Direct Reprogramming of Mouse Fibroblasts," Cell Stem Cell, 2: 10-12 (2008).

Wernig et al., "A drug-inducible transgenic system for direct reprogramming of multiple somatic cell types", Nat Biotechnol, 26: 916-924 (2008).

Wernig, et al., "In vitro reprogramming of fibroblasts into a pluripotent ES-cell-like state," Nature, 448(7151): 318-324 (2007).

Willis et al., "TGF-beta-induced EMT: mechanisms and implications for fibrotic lung disease", Am. J Physiol. Lung Cell Physiol., 293: L525-L534 (2007).

Wilson et al., "Implantation of vascular grafts lined with genetically modified endothelial cells", Science, 244(4910): 1344-1346 (1989).

(56) References Cited

OTHER PUBLICATIONS

Wissmann et al., "Cooperative demethylation by JMJDC2 and LSD1 promotes androgen receptor-dependent gene expression", Nature Cell Biology, 9(3): 347-353; and Supplementary Information (12 pages) (2007).

Woltjen et al., "piggyBac transposition reprograms fibroblasts to induced pluripotent stem cells", Nature, 458(7239): 766-770 (2009).

Wong et al. (Apr. 29, 2011). "L1TD1 is a marker for undifferentiated human embryonic stem cells," *PLoS One* 6(4):e19355.

Wong et al., "Appearance of beta-lactamase activity in animal cells upon liposome-mediated gene transfer", Gene, 10: 87-94 (1980).

Wrzesinski et al., "Transforming growth factor-beta and the immune response: implications for anticancer therapy", Clinical Cancer Research, 13(18): 5262-5270 (2007).

Wu et al., "Evidence for targeted gene delivery to Hep G2 hepatoma cells in vitro", Biochemistry, 27: 887-892 (1988).

Wu et al., "Receptor-mediated in vitro gene transformation by a soluble DNA carrier system", J Biol. Chem., 262(10): 4429-4432 (1987).

Wu et al., "Cellular senescence is an important mechanism of tumor regression upon c-Myc inactivation," PNAS, 104(32): 13028-13033 (2007).

Xiong et al., "Histone deacetylase inhibitors DNA methyltransferase-3B messenger RNA stability and down-regulate de novo DNA methyltransferase activity in human endometrial cells," Cancer Res., 65(7): 2684-2689 (2005).

Xu et al., "A chemical approach to stem-cell biology and regenerative medicine", Nature, 453: 338-344 (2008).

Xu et al., "BMP4 initiates human embryonic stem cell differentiation to trophoblas", Nat. Biotechnol, 20(12): 1261-1264 (2002).

Xu et al., "Revealing a core signaling regulatory mechanism for pluripotent stem cell survival and self-renewal by small molecules," PNAS, 107(8): 8129-8134 (2010).

Yamanaka, "Strategies and New Developments in the Generation of Patient-Specific Pluripotent Stem Cells," Cell Stem Cell, 1(1): 39-49 (2007).

Yamanaka, et. al. "Induction of pluripotent stem cells from mouse embryonic and adult fibroblast cultures by defined factors", Cell, 126: 663-676 (2006).

Ying et al., "BMP induction of Id proteins suppresses differentiation and sustains embryonic stem cell self-renewal in collaboration with STAT3", Cell, 115(3): 281-292 (2003).

Ying et al., "Changing potency by spontaneous fusion", Nature, 416: 545-548 (2002).

Ying et al., "The ground state of embryonic stem cell self-renewal", Nature, 453: 519-523 (2008).

Yu et al., "Human induced pluripotent stem cells free of vector and transgene sequences", Science, 324(5928): 797-801 (2009).

Yu et al., "Induced pluripotent stem cell lines derived from human somatic cells", Science, 318: 1917-1920 (2007).

Zhang et al., "Sall4 modulates embryonic stem cell pluripotency and early embryonic development by the transcriptional regulation of Pou5f1", Nat. Cell Biol., 8(10): 1114-1123 (2006).

Zhao et al., "Granzyme K cleaves the nucleosome assembly protein SET to induce single-stranded DNA nicks of target cells", Cell Death and Differentiation, 14(3): 489-499 (2007).

Zhao et al., "Resorcylic Acid Lactones: Naturally Occurring Potent and Selective Inhibitors of MEK", The Journal of Antibiotics, 52(12): 1086-1094 (1999).

Zhao et al., "Two supporting factors greatly improve the efficiency of human iPSC generation", Cell Stem Cell, 3(5): 475-479 (2008).

Zhao, et al., "Inhibition of transforming growth factor-beta1-induced signaling and epithelial-to-mesenchymal transition by the Smad-binding peptide aptamer Trx-SARA", Molecular Biology of the Cell, 17(9): 3819-3831 (2006).

Zheng et al., "Lipid-mediated protein delivery of suicide nucleoside kinases", Cancer Res., vol. 63(20): 6909-6913 (2003).

Zhou et al., "In vivo reprogramming of adult pancreatic exocrine cells to beta-cells", Nature, 455(7213): 627-632 (2008).

Zhou et al., "Conversion of Mouse Epiblast Stem Cells to an Earlier Pluripotency State by Small Molecules," Journal of Biological Chemistry, 285(39): 29676-29680 (2010). DOI: 10.1074/jbc.C110.150599.

Zhou Hongyan et al., "Generation of Induced Pluripotent Stem Cells Using Recombinant Proteins", Cell Stem Cell, 4: 381-384 (2009).

Zhu and Otterson et al., "The interaction of histone deacetylase inhibitors and DNA methyltransferase inhibitors in the treatment of human cancer cells", Current Medicinal Chemistry, 3(3): 187-199 (2003).

Zhu et al., "Induction of S-phase arrest and p21 overexpression by a small molecule 2[[3-(2,3-dichlorophenoxy)propyl] amino]ethanol in correlation with activation of ERK", Oncogene, 23: 4984-4992 (2004).

Zhu et al., "Reprogramming of human primary somatic cells by OCT4 and chemical compounds," Cell Stem Cell, 7(6): 651-655 (2010).

Tsutsui et al., "An optimized small molecule inhibitor cocktail supports long-term maintenance of human embryonic stem cells," Nat. Comm., 2:167 (2011).

Jung et al., "ONSL and OSKM cocktails act synergistically in reprogramming human somatic cells into induced pluripotent stem cells", Molecular Human Reproduction, 20(6): 538-549 (2014).

Radzisheuskaya et al., "Do all roads lead to Oct4? The emerging concepts of induced pluripotency", Trends Cell Biol., 24(5):275-284 (2013).

Zhou et al., "Evolution of induced pluripotent stem cell technology", *Current Opinions in Hematology*, 17:276-280 (2010).

Takashima et al., "Resetting transcription factor control circuitry toward ground-state pluripotency in human," *Cell*, 158:1254-1269 (2014).

Ning ed., *Animal Cloning and Genome Editing*, China Agricultural University Press, Beijing, China, pp. 175 (2012).

* cited by examiner

FTC007-c21

FTC007-c21          FTC016-c25

FTC017-c11_p15

| Vector System | Abbreviation |
|---|---|
| EF1a-OCT4-2A-NANOG-2A-SOX2 | ONS |
| EF1a-OCT4-2A-SOX2 | OS |
| EF1a-OCT4-2A-OCT4 | 2xO |
| EF1a-SV40LT | T |

2x0+OS+ONS+T-c10 p12

| 213 Probe sets upregulated in conventional hESC culture group vs. FMM culture group | | | |
|---|---|---|---|
| GO ID | GO Term | % | p-value |
| GO:0007389 | pattern specification process | 11.2 | 2.20E-10 |
| GO:0003002 | regionalization | 8.1 | 1.90E-07 |
| GO:0048598 | embryonic morphogenesis | 8.1 | 1.90E-05 |
| GO:0009952 | anterior/posterior pattern formation | 5.6 | 3.60E-05 |
| GO:0043009 | chordate embryonic development | 6.2 | 2.90E-03 |
| GO:0009792 | embryonic development ending in birth or egg hatching | 6.2 | 3.10E-03 |
| GO:0001756 | somitogenesis | 2.5 | 3.40E-03 |
| GO:0001775 | cell activation | 5.6 | 4.20E-03 |
| GO:0001667 | ameboidal cell migration | 2.5 | 4.30E-03 |
| GO:0048568 | embryonic organ development | 4.4 | 4.50E-03 |
| GO:0040029 | regulation of gene expression, epigenetic | 3.1 | 5.00E-03 |
| GO:0010557 | positive regulation of macromolecule biosynthetic process | 8.8 | 5.70E-03 |
| GO:0010628 | positive regulation of gene expression | 8.1 | 5.80E-03 |
| GO:0045321 | leukocyte activation | 5 | 6.00E-03 |
| GO:0048562 | embryonic organ morphogenesis | 3.8 | 6.80E-03 |
| GO:0030111 | regulation of Wnt receptor signaling pathway | 2.5 | 8.00E-03 |
| GO:0031328 | positive regulation of cellular biosynthetic process | 8.8 | 8.20E-03 |
| GO:0046649 | lymphocyte activation | 4.4 | 8.90E-03 |
| GO:0035282 | segmentation | 2.5 | 9.00E-03 |
| GO:0009891 | positive regulation of biosynthetic process | 8.8 | 9.20E-03 |
| GO:0010604 | positive regulation of macromolecule metabolic process | 10 | 9.40E-03 |

*FIG. 7B*

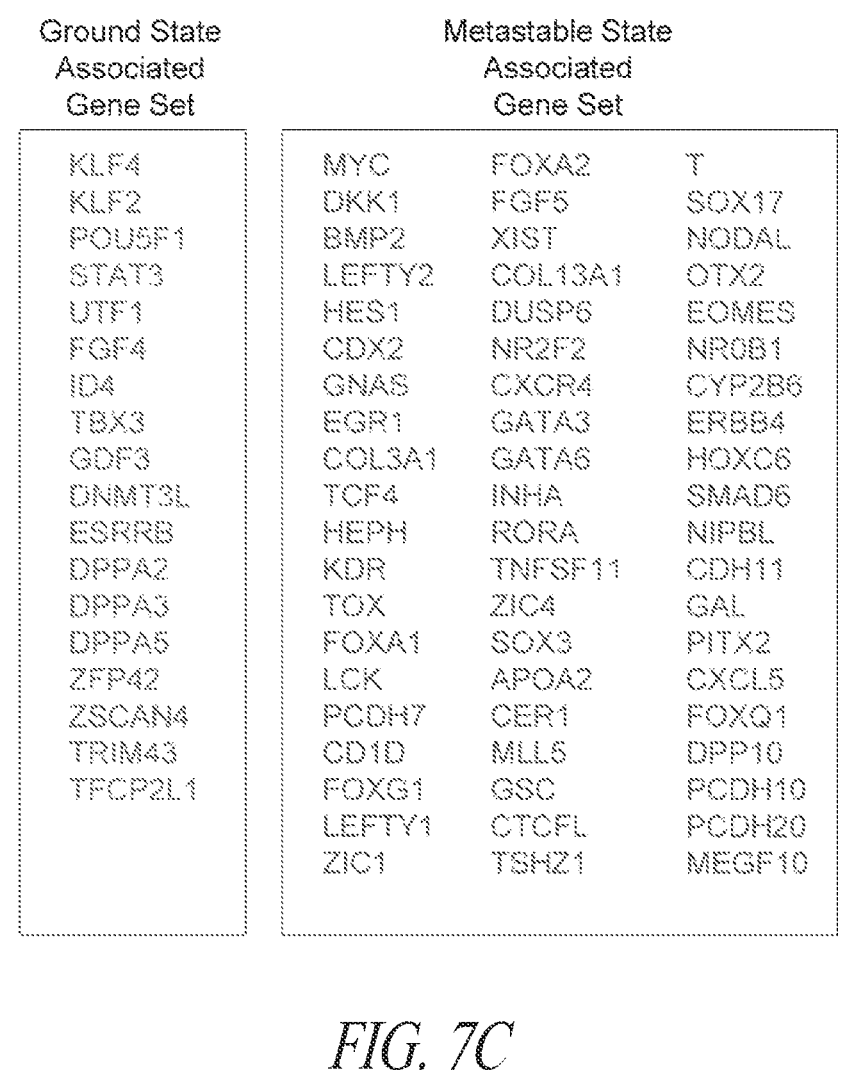

Ground State
Associated
Gene Set

Metastable State
Associated
Gene Set

| | | |
|---|---|---|
| KLF4 | MYC | FOXA2 | T |
| KLF2 | DKK1 | FGF5 | SOX17 |
| POU5F1 | BMP2 | XIST | NODAL |
| STAT3 | LEFTY2 | COL13A1 | OTX2 |
| UTF1 | HES1 | DUSP6 | EOMES |
| FGF4 | CDX2 | NR2F2 | NR0B1 |
| ID4 | GNAS | CXCR4 | CYP2B6 |
| TBX3 | EGR1 | GATA3 | ERBB4 |
| GDF3 | COL3A1 | GATA6 | HOXC6 |
| DNMT3L | TCF4 | INHA | SMAD6 |
| ESRRB | HEPH | RORA | NIPBL |
| DPPA2 | KDR | TNFSF11 | CDH11 |
| DPPA3 | TOX | ZIC4 | GAL |
| DPPA5 | FOXA1 | SOX3 | PITX2 |
| ZFP42 | LCK | APOA2 | CXCL5 |
| ZSCAN4 | PCDH7 | CER1 | FOXQ1 |
| TRIM43 | CD1D | MLL5 | DPP10 |
| TFCP2L1 | FOXG1 | GSC | PCDH10 |
| | LEFTY1 | CTCFL | PCDH20 |
| | ZIC1 | TSHZ1 | MEGF10 |

*FIG. 7C*

3F Lenti-hiPSC-c3: SMC4

3F Lenti-hiPSC-c2: SMC4

Epi-FTC007-c21: FMM

Epi-FTC016-c28: FMM

3F Lenti-hiPSC-c4: Conv→FMM

6F Lenti-hiPSC-c3: Conv→FMM

Epi-FTC016-c36: FMM

HUE9 hESC: Conv

6F Lenti-hiPSC-c3: Conv

6F Lenti-hiPSC-c2: Conv

6F Lenti-hiPSC-c1: Conv

Epi-FTC016-c28: FMM→Conv

H1 hESC: Conv

3F Lenti-hiPSC-c4: Conv

3F Lenti-hiPSC-c1: Conv

| Nomenclature | Cell Type | Source | Ethnicity | Gender | Age | Culture Medium | Percent SSEA4/TRA181 Positive Population At Time of 96-Well Plate FACS |
|---|---|---|---|---|---|---|---|
| FTC007 | Fibroblast | Neonatal Foreskin | Caucasian | Male | Neonatal | DMEM + 10%FBS | 8.55% (Day 19 post induction) |
| FTC008 | Fibroblast | Dermal Skin | Asian | Female | Adult | DMEM + 10%FBS | 1.81% (Day 16 post induction) |
| FTC016 | CD34+ Hematopoietic Cells | Cord Blood, AllCells | Pool | Pool | Neonatal | Stempro + CC110 | 29.3% (Day 19 post induction) |
| FTC017 | CD34+ Hematopoietic Cells | Cord Blood, Fate derived | African American | Male | Neonatal | Stempro + CC110 | 41.2% (Day 21 post induction) |

*FIG. 9A*

Continuous Culture on Matrigel       Continuous Culture on Vitronectin

Continuous Culture on Matrigel       Continuous Culture on Vitronectin

OCT4 NANOG DAPI

2xO + ONS                          2xO + ONS + T

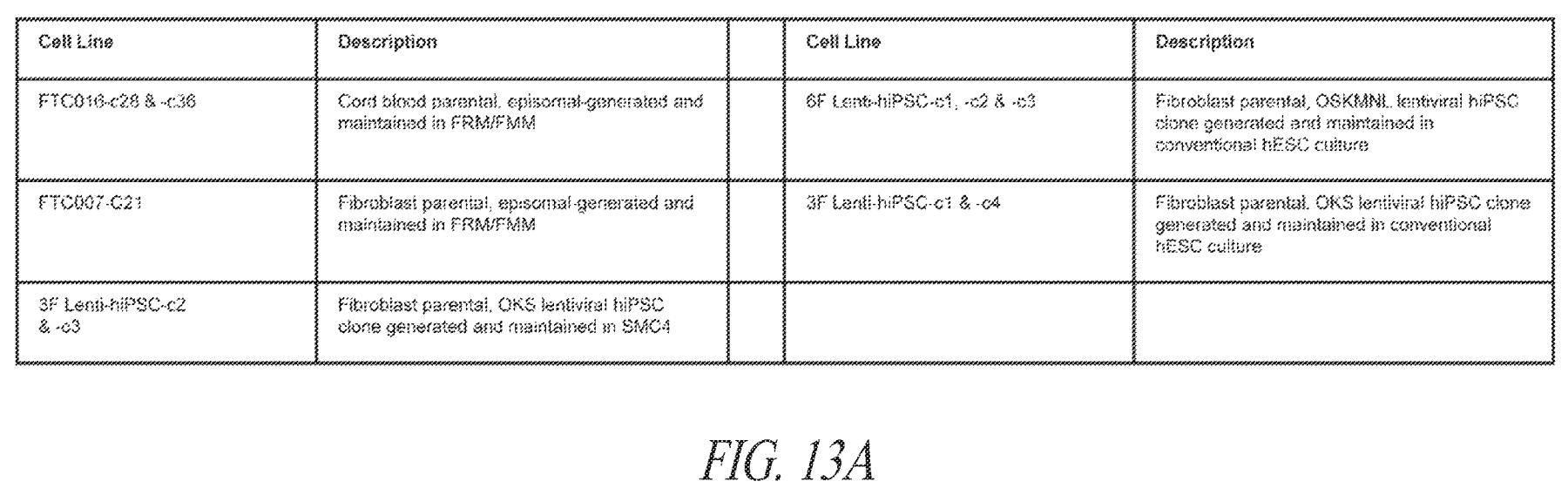

| Cell Line | Description | | Cell Line | Description |
|---|---|---|---|---|
| FTC016-c28 & -c36 | Cord blood parental, episomal-generated and maintained in FRM/FMM | | 6F Lenti-hiPSC-c1, -c2 & -c3 | Fibroblast parental, OSKMNL lentiviral hiPSC clone generated and maintained in conventional hESC culture |
| FTC007-C21 | Fibroblast parental, episomal-generated and maintained in FRM/FMM | | 3F Lenti-hiPSC-c1 & -c4 | Fibroblast parental, OKS lentiviral hiPSC clone generated and maintained in conventional hESC culture |
| 3F Lenti-hiPSC-c2 & -c3 | Fibroblast parental, OKS lentiviral hiPSC clone generated and maintained in SMC4 | | | |

*FIG. 13A*

| 133 Probe sets upregulated in conventional hESC culture group vs. FMM/SMC4 culture group | | |
|---|---|---|
| GO ID | GO Term | % | p-value |
| GO:0007389 | pattern specification process | 9.7 | 3.50E-05 |
| GO:0048598 | embryonic morphogenesis | 8.6 | 5.90E-04 |
| GO:0001775 | cell activation | 7.5 | 2.30E-03 |
| GO:0046649 | lymphocyte activation | 6.5 | 2.50E-03 |
| GO:0042110 | T cell activation | 5.4 | 3.00E-03 |
| GO:0002521 | leukocyte differentiation | 5.4 | 3.40E-03 |
| GO:0030217 | T cell differentiation | 4.3 | 3.60E-03 |
| GO:0030097 | hemopoiesis | 6.5 | 5.10E-03 |
| GO:0045321 | leukocyte activation | 6.5 | 5.70E-03 |
| GO:0007610 | behavior | 8.6 | 6.50E-03 |
| GO:0048534 | hemopoietic or lymphoid organ development | 6.5 | 7.60E-03 |
| GO:0048568 | embryonic organ development | 5.4 | 8.90E-03 |
| GO:0002520 | immune system development | 6.5 | 9.80E-03 |

*FIG. 13C*

| 167 Probe sets upregulated in small molecule culture group vs. conventional culture group | | | |
|---|---|---|---|
| GO ID | GO Term | % | p-value |
| GO:0042127 | regulation of cell proliferation | 12.4 | 5.20E-04 |
| GO:0051205 | protein insertion into membrane | 2.5 | 1.50E-03 |
| GO:0009725 | response to hormone stimulus | 7.4 | 2.60E-03 |
| GO:0051668 | localization within membrane | 2.5 | 4.20E-03 |
| GO:0009719 | response to endogenous stimulus | 7.4 | 4.80E-03 |
| GO:0008284 | positive regulation of cell proliferation | 7.4 | 5.50E-03 |
| GO:0008406 | gonad development | 4.1 | 6.10E-03 |
| GO:0009636 | response to toxin | 3.3 | 7.30E-03 |
| GO:0014070 | response to organic cyclic substance | 4.1 | 8.00E-03 |
| GO:0043066 | negative regulation of apoptosis | 6.6 | 8.20E-03 |
| GO:0048545 | response to steroid hormone stimulus | 5 | 8.30E-03 |
| GO:0008585 | female gonad development | 3.3 | 8.30E-03 |
| GO:0043069 | negative regulation of programmed cell death | 6.6 | 8.80E-03 |
| GO:0060548 | negative regulation of cell death | 6.6 | 9.00E-03 |
| GO:0048608 | reproductive structure development | 4.1 | 9.20E-03 |
| GO:0045137 | development of primary sexual characteristics | 4.1 | 9.40E-03 |
| GO:0046660 | female sex differentiation | 3.3 | 1.00E-02 |
| GO:0046545 | development of primary female sexual characteristics | 3.3 | 1.00E-02 |

*FIG. 13D*

| 126 Probe sets upregulated in FMM samples group vs. conventional culture group | | | |
|---|---|---|---|
| GO ID | GO Term | % | p-value |
| GO:0007267 | cell-cell signaling | 16.5 | 8.20E-07 |
| GO:0040008 | regulation of growth | 10.3 | 1.10E-04 |
| GO:0042981 | regulation of apoptosis | 15.5 | 1.20E-04 |
| GO:0043067 | regulation of programmed cell death | 15.5 | 1.30E-04 |
| GO:0010941 | regulation of cell death | 15.5 | 1.30E-04 |
| GO:0010817 | regulation of hormone levels | 7.2 | 1.90E-04 |
| GO:0045926 | negative regulation of growth | 6.2 | 3.60E-04 |
| GO:0031100 | organ regeneration | 4.1 | 3.90E-04 |
| GO:0001558 | regulation of cell growth | 7.2 | 7.10E-04 |
| GO:0043066 | negative regulation of apoptosis | 9.3 | 7.40E-04 |
| GO:0043069 | negative regulation of programmed cell death | 9.3 | 8.20E-04 |
| GO:0060548 | negative regulation of cell death | 9.3 | 8.30E-04 |
| GO:0016358 | dendrite development | 4.1 | 9.40E-04 |
| GO:0006916 | anti-apoptosis | 7.2 | 9.70E-04 |
| GO:0045596 | negative regulation of cell differentiation | 7.2 | 1.20E-03 |
| GO:0030308 | negative regulation of cell growth | 5.2 | 1.70E-03 |
| GO:0050768 | negative regulation of neurogenesis | 4.1 | 2.00E-03 |
| GO:0045792 | negative regulation of cell size | 5.2 | 2.20E-03 |
| GO:0010721 | negative regulation of cell development | 4.1 | 2.40E-03 |
| GO:0042445 | hormone metabolic process | 5.2 | 2.80E-03 |
| GO:0032535 | regulation of cellular component size | 7.2 | 3.90E-03 |
| GO:0034754 | cellular hormone metabolic process | 4.1 | 4.30E-03 |
| GO:0051270 | regulation of cell motion | 6.2 | 4.30E-03 |
| GO:0048754 | branching morphogenesis of a tube | 4.1 | 5.60E-03 |
| GO:0008361 | regulation of cell size | 6.2 | 5.70E-03 |
| GO:0001569 | patterning of blood vessels | 3.1 | 5.90E-03 |
| GO:0031099 | regeneration | 4.1 | 6.60E-03 |
| GO:0035295 | tube development | 6.2 | 7.50E-03 |
| GO:0009991 | response to extracellular stimulus | 6.2 | 7.50E-03 |
| GO:0001763 | morphogenesis of a branching structure | 4.1 | 8.00E-03 |
| GO:0006917 | induction of apoptosis | 7.2 | 8.60E-03 |
| GO:0012502 | induction of programmed cell death | 7.2 | 8.70E-03 |

*FIG. 13E*

OCT4/NANOG/ECAT1/UTF1

OCT4/ESRRB/NANOG/ECAT1/UTF1

OCT4/ESRRB/LIN28/ECAT1/UTF-1

OCT4-P2A-OCT4 / NANOG-P2A-ESRRB-P2A-LIN28 / ECAT1-T2A-UTF1

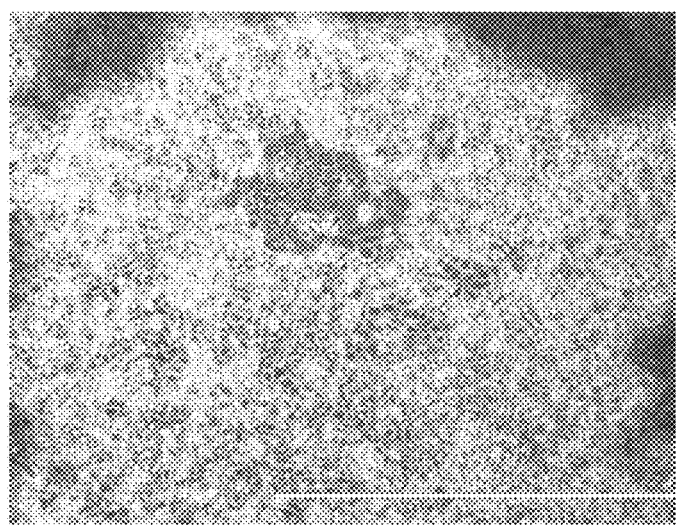
FIG. 16B
OCT4-P2A-ESRRB / OCT4-P2A-NANOG / ECAT1-T2A-UTF1
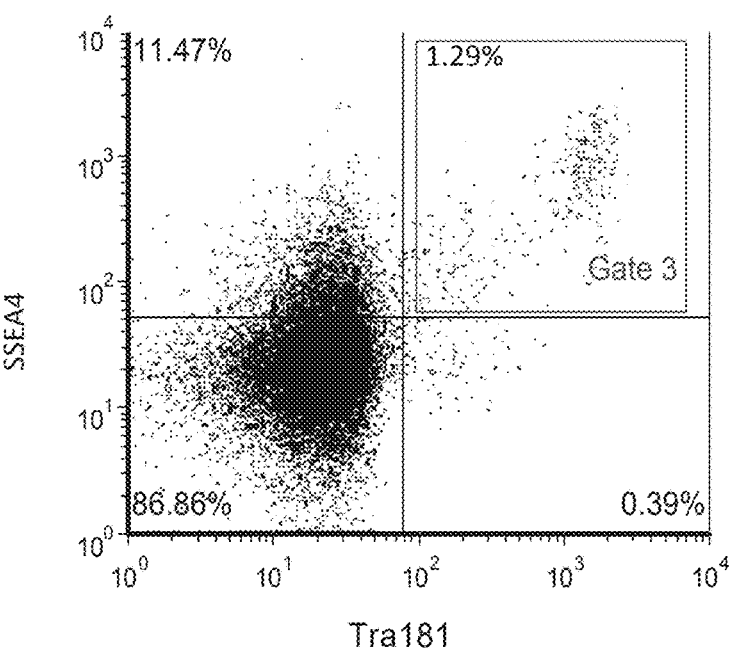

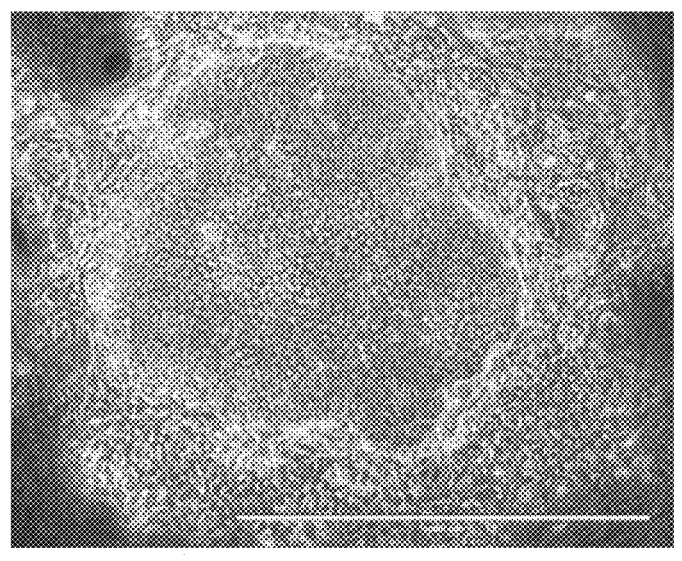
*FIG. 16C*
OCT4-P2A-OCT4 / ECAT1-T2A-UTF1
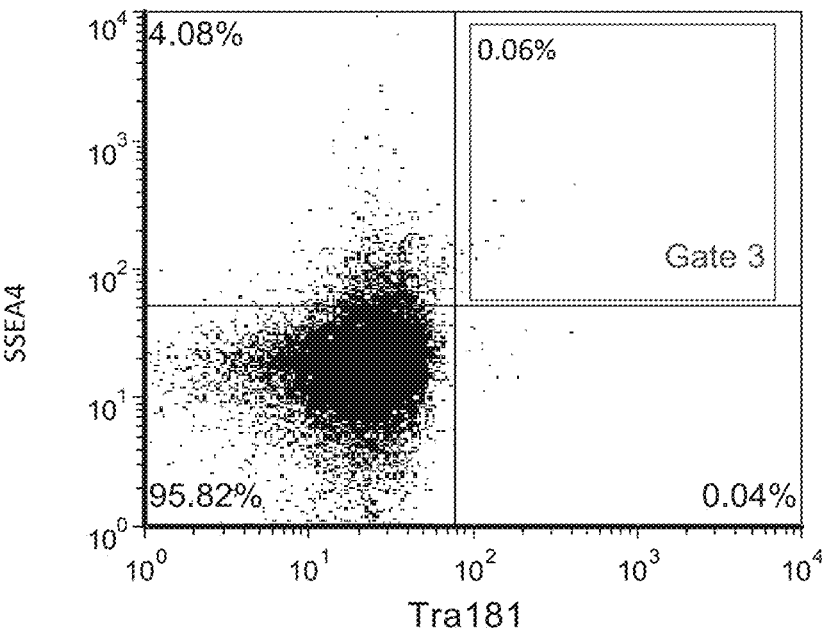

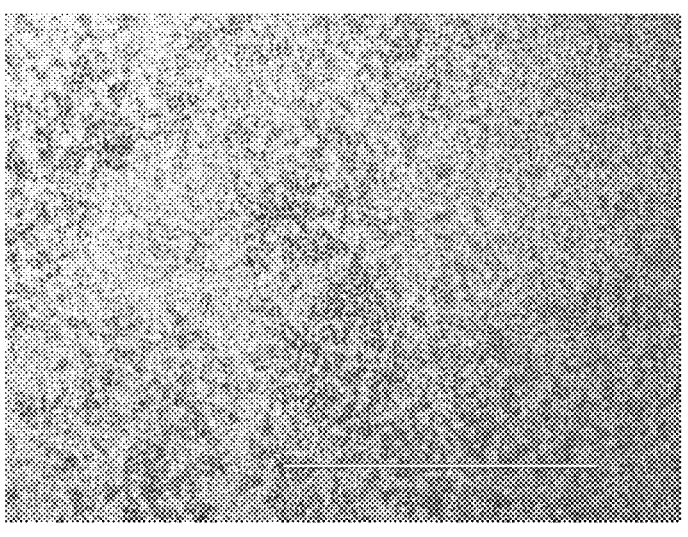
*FIG. 16D*
OCT4-P2A-NANOG / ECAT1-T2A-UTF1
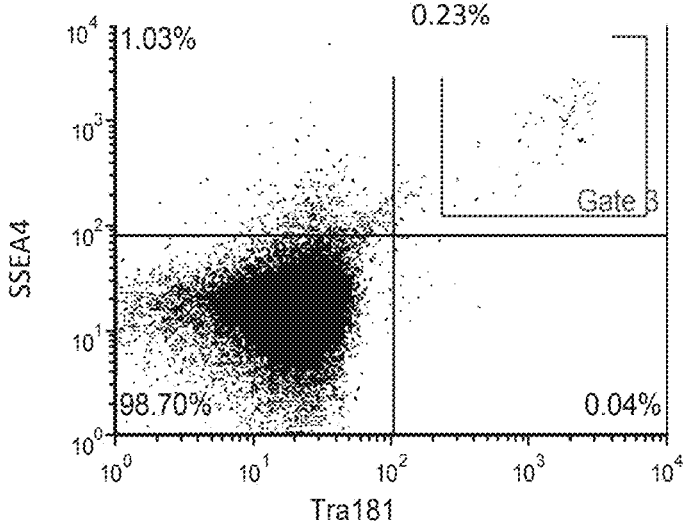

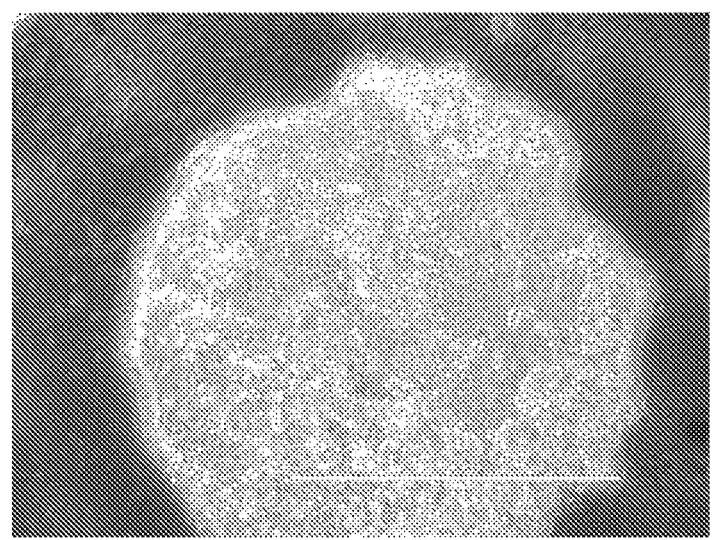
*FIG. 17A*
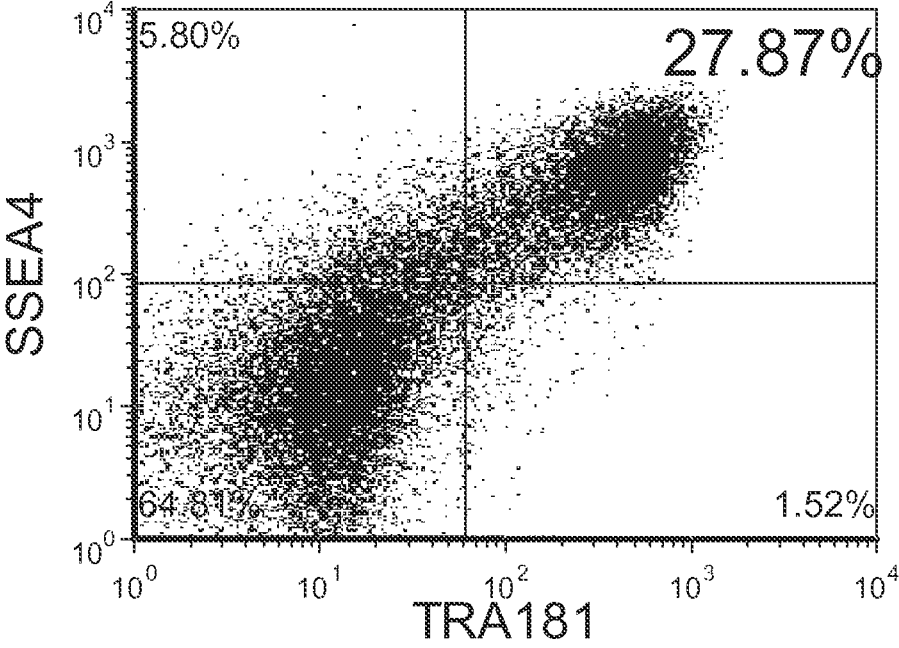

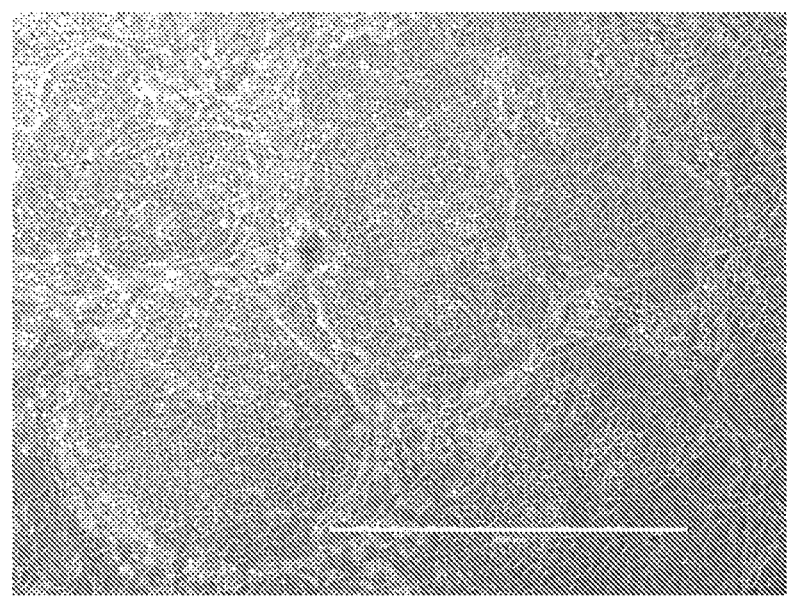
*FIG. 17B*
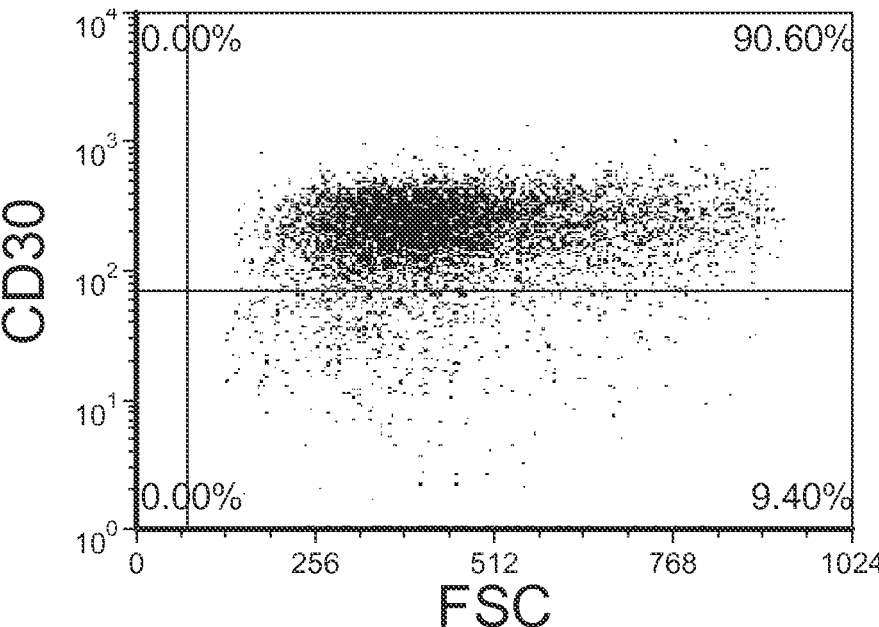

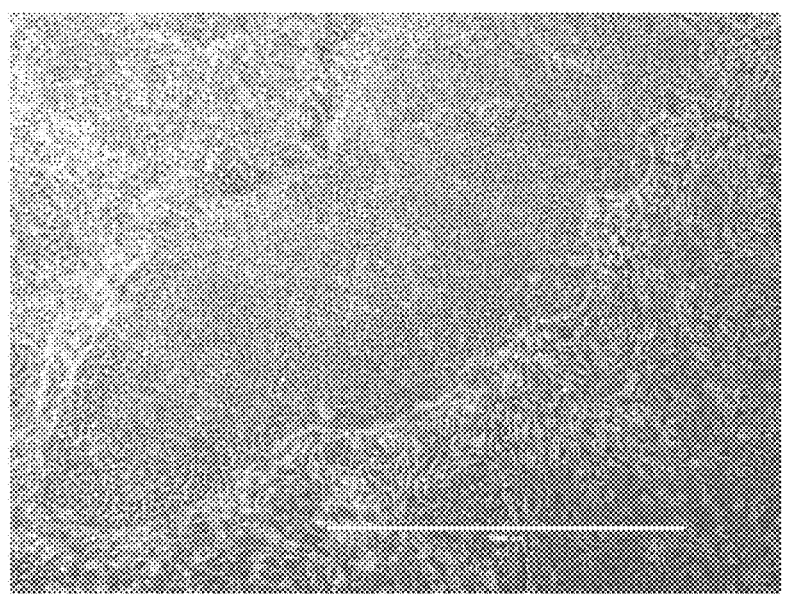
*FIG. 18A*
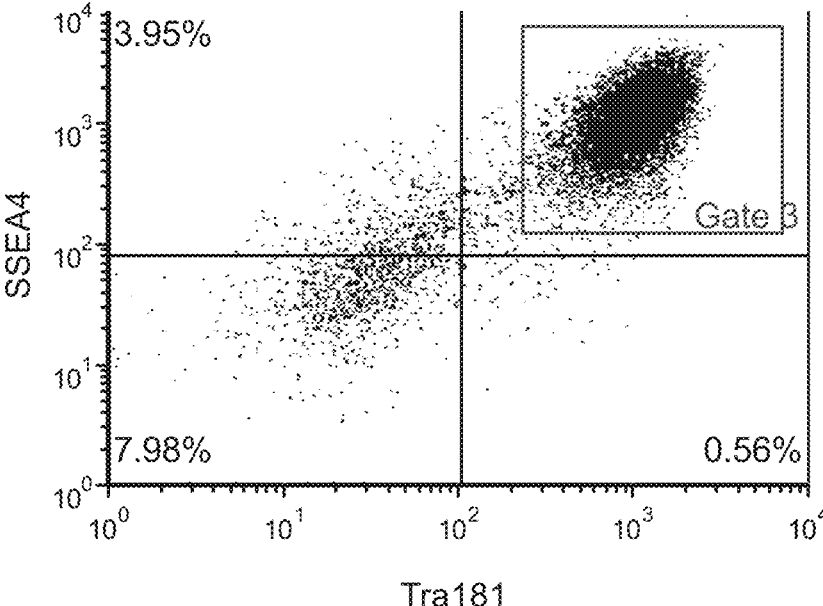

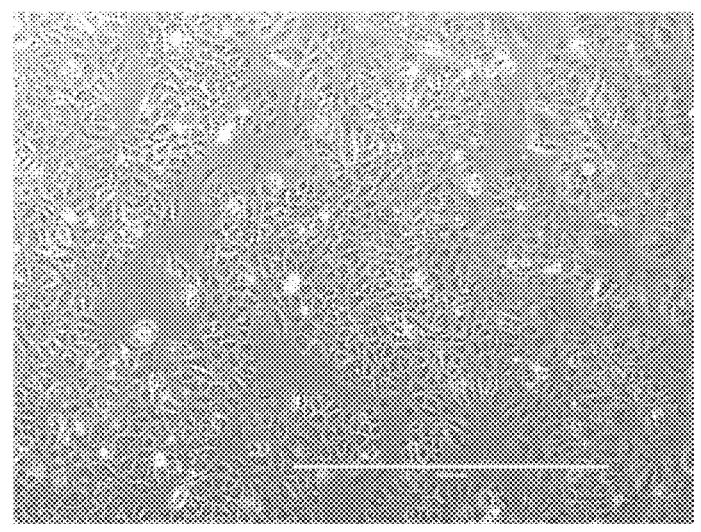
*FIG. 18B*
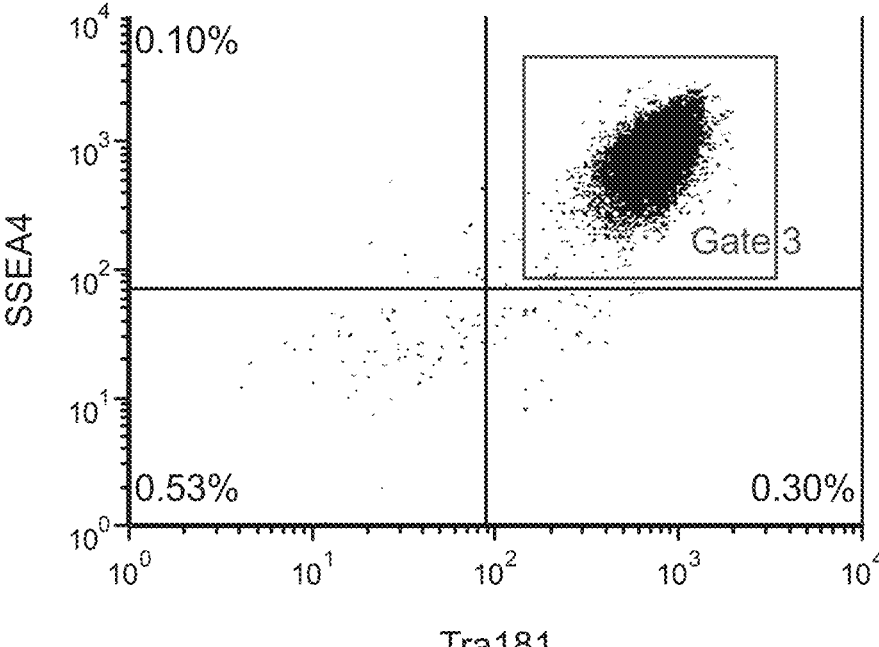

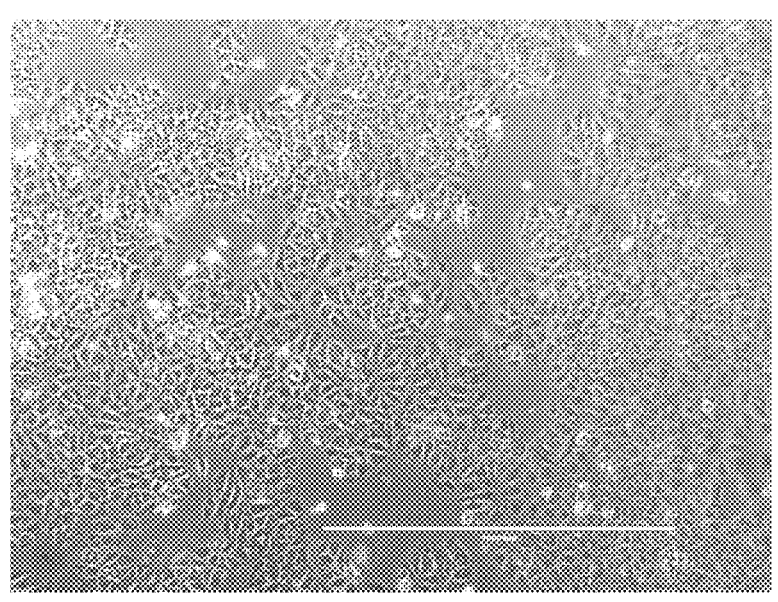
*FIG. 18C*
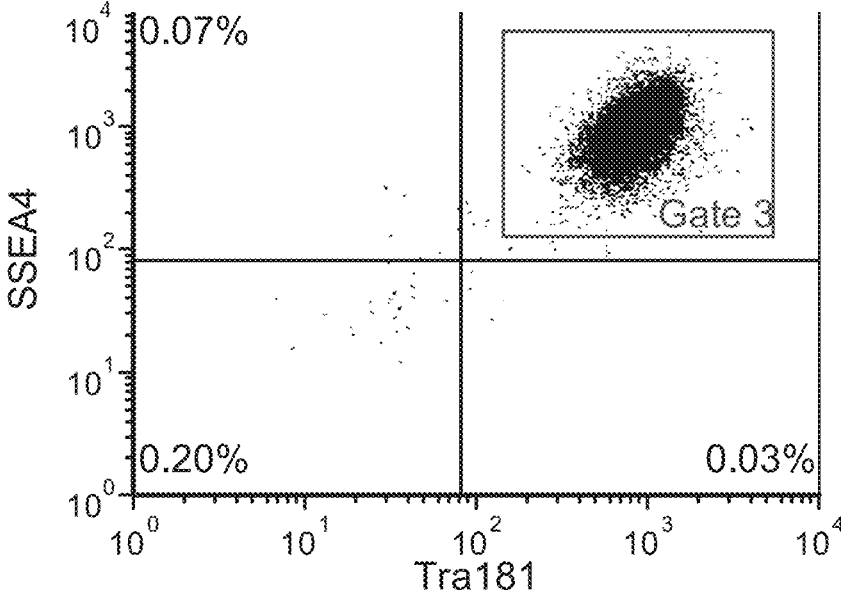

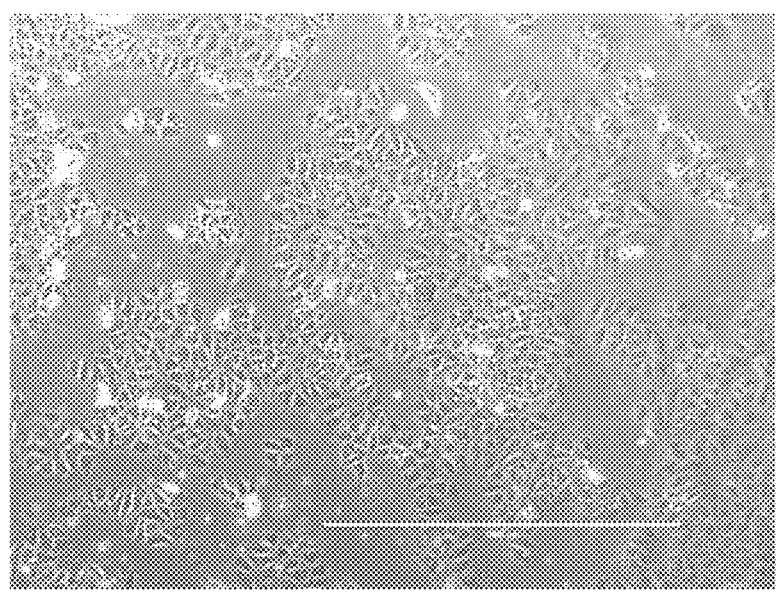
*FIG. 18D*
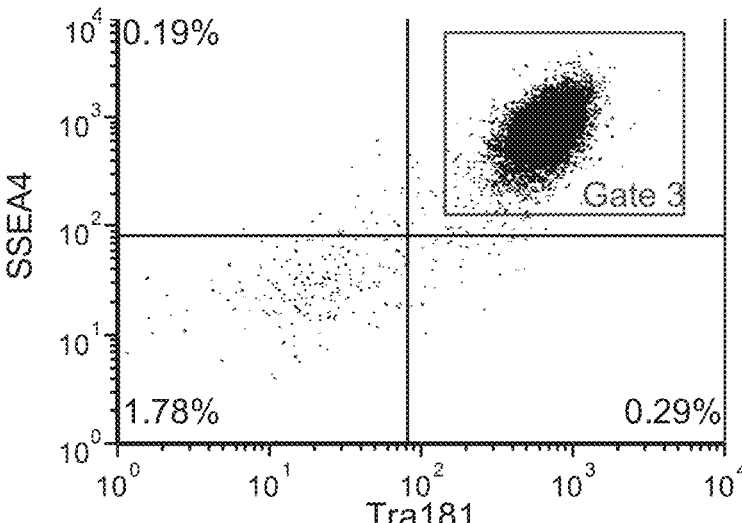

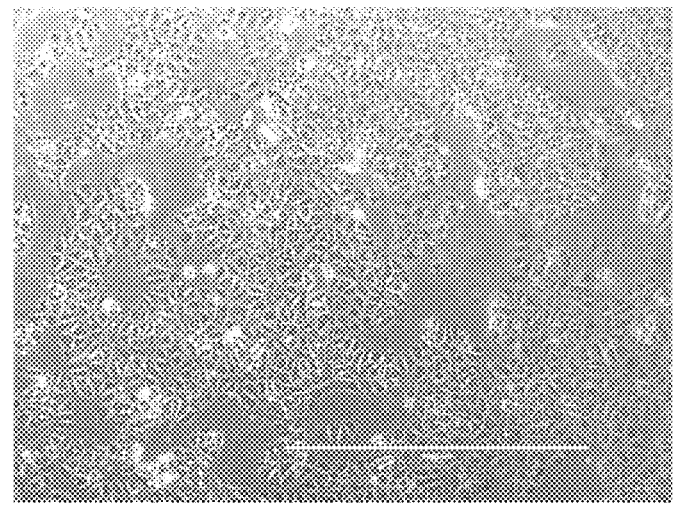
*FIG. 19A*
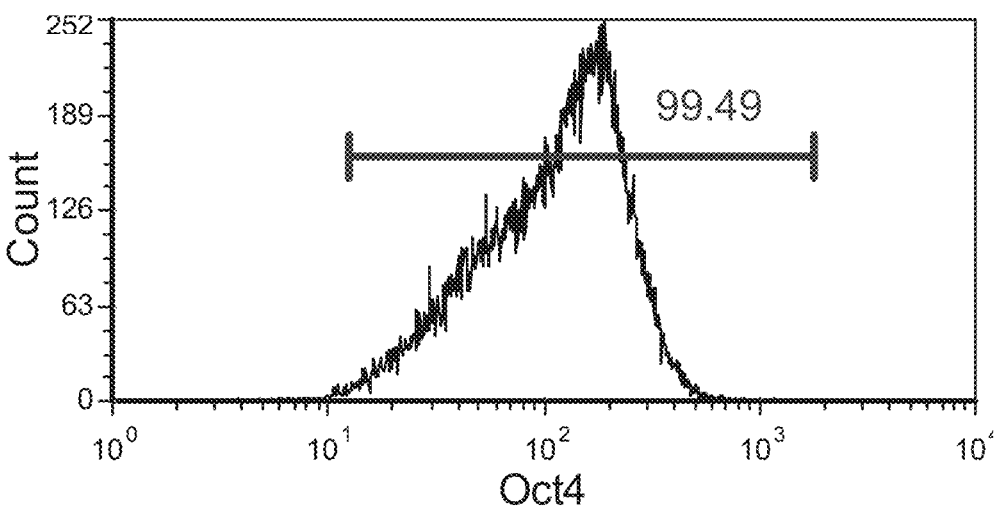

Clone 5, Passage 9

Clone 10, Passage 8

Clone 3, Passage 9

OCT4-P2A-OCT4 / NANOG-P2A-ESRRB-T2A-LIN28 / ECAT1-T2A-UTF1

OCT4-P2A-ESRRB / OCT4-P2A-NANOG / ECAT1-T2A-UTF1

| Constant Expression | Selection for | SSEA4/Tra181 Positive by flow analysis |
|---|---|---|
| OCT4-P2A-NANOG-T2A-SOX2 SV40 Large T Antigen | No Selection | 0.9% |
| OCT4-P2A-NANOG-T2A-SOX2 SV40 Large T Antigen OCT4-P2A-SOX2-Puro | OCT4/SOX2 | 0.24% |
| OCT4-P2A-NANOG-T2A-SOX2 SV40 Large T Antigen OCT4-P2A-NANOG-T2A-SOX2-Puro | OCT4/NANOG/SOX2 | 0.86% |
| OCT4-P2A-NANOG-T2A-SOX2 SV40 Large T Antigen OCT2-P2A-OCT4-Puro | OCT4 | 13.93% |

OCT4-P2A-NANOG-T2A-SOX2 /SV40 Large T Antigen

OCT4-P2A-NANOG-T2A-SOX2 / SV40 Large T Antigen / OCT2-P2A-OCT4-Puro

SEQUENCE LISTING

<160> NUMBER OF SEQ ID NOS: 31

<210> SEQ ID NO 1
<211> LENGTH: 19
<212> TYPE: PRT
<213> ORGANISM: Artificial Sequence
<220> FEATURE:
<223> OTHER INFORMATION: Synthetic made in lab

<400> SEQUENCE: 1

Leu Leu Asn Phe Asp Leu Leu Lys Leu Ala Gly Asp Val Glu Ser Asn
1               5                   10                  15

Pro Gly Pro

<210> SEQ ID NO 2
<211> LENGTH: 19
<212> TYPE: PRT
<213> ORGANISM: Artificial Sequence
<220> FEATURE:
<223> OTHER INFORMATION: Synthetic made in lab

<400> SEQUENCE: 2

Thr Leu Asn Phe Asp Leu Leu Lys Leu Ala Gly Asp Val Glu Ser Asn

```
1               5               10              15

Pro Gly Pro

<210> SEQ ID NO 3
<211> LENGTH: 14
<212> TYPE: PRT
<213> ORGANISM: Artificial Sequence
<220> FEATURE:
<223> OTHER INFORMATION: Synthetic made in lab

<400> SEQUENCE: 3

Leu Leu Lys Leu Ala Gly Asp Val Glu Ser Asn Pro Gly Pro
1               5               10

<210> SEQ ID NO 4
<211> LENGTH: 17
<212> TYPE: PRT
<213> ORGANISM: Artificial Sequence
<220> FEATURE:
<223> OTHER INFORMATION: Synthetic made in lab

<400> SEQUENCE: 4

Asn Phe Asp Leu Leu Lys Leu Ala Gly Asp Val Glu Ser Asn Pro Gly
1               5               10              15

Pro

<210> SEQ ID NO 5
<211> LENGTH: 20
<212> TYPE: PRT
<213> ORGANISM: Artificial Sequence
<220> FEATURE:
<223> OTHER INFORMATION: Synthetic made in lab

<400> SEQUENCE: 5

Gln Leu Leu Asn Phe Asp Leu Leu Lys Leu Ala Gly Asp Val Glu Ser
1               5               10              15

Asn Pro Gly Pro
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic made in lab

<400> SEQUENCE: 6

Ala Pro Val Lys Gln Thr Leu Asn Phe Asp Leu Leu Lys Leu Ala Gly
1               5               10              15

Asp Val Glu Ser Asn Pro Gly Pro
            20

<210> SEQ ID NO 7
<211> LENGTH: 40
<212> TYPE: PRT
<213> ORGANISM: Artificial Sequence
<220> FEATURE:
<223> OTHER INFORMATION: Synthetic made in lab

<400> SEQUENCE: 7

Val Thr Glu Leu Leu Tyr Arg Met Lys Arg Ala Glu Thr Tyr Cys Pro
1               5               10              15

Arg Pro Leu Leu Ala Ile His Pro Thr Glu Ala Arg His Lys Gln Lys
            20              25              30
```

Ile Val Ala Pro Val Lys Gln Thr
        35                  40

<210> SEQ ID NO 8
<211> LENGTH: 18
<212> TYPE: PRT
<213> ORGANISM: Artificial Sequence
<220> FEATURE:
<223> OTHER INFORMATION: Synthetic made in lab

<400> SEQUENCE: 8

Leu Asn Phe Asp Leu Leu Lys Leu Ala Gly Asp Val Glu Ser Asn Pro
1               5                   10                  15

Gly Pro

<210> SEQ ID NO 9
<211> LENGTH: 40
<212> TYPE: PRT
<213> ORGANISM: Artificial Sequence
<220> FEATURE:
<223> OTHER INFORMATION: Synthetic made in lab

<400> SEQUENCE: 9

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 10
<211> LENGTH: 33
<212> TYPE: PRT
<213> ORGANISM: Artificial Sequence
<220> FEATURE:
<223> OTHER INFORMATION: Synthetic made in lab

<400> SEQUENCE: 10

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gcccccaccc tttgtgtt                                                  18

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ttgaaaactt tggcttcctt gtt                                            23

```
<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
caggcccgaa agagaaagcg                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggagggcctt ggaagcttag                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tatacacagg ccgatgtggg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ttgaccggga ccttgtcttc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gtggtccgag tgtggttctg                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gttctcctgg gccatcttgc                                              20

<210> SEQ ID NO 19
<211> LENGTH: 20
<212> TYPE: DNA
<213> ORGANISM: Artificial Sequence
<220> FEATURE:
```

-continued

```
<223> OTHER INFORMATION: Primer

<400> SEQUENCE: 19
aagcgcagat caaaaggaga                                        20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 cccccctgaac ctgaaacata                                       20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
tgcttcccgt atggctttc                                         19

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
aaagggagat ccgactcgtc tg                                     22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atcgtcaaag ctgcacacag                                        20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cccaggagtc ccagtagtca                                        20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gtggacctga cctgccgtct                                        20
```

```
<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ggaggagtgg gtgtcgctgt                                                  20

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
gggtttttgg gattaagttc ttca                                             24

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
agcctaaatg atggtgcttg gt                                               22

<210> SEQ ID NO 29
<211> LENGTH: 7
<212> TYPE: PRT
<213> ORGANISM: Artificial Sequence
<220> FEATURE:
<223> OTHER INFORMATION: Polypeptide cleavage recognition site
<220> FEATURE:
<221> NAME/KEY: MISC_FEATURE
<222> LOCATION: (2)..(2)
<223> OTHER INFORMATION: Xaa represent any amino acid
<220> FEATURE:
<221> NAME/KEY: MISC_FEATURE
<222> LOCATION: (3)..(3)
<223> OTHER INFORMATION: Xaa represent any amino acid
<220> FEATURE:
<221> NAME/KEY: MISC_FEATURE
<222> LOCATION: (5)..(5)
<223> OTHER INFORMATION: Xaa represent any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 29

Glu Xaa Xaa Tyr Xaa Gln Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Polypeptide cleavage recognition site

<400> SEQUENCE: 30

Glu Asn Leu Tyr Phe Gln Gly
1               5

<210> SEQ ID NO 31
```

-continued

```
<211> LENGTH: 7
<212> TYPE: PRT
<213> ORGANISM: Artificial Sequence
<220> FEATURE:
<223> OTHER INFORMATION: Polypeptide cleavage recognition site

<400> SEQUENCE: 31

Glu Asn Leu Tyr Phe Gln Ser
1               5
```

REPROGRAMMING METHODS AND CELL CULTURE PLATFORMS

CROSS REFERENCE TO RELATED APPLICATIONS

This application claims the benefit under 35 U.S.C. § 119(e) of U.S. Provisional Application No. 61/947,979, filed Mar. 4, 2014, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FATE_122_01WO_ST25.txt. The text file is 8 KB, was created on Mar. 4, 2015, and is being submitted electronically via EFS-Web, concurrent with the filing of the specification.

BACKGROUND

Technical Field

The invention relates generally to compositions and methods for manufacturing pluripotent cells. In particular, the invention relates to improved culture platforms for manufacturing pluripotent cells with ground state pluripotency.

Description of the Related Art

Today's pluripotent stem cell-based disease and toxicology screening efforts and tomorrow's auto/allogeneic pluripotent stem cell therapies will require robust, reproducible methods of cell line generation and expansion of human embryonic stem cells (hESCs) and human induced pluripotent stem cells (hiPSCs). hiPSCs have been generated by the ectopic expression of pluripotency factors introduced through genome-integrating retro- and lentiviral expression systems. Efforts to eliminate as many integrating events as possible have included substituting small molecule inhibitors for a number of reprogramming factors. In addition, non-integrative methods have proven to be inefficient and labor intensive, requiring additional reprogramming factors or not being effective in reprogramming all somatic cells (Lee et al., 2013).

Several challenges associated with the culture of pluripotent stem cells have yet to be addressed to allow the cells to become suitable for future industrial and clinical applications. In the most commonly used conventional culture system, hESCs and hiPSCs are maintained on feeder cells while passaged as clumps to prevent extensive cell death and genomic aberrations (Thomson et al., 1998). The inability to single cell culture hiPSCs in a feeder-free (FF) environment severely limits potential industrial scale screening or cell therapy applications (Skottman et al., 2007; Valamehr et al., 2011). In addition, recent efforts on improving hiPSCs have focused on lentiviral derived hiPSC that were not transgene-free, limiting the therapeutic relevance of such efforts.

Another challenge yet to be successfully addressed, short of genome modification, is the propensity for spontaneous differentiation of human pluripotent stem cells in culture (Pera and Trounson, 2004; Sathananthan and Trounson, 2005; Valamehr et al., 2011).

Studies in hESCs and hiPSCs have been described, but continuous ectopic expression of pluripotency genes were necessary to maintain the ground state resulting in genome modified human pluripotent stem cells (Hanna et al., 2010a), which are unsuitable for industrial- and clinical-grade pluripotent cells.

Accordingly, the absence of compositions and methods for high-throughput, transgene or footprint free generation of human pluripotent cell products has thus far proven to be a substantial hurdle in the development and commercialization of future pluripotent stem cell therapies.

BRIEF SUMMARY

The invention generally provides improved cell culture platforms.

In various embodiments, the invention contemplates, in part, a composition comprising: (a) a Wnt pathway agonist; (b) a MEK inhibitor; and (c) a ROCK inhibitor, wherein the composition does not comprise a TGFβR inhibitor.

In particular embodiments, the Wnt pathway agonist is a GSK3 inhibitor.

In certain embodiments, the GSK3 inhibitor is CHIR99021 or BIO.

In additional embodiments, the MEK inhibitor is PD98059 or PD032901.

In further embodiments, the ROCK inhibitor is thiazovivin or Y27632.

In some embodiments, the GSK3 inhibitor is CHIR99021; the MEK inhibitor is PD032901; and the ROCK inhibitor is thiazovivin.

In certain embodiments, any of the foregoing compositions further comprises bFGF or LIF.

In further embodiments, any of the foregoing compositions further comprises bFGF and LIF.

In various embodiments, a culture medium is provided comprising any of the foregoing compositions, wherein the medium does not comprise a TGFβR inhibitor.

In some embodiments, a method of culturing one or more pluripotent cells comprising culturing the one or more pluripotent cells in a cell culture medium according to any of the foregoing culture media.

In additional embodiments, the one or more pluripotent cells are embryonic stem cells (ESCs) or induced pluripotent stem cells (iPSCs).

In particular embodiments, the one or more pluripotent cells are iPSCs.

In certain embodiments, the composition comprises a population of pluripotent cells.

In further embodiments, the population of pluripotent cells is a homogenous population of pluripotent cells.

In particular embodiments, at least 95% of the population of pluripotent cells expresses SSEA4-FITC and TRA1-81 or TRA1-60.

In some embodiments, at most 5% of the population of pluripotent cells expresses α-smooth muscle actin (SMA), TUJ1, or FoxA2.

In particular embodiments, the pluripotent cells were previously cultured in a cell culture medium comprising a TGFβR inhibitor.

In additional embodiments, culturing the pluripotent cells in the cell culture medium reduces spontaneous differentiation of the cultured cells.

In one embodiment, expression of one or more differentiation marker genes in the cultured cells is decreased by at least about 10%, 20%, 25%, 30%, 40%, 50%, 60%, 70%, 80%, or 90% compared to the expression of the one or more differentiation marker genes in a pluripotent cell cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In another embodiment, the one or more differentiation marker genes is selected from the group consisting of T gene, CXCR4, NODAL, GATA4, SOX17, FOXA2, OTX2, and TUJ1.

In yet another embodiment, expression of two or more differentiation marker genes is decreased in the cultured cells by at least about 10%, 20%, 25%, 30%, 40%, 50%, 60%, 70%, 80%, or 90% compared to the expression of the two or more differentiation marker genes in a pluripotent cell cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In still yet another embodiment, the two or more differentiation marker genes are selected from the group consisting of T gene, CXCR4, NODAL, GATA4, SOX17, FOXA2, OTX2, and TUJ1.

In a particular embodiment, expression of three or more differentiation marker genes is decreased in the cultured cells by at least about 10%, 20%, 25%, 30%, 40%, 50%, 60%, 70%, 80%, or 90% compared to the expression of the three or more differentiation marker genes in a pluripotent cell cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In a certain embodiment, the three or more differentiation marker genes are selected from the group consisting of T gene, CXCR4, NODAL, GATA4, SOX17, FOXA2, OTX2, and TUJ1.

In an additional embodiment, expression of five or more differentiation marker genes is decreased in the cultured cells by at least about 10%, 20%, 25%, 30%, 40%, 50%, 60%, 70%, 80%, or 90% compared to the expression of the five or more differentiation marker genes in a pluripotent cell cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In a further embodiment, the five or more differentiation marker genes are selected from the group consisting of T gene, CXCR4, NODAL, GATA4, SOX17, FOXA2, OTX2, and TUJ1.

In a certain embodiment, culturing the pluripotent cells in the cell culture medium maintains or induces a ground state of pluripotency.

In particular embodiments, the ground state of pluripotency of the one or more pluripotent cells is maintained for at least 5 passages.

In certain particular embodiments, the ground state of pluripotency of the one or more pluripotent cells is maintained for at least 10 passages.

In further particular embodiments, the ground state of pluripotency of the one or more pluripotent cells is maintained for at least 50 passages.

In additional particular embodiments, the ground state of pluripotency of the one or more pluripotent cells is maintained for at least 100 passages.

In various embodiments, the foregoing methods further comprise dissociating the one or more pluripotent cells during passaging.

In certain embodiments, the viability of the one or more pluripotent cells is maintained during passaging.

In certain particular embodiments, the one or more pluripotent cells comprise a normal karyotype.

In certain additional embodiments, the one or more pluripotent cells are cultured in a feeder free environment.

In certain further embodiments, the genomic stability of the one or more pluripotent cells is maintained for at least 10 passages.

In certain related embodiments, the genomic stability of the one or more pluripotent cells is maintained for at least 50 passages.

In certain other embodiments, the genomic stability of the one or more pluripotent cells is maintained for at least 100 passages.

In various embodiments, the present invention contemplates, in part, a method of adapting pluripotent cells to a feeder-free culture comprising: (a) isolating one or more pluripotent cells that are cultured in the presence of feeder cells; (b) culturing the one or more pluripotent cell in a chemically defined cell culture medium comprising: a Wnt pathway agonist, optionally wherein the Wnt pathway agonist is a GSK3 inhibitor; a MEK inhibitor; and a ROCK inhibitor, wherein the medium does not comprise a TGFβR inhibitor.

In various particular embodiments, the present invention contemplates, in part, a method of culturing pluripotent cells enzymatically passaged as single cells comprising: (a) enzymatically treating one or more pluripotent cells to passage a single pluripotent cell; (b) culturing the single pluripotent cell in a feeder free environment; (c) culturing the single pluripotent cell in a chemically defined cell culture medium comprising: a Wnt pathway agonist, optionally wherein the Wnt pathway agonist is a GSK3 inhibitor; a MEK inhibitor; and a ROCK inhibitor, wherein the medium does not comprise a TGFβR inhibitor.

In various certain embodiments, the present invention contemplates, in part, a method of reducing spontaneous differentiation of one or more pluripotent cells comprising: (a) culturing the one or more pluripotent cells in a feeder free environment; (b) culturing the one or more pluripotent cells in a chemically defined cell culture medium comprising: a Wnt pathway agonist, optionally wherein the Wnt pathway agonist is a GSK3 inhibitor; a MEK inhibitor; and a ROCK inhibitor, wherein the medium does not comprise a TGFβR inhibitor.

In various additional embodiments, the present invention contemplates, in part, a method of manufacturing induced pluripotent stem cells (iPSCs) comprising: (a) obtaining one or more non-pluripotent cells; (b) reprogramming the one or more non-pluripotent cells to a pluripotent state; (c) culturing the pluripotent cells in a cell culture medium that does not comprise a TGFβR inhibitor thereby producing iPSCs.

In particular embodiments, the one or more non-pluripotent cells comprise a somatic cell.

In some embodiments, the one or more non-pluripotent cells comprise an adult stem cell.

In certain embodiments, the one or more non-pluripotent cells are reprogrammed to a pluripotent state by increasing the expression of endogenous OCT4 in the cell.

In further embodiments, reprogramming the one or more non-pluripotent cells to the pluripotent state comprises introducing one or more polynucleotides encoding one or more reprogramming factors selected from the group consisting of: OCT4, SOX2, NANOG, KLF4, LIN28, C-MYC, ECAT1, UTF1, ESRRB, and SV40LT into the one or more non-pluripotent cells.

In additional embodiments, reprogramming the one or more non-pluripotent cells to the pluripotent state comprises introducing one or more polynucleotides encoding one or more copies of reprogramming factors selected from the group consisting of: OCT4, SOX2, NANOG, KLF4, LIN28, C-MYC, ECAT1, UTF1, ESRRB, and SV40LT into the one or more non-pluripotent cells.

In certain embodiments, reprogramming the one or more non-pluripotent cells to the pluripotent state comprises introducing one or more polynucleotides encoding one or more copies of reprogramming factors selected from the group consisting of: OCT4, SOX2, and NANOG into the one or more non-pluripotent cells.

In certain embodiments, reprogramming the one or more non-pluripotent cells to the pluripotent state comprises introducing one or more polynucleotides encoding one or more copies of reprogramming factors selected from the group consisting of: OCT4, NANOG, ECAT1, UTF1, and ESRRB into the one or more non-pluripotent cells.

In certain embodiments, reprogramming the one or more non-pluripotent cells to the pluripotent state comprises introducing one or more polynucleotides encoding one or more copies of reprogramming factors selected from the group consisting of: OCT4, ECAT1, and UTF1 into the one or more non-pluripotent cells.

In particular embodiments, the one or more polynucleotides are a lentiviral vector.

In some embodiments, the one or more polynucleotides are an episomal vector.

In related particular embodiments, the cell culture medium comprises a Wnt pathway agonist, optionally wherein the Wnt pathway agonist is a GSK3 inhibitor; a MEK inhibitor; and a ROCK inhibitor.

In further particular embodiments, reprogramming the one or more non-pluripotent cells comprises contacting the one or more non-pluripotent cells with a Wnt pathway agonist, optionally wherein the Wnt pathway agonist is a GSK3 inhibitor; a MEK inhibitor; and a TGFβR inhibitor, and optionally a ROCK inhibitor.

In additional embodiments, the iPSCs comprise a population of iPSCs.

In particular embodiments, the population of iPSCs is a homogenous population of iPSCs.

In particular embodiments, at least 95% of the population of iPSCs expresses SSEA4 and TRA1-81 or TRA1-60.

In certain embodiments, at most 5% of the population of pluripotent cells expresses α-smooth muscle actin (SMA), TUJ1, or FoxA2.

In particular embodiments, culturing the pluripotent cells in the cell culture medium reduce spontaneous differentiation, or maintain or induce a ground state of pluripotency.

In additional embodiments, expression of one or more, two or more, three or more, four or more, or five or more differentiation marker genes is decreased in the iPSCs by at least about 10%, 20%, 25%, 30%, 40%, 50%, 60%, 70%, 80%, or 90% compared to the expression of the one or more differentiation marker genes in iPSCs cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In particular embodiments, the one or more differentiation marker genes is selected from the group consisting of T gene, CXCR4, NODAL, GATA4, SOX17, FOXA2, OTX2, and TUJ1.

In certain embodiments, the reduction in spontaneous differentiation is maintained for at least 5 passages.

In other embodiments, the reduction in spontaneous differentiation is maintained for at least 10 passages.

In particular embodiments, the reduction in spontaneous differentiation is maintained for at least 50 passages.

In additional embodiments, the reduction in spontaneous differentiation is maintained for at least 100 passages.

In further embodiments, the foregoing methods comprise dissociating the iPSCs during passaging.

In additional embodiments, the viability of the iPSCs is maintained during passaging.

In certain embodiments, the iPSCs comprise a normal karyotype.

In other embodiments, the iPSCs are cultured in a feeder free environment.

In particular embodiments, the genomic stability of the iPSCs is maintained for at least 10 passages.

In additional embodiments, the genomic stability of the iPSCs is maintained for at least 50 passages.

In particular additional embodiments, the genomic stability of the iPSCs is maintained for at least 100 passages.

In various embodiments, the invention provides, in part, an induced pluripotent stem cell (iPSC) comprising ground state pluripotency produced according to any one of foregoing embodiments.

In various certain embodiments, the invention provides, in part, an induced pluripotent stem cell (iPSC) comprising ground state pluripotency, wherein the iPSC does not comprise an exogenously introduced polynucleotide encoding a reprogramming factor polypeptide.

In various particular embodiments, the invention provides, in part, an method of manufacturing induced pluripotent stem cells (iPSCs) comprising: a) obtaining one or more pluripotent stem cells; (b) culturing the one or more pluripotent stem cells in a cell culture medium that does not comprise a TGFβR inhibitor thereby producing ground state iPSCs.

In certain embodiments, the one or more iPSCs comprises a reprogrammed somatic cell.

In additional embodiments, the one or more iPSCs comprises a reprogrammed adult stem cell.

In other embodiments, the one or more iPSCs were reprogrammed to a pluripotent state by increasing the expression of endogenous OCT4 in the one or more iPSCs.

In particular embodiments, the one or more iPSCs were reprogrammed by introducing one or more polynucleotides encoding one or more reprogramming factors selected from the group consisting of: OCT4, SOX2, NANOG, KLF4, LIN28, C-MYC, ECAT1, UTF1, ESRRB, and SV40LT into the one or more non-pluripotent cells.

In certain particular embodiments, the one or more iPSCs were reprogrammed by introducing one or more polynucleotides encoding one or more copies of reprogramming factors selected from the group consisting of: OCT4, SOX2, NANOG, KLF4, LIN28, C-MYC, ECAT1, UTF1, ESRRB, and SV40LT.

In additional embodiments, the one or more iPSCs were reprogrammed by introducing one or more polynucleotides encoding one or more copies of reprogramming factors selected from the group consisting of: OCT4, SOX2, and NANOG into the one or more non-pluripotent cells.

In additional embodiments, the one or more iPSCs were reprogrammed by introducing one or more polynucleotides encoding one or more copies of reprogramming factors selected from the group consisting of: OCT4, NANOG, ECAT1, UTF1, and ESRRB into the one or more non-pluripotent cells.

In another embodiment, the one or more iPSCs were reprogrammed by introducing one or more polynucleotides encoding one or more copies of reprogramming factors selected from the group consisting of: OCT4, ECAT1, and UTF1 into the one or more non-pluripotent cells.

In various embodiments, a lentiviral vector comprises the one or more polynucleotides.

In particular embodiments, an episomal vector comprises the one or more polynucleotides.

In other embodiments, the cell culture medium comprises a Wnt pathway agonist, optionally wherein the Wnt pathway agonist is a GSK3 inhibitor; a MEK inhibitor; and a ROCK inhibitor.

In certain embodiments, obtaining the one or more iPSCs comprises contacting the one or more non-pluripotent cells or partially pluripotent cells with a Wnt pathway agonist, optionally wherein the Wnt pathway agonist is a GSK3 inhibitor; a MEK inhibitor; and a TGFβR inhibitor, and optionally a ROCK inhibitor to produce the one or more iPSCs.

In additional embodiments, the iPSCs comprise a population of iPSCs.

In additional embodiments, the population of iPSCs is a homogenous population of iPSCs.

In particular embodiments, at least 95% of the population of iPSCs expresses SSEA4 and TRA1-81 or TRA1-60.

In particular embodiments, the one or more iPSCs are obtained by reprogramming a population of pluripotent cells, wherein at most 5% of the population of pluripotent cells expresses α-smooth muscle actin (SMA), TUJ1, or FoxA2.

In further embodiments, the foregoing methods comprise culturing the one or more iPSCs in the cell culture medium reduces spontaneous differentiation or maintains or induces a ground state of pluripotency.

In certain embodiments, the iPSCs with reduced spontaneous differentiation comprise a gene expression wherein expression of one or more, two or more, three or more, four or more, or five or more differentiation marker genes is decreased in the iPSCs by at least about 10%, 20%, 25%, 30%, 40%, 50%, 60%, 70%, 80%, or 90% compared to the expression of the one or more differentiation marker genes in iPSCs cultured in a medium comprising a TGFβR inhibitor, wherein the differentiation marker genes are selected from the group consisting of: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In additional embodiments, the one or more differentiation marker genes is selected from the group consisting of T gene, CXCR4, NODAL, GATA4, SOX17, FOXA2, OTX2, and TUJ1.

In other embodiments, the reduced spontaneous differentiation is maintained for at least 5 passages.

In certain embodiments, the reduced spontaneous differentiation is maintained for at least 10 passages.

In additional embodiments, the reduced spontaneous differentiation is maintained for at least 50 passages.

In particular embodiments, the reduced spontaneous differentiation is maintained for at least 100 passages.

In further embodiments, the foregoing methods comprise dissociating the one or more iPSCs during passaging.

In particular embodiments, the viability of the one or more iPSCs are maintained during passaging.

In other embodiments, the one or more iPSCs comprise a normal karyotype.

In additional embodiments, the one or more iPSCs are cultured in a feeder free environment.

In certain embodiments, the genomic stability of the one or more iPSCs is maintained for at least 10 passages.

In additional embodiments, the genomic stability of the one or more iPSCs is maintained for at least 50 passages.

In particular embodiments, the genomic stability of the one or more iPSCs is maintained for at least 100 passages.

In various particular embodiments, the invention provides, in part, an induced pluripotent stem cell (iPSC) comprising ground state pluripotency produced according to any one of the foregoing embodiments.

In various embodiments, the invention provides, in part, an induced pluripotent stem cell (iPSC) comprising ground state pluripotency, wherein the iPSC does not comprise an exogenously introduced polynucleotide encoding a reprogramming factor polypeptide.

In some embodiments, a method for reprogramming a non-pluripotent cell to a pluripotent cell is provided comprising introducing into the nonpluripotent cell (i) one or more polynucleotides that encode at least one polypeptide selected from the group consisting of an OCT4 polypeptide, an ECAT1 polypeptide, a UTF1 polypeptide, a NANOG polypeptide, and an ESRRB polypeptide, or (ii) at least one polypeptide selected from the group consisting of an OCT4 polypeptide, an ECAT1 polypeptide, a UTF1 polypeptide, a NANOG polypeptide, and an ESRRB polypeptide, thereby reprogramming the non-pluripotent cell to a pluripotent cell.

In a particular embodiment, introducing comprises (i) introducing one or more polynucleotides that encode an OCT4 polypeptide, an ECAT1 polypeptide, a UTF1 polypeptide, a NANOG polypeptide, and an ESRRB polypeptide, or (ii) introducing a OCT4 polypeptide, an ECAT1 polypeptide, a UTF1 polypeptide, a NANOG polypeptide, and an ESRRB polypeptide.

In another embodiment, introducing comprises (i) introducing one or more polynucleotides that encode an OCT4 polypeptide, an ECAT1 polypeptide, and a UTF1 polypeptide, or (ii) introducing an OCT-4 polypeptide, an ECAT1 polypeptide, and a UTF1 polypeptide.

In some embodiments, the one or more polynucleotides are introduced by a retrovirus, Sendai virus, an adenovirus, an episome, mini-circle, vector system with expression cassette, or mRNA.

In a particular embodiment, the retrovirus is a lentivirus.

In another embodiment, the pluripotent cell is free of exogenous polynucleotides.

In another embodiment, the one or more polynucleotides is excised by CRE-mediated excision.

In some embodiments, the method further comprises introducing into the non-pluripotent cell (i) a polynucleotide that encodes a SV40LT polypeptide, or (ii) a SV40LT polypeptide.

In one embodiment, the method comprises contacting the nonpluripotent cell with at least one of a TGFβR inhibitor, a Wnt pathway agonist, a MEK inhibitor and a ROCK inhibitor, wherein the Wnt pathway agonist is optionally a GSK3 inhibitor.

In another embodiment, the nonpluripotent cell is contacted with a TGFβR inhibitor, a Wnt pathway agonist, a MEK inhibitor and a ROCK inhibitor, wherein the Wnt pathway agonist is optionally a GSK3 inhibitor.

In a particular embodiment, the method further comprises culturing the pluripotent cell in a culture medium comprising a Wnt pathway agonist, a MEK inhibitor and a ROCK inhibitor, wherein the Wnt pathway agonist is optionally a GSK3 inhibitor, and wherein the culture medium does not contain TGFβR inhibitor.

In some embodiments, the Rock inhibitor is thiazovivin or Y27632, the TGFβR inhibitor is A-83-01 or SB431542, the GSK3 inhibitor is CHIR99021 or BIO, or the MEK inhibitor is PD98059 or PD032901.

In another embodiment, pluripotency of the pluripotent cell is maintained for at least 5 cell divisions or at least 10 cell divisions.

In a particular embodiment, the one or more polynucleotides is introduced as a polycistronic vector comprising a plurality of polynucleotides that are separated by at least one 2A peptide.

In one embodiment, the polycistronic vector comprises a plurality of polynucleotides that encode an OCT4 polypeptide.

In some embodiments, the method comprises identifying the pluripotent cell by selecting for OCT4 expression in the pluripotent cell.

In one embodiment, selecting for OCT4 expression comprises selecting for ectopic Oct-4 expression.

In another embodiment, culturing produces a population of pluripotent stem cells.

In another embodiment, the population of pluripotent stem cells are at least 70% homogenous, at least 80% homogenous, or at least 90% homogenous.

In yet another embodiment, at least 70%, at least 80%, or at least 90% of the population of pluripotent cells expresses SSEA and Tra-181.

In an embodiment, the pluripotent cell or population of pluripotent cells are capable of single cell passaging.

In one embodiment, the cells produced by single cell passaging have a normal karyotype.

In one embodiment, the invention provides a pluripotent cell produced according to the method of any one of the methods above.

In another embodiment, the invention provides a composition comprising an isolated non-pluripotent cell that comprises (i) one or more exogenous polynucleotides that encode at least one polypeptide selected from the group consisting of an OCT4 polypeptide, an ECAT1 polypeptide, a UTF1 polypeptide, a NANOG polypeptide, and an ESRRB polypeptide, or (ii) at least one exogenous polypeptide selected from an OCT4 polypeptide, an ECAT1 polypeptide, a UTF1 polypeptide, a NANOG polypeptide, and an ESRRB polypeptide.

In one embodiment, the cell comprises (i) one or more exogenous polynucleotides that encode at least two of an OCT4 polypeptide, an ECAT1 polypeptide, a UTF1 polypeptide, a NANOG polypeptide, and an ESRRB polypeptide, or (ii) at least two exogenous polypeptides selected from an OCT4 polypeptide, an ECAT1 polypeptide, a UTF1 polypeptide, a NANOG polypeptide, and an ESRRB polypeptide.

In another embodiment, the cell comprises (i) one or more exogenous polynucleotides that encode at least three of an OCT4 polypeptide, an ECAT1 polypeptide, a UTF1 polypeptide, a NANOG polypeptide, and an ESRRB polypeptide, or (ii) at least three exogenous polypeptides selected from an OCT4 polypeptide, an ECAT1 polypeptide, a UTF1 polypeptide, a NANOG polypeptide, and an ESRRB polypeptide.

In one particular embodiment, the cell comprises (i) one or more exogenous polynucleotides that encode an OCT4 polypeptide, an ECAT1 polypeptide, a UTF1 polypeptide, a NANOG polypeptide, and an ESRRB polypeptide, or (ii) an exogenous OCT4 polypeptide, an exogenous ECAT1 polypeptide, an exogenous UTF1 polypeptide, an exogenous NANOG polypeptide, and an exogenous ESRRB polypeptide.

In another embodiment, the cell comprises one or more exogenous polynucleotides that encode an OCT4 polypeptide, an ECAT1 polypeptide, and a UTF1 polypeptide, or an exogenous OCT4 polypeptide, an exogenous ECAT1 polypeptide, and an exogenous UTF1 polypeptide.

In one embodiment, the cell has been contacted with at least one of a TGFβR inhibitor, a GSK3 inhibitor, a MEK inhibitor and a ROCK inhibitor.

In another embodiment, the cell has been contacted with a TGFβR inhibitor, a Wnt pathway activator, a MEK inhibitor and a ROCK inhibitor, wherein the Wnt pathway activator is optionally a GSK3 inhibitor.

In a particular embodiment, the Rock inhibitor is thiazovivin or Y27632, the TGFβR inhibitor is A-83-01 or SB431542, the GSK3 inhibitor is CHIR99021 or BIO, or the MEK inhibitor is PD98059 or PD032901.

In another embodiment, the one or more exogenous polynucleotides are introduced to the non-pluripotent cell by a retrovirus, Sendai virus, an adenovirus, an episome, mini-circle, vector system with expression cassette, or mRNA.

In another embodiment, the retrovirus is a lentivirus.

In a particular embodiment, the cell is free of exogenous polynucleotides.

In an embodiment, the one or more exogenous polynucleotides are removed by CRE-mediated excision.

In another embodiment, the cell comprises an exogenous polynucleotide that encodes a SV40LT antigen polypeptide, or an exogenous a SV40LT antigen polypeptide.

In one embodiment, the one or more exogenous polynucleotides is introduced as a polycistronic vector comprising a plurality of polynucleotides that are separated by at least one 2A peptide.

In another embodiment, the polycistronic vector comprises a plurality of polynucleotides that encode an OCT4 polypeptide.

In an embodiment, the exogenous polynucleotide encoding an OCT4 polypeptide is linked to a selectable marker.

In one particular embodiment, the invention provides a composition consisting of at least one of, at least two of, or at least three of (i) a cDNA encoding an OCT4 polypeptide, (ii) a cDNA encoding an ECAT1 polypeptide, (iii) a cDNA encoding a UTF1 polypeptide, (iv) a cDNA encoding a NANOG polypeptide, and (v) a cDNA encoding an ESRRB polypeptide.

In an embodiment, the composition consists of a cDNA encoding an OCT4 polypeptide, a cDNA encoding an ECAT1 polypeptide, a cDNA encoding a UTF1 polypeptide, a cDNA encoding a NANOG polypeptide, and a cDNA encoding an ESRRB polypeptide.

In another embodiment, the composition consists of a cDNA encoding an OCT4 polypeptide, a cDNA encoding an ECAT1 polypeptide, and a cDNA encoding a UTF1 polypeptide.

In a particular embodiment, each cDNA is encoded in a retrovirus, Sendai virus, an adenovirus, an episome, a mini-circle, a vector system with expression cassette, or mRNA.

In one embodiment, the invention provides a vector comprising of one or more polynucleotides that encode at least one reprogramming factor polypeptide selected from the group consisting of an OCT4 polypeptide, an ECAT1 polypeptide, a UTF1 polypeptide, a NANOG polypeptide, and an ESRRB polypeptide.

In an embodiment, the one or more polynucleotides encode an OCT polypeptide, an ECAT1 polypeptide, a UTF1 polypeptide, a NANOG polypeptide, and an ESRRB polypeptide.

In another embodiment, the one or more polynucleotides encode an OCT polypeptide, an ECAT1 polypeptide, and a UTF1 polypeptide.

In another particular embodiment, the vector further comprises a polynucleotide that encodes an SV40LT antigen polypeptide.

In one embodiment, the vector is a retrovirus, Sendai virus, an adenovirus, an episome, mini-circle, vector system with expression cassette, or mRNA.

In one embodiment, the retrovirus is a lentivirus.

In one particular embodiment, the invention provides a kit for reprogramming a non-pluripotent cell to a pluripotent cell, the kit comprising: one or more polynucleotides that encode at least one polypeptide selected from the group consisting of an OCT4 polypeptide, an ECAT1 polypeptide, a UTF1 polypeptide, a NANOG polypeptide, or an ESRRB polypeptide; or at least one polypeptide selected from the group consisting of an OCT4 polypeptide, an ECAT1 polypeptide, a UTF1 polypeptide, a NANOG polypeptide, or an ESRRB polypeptide; and at least one of a TGFβR inhibitor, a Wnt pathway activator, a MEK inhibitor and a ROCK inhibitor, wherein the Wnt pathway activator is optionally a GSK3 inhibitor.

In an embodiment, the one or more polynucleotides encode an OCT4 polypeptide, an ECAT1 polypeptide, a UTF1 polypeptide, a NANOG polypeptide, and an ESRRB polypeptide, or the at least one polypeptide comprises an OCT4 polypeptide, an ECAT1 polypeptide, a UTF1 polypeptide, a NANOG polypeptide, and an ESRRB polypeptide.

In another embodiment, the one or more one or more polynucleotides encode an OCT4 polypeptide, an ECAT1 polypeptide, and a UTF1 polypeptide, or the at least one polypeptide comprises an OCT4 polypeptide, an ECAT1 polypeptide, and a UTF1 polypeptide.

In one embodiment, the kit comprises a polynucleotide that encodes a SV40LT antigen polypeptide, or a SV40LT antigen polypeptide.

In another embodiment, the kit comprises a TGFβR inhibitor, a Wnt pathway activator, a MEK inhibitor and a ROCK inhibitor, wherein the Wnt pathway activator is optionally a GSK3 inhibitor.

In one embodiment, the Rock inhibitor is thiazovivin or Y27632, the TGFβR inhibitor is A-83-01 or SB431542, the GSK3 inhibitor is CHIR99021 or BIO, or the MEK inhibitor is PD98059 or PD032901.

In another embodiment, the at least one polynucleotide is encoded in a retrovirus, Sendai virus, an adenovirus, an episome, a mini-circle, a vector system with expression cassette, or mRNA.

In another embodiment, the retrovirus is a lentivirus.

In one embodiment, the at least one polynucleotide is encoded in a polycistronic vector with each polynucleotide being separated by a 2A peptide.

In yet another embodiment, the polycistronic vector comprises two or more polynucleotides that encode an OCT4 polypeptide.

In a particular embodiment, the at least one polynucleotide that encodes an OCT4 polypeptide is linked to a selectable marker.

In another particular embodiment, the invention provides a method for producing a population of pluripotent stem cells comprising: providing a population of non-pluripotent cells; introducing into the population of non-pluripotent cells a polynucleotide that encodes an OCT4 polypeptide that is linked to a selectable marker; incubating the population of non-pluripotent cells with the polynucleotide under conditions sufficient to reprogram at least a portion of the population of non-pluripotent cells to pluripotent cells; selecting cells that express the selectable marker thereby providing a population of pluripotent stem cells.

In another embodiment, the polynucleotide is introduced as a polycistronic vector comprising a plurality of polynucleotides that encode an OCT4 polypeptide.

In one embodiment, the plurality of polynucleotides are separated by at least one 2A peptide.

In yet another embodiment, at least 10% of the cells in the population of cells express SSEA and TRA-181.

Figure 1A:
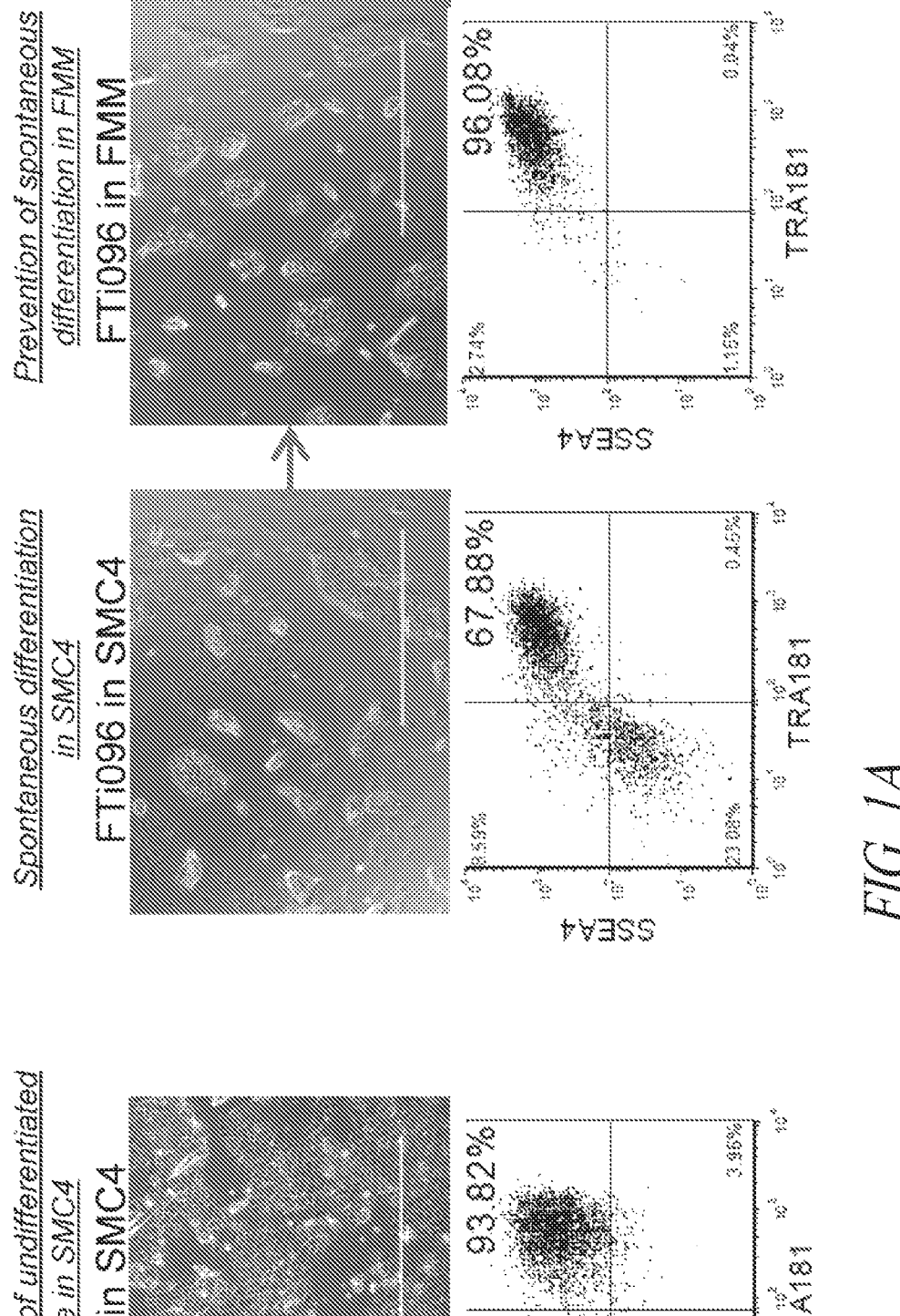
FIGS. 1A-1E show results from a multistage culture platform for enhanced reprogramming and hiPSC maintenance. (1A) Lentiviral generated hiPSC clone FTi088 maintained a homogeneous population of undifferentiated cells in SMC4 while spontaneous differentiation was seen in the lentiviral generated hiPSC line FTi096 cultured in SMC4. Spontaneous differentiation was minimized when FTi096 was transitioned to FMM for 3 passages as shown by morphology (upper panels) and flow cytometry for SSEA4 and TRA1-81 (lower panels). (1B) qRT-PCR for transgene expression of viral element WPRE. Expression was normalized to GAPDH and relative to WPRE expression of parental fibroblast line four days post lentiviral infection (Day 4 P.I.). Uninfected fibroblast line (fibroblast) and human ESC line HUES9 were used as negative controls. Value of each set is indicated above the bar. (1C) Screen of various medium components' effect on SSEA4 and TRA1-81 population of transgene free lentiviral-induced hiPSC after 10 passages; removal of SB431542 (−TGFβRi), increase from 10 to 100 ng/mL bFGF, addition of 10 ng/mL LIF. (1D) Fibroblast cell line was transfected with lentiviral construct containing gene set OCT4/KLF4/SOX2 and split into various media (conventional medium; Conv.), cultured for 17 days and sorted for SSEA4 and TRA1-81 double positive population at day 17. Sort gate is highlighted in blue. Each set was cultured for an additional 10 days in respective media except for the SMC4 set which was split into FMM and SMC4. At day 27, the cultures were resorted for SSEA4 and TRA1-81 double positive population, seeded at normalized density of sorted events and maintained in respective media for an additional 9 days. Conventional culture set gating was expanded to achieve normalized number of cells. At day 36, each culture was stained for OCT4 and NANOG expression. Representative immunocytochemistry images shown in the right panel for each set. (1E) Colony counts of day 36 staining as discussed in (1D). Error bars represent triplicates for FRM to FMM and FRM and duplicates for FMM and hESC.
Figure 1B:
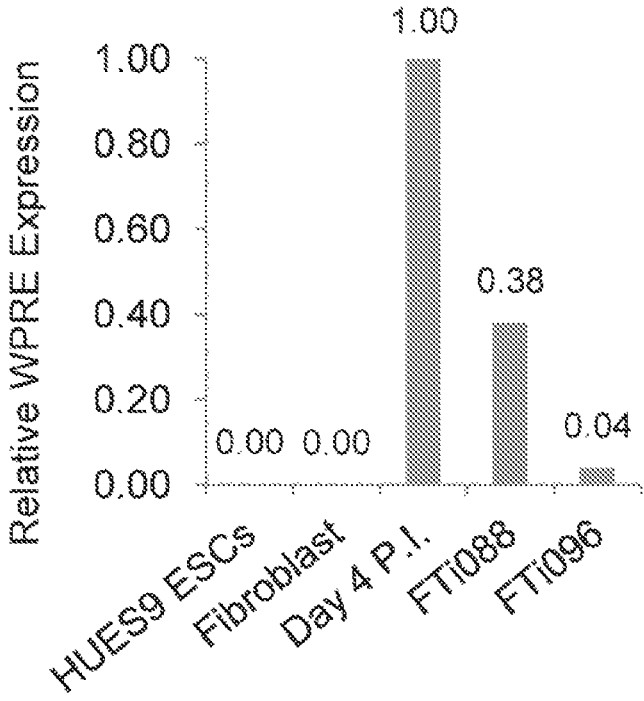

Lane 3, FTC016-c25 p5; Lane 4, FTC016-c36 p5; Lane 5, FTC017-c11 p7; Lane 6, FTC017-c14 p7; Lane 7, FTC017-c17 p6 (a line maintaining episomal constructs used a positive control); Lane 8, untransfected FTC007; Lane 9, hiPSC generated using lentiviral constructs (to serve as a control against cross contamination); Lane 10, episomal vector used as positive control. Input of 100 ng genomic DNA and 35 PCR cycles were used for all sets. (3D) Pluripotency markers detected by immunofluorescence for the expression of OCT4, NANOG, TRA1-81 and TRA160. (3E) Flow cytometry profile for selected hiPSC clones from various parental lines. Upper row profiles SSEA4/TRA1-81 surface expression. Bottom row profiles OCT4/NANOG intracellular expression. (3F) qRT-PCR analysis for endogenous pluripotent gene expression. Data was normalized to GAPDH and relative to HUES9 hESCs. In the case of KLF4 expression two data points exceeded 15-times greater than HUES9 and were noted on the graph. Error bars represent standard deviation of replicates.

FIGS. 4A-4E show that genomic stability and pluripotency is maintained during continuous single cell and FF culture. (4A) Cytogenetic analysis on 20 to 40 G-banded metaphase cells from various hiPSC clones maintained in FF and single cell culture. (4B) Flow cytometry profile and cytogenetic analysis of long-term passaged (p25-30) hiPSC clones in FF and single cell culture. (4C) Three to four day directed differentiation of FTC017-c11. (4D) Embryoid body formation and differentiation of hiPSC clones demonstrating trilineage differentiation. Immunocytochemistry conducted 28 days post differentiation: Ectoderm, TUJ1; Mesoderm, alpha smooth muscle actin (aSMA); Endoderm, AFP. (4E) Histological sections of teratoma derived from FTC007-c21 and FTC016-c25 representing each somatic lineage. Black arrows, endoderm; white arrows, ectoderm; gray arrows, mesoderm.

FIGS. 5A-5J show derivation of hiPSC clones with minimal number of reprogramming factors. (5A) OCT4, SOX2 and NANOG were cloned into pCEP4 in various formats. Table represents vector systems and abbreviations. (5B) SSEA4 and TRA1-81 flow cytometry profile of reprogramming kinetics induced by various gene combinations at day 13 post induction. (5C) Efficiency histogram representing the presence of TRA1-81 positive hiPSC clones in wells of 96-well plate at 3 and 9 cells per well. (5D) PCR analysis for episomal DNA derived from various hiPSC clones. Lane 1 2xO+OS+ONS+T-c7 p6; Lane 2, 2xO+OS+ONS+T-c10 p6; Lane 3, 2xO+ONS+T-c5 p5; Lane 4, 2xO+ONS+T-c9 p5; Lane 5, 2xO+OS+T-c7 p7; Lane 6, 2xO+OS+T-c9 p6; Lane 7, untransfected FTC007; Lane 8, hiPSC generated using lentiviral constructs; Lane 9, episomal vector used as positive control. Input of 100 ng genomic DNA and 35 PCR cycles were used for all sets. (5E) Morphology of clone 9 derived from 2xO+OS+T. (5F) Pluripotency markers detected by immunofluorescence for the expression of OCT4, NANOG, TRA1-81 and TRA160. Images taken at 10× magnification. (5G) Flow profile of hiPSC clones derived from selected gene sets. Upper row profiles SSEA4/ TRA1-81 surface expression. Bottom row profiles OCT4/ NANOG intracellular expression. (5H) Directed differentiation of selected hiPSC clones approximately 72 to 96 hrs post induction. (5I) Cytogenetic analysis of G-banded metaphase cells from various hiPSC clones maintained in FF and single cell culture. (5J) Histological sections of teratoma derived from hiPSC clone 2xO+OS+ONS+T-c10 representing each somatic lineage. Left panel, endoderm; middle panel, mesoderm; right panel, ectoderm.

Figure 6A:
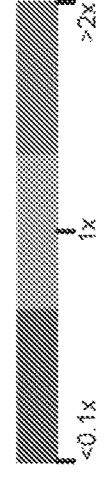
Figure 6B:
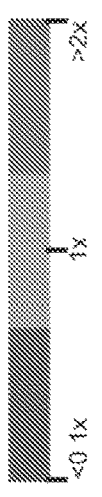

FIGS. 6A-6B show the relative gene expression profile of minimal factor episomal-induced hiPSCs in FMM. Heatmap results derived from a Fluidigm dynamic array depicting relative gene expression levels (RQ) of pluripotency (6A) and differentiation (6B) genes of conventionally maintained hiPSC lines, conventionally maintained H1 hESCs, and episomal hiPSC lines derived using various gene combinations maintained in FMM. Relative gene expression for each line is noted within each box and color coded based on three expression levels summarized in the legend (lower right). All sets were conducted in duplicates, normalized to the average expression of two housekeeping genes (GAPDH and HPRT1) and referenced to the median expression level of six control conventional lines (OSK hiPSCs and H1 hESCs on MEF) representing 1× value.

FIGS. 7A-7G show that FMM maintained hiPSCs have reduced expression of differentiated genes and represent the ground state. (7A) A total of 339 probe sets were differentially expressed between conventional and FMM culture by greater or less than 2.5-fold. Hierarchical clustering on the 339 probe sets using a complete linkage method based on Euclidean distance measurements. (7B) Gene ontology biological process enrichment analysis (D.A.V.I.D.) of the 213 probe sets up-regulated 2.5-fold or greater with conventional culture (in comparison to FMM culture). (7C) Gene lists representative of ground or metastable pluripotency states. List derived from references noted in text. 7(D) Hierarchical clustering on the 231 probe sets corresponding to the genes in (7C) using a complete linkage method based on Euclidean distance measurements. (7E) RMA (log 2) intensities for the probe sets corresponding to the genes in (7C). Left panel represents 39 probe sets for ground state, right panel represents 188 probe sets for metastable state. Average conventional culture intensity levels are plotted on the X-axis while the average FMM/SMC4 intensity is on the Y-axis, black line indicates equal expression. (7F) Gene expression comparison of X chromosome located genes between hiPSC clone derived and cultured in conventional medium culture and its counterpart adapted to SMC4 culture using Affymetrix probe sets. Probe sets associated with XIST gene expression are highlighted. (7G) Representative images of HEK27me3 on hiPSC clone maintained in FMM or adapted to conventional culture for 5 passages. Dotted arrow in the left panel points to a representative nucleus absent of H3K27me3 staining while solid arrow in the right panel points to a nucleus positive for H3K27me3 staining. Percentages of nucleus positive staining are indicated in the lower left side of each panel. FMM cultured cells have a larger nuclei. Scale bar=50 μm.

FIGS. 8A-8D show episomal induced reprogramming with FRM and FMM. (8A) Day 10 SSEA4 and TRA1-81 flow profile of reprogramming pool. (8B) Representative morphology of typical colony seen during reprogramming. Image taken at day 13 post transfection. (8C) Episomal reprogrammed fibroblast cells maintained in FRM for the first 14 days were split and either maintained in FRM or switched to FMM. The reprogramming cultures were then sorted for SSEA4/TRA1-81/CD30 on day 21 post transfection and maintained in FRM or FMM for an additional 10 days prior to analysis. (8D) Morphology and flow profile of representative cultures in FRM or FMM. White arrow points to regions of differentiated cells in a culture that consists of a mixture of undifferentiated and differentiated population. Black arrow points to sharp edges of a mostly undifferentiated population. Lower panels are representative flow profiles. FSC; Forward Side Scatter.

Figure 9B:
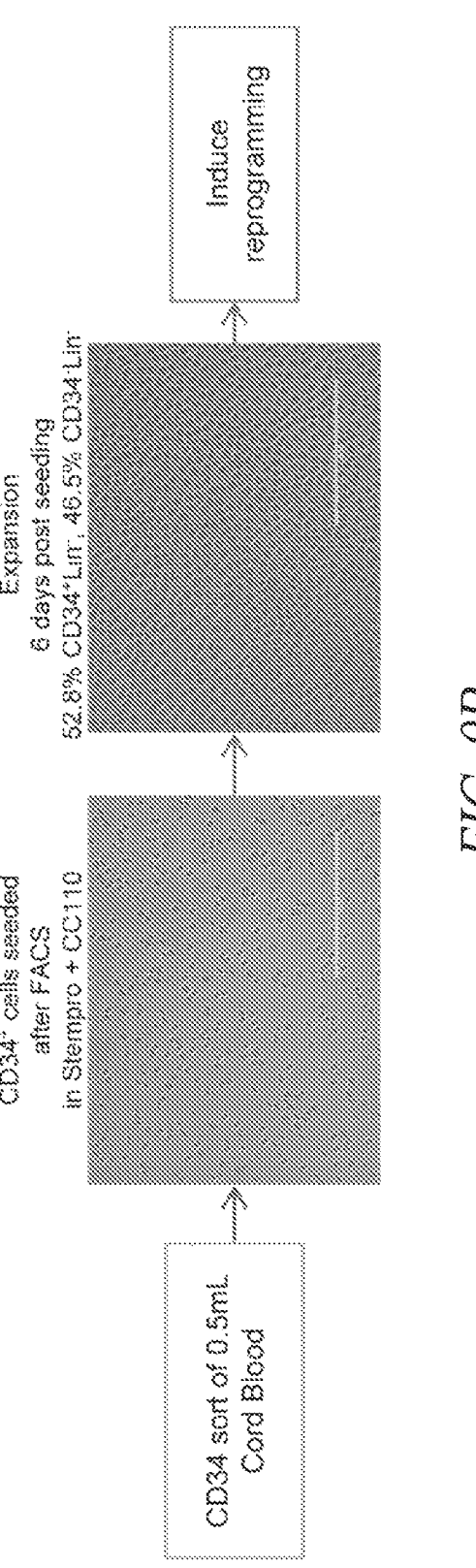

FIGS. 9A-9B show reprogramming of various parental lines. (9A) Summary table of the starting cell lines used in this study. In addition to specific information related to each line, the percent positive SSEA4/TRA1-81/CD30 population at time of sort post episomal transfection is noted. (9B) Illustration depicting the sort and culture of CD34 enriched cord blood cells. A volume of 0.5 ml cord blood previously maintained in a bank was used to extract 65,000 CD34+ CD45+Lin− cells which were cultured in suspension for 6 days prior to episomal transfection.

FIGS. 10A-10G show the characterization of hiPSCs during the reprogramming and maintenance process. (10A) Typical colony morphology three days post single cell 96-well plate sorting. Scale bar represents 400 μm. (10B) Representative morphology of single cell derived hiPSC-like colony 7-9 days post sort from various starting cells. Scale bar represents 1000 μm. (10C) Immunocytochemistry for NANOG expression of hiPSC-like colonies in 96-well plates. (10D) Day 16 flow profile analysis of FTC007 induced to reprogram and maintained either on Matrigel or vitronectin coated culture plates. (10E) Bright-field image, (10F) immunofluorescence for OCT4 and NANOG or (10G) flow cytometry analysis for SSEA4 and TRA1-81 of FTC016-c28 maintained in FMM either continuously on Matrigel or for 5 passages Vitronectin.

Figure 11A:
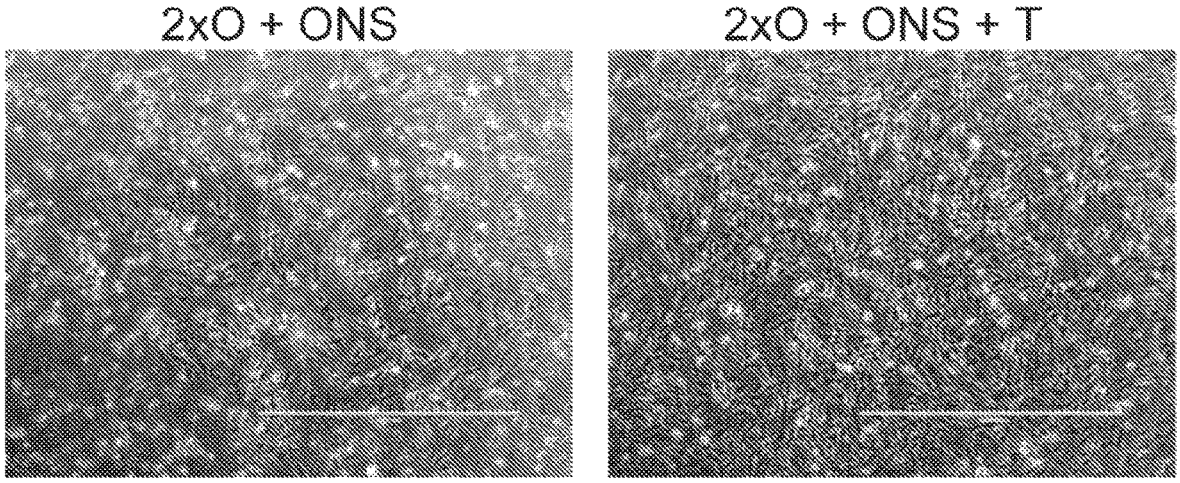
Figure 11B:
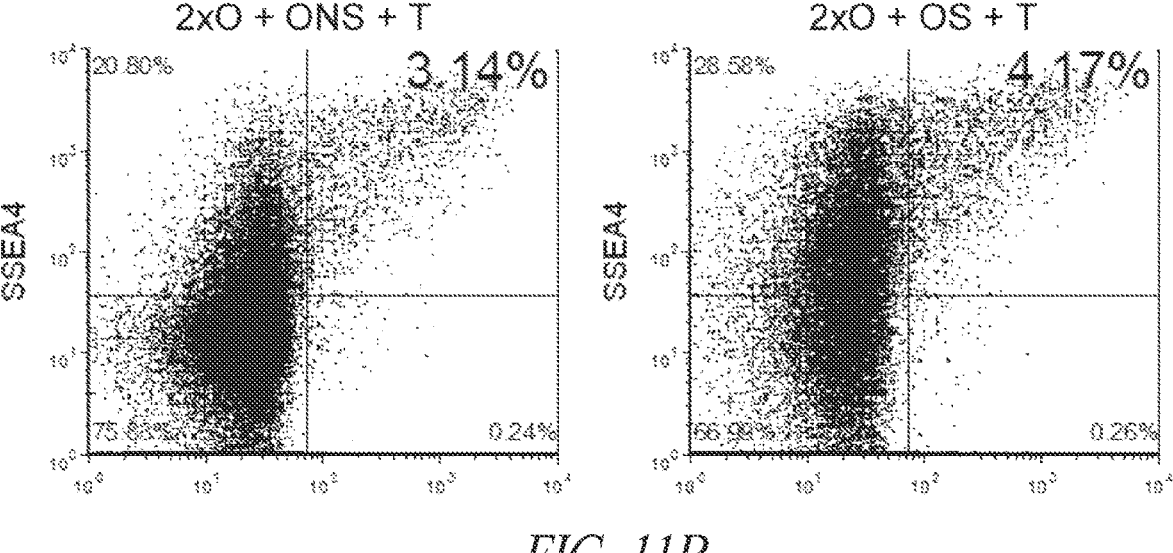
Figure 11C:
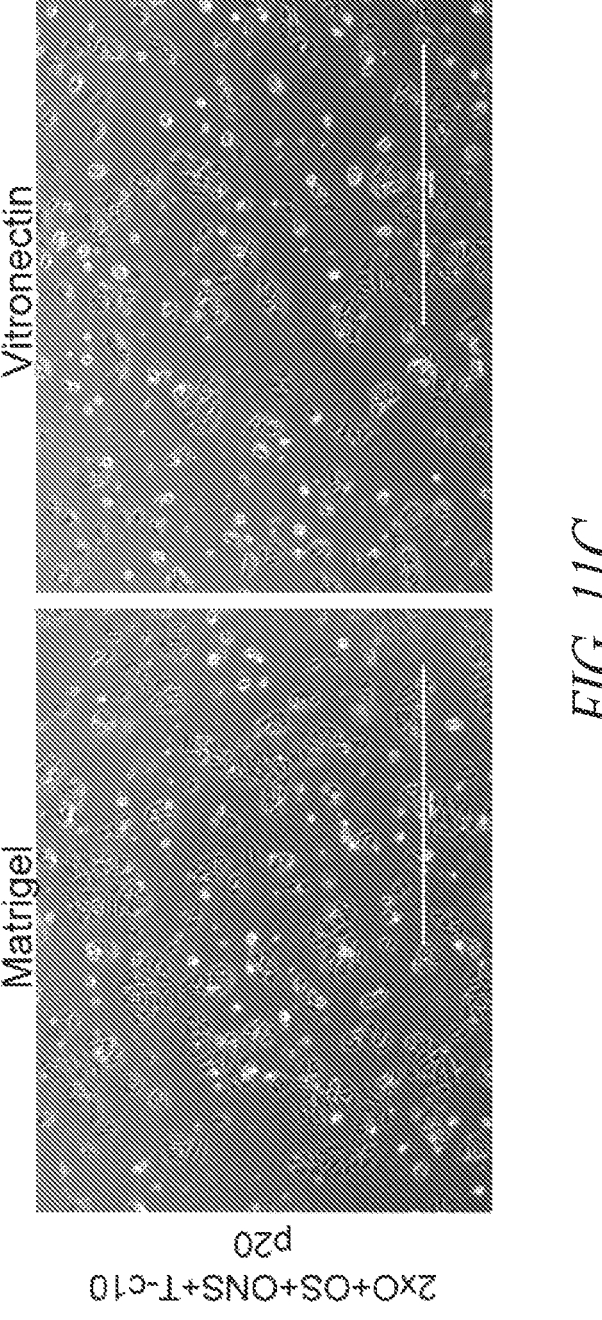

FIGS. 11A-11C show examples of minimal gene reprogramming with the FMM culture platform. (11A) Morphology of cells treated with hygromycin from day 2 to 5 post transfection with episomal construct containing hygromycin selection cassette. (11B) Reprogramming pools were maintained for longer duration and profiled on day 16 post transfection. (11C) Appearance of culture maintained on either Matrigel or Vitronectin.

FIGS. 12A-12E show the characteristics of hiPSC cultured in multiple conditions. (12A) Lentiviral derived and SMC4 maintained FTi111 displayed the hallmarks of pluripotency and maintained genomic integrity. (12B) Depiction of thaw strategy of FTi111 p43. A single vial was thawed into four culture environments as noted. Surviving cultures were passaged in respective culture with the exception of conventional culture supplemented with thiazovivin on feeder cells, which was transitioned to conventional culture without Thiazovivin in the presence of feeder cells and passaged as clump. (12C) Morphology of recovering cells in various culture post thaw. No surviving cells were identified in the conventional culture without Thiazovivin in the presence of feeder cells. (12D) Morphology of culture sets at passage 3 post thaw. Larger colony morphology was associated with conventional culture. Scale bar 1000 μm. (12E) qRT-PCR analysis for endogenous pluripotent gene expression of each culture set. Data was normalized to GAPDH and relative to H1 hESCs.

FIGS. 13A-13E show the gene ontology of gene expression profiles of hiPSCs cultured in various conditions. (13A) Table describing the derivation and maintenance of each line described in global gene expression studies. (13B) A total of 300 probe sets were differentially expressed between the conventional and small molecule (FMM and SMC4) culture conditions by greater or less than 2.5-fold. Hierarchical clustering on the 300 probe sets using a complete linkage method based on Euclidean distance measurements. (13C) Gene ontology biological process enrichment analysis (D.A.V.I.D.) of the 133 probe sets up-regulated 2.5-fold or greater with conventional culture (in comparison to small molecule culture). (13D) Gene ontology biological process enrichment analysis (D.A.V.I.D.) of the 167 probe sets up-regulated 2.5-fold or greater with small molecule culture (in comparison to conventional culture). (13E) Gene ontology biological process enrichment analysis of the 126 probe sets up-regulated 2.5-fold or greater with FMM culture (in comparison to conventional culture).

FIGS. 14A-14F show cloning maps illustrating examples of the lentiviral constructs (14A-14B) and episomal constructs (14C-14F) used for reprogramming. Lentiviral constructs include an EF1α promoter and a LOXP site for CRE-mediated excision of transgenes. Episomal constructs also include an EF1α promoter.

Figure 15A:
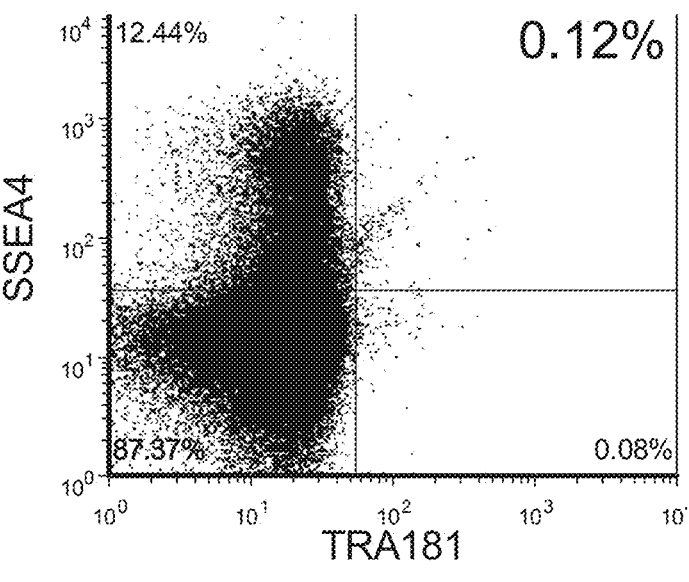
Figure 15B:
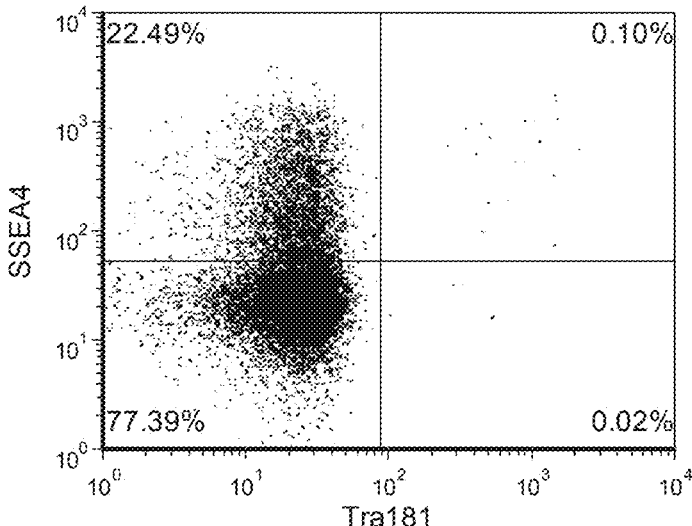
Figure 15C:
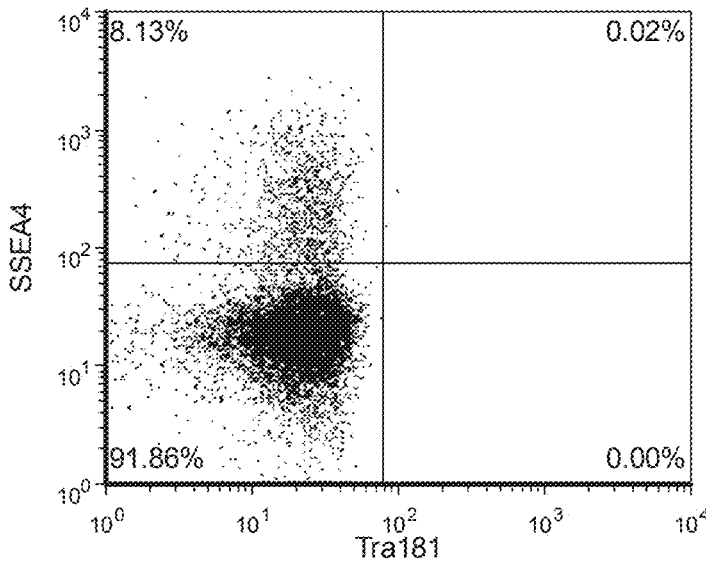
Figure 16A:
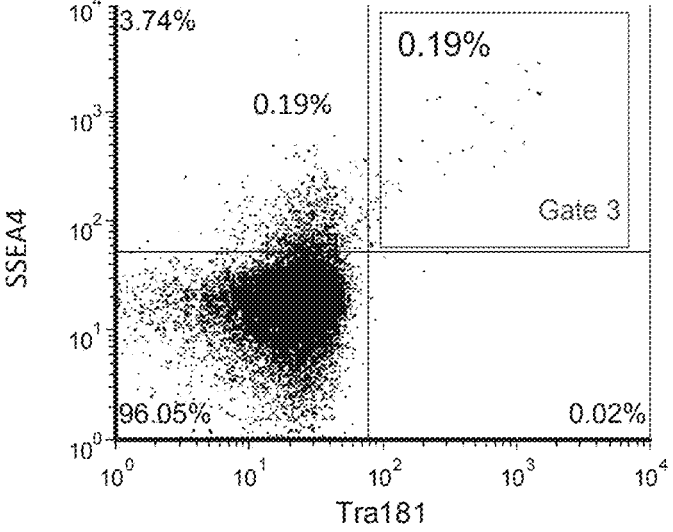

FIGS. 15A-15C show representative flow analysis for various reprogramming factor combinations at days 8-15. Human fibroblast cells were induced with various combinations of lentiviral mediated reprogramming factors including OCT4, ECAT1, and UTF1.

FIGS. 16A-16D show representative flow analysis and iPSC morphology characteristics for various reprogramming factor combinations at days 21-27. Data shows unique reprogramming combinations can be used to derive SSEA4+/TRA181+ hiPSCs.

FIGS. 17A-17B show highly enhanced lentiviral reprogramming efficiency as illustrated by flow analysis (SSEA4+/TRA181+ and CD30+ populations) and iPSC morphology characteristics. Human fibroblast cells were reprogrammed with OCT4, ECAT1, UTF1, ESRRB, and NANOG. Cells were reprogrammed using FRM and maintained in FMM.

FIGS. 18A-18D show representative flow analysis and phase images of established four iPSC clones after 7-9 passages after 96-well sort. Clones were generated with lentiviral reprogramming factors (OCT4, ECAT1, UTF1, ESRRB, and NANOG) with FRM and maintained in FMM. Populations expressing high SSEA4+/TRA181+ indicate pluripotency.

Figure 19B:
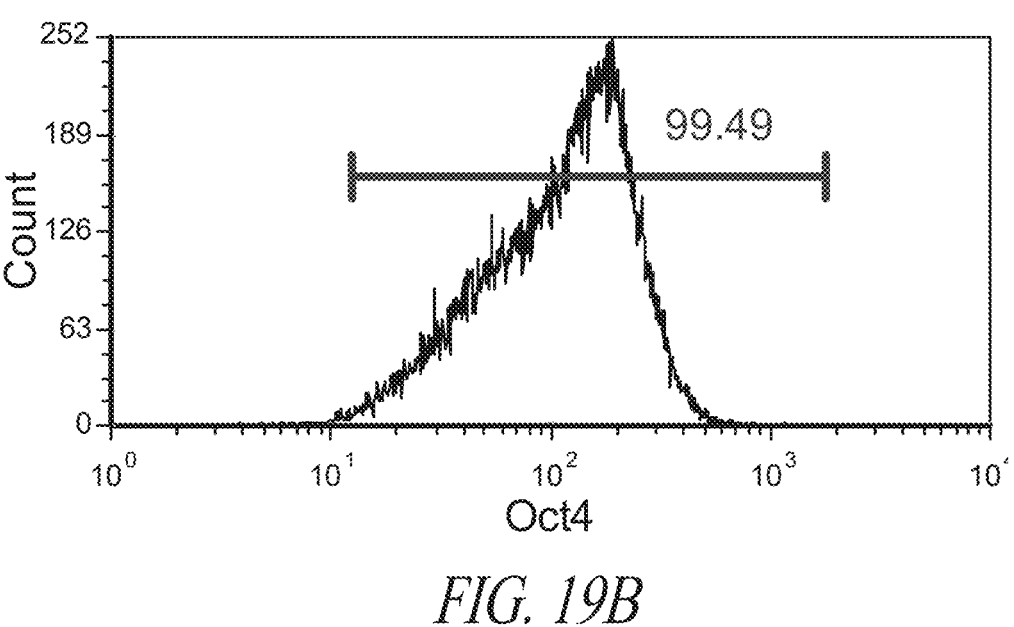

FIGS. 19A-19B show representative flow analysis for expression of OCT4 and NANOG in human fibroblast cells reprogrammed with lentiviral reprogramming factors OCT4, ECAT1, UTF1, NANOG and ESRRB. Clones were reprogrammed using FRM and maintained in FMM. Populations expressing high OCT4+/NANOG+ indicate pluripotency.

Figure 20A:
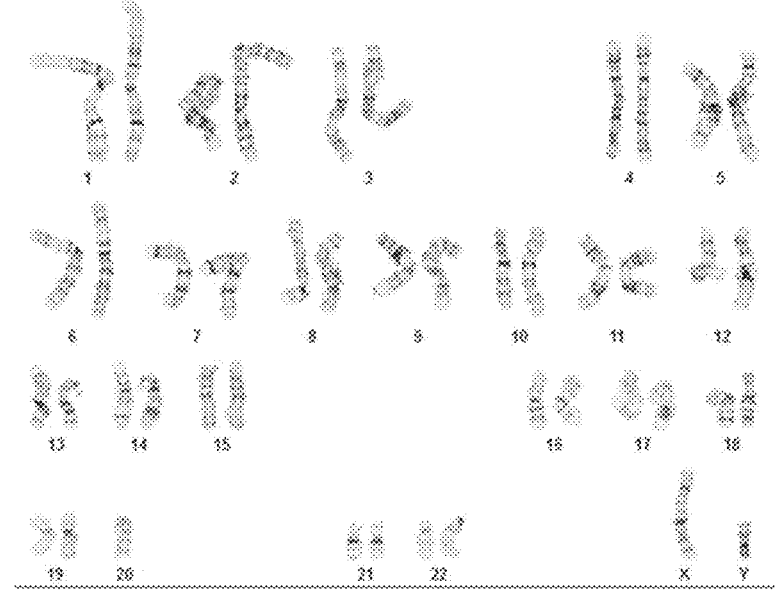
Figure 20B:
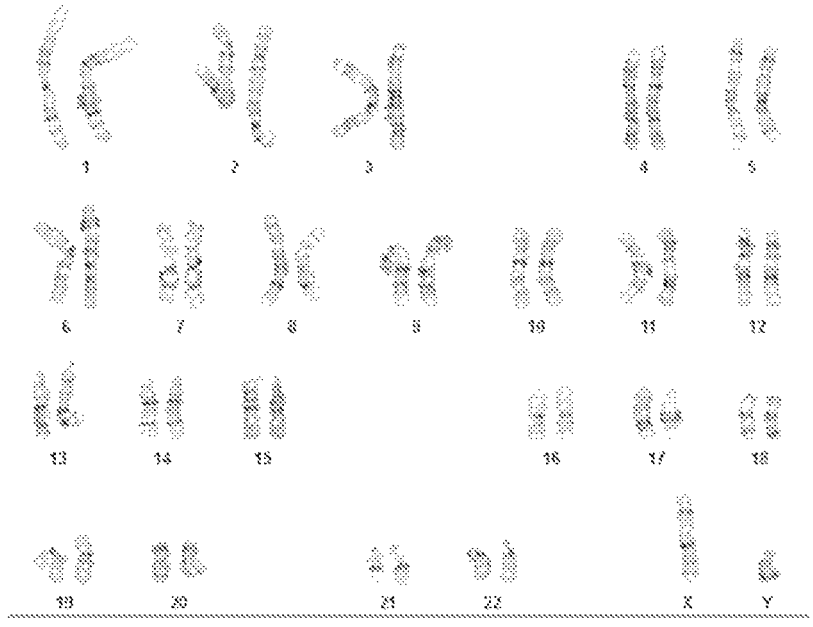
Figure 20C:
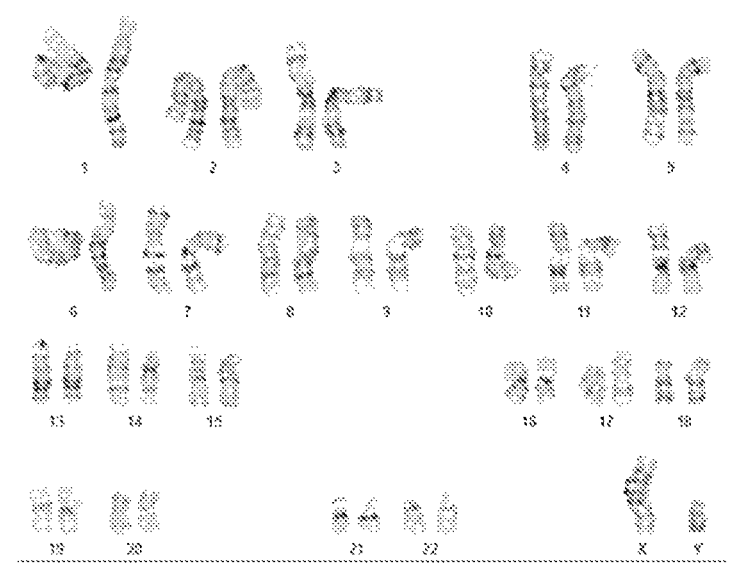

FIGS. 20A-20C show the karyotype analysis of hIPSC clones derived from human fibroblast cells reprogrammed with lentiviral reprogramming factors OCT4, ECAT1, UTF1, NANOG and ESRRB. Clones were reprogrammed using FRM and maintained in FMM. Clones exhibit a normal, male karyotype.

Figure 21:
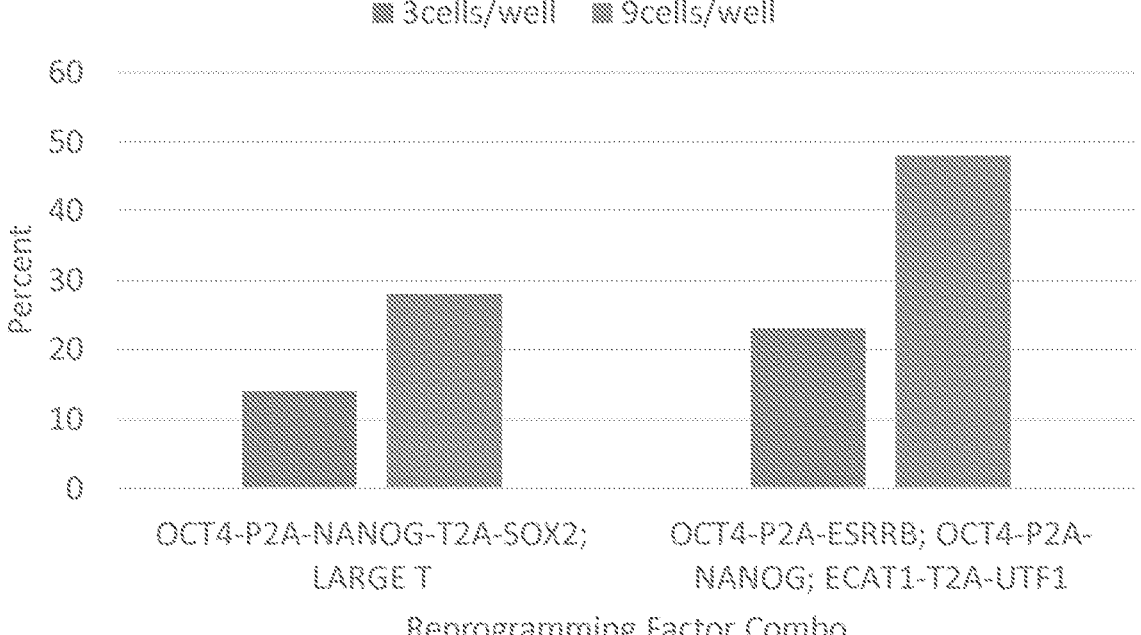

FIG. 21 shows 96 well plate sorting efficiency of reprogramming factor combination OCT4/ESRRB/NANOG/ECAT1/UTF1 compared to the reprogramming factor combination OCT4/NANOG/SOX2/LARGE T.

Figure 22A:
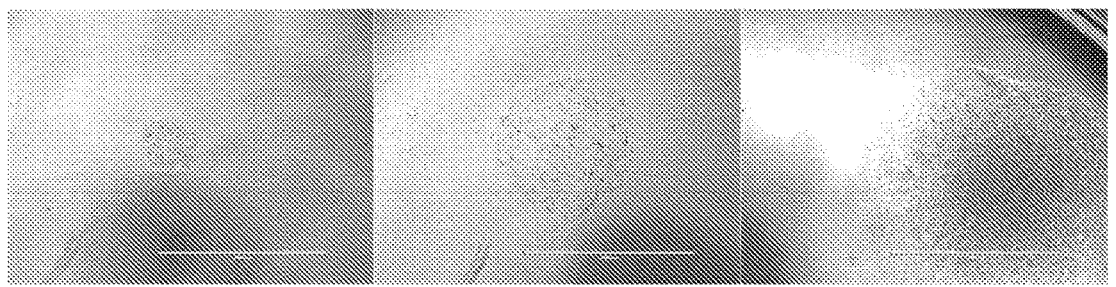
Figures 22B, 23A:
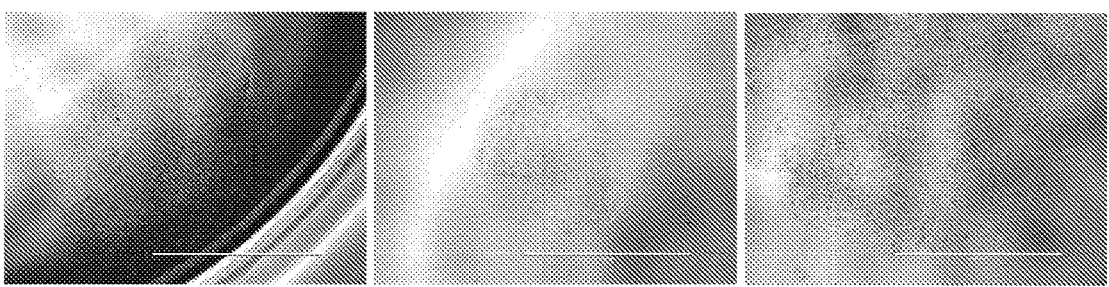

FIGS. 22A-22B show images of colonies during expansion out of 96 well for cells reprogrammed with (22A) OCT4-P2A-OCT4/NANOG-P2A-ESRRB-T2A-LIN28/ECAT1-T2A-UTF1 at 4, 6 and 11 days, and (22B) OCT4-P2A-ESRRB/OCT4-P2A-NANOG/ECAT1-T2A-UTF1 for two wells at 7 days and one well at 10 days.

Figure 23B:
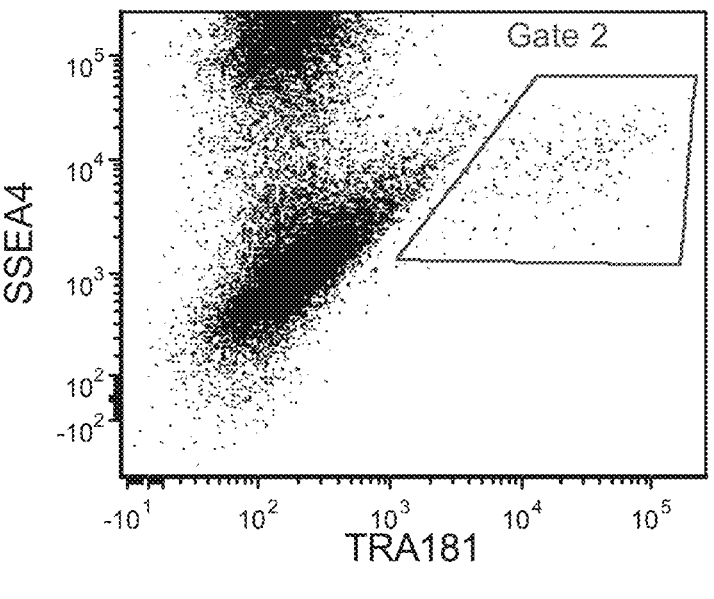
Figure 23C:
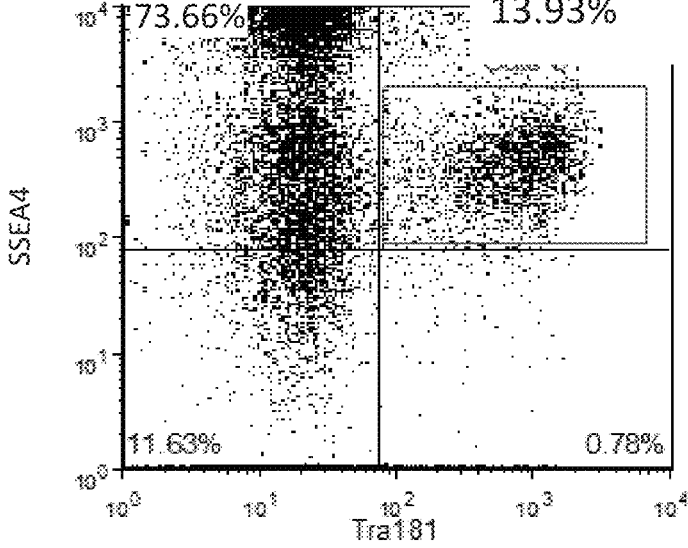

FIGS. 23A-23C show (23A) a summary the results of flow analysis demonstrating the effect of reprogramming factor stoichiometry and use of a genetic marker for selection of cells with ectopic OCT4 expression, (23B) flow analysis for human fibroblasts reprogrammed with episomal OCT4-P2A-NANOG-T2A-SOX2/SV40 Large T Antigen without selection of OCT4, and (23C) flow analysis for human fibroblasts reprogrammed with episomal OCT4-P2A-NANOG-T2A-SOX2/SV40 Large T Antigen/OCT2-P2A-OCT4-Puromycin.

Figure 24:
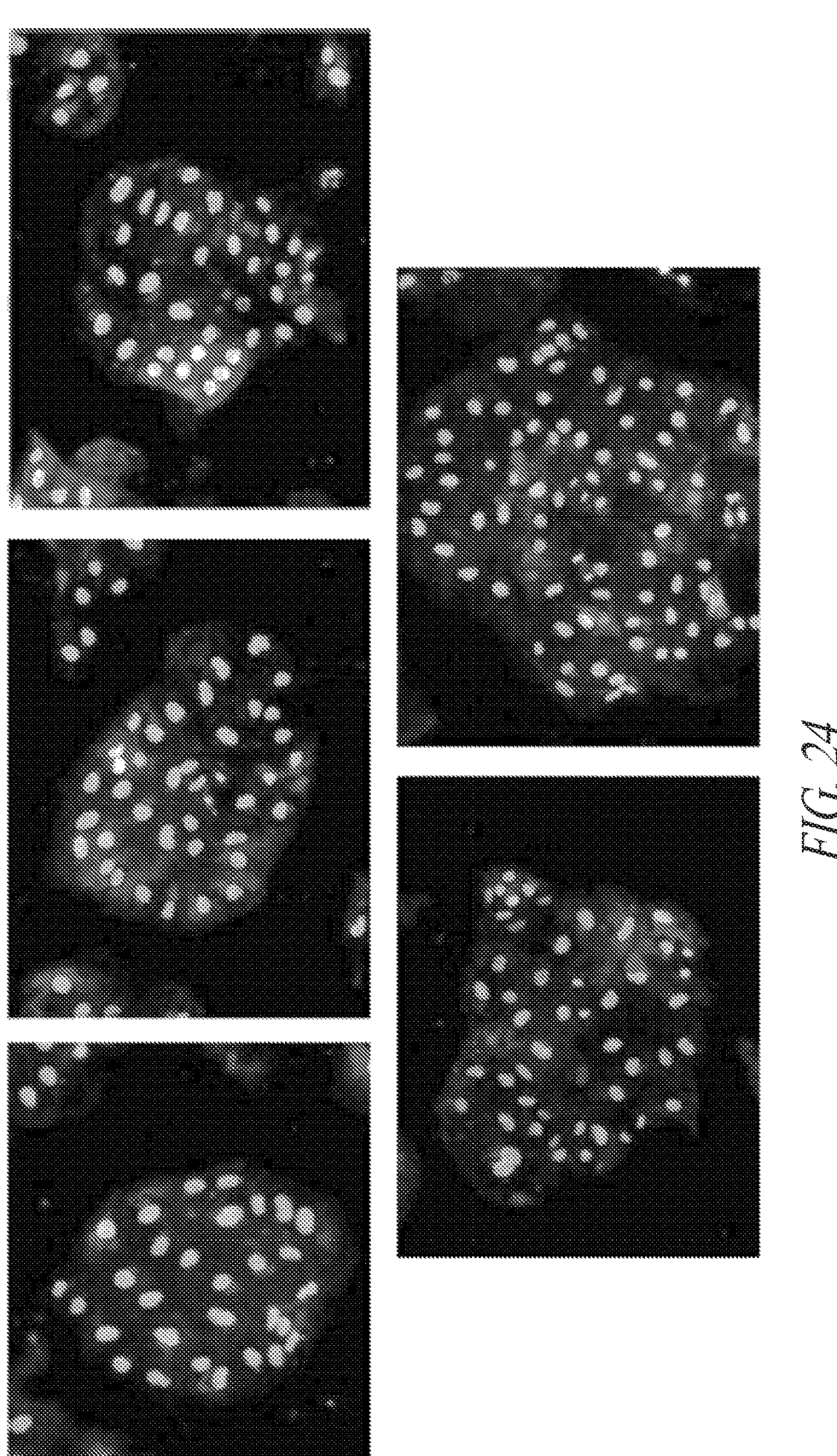

FIG. 24 shows immunofluorescent analysis of derived iPSC clones stained for pluripotency markers OCT4 (green) and TRA181 (red) with DAPI in blue.

Figure 25:
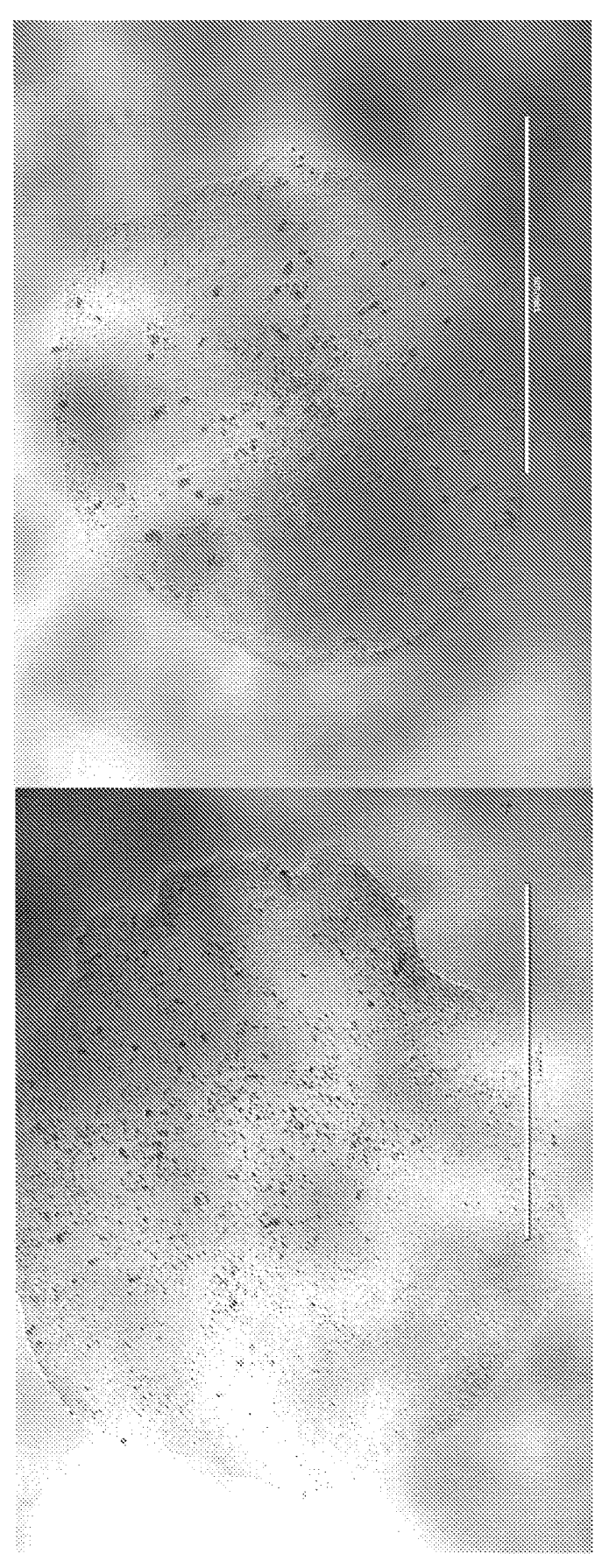

FIG. 25 shows images of SSEA4+/TRA181+/CD30+ 96-well plate sorted clones post CRE-mediated excision. Colonies were sorted from an iPSC clone originally derived from human fibroblast cells, reprogrammed with lentiviral factors OCT4, ECAT1, UTF1, NANOG, and ESRRB, and then excised for transgenes. Sorted colonies show an iPSC phenotype.

DETAILED DESCRIPTION

A. Overview

Existing methods for the production and maintenance of pluripotent cells have not yet realized homogenous cultures of footprint-free pluripotent cells free from spontaneous differentiation and amenable to high-resolution/high-clonality single cell passage and large scale expansion. Ground State pluripotent cells may confer qualities and characteristics that overcome these challenges. However, to date, no reliable or robust methods exist for the high-throughput generation of ground state pluripotent cells in feeder-free conditions. Thus, existing methods may not be suitable for the production of industrial- or clinical grade pluripotent cells. The invention contemplated herein addresses a need for the robust generation of stable pluripotent cells in or with characteristics of ground state pluripotency and solves problems in the manufacture of stable pluripotent cells suitable for industrial and clinical use.

In general, the invention relates to compositions and methods for the improved manufacture of pluripotent cells, particularly cells with reduced spontaneous differentiation, including ground state pluripotent cells. More particularly, the invention relates to a multistage culture platform that utilizes small molecule modulators of cellular signal transduction pathways, in a stage-specific manner and enables pluripotent cell derivation and maintenance to the point where culturing methods and methods of deriving pluripotent cells are no longer a source of variability and/or gating activity for downstream use. Moreover, the culture platform contemplated herein enables the derivation and maintenance of pluripotent cells in feeder-free conditions, with improved genomic stability, improved undifferentiated state, reduced spontaneous differentiation, improved culture homogeneity, improved survival in the culturing, dissociation, and passaging of single pluripotent cells, and improved methods of transgene or footprint free reprogramming cells to ground state pluripotency. Thus, the compositions and methods contemplated herein enable the manufacture of pluripotent cells that are appropriate for industrial and clinical use and/or ground state pluripotent cells.

To date no small molecule driven platform has demonstrated the ability to enhance reprogramming and support single cell and FF culture of footprint-free induced pluripotent stem cells (iPSCs) derived from human cells (Nichols and Smith, 2012). The culture platforms contemplated herein, provide for, in part, the application of specific combinations of small molecule inhibitors in a stage-specific manner to enable rapid and robust reprogramming and stable long term culture of pluripotent stem cells. In various embodiments, a culture platform for inducing or maintaining improved undifferentiated pluripotent state including ground state pluripotency is provided. The platform contemplated herein also provides a robust culture system for the production and maintenance of ground state pluripotency in human iPSCs (hiPSCs). In one embodiment, the culture platforms enable a transgene or footprint-free method of reprogramming. In particular embodiments, the platform contemplated herein represents an improved method for the manufacture of hiPSCs that overcomes key challenges in the multiplex derivation and maintenance of transgene-free hiPSC.

The practice of the present invention will employ, unless indicated specifically to the contrary, conventional methods of chemistry, biochemistry, organic chemistry, molecular biology, microbiology, recombinant DNA techniques, genetics, immunology, cell biology, stem cell protocols, cell culture and transgenic biology that are within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Fire et al., *RNA Interference Technology: From Basic Science to Drug Development* (Cambridge University Press, Cambridge, 2005); Schepers, *RNA Interference in Practice* (Wiley-VCH, 2005); Engelke, *RNA Interference (RNAi): The Nuts & Bolts of siRNA Technology* (DNA Press, 2003); Gott, *RNA Interference, Editing, and Modification: Methods and Protocols* (Methods in Molecular Biology; Human Press, Totowa, NJ, 2004); Sohail, *Gene Silencing by RNA Interference: Technology and Application* (CRC, 2004); Clarke and Sanseau, *microRNA: Biology, Function & Expression* (Nuts & Bolts series; DNA Press, 2006); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C. Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Pro-*

*tocols* (Methods in Molecular Biology) (Kevin D. Bunting Ed., 2008) *Neural Stem Cells: Methods and Protocols* (Methods in Molecular Biology) (Leslie P. Weiner Ed., 2008); Hogan et al., *Methods of Manipulating the Mouse Embryo* ($2^{nd}$ Edition, 1994); Nagy et al., *Methods of Manipulating the Mouse Embryo* ($3^{rd}$ Edition, 2002), and *The Zebrafish book. A guide for the laboratory use of zebrafish* (Danio rerio), 4th Ed., (Univ. of Oregon Press, Eugene, OR, 2000).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. For the purposes of the present invention, the following terms are defined below.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "appreciable" refers to a range of quantity, level, value, number, frequency, percentage, dimension, size, amount, weight or length or an event that is readily detectable by one or more standard methods. The terms "not-appreciable" and "not appreciable" and equivalents refer to a range of quantity, level, value, number, frequency, percentage, dimension, size, amount, weight or length or an event that is not readily detectable or undetectable by standard methods. In one embodiment, an event is not appreciable if it occurs less than 5%, 4%, 3%, 2%, 1%, 0.1%, 0.01%, 0.001% or less of the time.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a repro-grammed cell is one that is in a less differentiated state than the same cell in a non-reprogrammed state.

As used herein, the term "potency" refers to the sum of all developmental options accessible to the cell (i.e., the developmental potency). One having ordinary skill in the art would recognize that cell potency is a continuum, ranging from the most plastic cell, a totipotent stem cell, which has the most developmental potency to the least plastic cell, a terminally differentiated cell, which has the least developmental potency. The continuum of cell potency includes, but is not limited to, totipotent cells, pluripotent cells, multipotent cells, oligopotent cells, unipotent cells, and terminally differentiated cells.

As used herein, the term "pluripotent" refers to the ability of a cell to form all lineages of the body or soma (i.e., the embryo proper). For example, an embryonic stem cell is a type of pluripotent stem cell that is able to form cells from each of the three germs layers: the ectoderm, the mesoderm, and the endoderm.

Pluripotency can be determined, in part, by assessing pluripotency characteristics of the cells. Pluripotency characteristics include, but are not limited to: (i) pluripotent stem cell morphology; (ii) the potential for unlimited self renewal (iii) expression of pluripotent stem cell markers including, but not limited to SSEA1 (mouse only), SSEA3/4; SSEA5, TRA1-60/81; TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm) (v) teratoma formation consisting of the three somatic lineages; and (vi) formation of embryoid bodies consisting of cells from the three somatic lineages;

Two types of pluripotency have previously been described: the "primed" or "metastable" state of pluripotency akin to the epiblast stem cells (EpiSC) of the late blastocyst and the "Naïve" or "Ground" state of pluripotency akin to the inner cell mass of the early/preimplantation blastocyst. While both pluripotent states exhibit the characteristics as described above, the naïve or ground state further exhibits; (i) preinactivation or reactivation of the X-chromosome in female cells (ii) improved clonality and survival during single-cell culturing (iii) global reduction in DNA methylation, (iv) reduction of H3K27me3 repressive chromatin mark deposition on developmental regulatory gene promoters, and (v) reduced expression of differentiation markers relative to primed state pluripotent cells. Standard methodologies of cellular reprogramming in which exogenous pluripotency genes are introduced to a somatic cell, expressed and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical intercell spacing.

As used herein, the term "gene expression profile," "gene expression signature," "gene expression panel," "gene panel," or "gene signature" refers to the expression or levels of expression of a plurality of genes which serves to distinguish a cell or population of cells from another cell or population of cells. For example, a population of pluripotent cells maintained in a medium to prevent spontaneous differentiation may display a gene expression profile comprising decreased expression of differentiation genes relative to a control population of pluripotent cells of the same origin that are not maintained in the same medium.

As used herein, the term "differentiation marker gene," or "differentiation gene," refers to genes whose expression are indicative of cell differentiation occurring within a cell, such as a pluripotent cell. Differentiation marker genes include, but are not limited to, the following genes: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

As used herein, the term "differentiation marker gene profile," or "differentiation gene profile," "differentiation gene expression profile," "differentiation gene expression signature," "differentiation gene expression panel," "differentiation gene panel," or "differentiation gene signature" refers to the expression or levels of expression of a plurality of differentiation marker genes.

In particular embodiments, a population of pluripotent cells showing decreased spontaneous differentiation may be characterized by a decrease in expression of a differentiation marker gene or a differentiation marker gene profile. For example, decreased spontaneous differentiation in a pluripotent cell or population of pluripotent cells may be indicated where a given set of culture conditions causes a decrease in expression of one or more a differentiation marker genes of at least 10%, 20%, 25%, 30%, 40%, 50%, 60%, 70%, 80%, 90%, or more compared to the expression of the differentiation marker genes of a control pluripotent cell or population of pluripotent cells lacking the same culture conditions.

"Gene expression" as used herein refers to the relative levels of expression and/or pattern of expression of a gene in a biological sample, such as pluripotent cells, or a population of cells comprising pluripotent cells. In particular embodiments, the pluripotent cells are iPSCs.

Any methods available in the art for detecting expression of the genes characterizing the cells of the invention are encompassed herein. As used herein, the term "detecting expression" means determining the quantity or presence of an RNA transcript or its expression product of a gene. Methods for detecting expression of genes, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR (RT-PCR) (Weis et al., TIG 8:263-64, 1992), and array-based methods such as microarray (Schena et al., Science 270:467-70, 1995) are used.

"Adhere" refers to cells attaching to a vessel, for example, a cell attaching to a sterile plastic (or coated plastic) cell culture dish or flask in the presence of an appropriate culture medium. Certain classes of cells are not sustained or do not grow in a culture unless they adhere to the cell culture vessel. Certain classes of cells ("non-adherent cells") are maintained and/or proliferate in culture without adhering.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate" refers to the sustaining, propagating (growing) and/or differentiating of cells outside of tissue or the body, for example in a sterile plastic (or coated plastic) cell culture dish or flask. "Cultivation" may utilize a culture medium as a source of nutrients, hormones and/or other factors helpful to propagate and/or sustain the cells.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, the terms "enrich" and "enriching" refer to increasing the amount of a specified component in a composition, such as a composition of cells, and "enriched", when used to describe a composition of cells such as a cell population, refers to a population of cells having an increased amount proportionally of a specified component as compared to the proportion of such component in the population of cells prior to being enriched. For example, a composition such as a population of cells may be enriched with respect to a target cell type (i.e., cells having specified characteristics), thus having an increased proportion or percent of the target cell type as compared to the proportion of the target cells present in the population of cells before being enriched. A population of cells may be enriched for a target cell type by cell selection and sorting methods known in the art. In some embodiments, a population of cells is enriched by a sorting or selection process as described in the examples herein. In a particular embodiment, a method that enriches for a target cell population enriches the cell population with respect to the target cell population by at least about 20%, meaning that the enriched cell population comprises proportionately about 20% more of the target cell type than in the population before the population was enriched. In one embodiment, a method that enriches for a target cell population enriches the cell population with respect to the target cell population proportionately by at least about 30+%, 40+%, 50+%, 60+%, 70+%, 80%, 85%, 90%, 95%, 97%, 98% or 99%, or at least about 98%, or in particular embodiments, about 99%.

In certain embodiments, a population of cells is enriched with respect to the amount of pluripotent cells or cells exhibiting pluripotency characteristics. In particular embodiments of the invention, a population of cells undergoing reprogramming is enriched for target cells having characteristics of pluripotency, such as expression of pluripotency markers including, without limitation, SSEA3, SSEA4, TRA 1-60, TRA-1-81, CD30 or CD50.

In particular embodiments, a population of cells, such as a population of cells undergoing reprogramming, is depleted of nonpluripotent cells using surface markers specific to differentiated cell lineages or nonpluripotent cells, which may include, for example, CD13, CD26, CD34, CD45, CD31, CD46, or CD7. The resulting cell population can thus be described as a population of cells enriched for pluripotent cells.

In particular embodiments, the enriched cells comprises a distinct gene or protein expression profile, for example, cell surface expression of at least two pluripotency markers such as SSEA3, SSEA4, TRA 1-60, TRA-1-81, CD30 and CD50. In some embodiments, the enriched cells comprise two or more pluripotency markers. In particular embodiments, the enriched cells express SSEA4 in combination with either TRA-181 or TRA-160. In more particular embodiments, the enriched cells express SSEA4, TRA181, and CD30. In one embodiment, a population of cells comprises at least about 5%, 10%, 15%, 20%, 25%, 30%, 40%, 50%, 70%, 75%, 80%, 90%, 95%, 97%, 98%, or 99% of the enriched cells, such as pluripotent cells.

Thus, in some embodiments, methods of enriching a population of cells for pluripotent cells comprise sorting the cell population based on cell surface expression of pluripotency markers, such as SSEA3, SSEA4, TRA 1-60, TRA-1-81, CD30 and CD50, and collecting the fraction of cells expressing such markers to obtain a population of cells that is enriched for pluripotent cells. In other embodiments, a population of cells is enriched for pluripotent cells by sorting the cell population based on cell surface expression of markers of differentiating or differentiated cells, such as CD13, CD26, CD34, CD45, CD31, CD46, and CD7, and depleting the cell population of such cells to obtain a population of cells that is enriched for pluripotent cells. In particular embodiments, the cell population is sorted based on the expression of CD13, and CD13$^+$ cells are removed from the cell population to obtain a population of cells enriched for pluripotent cells.

As used herein, "feeder cells" or "feeders" are terms used to describe cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, and immortalized mouse embryonic fibroblasts. The feeder cells may typically be inactivated when being co-cultured with other cells by irradiation or treatment with an anti-mitotic agent such as mitomycin c, to prevent them from outgrowing the cells they are supporting. Without limiting the foregoing, one specific feeder cell type may be a human feeder, such as a human skin fibroblast. Another feeder cell type may be mouse embryonic fibroblasts (MEF).

As used herein, a "feeder-free" (FF) environment refers to an environment such as a cell culture or culture media essentially free of feeder cells and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium.

Genomic stability refers to the ability of a cell to faithfully replicate DNA and maintain integrity of the DNA replication process. As used herein, the terms "genomically stable cells" and "cells having genomic stability" refer to cells that exhibit a frequency of mutations and chromosomal aberrations (such as translocations, aneuploidy, copy number variations and duplications) that is substantially similar to the frequency of mutations and chromosomal aberrations relative to normal somatic human cells.

"Ingredient" refers to any compound or other material, whether chemical or biological in origin that may be used in cell culture media to maintain and/or promote the growth and/or differentiation of cells. The terms "component" "nutrient" and "ingredient" may be used interchangeably. Conventional ingredients used for cell culture media may include but are not limited to amino acids, salts, metals, sugars, lipids, nucleic acids, hormones, vitamins, fatty acids, proteins and the like. Other ingredients that promote and/or maintain cultivation of cells ex vivo may be selected by those persons of ordinary skill in the art as required for a desired effect.

"Isolate" or "isolating" refers to separating and collecting a composition or material from its natural environment, such as the separating of individual cell or cell cultures from tissue or the body. In one aspect, a population or composition of cells is substantially free of cells and materials with which it can be associated in nature. "Isolated" or "purified" or "substantially pure", with respect to a target population of cells, refers to a population of cells that is at least about 50%, at least about 75%, at least about 85%, at least about 90%, and in particular embodiments, at least about 95% pure, with respect to the target cells making up a total cell population. Purity of a population or composition of cells can be assessed by appropriate methods that are well known in the art. For example, a substantially pure population of pluripotent cells refers to a population of cells that is at least about 50%, at least about 75%, at least about 85%, at least about 90%, and in particular embodiments at least about 95%, and in certain embodiments about 98% pure, with respect to pluripotent cells making up the total cell population. The term "essentially pure" is used interchangeably herein with "substantially pure".

"Passage" or "passaging" refers to the act of subdividing and plating cells into multiple cell culture surfaces or vessels when the cells have proliferated to a desired extent. In some embodiments "passage" or "passaging" refers to subdividing, diluting and plating the cells. As cells are passaged from the primary culture surface or vessel into a subsequent set of surfaces or vessels, the subsequent cultures may be referred to herein as "secondary culture" or "first passage," etc. Each act of subdividing and plating into a new culture vessel is considered one passage.

"Plating" refers to placing a cell or cells into a culture vessel such that the cells adhere to and spread on a cell culture vessel.

A "pluripotency factor" refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Proliferate" refers to the property of one cell dividing into two essentially identical cells or a population of cells increasing in number (e.g., to reproduce).

"Propagation" refers to growing (e.g., reproducing via cell proliferation) cells outside of tissue or the body, for example, in a sterile container such as a plastic (or coated plastic) cell culture dish or flask.

"Primary culture" refers to cells, tissue and/or culture where the isolated cells are placed in a first culture vessel with culture medium. The cells, tissue and/or culture may be sustained and/or may proliferate, however, as long as the cells, tissue and/or culture remain in the first vessel the cells, tissue and/or culture are referred to as the primary culture.

The terms "small molecule reprogramming agent" or "small molecule reprogramming compound" are used interchangeably herein and refer to small molecules that can increase developmental potency of a cell, either alone or in combination with other pluripotency factors. A "small molecule" refers to an agent that has a molecular weight of less than about 5 kD, less than about 4 kD, less than about 3 kD, less than about 2 kD, less than about 1 kD, or less than about 0.5 kD. Small molecules include, but are not limited to: nucleic acids, peptidomimetics, peptoids, carbohydrates, lipids or other organic or inorganic molecules. Libraries of chemical and/or biological mixtures, such as fungal, bacterial, or algal extracts, are known in the art and can be used as a source of small molecules in certain embodiments. In particular embodiments, the small molecule reprogramming agent used herein has a molecular weight of less than 10,000 daltons, for example, less than 8000, 6000, 4000, 2000 daltons, e.g., between 50-1500, 500-1500, 200-2000, 500-5000 daltons.

C. Cells

In a particular embodiment, one or more cells may be cultured, dissociated, and passaged using the compositions and methods contemplated herein. In one embodiment, single cells cultured, dissociated, and passaged using the compositions and methods contemplated herein. In another embodiment, a population of cells or a plurality of cells is cultured, dissociated, and passaged using the compositions and methods contemplated herein.

A starting population of cells suitable for use in particular embodiments may be derived from essentially any suitable source, and may be heterogeneous or homogeneous with respect to cell types or state of pluripotency. Suitable cells include fetal cells and adult cells. In addition, suitable cells may be mammalian in origin, e.g., from a rodent, a cat, a dog, a pig, a goat, a sheep, a horse, a cow, or a primate. In one embodiment, the cells are human cells.

The cells may be somatic, non-pluripotent, incompletely or partially pluripotent stem cells, multipotent cells, oligopotent cells, unipotent cells, terminally differentiated cells, or a mixed population of cells comprising any combination of the foregoing. Pluripotent cells suitable for use in particular embodiments include, but are not limited to, naturally-occurring stem cells, embryonic stem cells, or iPSCs. A "mixed" population of cells is a population of cells of varying degrees of developmental potency. For example, a mixed population of cells may comprise cells undergoing reprogramming, so that the mixed population comprises pluripotent cells, partially pluripotent cells, and non-pluripotent cells, such as fully differentiated cells.

In one embodiment, the starting population of cells is selected from adult or neonatal stem/progenitor cells. In particular embodiments, the starting population of stem/progenitor cells is selected from the group consisting of: mesodermal stem/progenitor cells, endodermal stem/progenitor cells, and ectodermal stem/progenitor cells.

Illustrative examples of mesodermal stem/progenitor cells include, but are not limited to: mesodermal stem/progenitor cells, endothelial stem/progenitor cells, bone marrow stem/progenitor cells, umbilical cord stem/progenitor cells, adipose tissue derived stem/progenitor cells, hematopoietic stem/progenitor cells (HSCs), mesenchymal stem/progenitor cells, muscle stem/progenitor cells, kidney stem/progenitor cells, osteoblast stem/progenitor cells, chondrocyte stem/progenitor cells, and the like.

Illustrative examples of ectodermal stem/progenitor cells include, but are not limited to neural stem/progenitor cells, retinal stem/progenitor cells, skin stem/progenitor cells, and the like.

Illustrative examples of endodermal stem/progenitor cells include, but are not limited to liver stem/progenitor cells, pancreatic stem/progenitor cells, epithelial stem/progenitor cells, and the like.

In certain embodiments, the starting population of cells may be a heterogeneous or homogeneous population of cells selected from the group consisting of: pancreatic islet cells, CNS cells, PNS cells, cardiac muscle cells, skeletal muscle cells, smooth muscle cells, hematopoietic cells, bone cells, liver cells, an adipose cells, renal cells, lung cells, chondrocyte, skin cells, follicular cells, vascular cells, epithelial cells, immune cells, endothelial cells, and the like.

D. Culture Platforms for Reducing Spontaneous Differentiation and Inducing Ground State Pluripotency Cell banking, disease modeling and cell therapy applications have placed increasing demands on manufacturing high quality pluripotent cells. For example, the high-throughput derivation of footprint-free iPSCs and their expansion in systems that allow scaled production remains technically elusive. In particular embodiments, culture platform are contemplated that allow for the rapid, parallel generation, selection and expansion of pluripotent cells using small molecule pathway inhibitors in stage-specific media compositions. The platforms contemplated herein support efficient and expedited reprogramming using minimal reprogramming factors in a completely feeder-free environment; enable single cell culture and expansion of pluripotent cells while maintaining a homogenous and genomically stable pluripotent population. Moreover, the culture platforms contemplated herein, provide culturing pluripotent cells, including hESCs and hiPSCs, to a reduced state of spontaneous differentiation and a common ground state of pluripotency, irrespective of genetic background and independent of transgene expression.

The culture platforms contemplated herein are useful, in part, for the production of industrial- or clinical-grade pluripotent cells having reduced spontaneous differentiation in culture. In one embodiment, non-pluripotent cells are induced to become pluripotent cells and cultured to maintain pluripotency. In another embodiment, non-pluripotent cells are induced to become pluripotent cells and cultured to achieve and/or maintain reduced spontaneous differentiation in culture. In another embodiment, non-pluripotent cells are induced to become pluripotent cells and cultured to achieve and/or maintain ground state pluripotency.

In various embodiments, the culture platforms contemplated herein maintain ground state pluripotency, normal karyotypes, and genomic stability of one or more pluripotency cells for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more passages, including any intervening number of passages.

In other embodiments, the culture platforms contemplated herein maintain reduced spontaneous differentiation in one or more pluripotency cells for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more passages, including any intervening number of passages.

In one embodiment, the culture platform comprises a cell culture medium comprising a cell culture medium and a GSK-3 inhibitor, a MEK inhibitor, and a Rho Kinase (ROCK) inhibitor. In various embodiments, the cell culture media contemplated herein do not comprise or lack an inhibitor of TGFβ/activin signaling pathways, including TGFβ receptor (TGFβR) inhibitors and ALK5 inhibitors. Without wishing to be bound to any particular theory, the inventors surprisingly discovered that while TGFβR/ALK5 inhibitors increase the efficiency of reprogramming, these inhibitors counteract the long-term maintenance, quality and homogeneity of a pluripotent cell population i.e. the inhibition of TGFβ pathway signaling improved the efficiency of cellular reprogramming but relief from this inhibition is required for subsequent maintenance of the pluripotent cell population in in vitro culture systems, particularly in systems using feeder-cell free and single cell, enzymatic passage where a homogeneous pluripotent population with reduced spontaneous differentiation is preferred and more particularly where transgene expression is absent. In addition, culturing metastable pluripotent cells in media comprising a GSK-3 inhibitor and a MEK inhibitor and optionally a ROCK inhibitor, but lacking TGFβR/ALK5 inhibitors, as disclosed herein, transition pluripotent cells to achieve reduced spontaneous differentiation and/or achieve ground state pluripotency. The culture media platform contemplated herein also enables efficient reprogramming and long-term culture of pluripotent cells in feeder free environments. Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J Mol. Pharmacol.* 62(1): 65-74 (2002).

In a preferred embodiment, the culture platform comprises a cell culture medium comprising a GSK-3 inhibitor, a MEK inhibitor, a Rho Kinase (ROCK) inhibitor, and optionally, LIF and/or bFGF, and does not comprise a small molecule inhibitor of a TGFβ/activin signaling pathway including but not limited to TGFβR or ALK5 inhibitors.

In additional embodiments, the cell culture media is substantially free of cytokines and/or growth factors, and optionally is a feeder-free environment. In other embodiments, the cell culture media contains supplements such as serums, extracts, growth factors, hormones, cytokines and the like.

In one preferred embodiment, the culture platform comprises feeder-free cultures.

The culture platforms contemplated herein also offer numerous advantages such as manufacturing a homogenous population of industrial- or clinical-grade pluripotent cells having reduced spontaneous differentiation and/or achieving ground state pluripotency. As used herein, the term "homogenous" refers to a population of cells wherein each cell is the same or substantially the same as the other cells in the population. In one embodiment, a cell is the same as other cells in the population if each cell expresses one or more of the same pluripotency markers as contemplated herein, e.g., SSEA4 and TRA1-81. In one embodiment, the population is homogenous if at least 90%, at least 95%, at least 96%, at least 97%, at least 98%, at least 99%, or more of the cells are the same or substantially the same as other cells in the population.

1. TGFβ Receptor/ALK5 Inhibitors

TGFβ receptor (e.g., ALK5) inhibitors can include antibodies to, dominant negative variants of, and antisense nucleic acids that suppress expression of, TGFβ receptors (e.g., ALK5). Exemplary TGFβ receptor/ALK5 inhibitors include, but are not limited to, SB431542 (see, e.g., Inman, et al., Molecular Pharmacology 62(1):65-74 (2002)), A-83-01, also known as 3-(6-Methyl-2-pyridinyl)-N-phenyl-4-(4-quinolinyl)-1H-p yrazole-1-carbothioamide (see, e.g., Tojo, et al., Cancer Science 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl] pyridin-2-yl}-N-(tetrahydro-2H-pyran-4-yl)benzamide) (see, e.g., Gellibert, et al., Journal of Medicinal Chemistry 49(7):2210-2221 (2006)), SM16 (see, e.g., Suzuki, et al., Cancer Research 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., Xenobiotica 38(3):325-339 (2008)), GW6604 (2-phenyl-4-(3-pyridin-2-yl-1H-pyrazol-4-yl)pyridine) (see, e.g., de Gouville, et al., Drug News Perspective 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., Molecular Pharmacology 65(3):744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data herein showing the effect of inhibiting ALK5, it is believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor (TGFβR) inhibitors can include antibodies to, dominant negative variants of and siRNA or antisense nucleic acids that target TGFβ receptors. Specific examples of TGFβ receptor inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., Clinical Cancer Research 13(18):5262-5270 (2007); Kaminska, et al., Acta Biochimica Polonica 52(2): 329-337 (2005); and Chang, et al., Frontiers in Bioscience 12:4393-4401 (2007)).

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et al., EP1992360, incorporated herein by reference).

Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., Oncogene 24:3864-3874 (2005) and Zhao, et al., Molecular Biology of the Cell, 17:3819-3831 (2006)).

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO-oligonucleotides. (See, e.g., Miyazono, et al., U.S. Pat. No. 6,534,476, and Steinbrecher, et al., US2005119203, both incorporated herein by reference).

2. Wnt Pathway Agonists

As used herein, the terms "Wnt signal-promoting agent," "Wnt pathway activating agent," or "Wnt pathway agonist," refers to an agonist of the Wnt signaling pathway, including but not limited to an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16. Wnt pathway agonists further include, but are not limited to, one or more of the following polypeptides or a fragment thereof: a Dkk polypeptide, a crescent polypeptide, a cerberus polypeptide, an axin polypeptide, a Frzb polypeptide, a T-cell factor polypeptide, or a dominant negative disheveled polypeptide.

Non-limiting examples of Wnt pathway agonists further include one or more of the following: a nucleic acid comprising a nucleotide sequence that encodes a Wnt polypeptide, a polypeptide comprising an amino acid sequence of a Wnt polypeptide, a nucleic acid comprising a nucleotide sequence that encodes an activated Wnt receptor, a polypeptide comprising an amino acid sequence of an activated Wnt receptor, a small organic molecule that promotes Wnt/β-catenin signaling, a small organic molecule that inhibits the expression or activity of a Wnt antagonist, an antisense oligonucleotide that inhibits expression of a Wnt antagonist, a ribozyme that inhibits expression of a Wnt antagonist, an RNAi construct, siRNA, or shRNA that inhibits expression of a Wnt antagonist, an antibody that binds to and inhibits the activity of a Wnt antagonist, a nucleic acid comprising a nucleotide sequence that encodes a β-catenin polypeptide, a polypeptide comprising an amino acid sequence of a β-catenin polypeptide, a nucleic acid comprising a nucleotide sequence that encodes a Lef-1 polypeptide, a polypeptide comprising an amino acid sequence of a Lef-1 polypeptide.

Wnt pathway agonists further include GSK3 inhibitors, such as, for example, a nucleic acid comprising a nucleotide sequence that encodes a dominant negative GSK-3, GSK3α, or GSK3β polypeptide, a polypeptide comprising an amino acid sequence of a dominant negative GSK-3, GSK3α, or GSK3β polypeptide, a small organic molecule that binds to and inhibits the expression or activity of GSK-3, GSK3α, or GSK3β, an RNAi construct, siRNA, or shRNA that binds to and inhibits the expression and/or activity of GSK-3, GSK3α, or GSK3β, an antisense oligonucleotide that binds to and inhibits the expression of GSK-3, GSK3α, or GSK3β, an antibody that binds to and inhibits the expression and/or activity of GSK-3, GSK3α, or GSK3β, a ribozyme that binds to and inhibits the expression of GSK-3, GSK3α, or GSK3β, and any GSK-3-independent reagent that activates β-catenin target genes similar in effect to GSK-3 inhibition.

3. GSK-3β Inhibitors

GSK-3β inhibitors are specific exemplary Wnt pathway agonists suitable for use in compositions contemplated herein, and may include, but are not limited to, polynucleotides, polypeptides, and small molecules. GSK-3β inhibitors contemplated herein may decrease GSK-3β expression and/or GSK-3β activity. Illustrative examples of GSK-3β inhibitors contemplated herein include, but are not limited to, anti-GSK-3β antibodies, dominant negative GSK-3β variants, siRNA, shRNA, miRNA and antisense nucleic acids that target GSK-3β.

Other illustrative GSK-3β inhibitors include, but are not limited to: Kenpaullone, 1-Azakenpaullone, CHIR99021, CHIR98014, AR-A014418, CT 99021, CT 20026, SB216763, AR-A014418, lithium, SB 415286, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione; TWS119 pyrrolopyrimidine compound, L803 H-KEAPPAPPQSpP-NH2 or its myristoylated form; 2-Chloro-1-(4,5-dibromo-thiophen-2-yl)-ethanone; GF109203X; RO318220; TDZD-8; TIBPO; and OTDZT.

In particular illustrative embodiments, the GSK-3β inhibitor is CHIR99021, BIO, or Kenpaullone.

In a preferred embodiment, the GSK-3β inhibitor is CHIR99021.

4. ERK/MEK Inhibitors

ERK/MEK inhibitors suitable for use in compositions contemplated herein include, but are not limited to, polynucleotides, polypeptides, and small molecules. ERK/MEK inhibitors contemplated herein may decrease MEK or ERK expression and/or MEK or ERK activity. Illustrative examples of MEK/ERK inhibitors contemplated herein include, but are not limited to, anti-MEK or anti-ERK antibodies, dominant negative MEK or ERK variants, siRNA, shRNA, miRNA and antisense nucleic acids that target MEK or ERK.

Other illustrative ERK/MEK inhibitors include, but are not limited to, PD0325901, PD98059, UO126, SL327, ARRY-162, PD184161, PD184352, sunitinib, sorafenib, Vandetanib, pazopanib, Axitinib, GSK1120212, ARRY-438162, RO5126766, XL518, AZD8330, RDEA119, AZD6244, FR180204 and PTK787.

Additional illustrative MEK/ERK inhibitors include those compounds disclosed in International Published Patent Applications WO 99/01426, WO 02/06213, WO 03/077914, WO 05/051301 and WO2007/044084.

Further illustrative examples of MEK/ERK inhibitors include the following compounds: 6-(4-Bromo-2-chlorophenylamino)-7-fluoro-3-methyl-3H-benzoimidazole-5-ca-rboxylic acid (2,3-dihydroxy-propoxy)-amide; 6-(4-Bromo-2-chloro-phenylamino)-7-fluoro-3-(tetrahydro-pyran-2-yl-methyl)-3H-benzoimidazole-5-carboxylic acid (2-hydroxy-ethoxy)-amide, 1-[6-(4-Bromo-2-chloro-phenylamino)-7-fl-uoro-3-methyl-3H-benzoimidazol-5-yl]-2-hydroxy-etha-none, 6-(4-Bromo-2-chloro-phenylamino)-7-fluoro-3-me-thyl-3H-benzoimidazole-5-carboxylic acid (2-hydroxy-1,1-dimethyl-ethoxy)-amide, 6-(4-Bromo-2-chloro-phenyl-amino)-7-fluoro-3-(tetrahydro-furan-2-ylmethyl)-3H-ben-zoimidazole-5-carboxylic acid (2-hydroxy-ethoxy)-amide, 6-(4-Bromo-2-fluoro-phenylamino)-7-fluoro-3-methyl-3H-benzoimidazole-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazole-5-carboxylic acid (2-hydroxy-ethoxy)-amide, referred to hereinafter as MEK inhibitor 1; 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6-oxo-1,6-dihydropyridazine-3-carboxamide or a pharma-ceutically acceptable salt thereof.

In a preferred embodiment, the MEK/ERK inhibitor is PD98059.

hydroxyl-HA-1077, GSK269962A, SB-772077-B, N-(4-Pyridyl)-N'-(2,4,6-trichlorophenyl)urea, 3-(4-Pyridyl)-1H-indole, and (R)-(+)-trans-N-(4-Pyridyl)-4-(1-aminoethyl)-cyclohexanecarboxamide and ROCK inhibitors disclosed in U.S. Pat. No. 8,044,201, which is herein incorporated by reference in its entirety.

In one embodiment, the ROCK inhibitor is thiazovivin, Y27632, or pyrintegrin.

In a preferred embodiment, the ROCK inhibitor is thiaz-ovivin.

The amount of the small molecules in the compositions and cell culture media contemplated herein can vary and may be optimized according to the specific culture condi-tions, including the specific molecules and combinations used, the type of cell being cultured in the media, and the specific application. In one embodiment, a small molecule is present in a composition at a concentration sufficient to induce pluripotency, improve the efficiency of reprogram-ming, increase or maintain the potency of a cell, or induce or maintain ground state pluripotency.

In particular embodiments, preferred concentrations and combinations of the small molecules in the cell culture media of the invention are shown in Table 1 as Fate Maintenance Medium (FMM). The components of the medium may be present in the medium in amounts within an optimal range of about the optimal concentrations shown in Table 1. Fate Reprogramming Medium (FRM) is useful in culture platforms contemplated herein that includes the reprogramming of cells, but is not suitable for establishment and long-term maintenance of ground state pluripotent cells.

TABLE 1

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum Replacement (20%) | Knockout Serum Replacement (20%) | Knockout Serum Replacement (20%) |
| | N2 (1x) | |
| | B27 (1x) | |
| Glutamine (1x) | Glutamine (1x) | Glutamine (1x) |
| Non-Essential Amino Acids (1x) | Non-Essential Amino Acids (1x) | Non-Essential Amino Acids (1x) |
| β-mercaptoethanol (100 μM) | β-mercaptoethanol (100 μM) | β-mercaptoethanol (100 μM) |
| bFGF (10 ng/mL) | bFGF (100 ng/mL) | bFGF (100 ng/mL) |
| | LIF (10 ng/mL) | LIF (10 ng/mL) |
| | Thiazovivin (5.0 μM) | Thiazovivin (5.0 μM) |
| | PD0325901 (0.4 μM) | PD0325901 (0.4 μM) |
| | CHIR99021 (1.0 μM) | CHIR99021 (1.0 μM) |
| | SB431542 (2.0 μM) | |
| In combination with MEF feeder cells | Feeder free, in combination with Matrigel or Vitronectin | |

5. ROCK Inhibitors

Rho associated kinases (ROCK) are serine/threonine kinases that serve downstream effectors of Rho kinases (of which three isoforms exist—RhoA, RhoB and RhoC). ROCK inhibitors suitable for use in compositions contem-plated herein include, but are not limited to, polynucleotides, polypeptides, and small molecules. ROCK inhibitors con-templated herein may decrease ROCK expression and/or ROCK activity. Illustrative examples of ROCK inhibitors contemplated herein include, but are not limited to, anti-ROCK antibodies, dominant negative ROCK variants, siRNA, shRNA, miRNA and antisense nucleic acids that target ROCK.

Illustrative ROCK inhibitors contemplated herein include, but are not limited to: thiazovivin, Y27632, Fasudil, AR122-86, Y27632 H-1152, Y-30141, Wf-536, HA-1077, 6. Cytokines and Growth Factors In particular embodiments, the cell culture media of the invention is substantially free of cytokines and/or growth factors. In certain embodiments, the cell culture media contains one or more supplements including, but not limited to sera, extracts, growth factors, hormones, cytokines and the like.

In one illustrative embodiment, the culture media may comprise one or more of, ECM proteins, laminin 1, fibronec-tin, collagen IV isotypes, proteases, protease inhibitors, cell surface adhesion proteins, cell-signaling proteins, cadherins, chloride intracellular channel 1, transmembrane receptor PTK7, insulin-like growth factor, or Inhibin beta A, but does not comprise inducers of the TGFβ/Activin/nodal signaling pathway, and Activin A In other embodiments, the media may comprise inducers of the TGFβ/Activin/nodal signaling pathway.

In another illustrative embodiment, a culture medium comprises one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ) and other cytokines having effects upon stem cells such as stem cell factor (SCF) and erythropoietin (Epo). These cytokines may be obtained commercially, for example from R&D Systems, Minneapolis, Minn., and may be either natural or recombinant. In particular embodiments, growth factors and cytokines may be added at concentrations contemplated herein. In certain embodiments growth factors and cytokines may be added at concentrations that are determined empirically or as guided by the established cytokine art.

7. Culture Substrates

Any suitable vessel or cell culture container may be used as a support for cell cultures in the basal media and/or the cell culture supplements. No substrate coating on the support is necessary. Coating the surface of a culture vessel with adhesion-promoting substrata (for example, collagens, fibronectins, RGD-containing polypeptides, gelatins, and the like) however promotes attachment of the cells and in particular embodiments may enhance the effect of the cell culture media and supplements disclosed herein. Suitable substrates for culturing and passaging cells are known in the art and include, without limitation, vitronectin, gelatin, Laminin, Fibronectin, Collagen, Elastin, osteopontin, mixtures of naturally occurring cell line-produced matrices such as Matrigel™ and synthetic or man-made surfaces such as Polyamine monolayers and carboxy-terminated monolayers.

In one embodiment, a culture platform contemplated herein comprises a substrate comprising Matrigel™ or vitronectin.

8. Feeder Free Environments

Existing methods for culturing pluripotent cells rely heavily on feeder cells or media pre-conditioned with feeder cells and containing fetal bovine serum; however, such environments may be unsuitable for producing cells for clinical and therapeutic use. For example, cells cultivated in such xeno-contaminated environments are generally considered unsuitable for human cell transplantation because the exposure to animal components may present a serious risk of immune rejection and transmitting unidentified pathogens to the treated patients, and could potentially reactivate animal retroviruses. Culture systems using animal-free culture media, such as the feeder free environments contemplated herein, facilitate the manufacture of clinical-grade cell lines, particularly hESC and hiPSC cell lines.

In particular embodiments, the feeder free environment is essentially free of human feeder cells, including without limitation mouse embryonic fibroblasts, human fibroblasts, keratinocytes, and embryonic stem cells, and is not pre-conditioned by feeder cells. The feeder free cell culture medium is suitable for use in culturing pluripotent cells, reprogramming cells, single-cell culture, dissociation, and passaging of pluripotent cells, cell sorting of pluripotent cells, generation of ground state pluripotent cells, and maintenance of ground state pluripotency. In particular embodiments, the feeder free environment is used to induce pluripotency, improve the efficiency of reprogramming, and/or increase or maintain the potency of a cell. In certain embodiments, the feeder free environment is substantially free of cytokines and growth factors, including bFGF.

9. Dissociation

One of the advantages offered by the culture platforms contemplated herein is the enhanced viability and survival of culturing, passaging, and dissociating single ground state pluripotent cells. Disassociation of cells into single cells, such as into a single cell suspension, can be accomplished by enzymatic or mechanical means. Any enzymatic agent known in the art to allow dissociation of cells into single cells may be used in the methods of the invention. In one embodiment, the dissociation agent is selected from Trypsin/EDTA, TrypLE-Select, Collagenase IV and Dispase.

A chelator, such as EDTA, Accutase, or AccuMax, may also be used, alone or in combination with an enzymatic agent, in dissociating cells in accordance with the methods contemplated herein. The dissociation agent may be dissolved in calcium and magnesium free PBS to facilitate dissociation to single cells.

To enhance the survival of the cells during and after dissociation, a survival promoting substance can be added (e.g., growth factor, inhibitors of cellular pathways involved in cell death and apoptosis, or conditioned media), e.g., a ROCK inhibitor such as thiazovivin.

Techniques in cell culture and media collection are outlined in Hu et al., *Curr. Opin. Biotechnol.* 8:148, 1997; K. Kitano, *Biotechnology* 17:73, 1991; *Curr. Opin. Biotechnol.* 2:375, 1991; Birch et al., *Bioprocess Technol.* 19:251, 1990; "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cell Differentiation in vitro" (M. V. Wiles, *Meth. Enzymol.* 225:900, 1993); "Properties and uses of Embryonic Stem Cells: Prospects for Application to Human Biology and Gene Therapy" (P. D. Rathjen et al., al., 1993).

Differentiation of stem cells is reviewed in Robertson, *Meth. Cell Biol.* 75:173, 1997; and Pedersen, *Reprod. Fertil. Dev.* 10:31, 1998.

10. Enrichment and Depletion Strategies

In particular embodiments, strategies for enriching a population of cells for pluripotent cells, e.g., iPSCs, are provided. In one embodiment, enrichment provides a method for deriving clonal iPSC colonies in a relatively short time, thereby improving the efficiency of iPSC generation. Enrichment may comprise sorting a population of cells, which have been induced to reprogram, to identify and obtain cells expressing markers of pluripotency, thereby obtaining a population of cells enriched for pluripotent cells. An additional enrichment methodology comprises the depletion of cells expressing markers of differentiation or non-pluripotent cells to obtain an enriched population of pluripotent cells. In some embodiments, the cells are cultured after reprogramming is induced for about 4 to 30 days, about 4 to 24 days, about 6 to 22 days, or about 8 to about 12 days.

In one embodiment, enriching a population of cells for pluripotent cells comprises making a single cell suspension by dissociating the cells in the population and resuspending the cells. The dissociated cells may be resuspended in any suitable solution or media for maintaining cells or performing cell sorting. In particular embodiments, the single cell suspension contains a GSK3 inhibitor, a MEK inhibitor, and a Rock inhibitor and lacks a TFGβ inhibitor. In certain embodiments, the GSK3 inhibitor is CHIR99021, the MEK inhibitor is PD0325901, and the Rock inhibitor is thiazovivin.

In a particular embodiment, a population of cells is sorted to positively select pluripotent cells, and/or the population is depleted of non-reprogrammed or non-pluripotent cells, thereby obtaining a population of cells enriched for pluripotent cells. In one embodiment, a single cell suspension is prepared, and then the single cells are prepared for sorting, such as by staining for markers of pluripotency using, e.g., appropriate antibodies. Cells may be sorted by any suitable method of sorting cells, such as by magnetic bead or flow cytometry (FACS) sorting.

Cells may be sorted based on various markers of pluripotency, including expression of SSEA3/4, TRA1-60/81, TRA1-85, TRA2-54, GCTM-2, TG343, TG30, CD9, CD29, CD133/prominin, CD140a, CD56, CD73, CD105, OCT4, NANOG, SOX2, KLF4, SSEA1 (Mouse), CD30, SSEA5, CD90 and CD50. In various embodiments, cells are sorted based on at least two, at least three, or at least four markers of pluripotency. In certain embodiments, cells are sorted based on expression of SSEA4, and in certain particular embodiments based on expression of SSEA4 in combination with TRA1-81 or TRA1-60. In certain embodiments, cells are sorted based on SSEA4, TRA1-81 or TRA1-60 and CD30 expression. In certain embodiments, cells are initially depleted for non-reprogrammed cells using surface markers of differentiating cells including, but not limited to, CD13, CD26, CD34, CD45, CD31, CD46, or CD7, and then enriched for pluripotent markers such as SSEA4, TRA1-81 and CD30.

A population enriched for pluripotent cells may be placed in a cell culture system, such as conventional hESC media or the cell culture media of the invention. The cell culture system may be supplemented with feeder cells, or optionally be a feeder free environment. In some embodiments, the sorted cells expressing markers of pluripotency are placed in a feeder cell supplemented culture system and then transferred to a feeder free environment. In one embodiment, the cell culture medium is a feeder free environment and comprises a GSK3 inhibitor, a MEK inhibitor, and a Rock inhibitor, and lacks a TGFβ inhibitor. In particular embodiments, the GSK3 inhibitor is CHIR99021, the MEK inhibitor is PD0325901, and the Rock inhibitor is thiazovivin. In other particular embodiments of the invention, the cell culture system is a feeder free environment comprising a Matrigel™ coated tissue plate. In one embodiment, the cell culture system comprises the FMM medium described in Table 1.

The enriched cell population may be cultured in the cell culture systems described herein to obtain ground state iPSC colonies, typically appearing about 3 to about 25 days post sort; about 5-9 days post sort, or about 5-7 days post sort. iPSC colonies can be picked or sorted for clonal expansion. Using the enrichment strategies contemplated herein, the cell population is enriched at least about 3-fold, 5-fold, or 10-fold or more for pluripotent cells.

In some embodiments, a population of cells undergoing reprogramming or a population of pluripotent cells is depleted of differentiated cells. In one embodiment, a population of pluripotent cells or cells induced to reprogram can be depleted of cells having cells surface markers of differentiated cells. Illustrative examples of cell surface markers of differentiating cells include but are not limited to, CD13, CD26, CD34, CD45, CD31, CD46, or CD7. In particular embodiments, CD13 is used as a surface marker of differentiating cells.

In other embodiments, a population of cells induced to differentiate into a desired lineage and is depleted of pluripotent cells to obtain an enriched population of differentiating or differentiated cells. In some embodiments, the population of differentiated cells comprises a population of cells, such as ESCs or iPSCs that has been induced to differentiate into a specific lineage. A population of cells may be depleted of pluripotent cells using the negative cell sorting techniques described above ("panning"), such as sorting cells in the population according to magnetic beads or FACs based on markers of pluripotency. In some embodiments, a population of cells comprising differentiated cells is sorted by FACs using pluripotency markers, and a fraction is obtained that is depleted of cells expressing pluripotency markers. In other embodiments, a population of cells is sorted by FACs based on markers of differentiation, such as lineage-specific markers like CD13, CD26, CD34, CD45, CD31, CD46, or CD7, to obtain a fraction depleted of markers of pluripotency. CD13 is used as a surface marker of differentiating cells in particular embodiments of the invention.

E. Culture Platforms for Reprogramming Cells

Various strategies are being pursued to induce pluripotency, or increase potency, in cells (Takahashi, K., and Yamanaka, S., *Cell* 126, 663-676 (2006); Takahashi et al., *Cell* 131, 861-872 (2007); Yu et al., *Science* 318, 1917-1920 (2007); Zhou et al., *Cell Stem Cell* 4, 381-384 (2009); Kim et al., *Cell Stem Cell* 4, 472-476 (2009); Yamanaka et al., 2009; Saha, K., Jaenisch, R., *Cell Stem Cell* 5, 584-595 (2009)), and improve the efficiency of reprogramming (Shi et al., *Cell Stem Cell* 2, 525-528 (2008a); Shi et al., *Cell Stem Cell* 3, 568-574 (2008b); Huangfu et al., *Nat Biotechnol* 26, 795-797 (2008a); Huangfu et al., *Nat Biotechnol* 26, 1269-1275 (2008b); Silva et al., *Plos Bio* 6, e253. doi: 10.1371/journal. pbio. 0060253 (2008); Lyssiotis et al., *PNAS* 106, 8912-8917 (2009); Ichida et al., *Cell Stem Cell* 5, 491-503 (2009); Maherali, N., Hochedlinger, K., *Curr Biol* 19, 1718-1723 (2009b); Esteban et al., *Cell Stem Cell* 6, 71-79 (2010); Feng et al., *Cell Stem Cell* 4, 301-312 (2009)). However, existing methods have yet to realize a high-throughput solution for the manufacture of industrial- or clinical-grade pluripotent cells, i.e. clonal transgene-free pluripotent cell populations with homogeneous pluripotency, no significant spontaneous differentiation and an ability to culture and expand the cell population using single cell, enzymatic passage in defined, xeno-free, feeder-cell culture systems.

The culture platforms contemplated herein are useful, in part, for the production of high-grade induced pluripotent stem cells (iPSCs). In one embodiment, non-pluripotent cells are reprogrammed to pluripotency and cultured to maintain pluripotency. In another embodiment, iPSCs are cultured to ground state pluripotency.

In various embodiments, the culture platforms enable a transgene and/or footprint-free method of reprogramming. The culture platforms contemplated herein provide highly efficient episomal reprogramming with a significant reduction in the time and effort required for hiPSC generation. Without wishing to be bound to any particular theory, it is contemplated that by both blocking differentiation cues early in the reprogramming process and promoting mesenchyme-to-epithelial transition (MET) through small molecule inhibition of specific pathways (MEK, ERK, TGFβ and ROCK) the efficiency of hiPSC generation is significantly improved using episomal vectors, in FF and single cell culture systems.

In one embodiment, the culture platform comprises reprogramming one or more non-pluripotent cells to a pluripotent state comprising increasing the expression of endogenous OCT4 in the cell. Expression of endogenous OCT4 in the cell may be increased by introducing one or more polynucleotides, polypeptides, or small molecule inducers of OCT4 expression. In one embodiment, introduction of a polynucleotide encoding OCT4 or an OCT4 polypeptide into a cell is sufficient to induce endogenous expression of OCT4 in the cell.

In one embodiment, the culture platform comprises reprogramming one or more non-pluripotent cells comprising introducing one or more polynucleotides encoding one or more reprogramming factors selected from the group consisting of: OCT4, SOX2, NANOG, KLF4, LIN28, C-MYC, and SV40LT into the one or more non-pluripotent cells. In another embodiment, the culture platform comprises reprogramming one or more non-pluripotent cells comprising introducing one or more polypeptides selected from the group consisting of: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1 into the one or more non-pluripotent cells.

In one embodiment, the culture platform comprises reprogramming one or more non-pluripotent cells comprising introducing one or more polynucleotides encoding one or more reprogramming factors selected from the group consisting of: OCT4, NANOG, ESRRB, ECAT1 and UTF1 into the one or more non-pluripotent cells. In another embodiment, the culture platform comprises reprogramming one or more non-pluripotent cells comprising introducing one or more polypeptides selected from the group consisting of: OCT4, NANOG, ESRRB, ECAT1 and UTF1 into the one or more non-pluripotent cells.

As used herein, in particular embodiments, the term "introducing" refers to a process that comprises contacting a cell with a polynucleotide, polypeptide, or small molecule. An introducing step may also comprise microinjection of polynucleotides or polypeptides into the cell, use of liposomes to deliver polynucleotides or polypeptides into the cell, or fusion of polynucleotides or polypeptides to cell permeable moieties to introduce them into the cell.

In particular embodiments, one or more polynucleotides encoding 1, 2, 3, 4, 5 or more copies of one or more of the reprogramming factors selected from the group consisting of: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1 may be introduced into a non-pluripotent cell to reprogram the cell. The copy number of each reprogramming factor introduced into the cell may be the same or different in any combination suitable to achieve ground state pluripotency as contemplated herein.

In one embodiment, one or more polynucleotides encoding 1, 2, 3, 4, 5 or more copies of one or more of the reprogramming factors selected from the group consisting of: OCT4, SOX2, and NANOG are introduced into the non-pluripotent cell.

In one embodiment, one or more polynucleotides encoding 1, 2, 3, 4, 5 or more copies of each of OCT4, SOX2, and NANOG are introduced into the non-pluripotent cell.

In one embodiment, one or more polynucleotides encoding 1, 2, 3, 4, 5 or more copies of each of OCT4 and SOX2 are introduced into the non-pluripotent cell.

In one embodiment, one or more polynucleotides encoding 1, 2, 3, 4, 5 or more copies of OCT4 are introduced into the non-pluripotent cell.

In one embodiment, one or more polynucleotides encoding 2 copies of OCT4, 2 copies of SOX2, and 2 copies of NANOG are introduced into the non-pluripotent cell, with SV40LT optionally being introduced into the non-pluripotent cell.

In another embodiment, one or more polynucleotides encoding 3 copies of OCT4, 2 copies of SOX2, one copy of NANOG, and one copy of UTF1 are introduced into the non-pluripotent cell.

In various illustrative embodiments, a culture platform comprising reprogramming a non-pluripotent cell comprises introducing 1 to 5 copies of a polynucleotide encoding OCT4; 1 to 3 copies of a polynucleotide encoding SOX2, and optionally, 1 to 2 copies of a polynucleotide encoding NANOG. The polynucleotides may be introduced into the cell as any combination of one or more larger polynucleotides. In one non-limiting example, one or more polynucleotides encoding 1 to 4 copies of OCT4, 1 or 2 copies of SOX2, and 1 copy of NANOG are introduced into a non-pluripotent cell. In another non-limiting example reprogramming a non-pluripotent cells to the pluripotent state comprises introducing a first polynucleotide encoding 2 copies of OCT4, a second polynucleotide encoding 1 copy of OCT4 and 1 copy of SOX2; and a third polynucleotide encoding 1 copy of OCT4, 1 copy of SOX2, and 1 copy of NANOG, into the non-pluripotent cells. In a further non-limiting example, reprogramming one or more non-pluripotent cells comprises introducing a first polynucleotide encoding 2 copies of OCT4 and a second polynucleotide encoding 1 copy of OCT4, 1 copy of SOX2, and 1 copy of NANOG, into the one or more non-pluripotent cells. In yet a further non-limiting example, a first polynucleotide encoding 2 copies of OCT4 and a second polynucleotide encoding 1 copy of OCT4 and 1 copy of SOX2 are introduced into the one or more non-pluripotent cells to produce a pluripotent cell.

In one embodiment, a single vector comprising a polynucleotide comprising any number and combination of the reprogramming factors contemplated herein is introduced into a non-pluripotent cell and is sufficient to reprogram the cell to a pluripotent state.

In one embodiment, one or more vectors comprising 1, 2, 3, 4, 5 or more polynucleotides comprising any number and combination of the reprogramming factors contemplated herein is introduced into a non-pluripotent cell and is sufficient to reprogram the cell to a pluripotent state.

In a preferred embodiment, one or more vectors comprising the one or more polynucleotides contemplated herein for reprogramming a non-somatic cell are used to introduce the one or more polynucleotides into the cell and are sufficient to reprogram the cell.

In the most preferred embodiment, one or more episomal vectors comprising the one or more polynucleotides contemplated herein for reprogramming a non-somatic cell are used to introduce the one or more polynucleotides into the cell and are sufficient to reprogram the cell. Pluripotent cells displaying reduced spontaneous differentiation and/or the ground state may be manufactured with episomal vectors as contemplated herein, and then cultured until loss of the vector to obtain pluripotent cells displaying reduced spontaneous differentiation and/or the ground state which do not comprise exogenous nucleic acids encoding reprogramming factors.

It is further contemplated that when polynucleotide or vector comprising the same comprises a polynucleotide encoding at least two reprogramming factors or at least two copies of a reprogramming factor, the polynucleotide comprises an IRES sequence or a polynucleotide encoding a self-cleaving polypeptide sequence between each of the reprogramming factors as contemplated herein.

In some aspects, the efficiency of reprogramming non-pluripotent cells is increased by selecting for the ectopic expression of one or more reprogramming factor polynucleotides after the reprogramming factors polynucleotides are introduced into the non-pluripotent cells. Such selection may take place, for example, by linking one or more of the reprogramming factor polynucleotides to a selectable marker, introducing the reprogramming factor polynucleotides and selectable marker into the non-pluripotent cells, and selecting those cells that express the selectable marker, wherein the selection identifies cells having increased reprogramming efficiency relative to the cells that lack expression of the marker and its associated reprogramming factor polynucleotides. One skilled in the art will appreciate that in particular embodiments any selectable marker that identifies the expression of the introduced reprogramming polynucleotides by the non-pluripotent cell may be used.

One non-limiting example of such a selectable marker includes, but is not limited to, antibiotic resistance genes such as puromycin resistance. Selectable markers may be linked to one or more of the following reprogramming factor polynucleotides: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1. In some embodiments, a specific combination of reprogramming factor polynucleotides are introduced as a polycistronic vector, with the selectable marker being linked to the specific combination of reprogramming factor polynucleotides. The specific combination of reprogramming factor polynucleotides may encode two or more copies of the reprogramming factor polynucleotides disclosed herein.

In one non-limiting embodiment, the polycistronic vector encodes two or more copies of an OCT4 polynucleotides linked to a selectable marker, such as a gene encoding puromycin resistance.

In some aspects, a polycistronic vector encoding one or more reprogramming factor polynucleotides and a selectable marker are introduced to non-pluripotent cells in addition to one or more separate reprogramming factor polynucleotides, wherein selecting for cells that express the selectable marker produces a population of cells having greater reprogramming efficiency than cells that lack expression of the selectable marker.

In one non-limiting example of this selection process, OCT4, NANOG and SOX2 polynucleotides are introduced to non-pluripotent cells in addition to a polycistronic vector encoding two or more copies of OCT4 linked to a puromycin resistance gene. The subsequent selection of non-pluripotent cells expressing the selectable marker identifies non-pluripotent cells with greater reprogramming efficiency relative to the non-pluripotent cells that do not express the selectable marker. The selected cells may have a reprogramming efficiency of at least 5%, at least 10%, at least 15%, at least 20%, at least 30% or at least 40%.

Small molecules are often included in the reprogramming steps of particular preferred embodiments. Without wishing to be bound to any particular theory, it is contemplated that include of small molecule inhibitors of various differentiation pathways increases the efficiency and kinetics of reprogramming. Accordingly, in particular embodiments, culture platforms comprising reprogramming non-pluripotent cells comprise introducing one or more reprogramming factors into the cells as contemplated herein and contacting the cells with a GSK3 inhibitor; a MEK inhibitor; a TGFβR inhibitor, and a ROCK inhibitor.

Improvements in efficiency of reprogramming can be measured by (1) a decrease in the time required for reprogramming and generation of pluripotent cells (e.g., by shortening the time to generate pluripotent cells by at least a day compared to a similar or same process without the small molecule), or alternatively, or in combination, (2) an increase in the number of pluripotent cells generated by a particular process (e.g., increasing the number of cells reprogrammed in a given time period by at least 10%, 30%, 50%, 100%, 200%, 500%, etc. compared to a similar or same process without the small molecule). In some embodiments, a 2-fold to 20-fold improvement in reprogramming efficiency is observed. In some embodiments, reprogramming efficiency is improved by more than 20 fold. In some embodiments, a more than 100 fold improvement in efficiency is observed over the method without the small molecule reprogramming agent (e.g., a more than 100 fold increase in the number of pluripotent cells generated).

In one embodiment, a culture platform contemplated herein comprises reprogramming non-pluripotent cells by introducing one or more reprogramming factors into the cells as contemplated herein and contacting the cells with a GSK3 inhibitor; a MEK inhibitor; and a TGFβR inhibitor, and optionally a ROCK inhibitor.

In one preferred embodiment, a culture platform contemplated herein comprises reprogramming non-pluripotent cells by introducing one or more reprogramming factors into the cells as contemplated herein and contacting the cells with a GSK3 inhibitor; a MEK inhibitor; a TGFβR inhibitor, and a ROCK inhibitor.

In a more preferred embodiment, a culture platform contemplated herein comprises reprogramming non-pluripotent cells by introducing one or more reprogramming factors into the cells as contemplated herein and contacting the cells with a GSK3 inhibitor; a MEK inhibitor; a TGFβR inhibitor, and a ROCK inhibitor, wherein the ROCK inhibitor is Thiazovivin.

However, to enable the long term culture of pluripotent cells in feeder-cell free and enzymatic passage culture systems with reduced or no significant spontaneous differentiation or to induce and/or maintain ground state pluripotency, iPSCs require subsequent culturing in a cell culture medium comprising a GSK-3 inhibitor, a MEK inhibitor, and optionally a Rho Kinase (ROCK) inhibitor, wherein the cell culture medium does not comprise, or lacks, an inhibitor of TGFβ/activin signaling pathways, including TGFβ receptor (TGFβR) inhibitors and ALK5 inhibitors, as contemplated herein. Without wishing to be bound to any particular theory, it is contemplated that long-term culture of pluripotent cells with a TGFβR/ALK5 inhibitor leads to spontaneous differentiation of the cultured transgene-free iPSCs and ultimately loss of ground state pluripotency.

In various embodiments, a two step culture platform is employed to stably reprogram somatic cells to achieve reduced spontaneous differentiation in culture, including ground state pluripotency. In certain embodiments, a non-pluripotent cell is reprogrammed by any suitable method disclosed in the art, and subsequently, the reprogrammed somatic cell is cultured to achieve reduced spontaneous differentiation in culture by culturing the cell in a medium comprising a GSK-3 inhibitor, a MEK inhibitor, and a Rho Kinase (ROCK) inhibitor, wherein the media lacks a TGFβR/ALK5 inhibitor. In some embodiments, the reprogrammed somatic cell is cultured to provide ground state pluripotent cells.

In particular embodiments, a non-pluripotent cell is reprogrammed by the methods disclosed herein and subsequently, the reprogrammed somatic cell is cultured to a stable ground state of pluripotency by culturing the cell in a medium comprising a GSK-3 inhibitor, a MEK inhibitor, and a Rho Kinase (ROCK) inhibitor, wherein the media lacks a TGFβR/ALK5 inhibitor.

In some embodiments, a non-pluripotent cell is reprogrammed by introducing one or more reprogramming factors and culturing the cell in a medium comprising a GSK-3 inhibitor, a MEK inhibitor, a Rho Kinase (ROCK) inhibitor, and a TGFβR/ALK5 inhibitor, and subsequently, the reprogrammed somatic cell is cultured to a provide cells with reduced spontaneous differentiation by culturing the cell in a medium comprising a GSK-3 inhibitor, a MEK inhibitor, and a Rho Kinase (ROCK) inhibitor, wherein the media lacks a TGFβR/ALK5 inhibitor.

In some embodiments, a non-pluripotent cell is reprogrammed by introducing one or more reprogramming factors and culturing the cell in a medium comprising a GSK-3 inhibitor, a MEK inhibitor, a Rho Kinase (ROCK) inhibitor, and a TGFβR/ALK5 inhibitor, and subsequently, the reprogrammed somatic cell is cultured to a stable ground state of pluripotency by culturing the cell in a medium comprising a GSK-3 inhibitor, a MEK inhibitor, and a Rho Kinase (ROCK) inhibitor, wherein the media lacks a TGFβR/ALK5 inhibitor.

In preferred embodiments, a non-pluripotent cell is reprogrammed by introducing one or more reprogramming factors and culturing the cell in a medium comprising a GSK-3 inhibitor, a MEK inhibitor, a Rho Kinase (ROCK) inhibitor, and a TGFβR/ALK5 inhibitor, and subsequently, the reprogrammed somatic cell is cultured to a stable ground state of pluripotency by culturing the cell in a medium comprising a GSK-3 inhibitor, a MEK inhibitor, and a Rho Kinase (ROCK) inhibitor, wherein the media lacks a TGFβR/ALK5 inhibitor and wherein there is not significant residual expression of reprogramming transgene.

In one embodiment, a non-pluripotent cell is reprogrammed by introducing one or more reprogramming factors selected from the group consisting of: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1 as disclosed elsewhere herein and culturing the cell in a medium comprising a GSK-3 inhibitor, a MEK inhibitor, a Rho Kinase (ROCK) inhibitor, and a TGFβR/ALK5 inhibitor, and subsequently, the reprogrammed somatic cell is cultured in a medium comprising a GSK-3 inhibitor, a MEK inhibitor, and a Rho Kinase (ROCK) inhibitor, wherein the media lacks a TGFβR/ALK5 inhibitor.

In a preferred embodiment, a non-pluripotent cell is reprogrammed by introducing one or more reprogramming factors selected from the group consisting of: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1 as disclosed elsewhere herein and culturing the cell in a medium comprising a GSK-3 inhibitor, a MEK inhibitor, a Rho Kinase (ROCK) inhibitor, and a TGFβR/ALK5 inhibitor, and subsequently, the reprogrammed somatic cell is cultured in a medium comprising a GSK-3 inhibitor, a MEK inhibitor, and a Rho Kinase (ROCK) inhibitor wherein the Rock Inhibitor is Thiazovivin, wherein the media lacks a TGFβR/ALK5 inhibitor.

In various embodiments, methods of manufacturing pluripotent cells with reduced spontaneous differentiation and/or ground state induced pluripotent stem cells (iPSCs) using the culture platforms contemplated herein are provided.

In particular embodiments, pluripotent cells with reduced spontaneous differentiation and/or ground state induced pluripotent stem cells (iPSCs) are manufactured using a starting material comprising one or more non-pluripotent or partially pluripotent stem cells and culturing the one or more pluripotent or partially-pluripotent stem cells in a culture medium that does not comprise a TGFβR inhibitor. The starting material may either be obtained or created. For example, non-pluripotent or partially pluripotent stem cells may be provided from a commercial supplier or other source or could be obtained de novo: non-pluripotent cells could also be isolated from a tissue or organ; and partially pluripotent cells could also be generated by reprogramming somatic cells or adult stem cells. In some embodiments, pluripotent embryonic stem cells, or pluripotent cells obtained by somatic nuclear transfer, may be induced to achieve ground state pluripotency using the culture media and platforms described herein.

In particular embodiments, a population of one or more IPSCs may comprise reprogrammed somatic cells or reprogrammed adult stem cells. In particular embodiments, the IPSCs may be generated by any known method either by performing the method or obtaining IPSCs generated by the method.

Exemplary methods of generating the IPSCs include, but are not limited to: increasing the expression of endogenous OCT4 in non-pluripotent cells; introducing one or more polynucleotides, optionally in one or more copies, encoding one or more reprogramming factors selected from the group consisting of: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1 into the one or more non-pluripotent cells; or introducing one or more polynucleotides, optionally in one or more copies, encoding one or more reprogramming factors selected from the group consisting of: OCT4, SOX2, and NANOG into the one or more non-pluripotent cells. Methods of generating IPSCs may further comprise contacting the one or more non-pluripotent cells or partially pluripotent cells with a GSK3 inhibitor; a MEK inhibitor; and a TGFβR inhibitor, and optionally a ROCK inhibitor to produce the one or more iPSCs.

In certain embodiments, the cell culture medium comprises a GSK3 inhibitor; a MEK inhibitor; and a ROCK inhibitor.

In preferred embodiments, the cell culture medium comprises a GSK3 inhibitor; a MEK inhibitor; and a ROCK inhibitor, wherein the ROCK inhibitor is Thiazovivin.

In particular embodiments, culturing the one or more pluripotent cells, e.g., IPSCs, in the cell culture medium maintains or induces a ground state of pluripotency, viability, normal karyotype, genomic stability, and decreased rate of spontaneous differentiation that can be maintained for at least 5 passages, at least 10 passages, at least 50 passages, at least 100 passages, or more, including any intervening number of passages.

F. Characterizing Pluripotent Cells

Pluripotent cell manufactured using the culture platforms contemplated herein may further comprise selection or validation of the pluripotent cell product, including, for example, ground state pluripotent cells or pluripotent cells with reduced spontaneous differentiation. The pluripotent cells may be selected and/or validated after reprogramming and subsequent culture with the compositions and methods contemplated herein, or after pluripotent cells were transitioned to the culture methods contemplated herein, if the pluripotent cells were not reprogrammed. The pluripotency of the cells may be characterized and/or selected based on relevant and detectable morphological, molecular and/or biochemical changes associated with pluripotency.

Specific characteristics of cell pluripotency which may be monitored, separately or in combination, in assessing the potency of a cell include, but are not limited to, gene expression, methylation, and in vivo and in vitro characteristics such as: i) pluripotent stem cell morphology that is round; ii) expression of pluripotent stem cell markers including SSEA3/4 (human pluripotent stem cells); TRA1-60/81; TRA1-85, TRA2-54, GCTM-2, TG343, TG30, CD9, CD29, CD133/prominin, CD140a, CD56, CD73, CD105, OCT4, NANOG, SOX2, CD30, SSEA5, CD90 and/or CD50, and combinations of the foregoing; iii) teratoma formation of pluripotent stem cells; iv) formation of embryoid bodies and in vitro trilineage differentiation: and v) inactive X chromosome reactivation. In certain embodiments, a subset of any of the above characteristics is used for monitoring cell potency. In one embodiment, pluripotent cells are characterized by having a round colony morphology, expression of SSEA4, TRA1-81, and OCT4, and the ability to form embryoid bodies and teratomas.

In another embodiment, pluripotent cells having reduced spontaneous differentiation in in vitro culture may be identified by a gene expression signature that comprises at least about a 10%, 20%, 25%, 30%, 40%, 50%, 60%, 70%, 80%, 90% decrease in the expression of one or more of the following differentiation marker genes compared to pluripotent cells cultured in the presence of a TGFβR inhibitor: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES1, CDX2, GNAS, EGR1, COL3A1, TCF4, HEPH, KDR, TOX, FOXA1, LCK, PCDH7, CD1D FOXG1, LEFTY1, TUJ1, T gene (Brachyury) and ZIC1.

In one embodiment, pluripotent cells having reduced spontaneous differentiation are characterized by the decreased expression of one or more differentiation marker genes, including but not limited to: T gene, CXCR4, NODAL, GATA4, SOX17, FOXA2, OTX2, and TUJ1. In particular embodiments, pluripotent cells having reduced spontaneous differentiation may be identified by a gene expression signature that comprises at least about a 10%, 20%, 25%, 30%, 40%, 50%, 60%, 70%, 80%, 90% decrease in the expression of one or more differentiation marker genes (e.g., T gene, CXCR4, NODAL, GATA4, SOX17, FOXA2, OTX2, TUJ1) compared to pluripotent cells cultured in the presence of a TGFβR inhibitor. [In another particular embodiments, pluripotent cells having reduced spontaneous differentiation may be identified by a gene expression signature that comprises at least about a 10%, 20%, 25%, 30%, 40%, 50%, 60%, 70%, 80%, 90% decrease in the expression of one or more differentiation marker genes (e.g., T gene, CXCR4, NODAL, GATA4, SOX17, FOXA2, OTX2, TUJ1).

In particular embodiments, ground state pluripotent cells have significantly repressed Xist expression and expression of early markers of differentiated cells, e.g., Foxa2, Sox17, and Brachyury, while conventional cultured pluripotent cells show only modest repression of Xist expression and significant expression of early differentiation markers.

In particular embodiments, ground state pluripotent cells retain characteristics of ground state pluripotency for multiple cell passages, such as for example, at least 1, 3, 5, 7, 10, 15, 20 or more passages.

G. Polynucleotides

In various illustrative embodiments, the present invention contemplates, in part, polynucleotides, polynucleotides encoding polypeptides and fusion polypeptides contemplated herein, and compositions comprising the same. In various other illustrative embodiments, the present invention contemplates, in part, reprogramming non-pluripotent cells with polynucleotides encoding one or more copies of at least one reprogramming factor. Reprogramming factors for use with the culture platforms described herein include, but are not limited to: OCT4, SOX2, NANOG, KLF4, LIN28, C-MYC, SV40LT, hTERT, SALL4, GLIS, ESRRB, DPPA2, ECAT1, SOX1, SOX3, KLF2, KLF5, L-MYC, N-MYC, LRH1 and UTF1. In preferred embodiments, a polynucleotide comprises a sequence of a reprogramming factor as set forth herein.

As used herein, the term "gene" may refer to a polynucleotide sequence comprising enhancers, promoters, introns, exons, and the like. In particular embodiments, the term "gene" refers to a polynucleotide sequence encoding a polypeptide, regardless of whether the polynucleotide sequence is identical to the genomic sequence encoding the polypeptide.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant DNA, or other polynucleotide that does not exist in nature and that has been made by the hand of man.

In particular embodiments, one or more polynucleotides may be arranged in any suitable order within a larger polynucleotide, such as a vector. In preferred embodiments, the vector is an episomal vector.

The polynucleotides contemplated herein, regardless of the length of the coding sequence itself, may be combined with other DNA sequences, such as expression control sequences, promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Aft sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated and/or expressed using any of a variety of well established techniques known and available in the art. In order to express a desired polypeptide, a nucleotide sequence encoding the polypeptide, can be inserted into appropriate vector.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

The term "operably linked", refers to a juxtaposition wherein the components described are in a relationship permitting them to function in their intended manner. In one embodiment, the term refers to a functional linkage between an expression control sequence (such as a promoter, and/or enhancer) and a second polynucleotide sequence, wherein the expression control sequence directs transcription of the nucleic acid corresponding to the second sequence.

Illustrative ubiquitous expression control sequences suitable for use in particular embodiments of the invention include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site specific DNA recombinase. According to certain embodiments of the invention, polynucleotides comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

In particular embodiments, polynucleotides contemplated herein, include one or more polynucleotides that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides. As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990).

H. Polypeptides

The present invention contemplates, in part, compositions comprising polypeptides, fusion polypeptides, and vectors that express polypeptides. In preferred embodiments, a polypeptide comprises the amino acid sequence set forth herein. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well known recombinant and/or synthetic techniques. Polypeptides are not limited to a specific length, e.g., they may comprise a full length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances.

In one embodiment, where expression of two or more polypeptides is desired, the polynucleotide sequences encoding them can be separated by and IRES sequence as discussed elsewhere herein. In another embodiment, two or more polypeptides can be expressed as a fusion protein that comprises a polypeptide cleavage signal between each of the polypeptide domains described herein. In addition, polypeptide site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO:29), for example, ENLYFQG (SEQ ID NO:30) and ENLYFQS (SEQ ID NO:31), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

TABLE 2

| Exemplary 2A sites include the following sequences: | |
| --- | --- |
| SEQ ID NO: 1 | LLNFDLLKLAGDVESNPGP |
| SEQ ID NO: 2 | TLNFDLLKLAGDVESNPGP |
| SEQ ID NO: 3 | LLKLAGDVESNPGP |
| SEQ ID NO: 4 | NFDLLKLAGDVESNPGP |
| SEQ ID NO: 5 | QLLNFDLLKLAGDVESNPGP |
| SEQ ID NO: 6 | APVKQTLNFDLLKLAGDVESNPGP |
| SEQ ID NO: 7 | VTELLYRMKRAETYCPRPLLAIHPTEARHKQKIV APVKQT |
| SEQ ID NO: 8 | LNFDLLKLAGDVESNPGP |
| SEQ ID NO: 9 | LLAIHPTEARHKQKIVAPVKQTLNFDLLKLAGDV ESNPGP |
| SEQ ID NO: 10 | EARHKQKIVAPVKQTLNFDLLKLAGDVESNPGP |

In preferred embodiments, a vector encoding one or more reprogramming factor polypeptides comprises one or more of the same or different protease cleavage sites between each of the reprogramming factors.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

The Examples disclosed herein identified a platform for the rapid, parallel generation, selection and expansion of hiPSCs using small molecule pathway inhibitors in stage-specific media compositions. The platform supported efficient and expedited episomal reprogramming using minimal reprogramming factors in a completely feeder-free environment. The resulting hiPSCs were free of transgene, readily cultured and expanded as single cells while maintaining a homogenous and genomically stable pluripotent population. hiPSCs generated or maintained in the media compositions contemplated in the Examples exhibit properties associated with the ground state of pluripotency and represent a robust high-throughput system for the manufacture of uniform industrial- or clinical-grade hiPSCs.

Example 1

Identification of a Medium Platform for Long-Term Maintenance and Expansion of iPSCs Overview The majority of lentiviral-derived hiPSC lines in SMC4-supplemented cultures maintain a homogeneous population of undifferentiated cells; however; silencing of the transgenic reprogramming factor in a subset of lines displayed various degrees of spontaneous differentiation in extended culture (FIGS. 1A and B). Therefore, various cell culture components were assessed in order to identify conditions for the maintenance of pluripotency during continuous FF culture and single-cell enzymatic passage irrespective of residual transgene expression. A multi-stage culture system that targets unique pathways at different stages of the reprogramming and maintenance process was identified as an efficient and robust approach to hiPSC generation.

Results

Figure 1C:
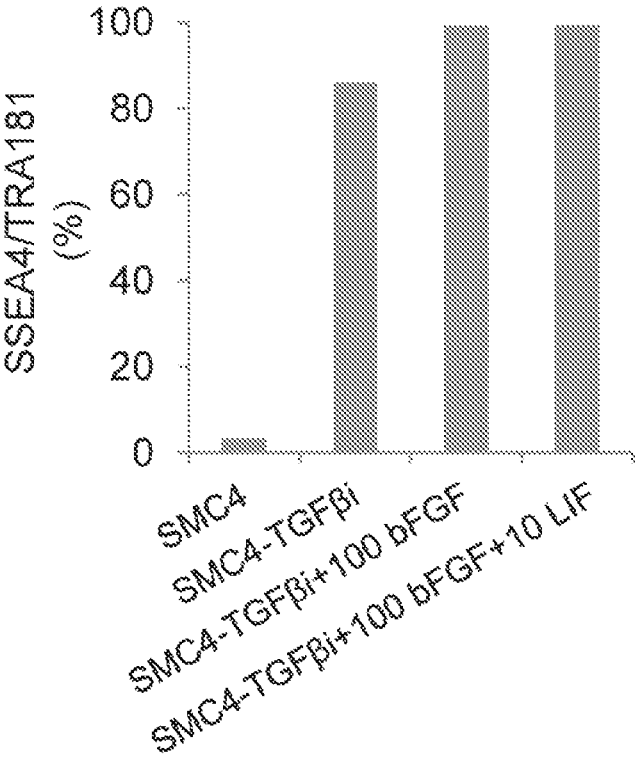

Inhibition of TGFβ pathway during long-term maintenance was identified as a significant factor in the spontaneous differentiation of hiPSC lines with silenced transgene expression (FIG. 1C). One of the iPSC cell lines found to undergo spontaneous differentiation was transitioned to culture in a new medium formulation, Fate Maintenance Medium (FMM) (Table 1). Spontaneous differentiation was eliminated and a homogenous population of SSEA4/TRA1-81 positive cells was established within 2-3 passages (FIG. 1A).

Figure 1D:
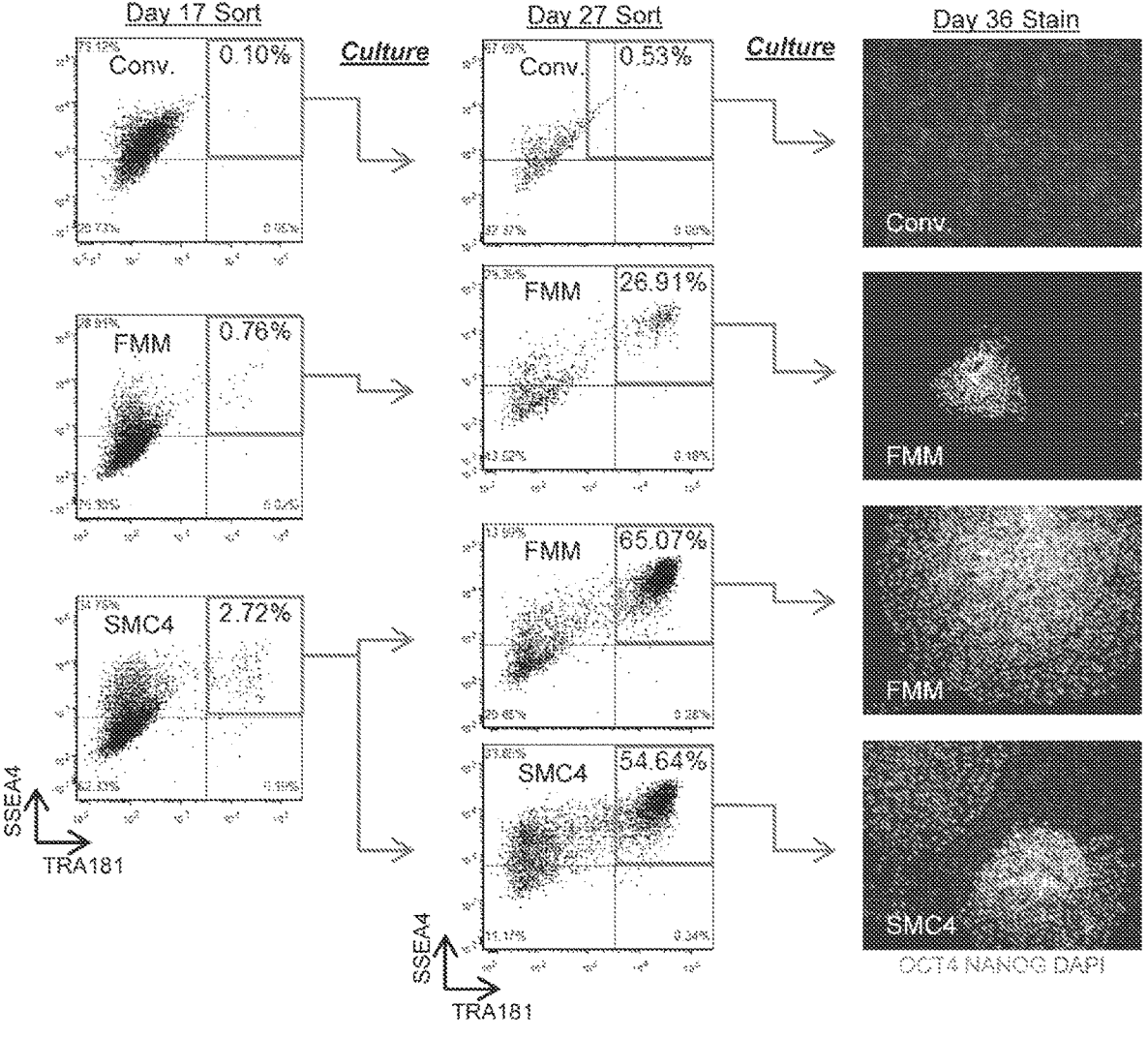

OCT4/KLF4/SOX2 (OKS) lentiviral reprogramming in conventional culture (hESC medium on MEF feeder cells), SMC4-supplemented medium in FF culture or the newly formulated FMM in FF culture (FIG. 1D) was also compared. Seventeen days after the induction of lentiviral reprogramming, SSEA4/TRA1-81 positive cells were selected by FACs and re-plated in either SMC4 or FMM for comparison (FIG. 1D). SMC4 improved the kinetics of reprogramming and resulted in significantly more SSEA4/TRA1-81 positive cells at day 17 post induction (2.72% versus 0.76% for FMM and 0.10% for conventional culture; FIG. 1D) than reprogramming with FMM.

Figure 1E:
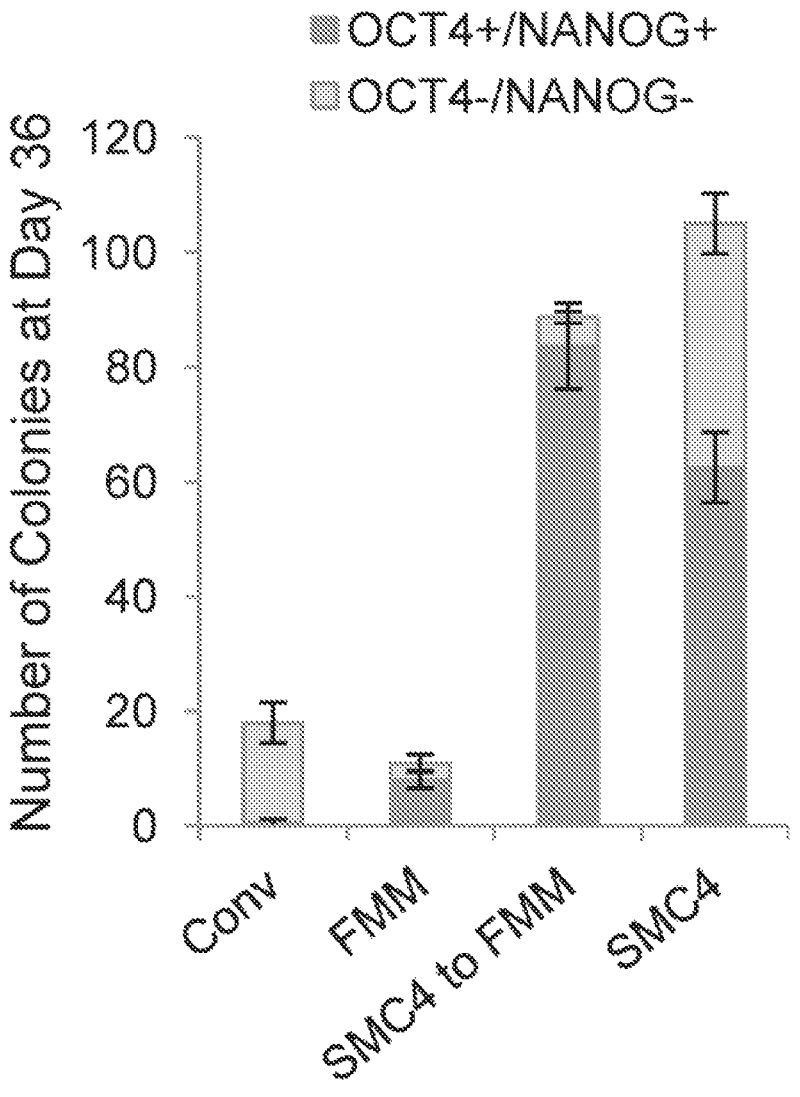

After the initial sort, cells were maintained in their respective conditions for 10 days, followed by a second SSEA4/TRA1-81 positive flow cytometry selection (FIG. 1D). The cultures were maintained for an additional 9 days (total of 36 days post infection) and scored for undifferentiated colonies based on OCT4 and NANOG co-expression (FIGS. 1D and 1E). The combination of initial reprogramming in SMC4 followed by a transition to FMM ultimately resulted in more OCT4/NANOG positive colonies and a significantly reduced number of OCT4/NANOG negative colonies relative to continuous maintenance in SMC4 (FIGS. 1D and 1E). Although OCT4/NANOG positive colonies were detected in cultures maintained exclusively in FMM, the number and size of the colonies appeared inferior to the stage-specific media approach.

These results show that a novel multi-stage culture system that targets unique pathways at different stages of the reprogramming and maintenance process resulted in the efficient manufacture of high quality hiPSCs.

Example 2

Figure 2A:
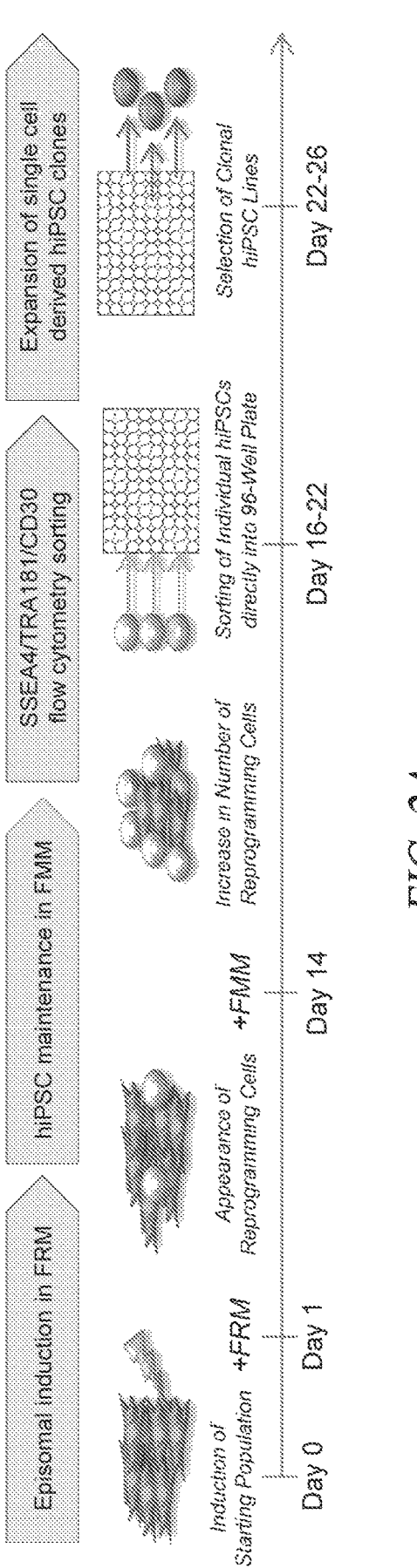
FIGS. 2A-2E show that individual episomal reprogrammed hiPSCs are efficiently selected and seeded in 96-well plates for clonal expansion. (2A) Schematic timing illustration of episomal induction, multistage culture platform, flow cytometry sorting and clonal expansion. (2B) Flow cytometry profile of episomal induced reprogramming maintained in FRM to FMM transition in FF culture (outlined in 2A) at indicated days post transfection. Sort gating strategy used for each parental line (SSEA4+/TRA1-81+/ CD30+ population) is illustrated in respective colors, corresponding to the bottom histogram panel representing the percent of wells of 96-well plate containing individual hiPSC clones. Wells containing multiple clones or differentiated clones were not scored. The solid line represents the average percentage amongst all derivations with dotted lines representing standard deviation. (2C) Flow profile of FTC007 induced to reprogram 19 days post transfection maintained in conventional medium in the presence of MEF cells. The induced population was taken from the same population of FTC007 in (2B), however treated in different culture thereafter. (2D) Immunocytochemistry analysis of various pluripotency markers of sorted colonies in 96-well plate. Right corner panels represent DAPI staining. (2E) qRT-PCR for NANOG expression for each well of a SSEA4/ TRA1-81/CD30 direct sorted (FACS) 96-well plate at 3 cells per well. The expression range is between zero and four times expression relative to H1 human ESCs as described in the legend and normalized to GAPDH.

Platform for Manufacturing Transgene-Free hiPCSs in a Single Cell Passage and FF Format Overview The efficiency of non-integrative reprogramming methods using episomal vector systems is extremely low (<0.001%), especially in FF environments (Narsinh et al., 2011; O'Doherty et al., 2013). Episomal-induction was tested in a multi-stage culture system including two media: Fate Reprogramming Medium (FRM) containing SMC4 and medium additives shown to improve reprogramming and FMM (FIG. 2A and Table 1).

Results

Figure 8A:
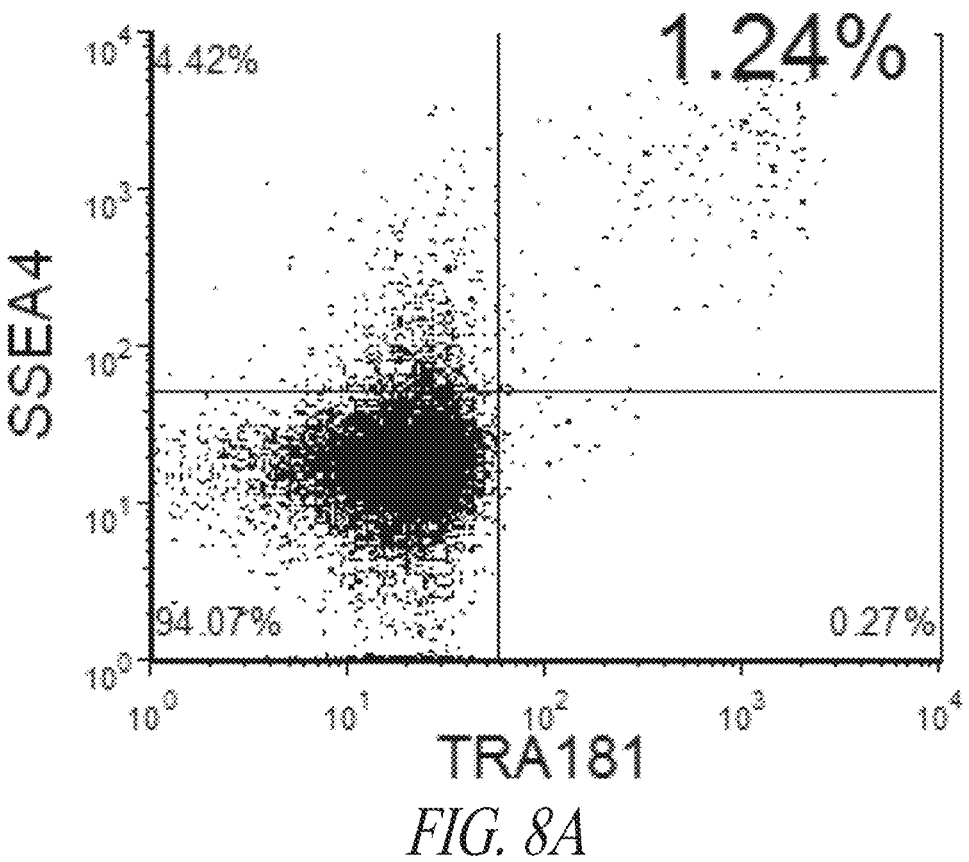
Figure 8B:
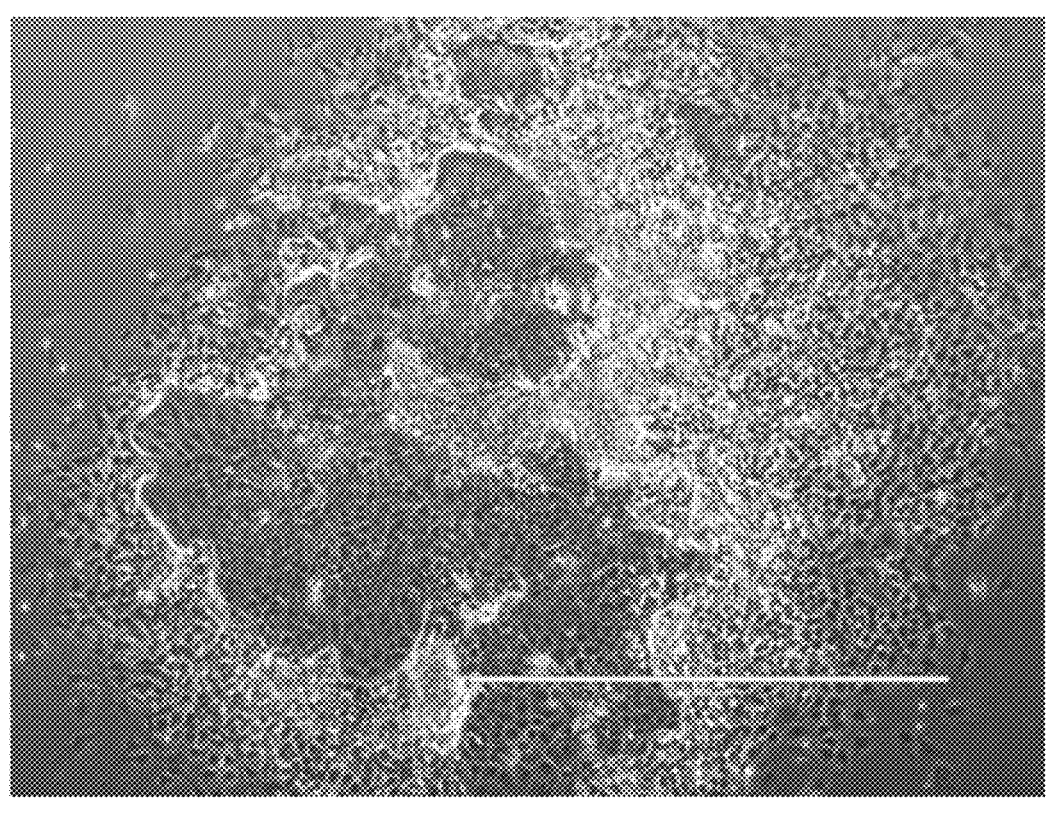
Figure 8C:
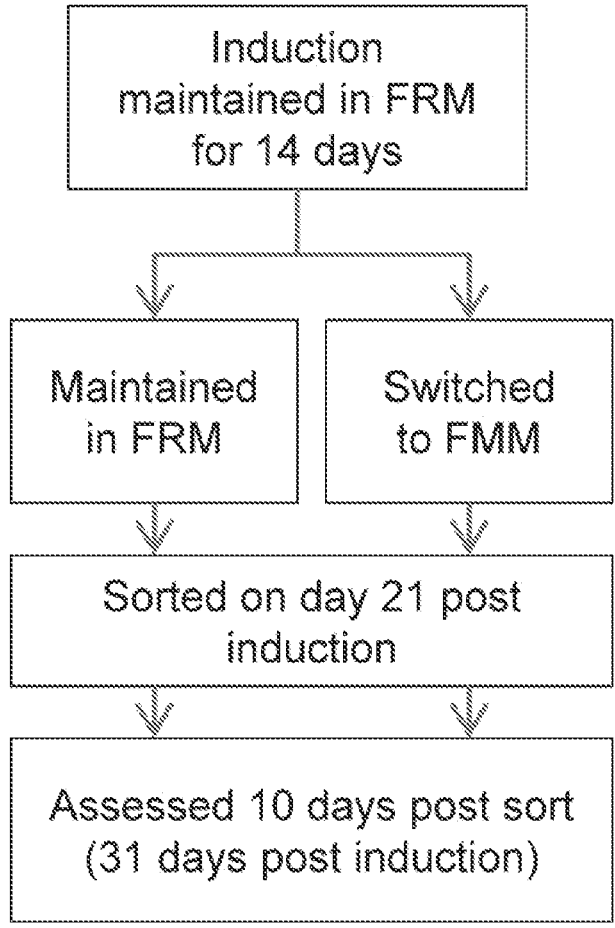
Figure 8D:
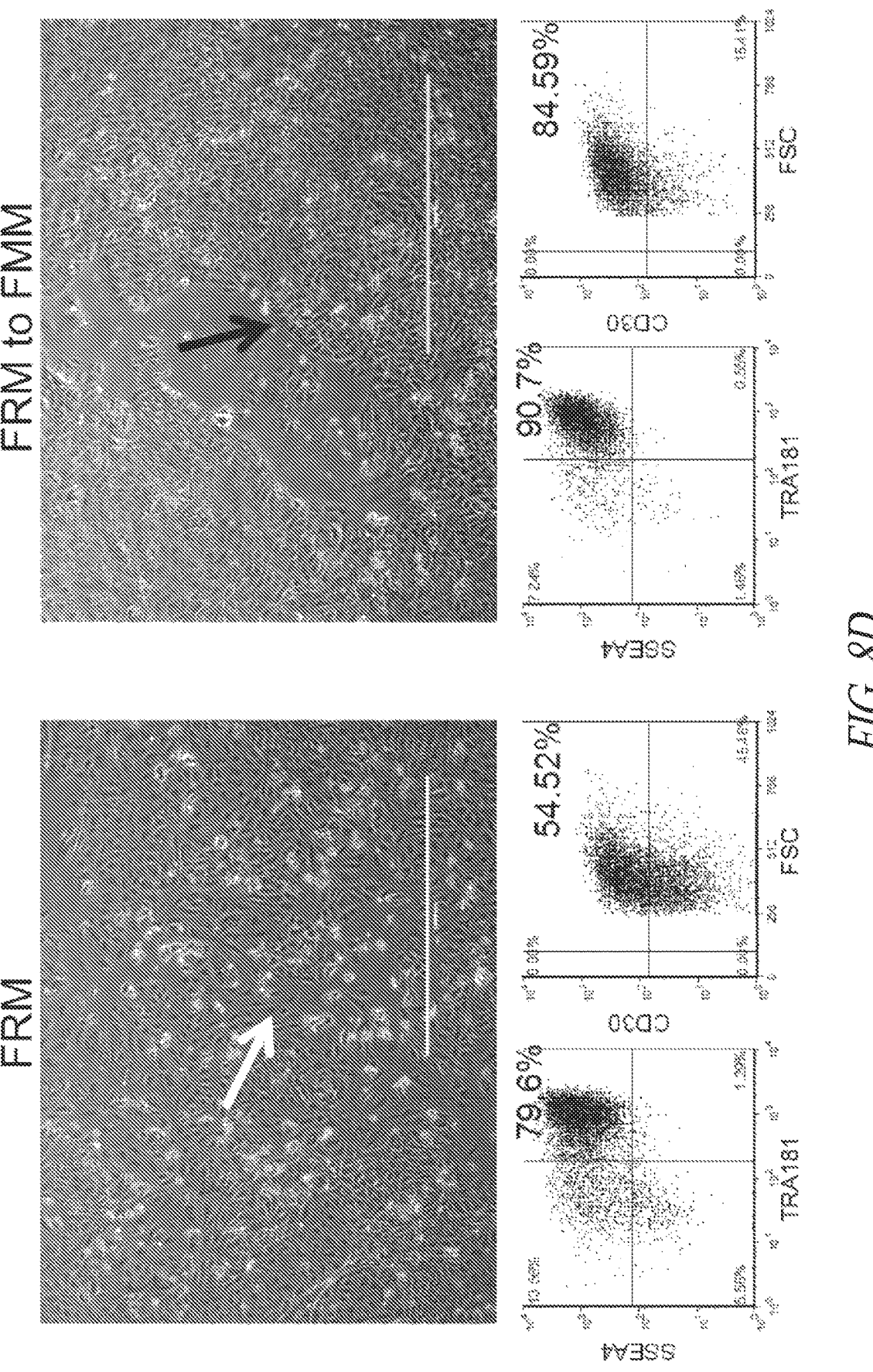

An episomal expression system consisting of gene combination OCT4/SOX2/NANOG/KLF4/LIN28/MYC/SV40LT (OSNKLMT) was used to transfect various fibroblast cells. Twenty-four hours after induction of episomal expression, the reprogramming culture is transitioned to FRM to enhance reprogramming kinetics. Early colony formation was observed within the first week and by day 10, a large population of SSEA4/TRA1-81 positive cells was detected (>1%) (FIGS. 8A and 8B). On Day 14, the reprogramming culture supported by FRM was split into either FRM or FMM media. On day 21, FACS was used to identify SSEA4/TRA1-81/CD30 positive cells in the cultures (FIG. 8C). FRM maintained cultures contained both differentiated and undifferentiated cells, whereas FMM cultures contained mostly undifferentiated cells (FIG. 8D).

Figure 2B:
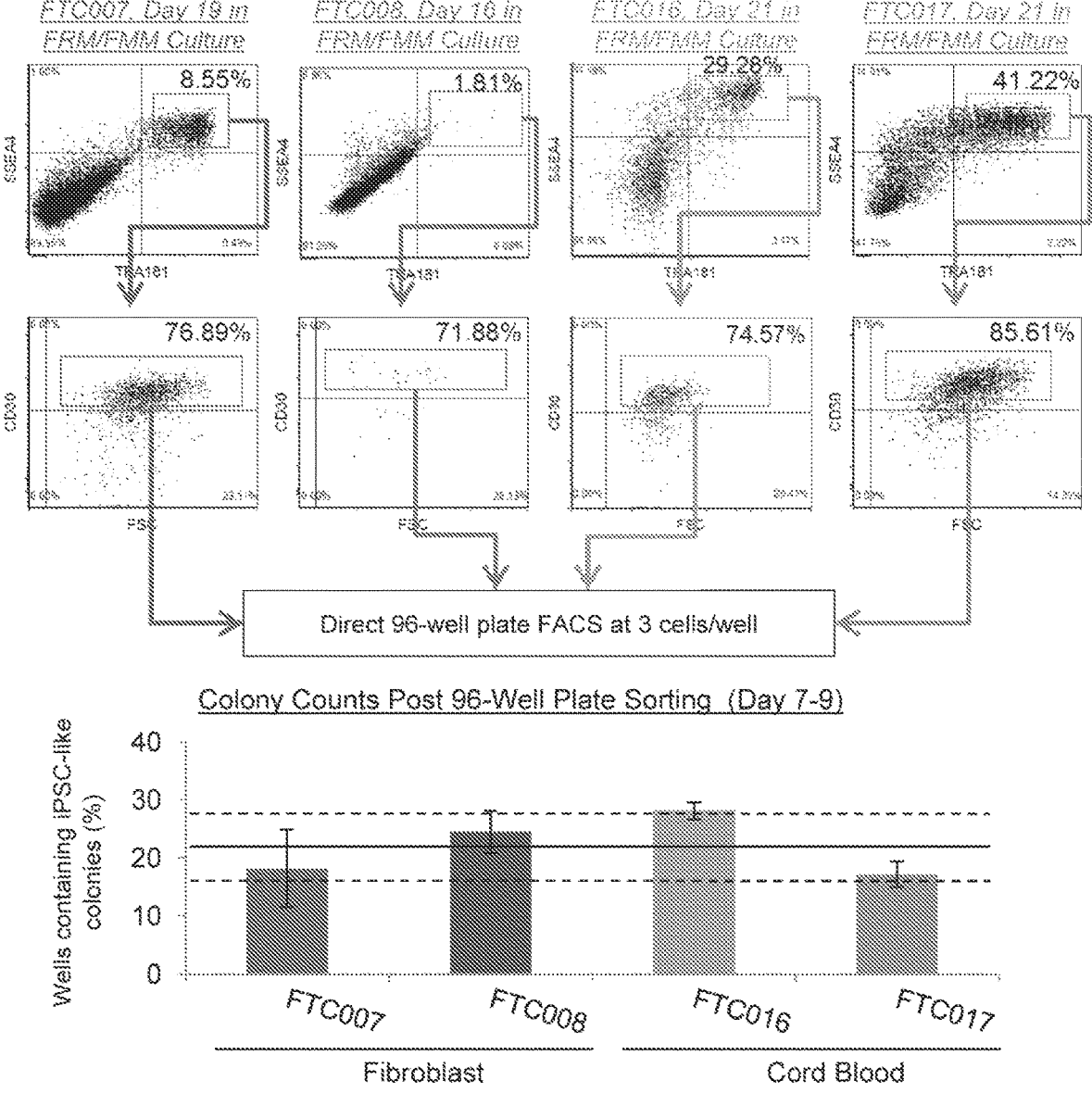
Figure 2C:
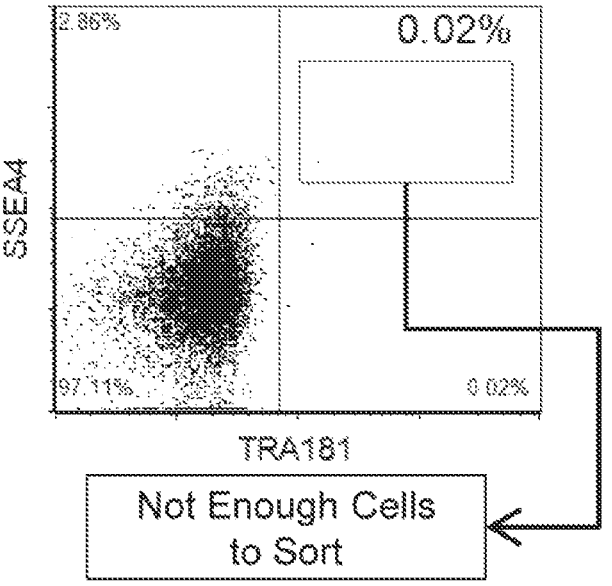
Figure 2D:
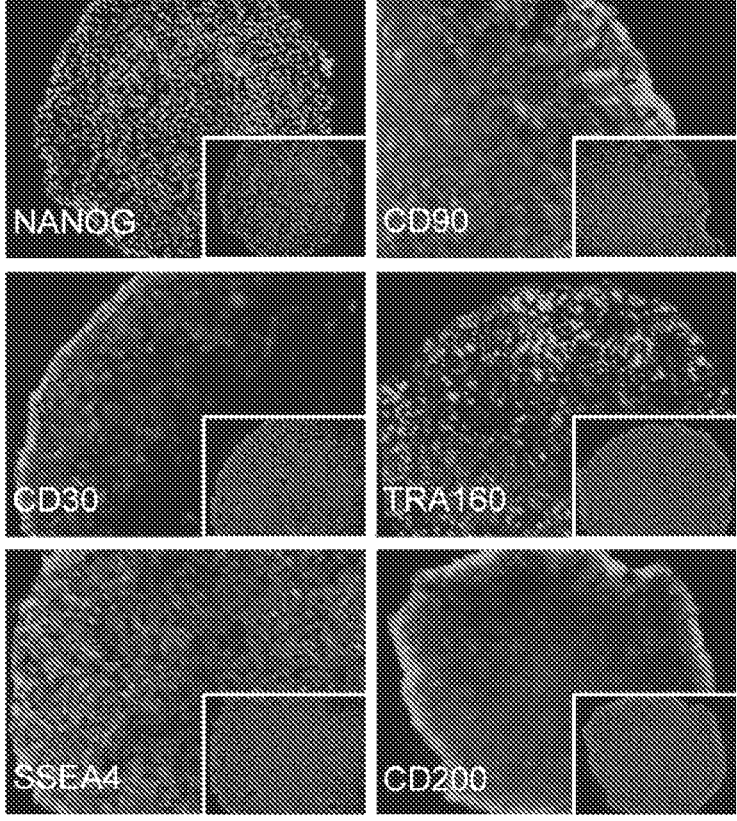
Figure 2E:
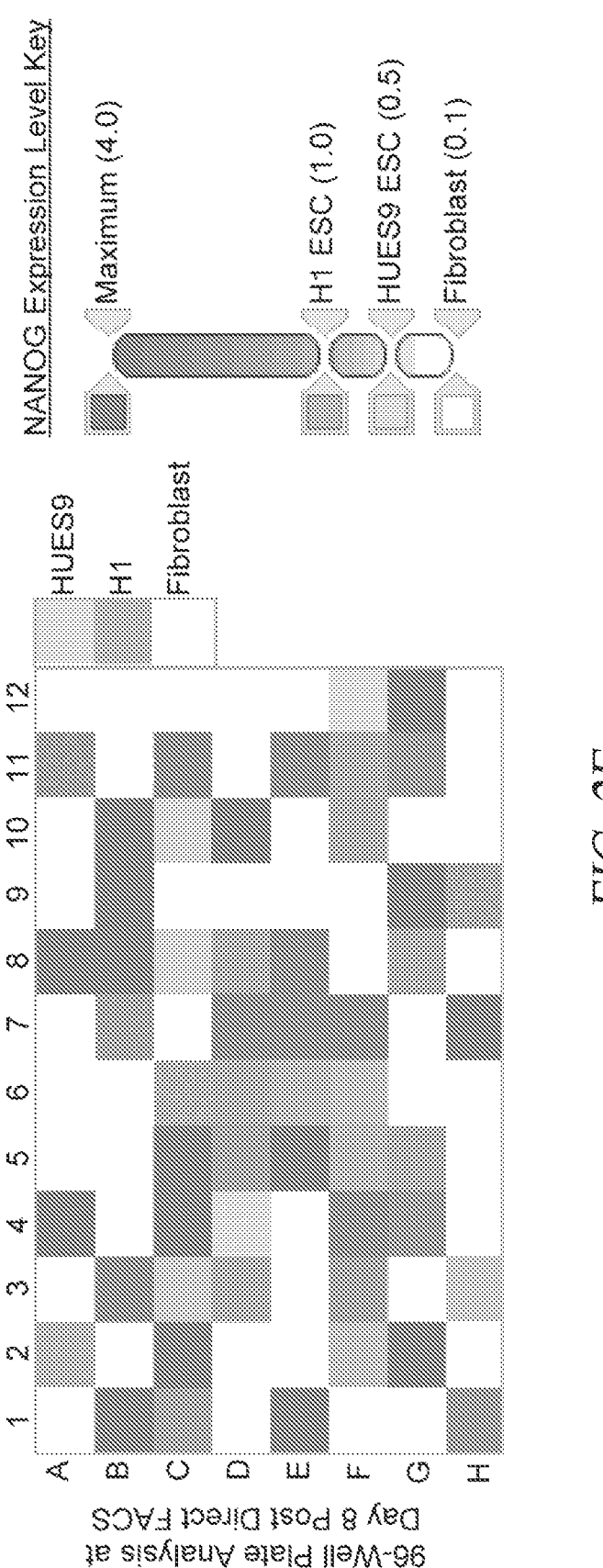
Figure 10B:
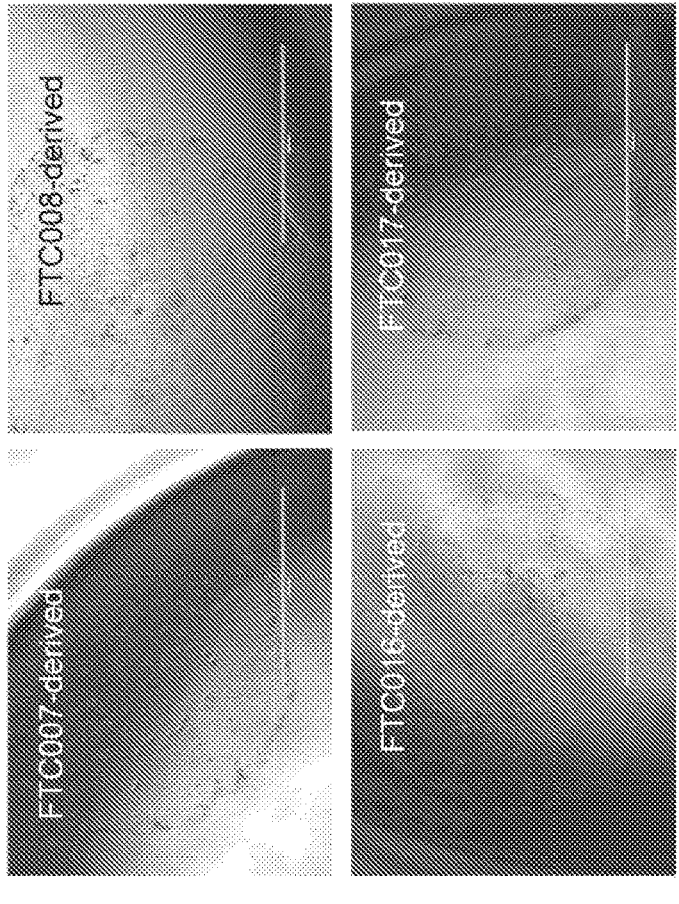
Figure 10A:
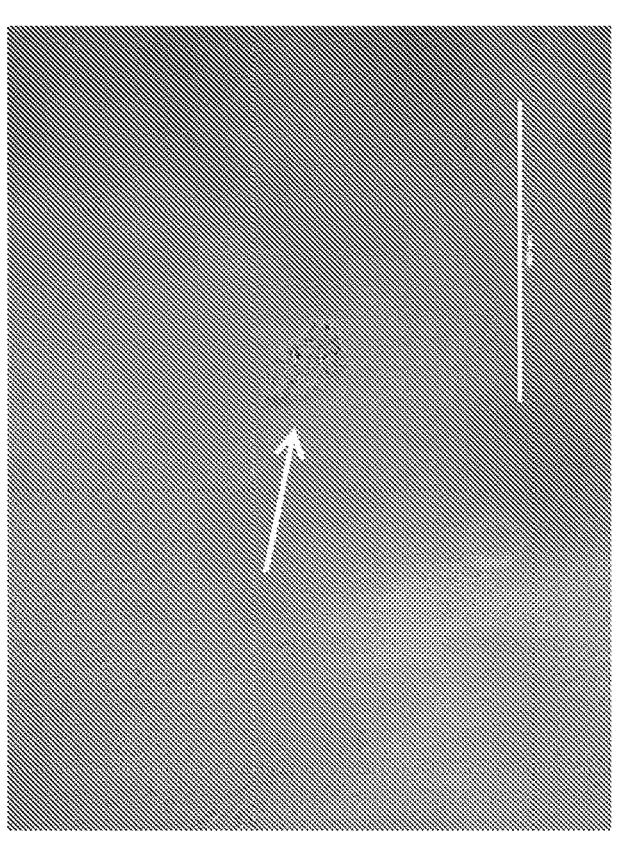
Figure 10C:
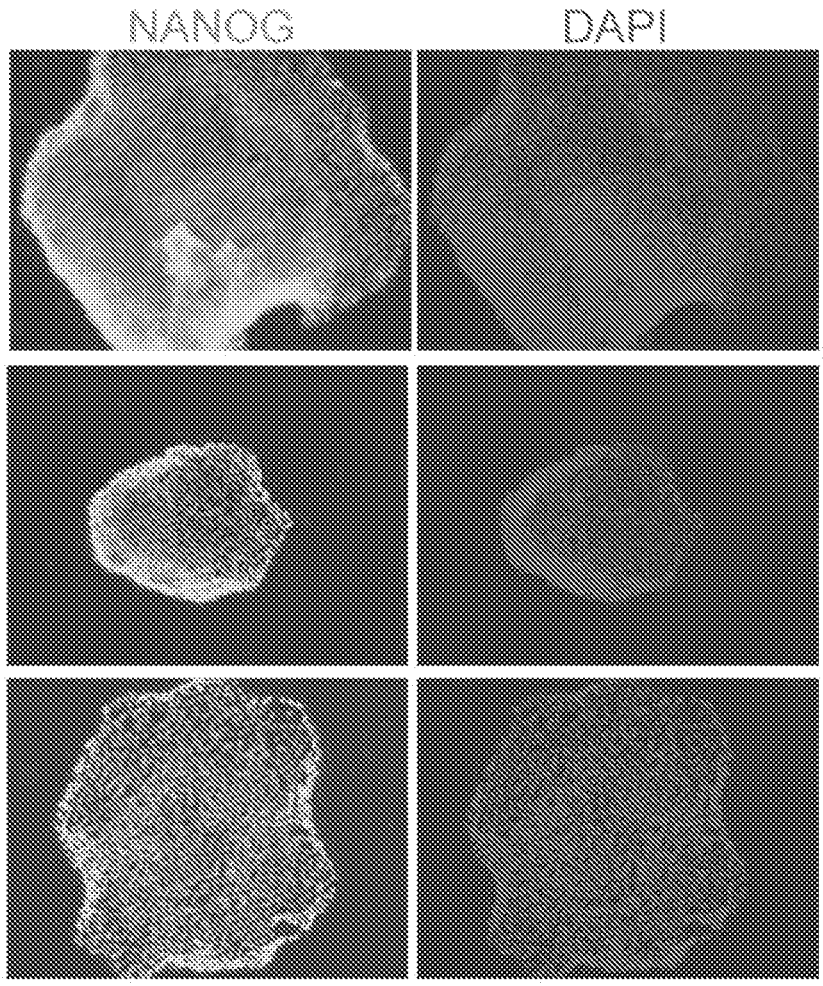
Figure 10D:
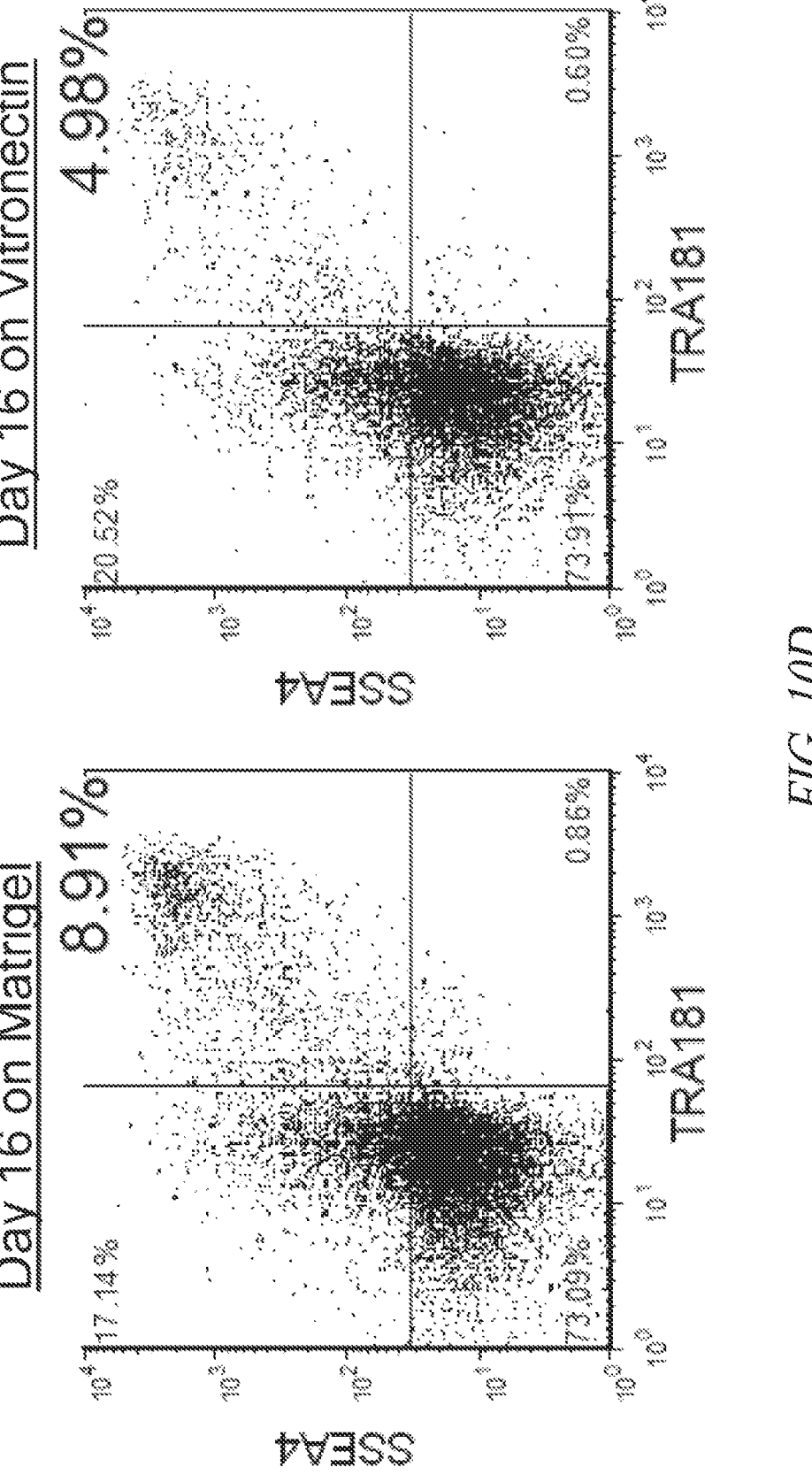

The throughput and robustness of this approach was tested with fibroblasts and CD34+ cells expanded from minimal volumes of umbilical cord blood from donors of different ages, genders and ethnicity (FIGS. 9A and 9B). Somatic cell reprogramming was induced as outlined in FIG. 2A with the episomal gene combination set OSNKLMT and 96-well plate flow cytometry sorted for individual hiPSCs between days 16 and 21 (FIG. 2B). A large population of SSEA4/TRA1-81/CD30 positive cells was observed for the majority of lines tested. Compared to a parallel reprogramming experiment using conventional medium and feeder cells, the FRM and FMM media system was resulted in a significant increase in the number of hiPSC clones (8.55% in FRM/FMM versus 0.02% in conventional culture for the FTC007 fibroblast line; FIGS. 2B and 2C). On average 22 clonal hiPSCs per 96-well plate were seen for each somatic line (FIGS. 2B, 10A and 10B) including the fibroblast FTC008 which had been previously observed to be refractory to lentiviral reprogramming with SMC4 medium. Colonies were subsequently confirmed as bona fide hiPSC clones by analysis of intracellular and surface marker expression and direct qRTPCR for NANOG (FIGS. 2D, 2E and 10C). The efficiency of reprogramming using the 96-well sorting and selection process was also increased (FIG. 2E). A similar reprogramming efficiency was also observed with the defined surface coating vitronectin (FIG. 10D).

These data showed that the platform was robust and reproducible when applied to episomal reprogramming and allowed for multiple reprogramming experiments to be performed in parallel in a high-throughput fashion with minimal effort and without compromising quality of the iPSC end product.

Example 3

Long-Term Passage and Expansion of Transgene-Free hiPSC Lines in FMM

Overview

Figure 3A:
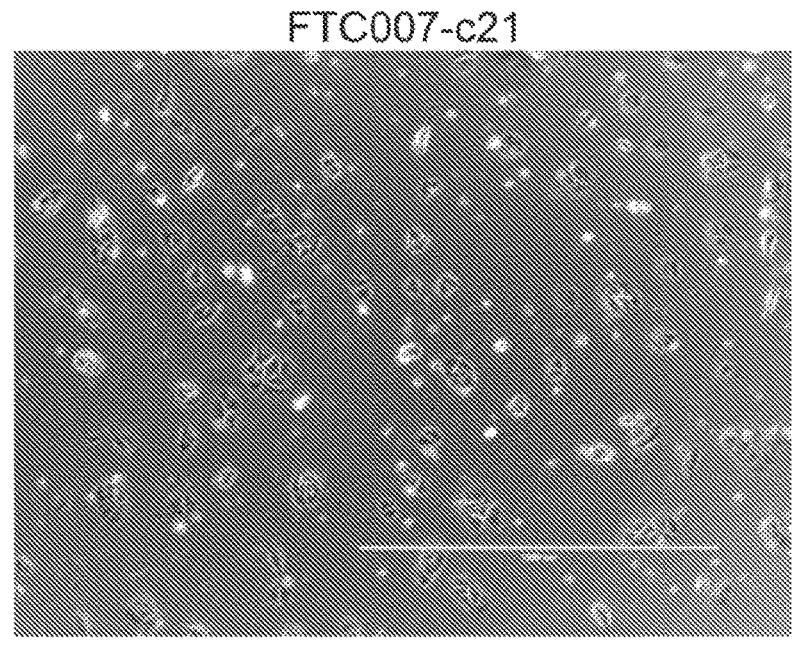
FIGS. 3A-3F show that episomal reprogrammed hiPSC clones maintain their undifferentiated state and are free of transgene sequence. (3A) Typical morphology of hiPSC clones 24 hours after single cell passage. (3B) Representative images of hiPSC clone during culture. (3C) PCR analysis for episomal DNA derived from various hiPSC clones. Lane 1, FTC007-c1 p4; Lane 2, FTC007-c21 p4.
Figure 3B:
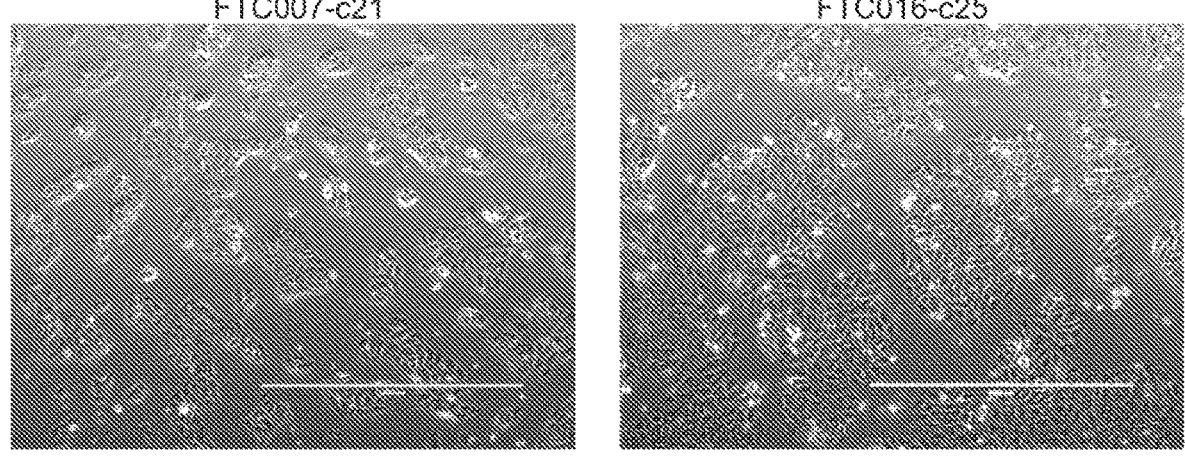

The long-term passage and expansion of hiPSC using the multi-stage media platform of FRM and FMM was studied using hiPSC clones from Example 2, expanded as single cells in FF culture (FIGS. 3A and 3B).

Figure 3C:
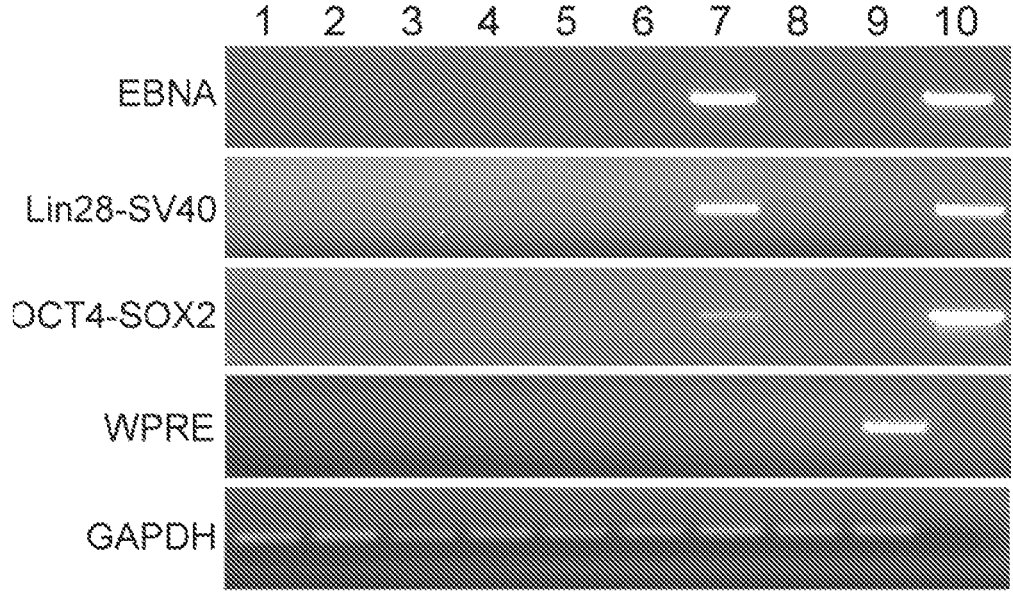
Figure 3D:
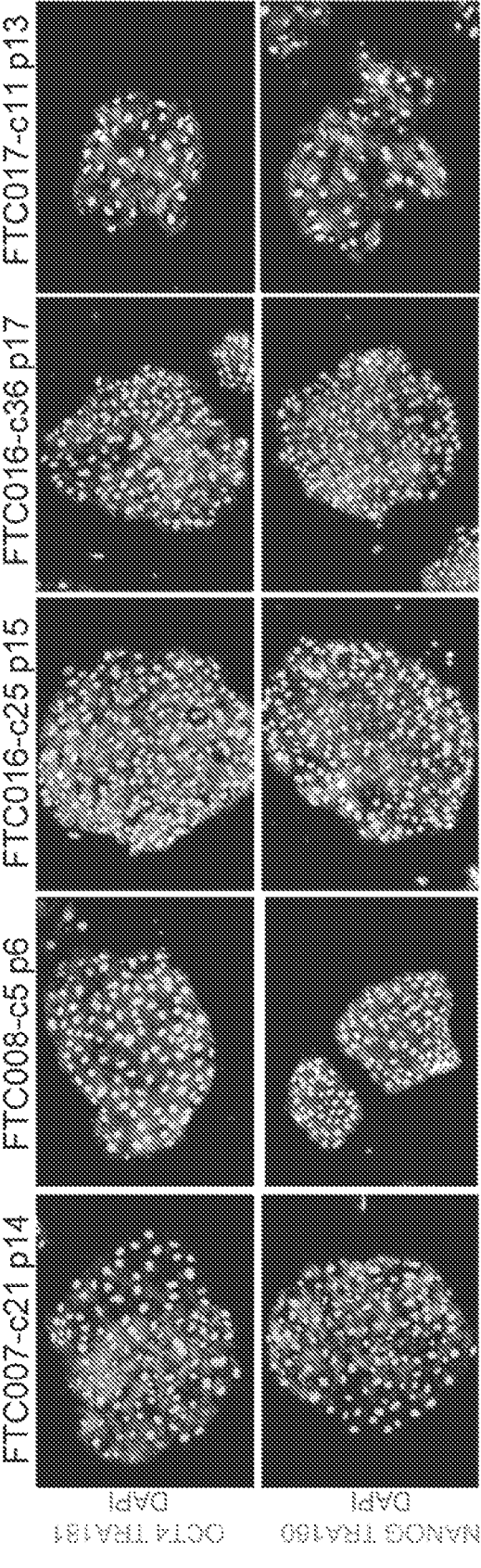
Figure 3E:
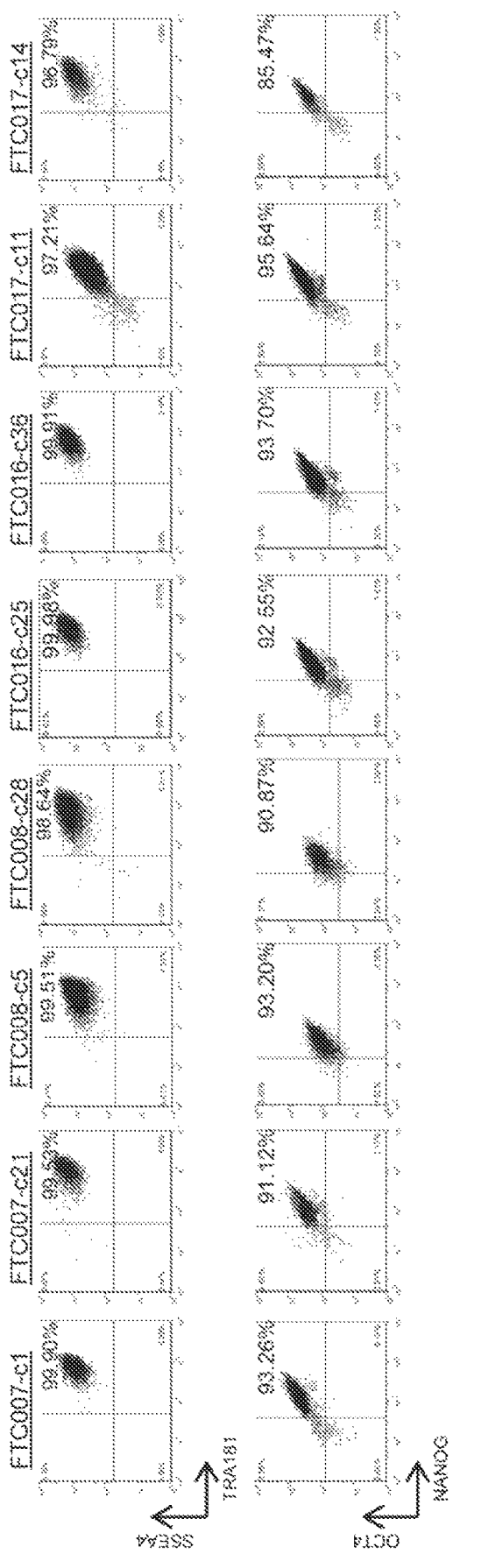
Figure 3F:
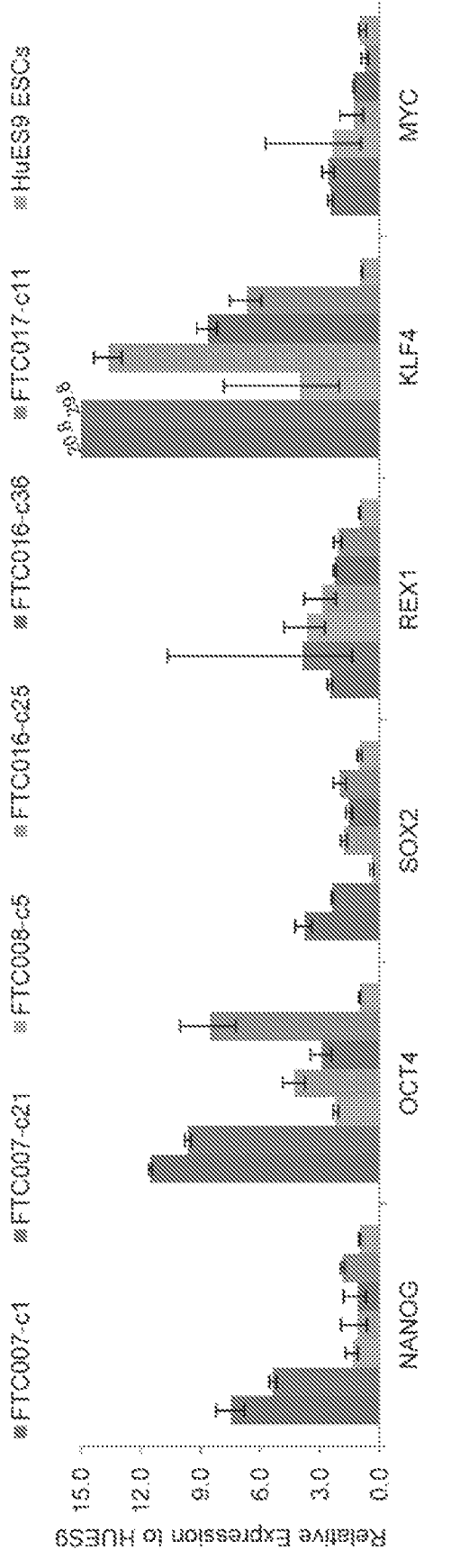
Figure 10E:
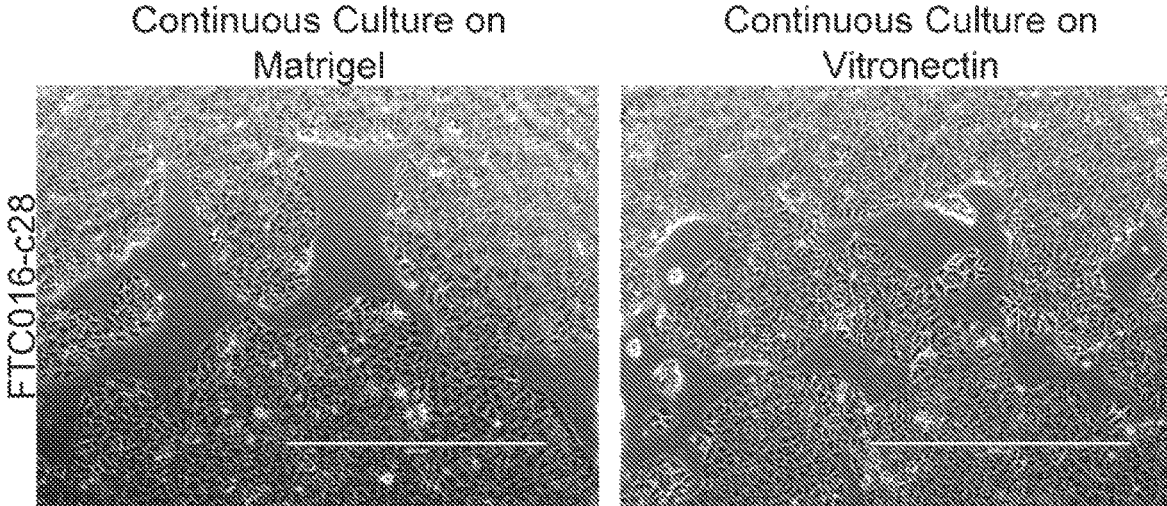
Figure 10F:
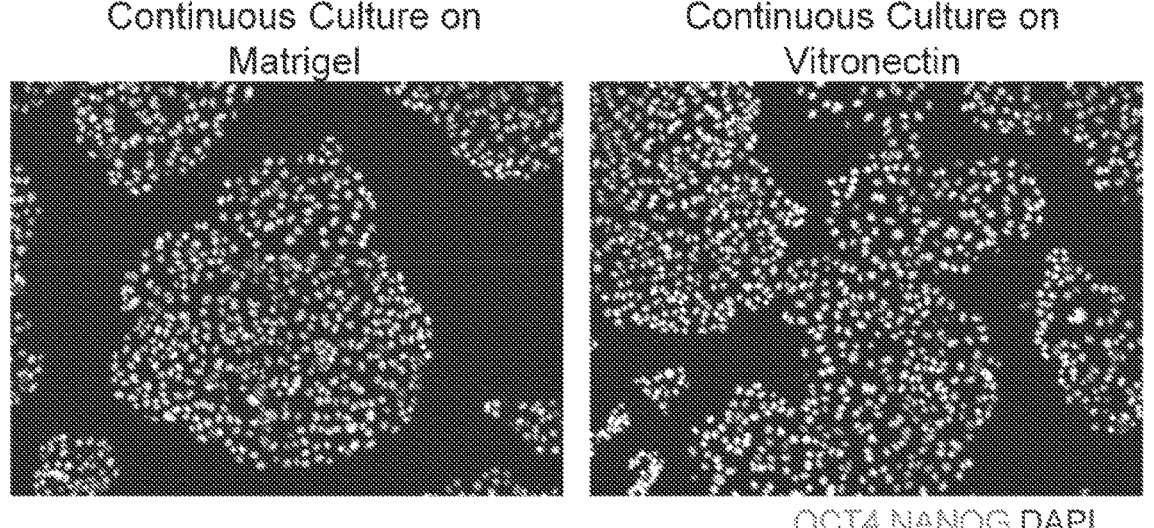
Figure 10G:
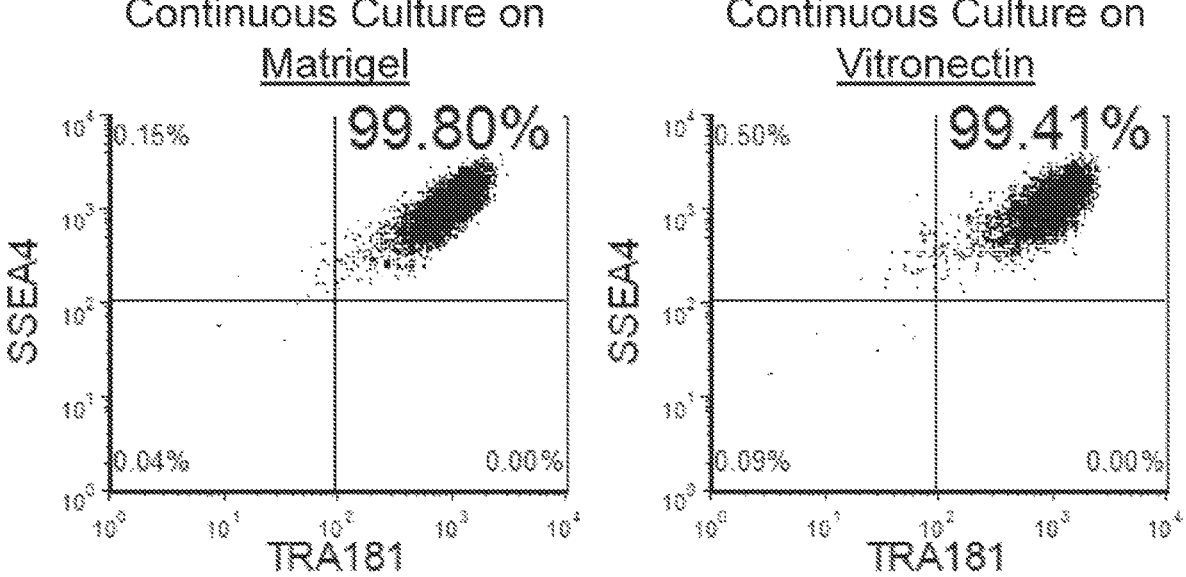

Results hiPSC lines reprogrammed according to Example 2 lost episomal DNA by passage 4-7 and thus, pluripotent independent of the transgene-based reprogramming factors (FIG. 3C). The hiPSC lines maintained a homogeneous population of undifferentiated cells positive for SSEA4, TRA1-81, OCT4 and NANOG. Moreover, these lines maintained pluripotent characteristics (FIG. 3F) in the absence of any cleanup strategies that are commonly utilized in pluripotent culture (FIGS. 3D and 3E). Similar expansion of uniform hiPSC cultures were observed when Matrigel was replaced with the defined surface coating Vitronectin during routine single cell passaged culture (FIGS. 10E-10G).

Figure 4A:
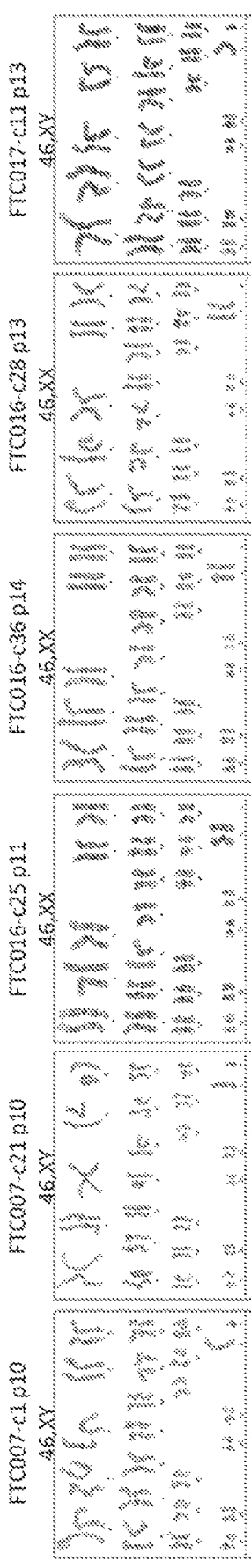
Figure 4B:
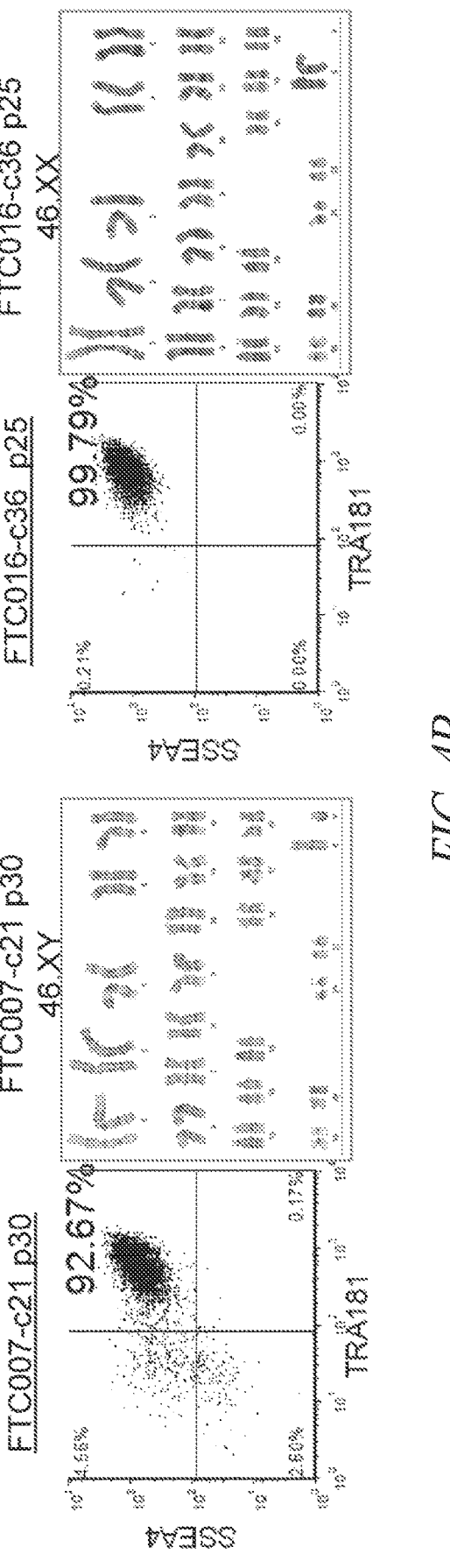

Genomic abnormalities are often detected in hESC and hiPSC lines cultured as single cells in a FF environment (Laurent et al., 2011; Taapken et al., 2011). Karyotype analysis of all analyzed hiPSC lines demonstrated genomic stability in FMM culture (FIG. 4A). In addition, single cell and FF cultured hiPSC clones maintained in FMM for an extended period (25-30 passages) continued to maintain their undifferentiated profile and genomic stability without the need for culture cleaning or selection (FIG. 4B).

Figure 4C:
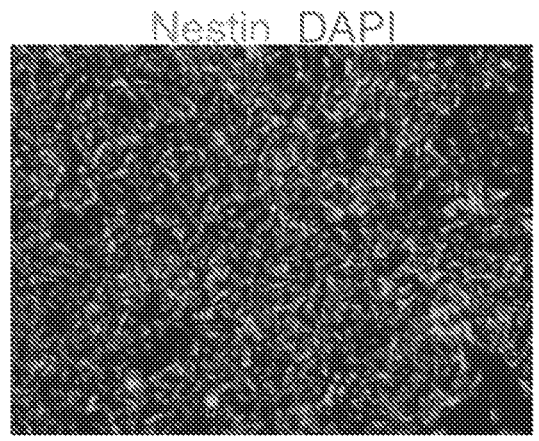
Figure 4C:
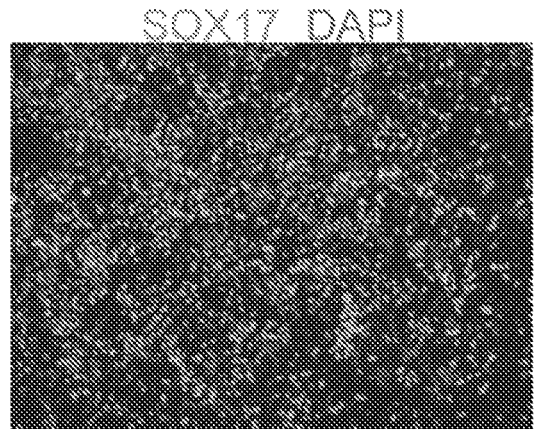
Figure 4C:
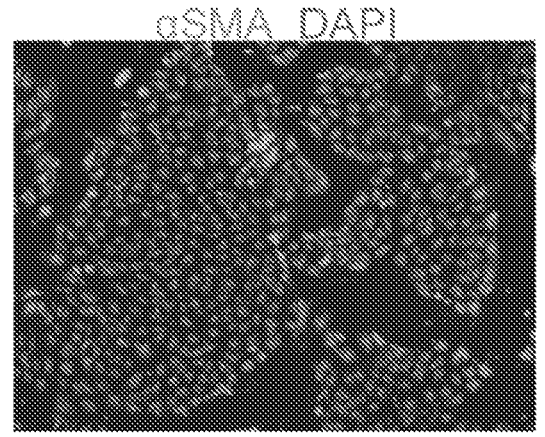
Figure 4D:
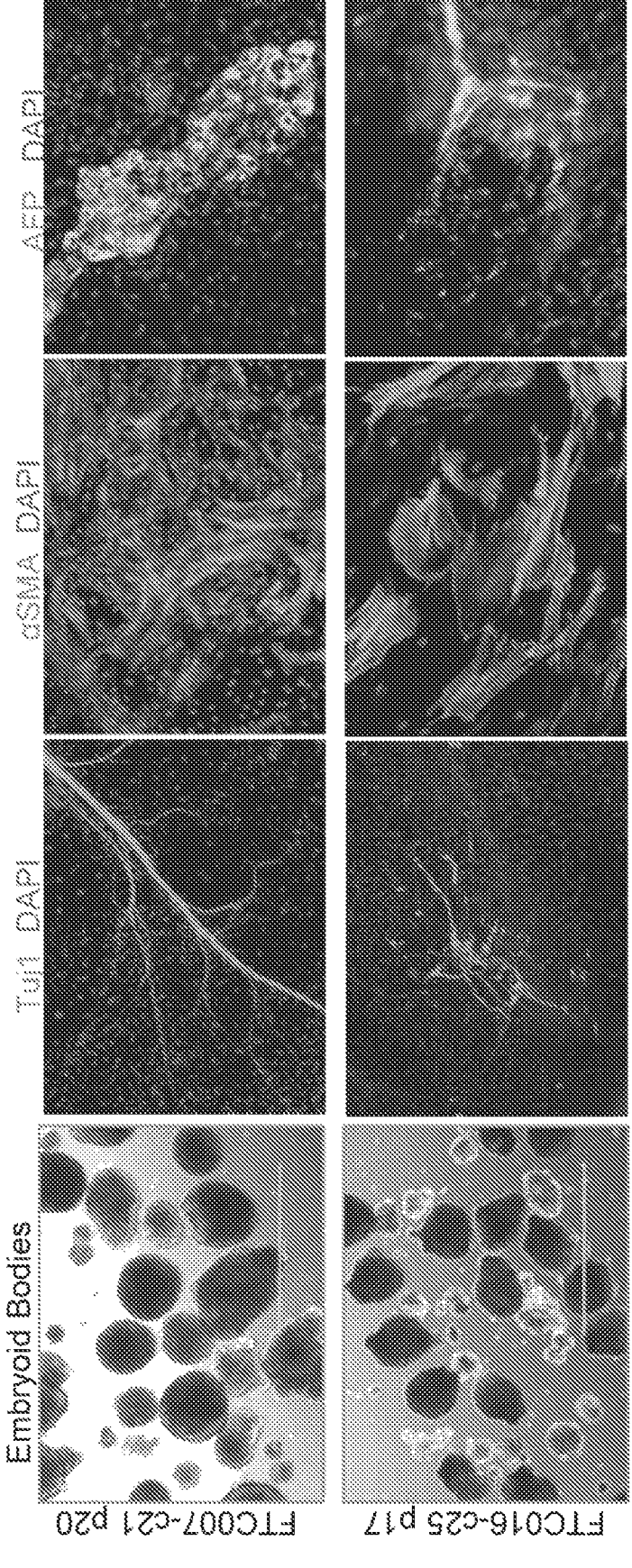
Figure 4E:
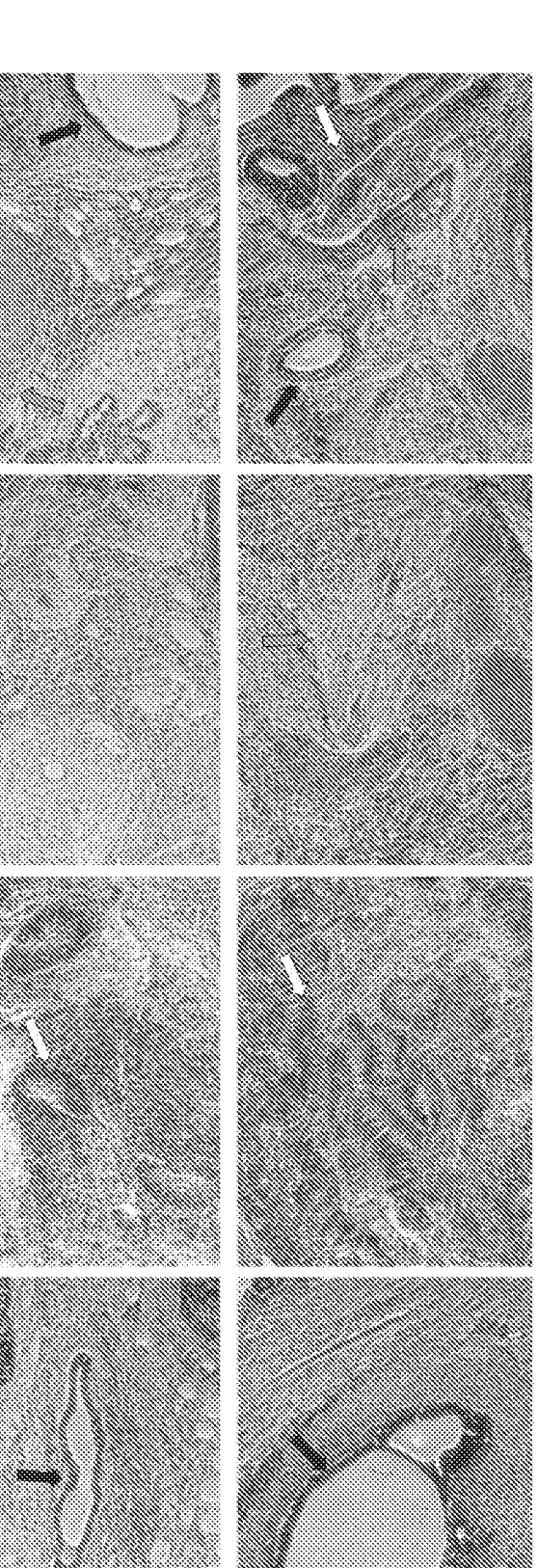

Episomal-derived hiPSC clones maintained in FMM also readily gave rise to all three somatic lineages, in vitro differentiation via embryoid bodies, and in vivo differentiation by teratoma formation (FIG. 4C-E).

These data demonstrated that the FRM and FMM multi-stage media platform enables transgene-free hiPSC clones to be readily generated and expanded in FF and single cell enzymatic passage format while maintaining homogeneous population of pluripotent and genomically stable cells.

Example 4

Figures 5A, 5B:
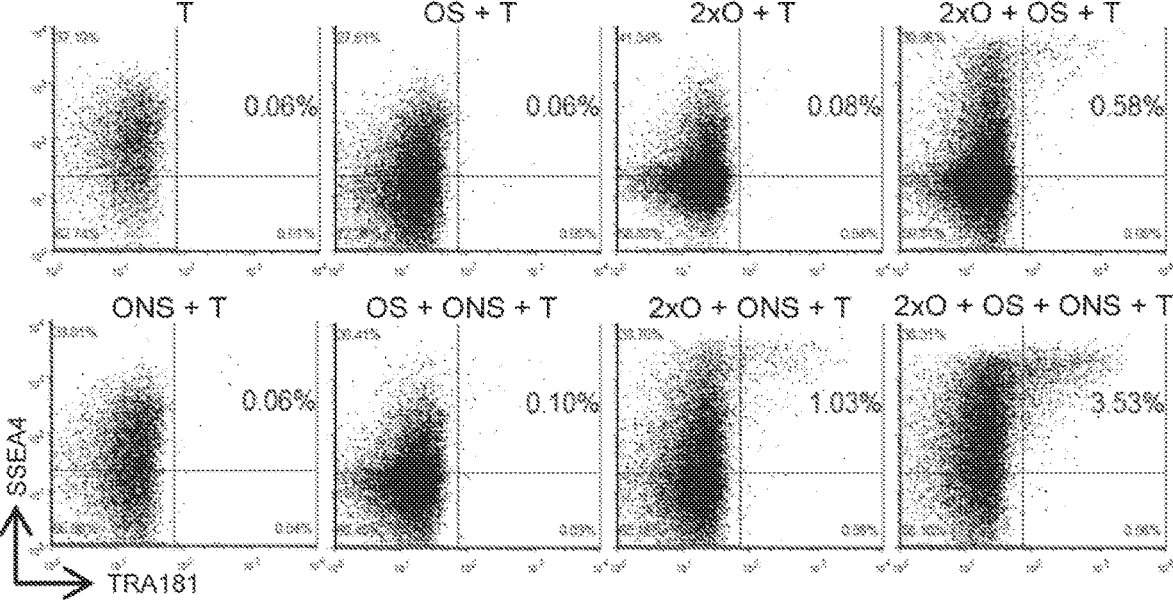

Multi-Stage Media Platform Enables Episomal Reprogramming with Minimal Genes
Overview An efficient footprint-free expression system with the reduced dependency for oncogenes such as KLF4, MYC and LIN28 or the need to knockdown P53 in the reprogramming process would be of great value for pluripotent stem cell therapies (Lee et al., 2013; Okita et al., 2011; Yu et al., 2009). Because the multi-stage media platform demonstrated an extremely efficient and robust platform for the generation and expansion of transgene-free hiPSC cells using OSNKLMT reprogramming factors, the robustness of the platform was measured against the requirement for reprogramming factor.
Results Several episomal-expression cassettes containing minimal gene sets were constructed, including OCT4/NANOG/SOX2 (ONS), OCT4/SOX2 (OS) or OCT4/OCT4 (2xO) in an attempt to vary gene expression combination and dosage (FIG. 5A). A fibroblast cell line was transfected with combinations of OCT4, NANOG, SOX2, and SV40LT and cultured using the FRM/FMM platform. SV40LT alone did not produce any true SSEA4/TRA1-81 positive cells at day 13 of reprogramming, but improved cell survival post transfection (FIGS. 5B and 11A). The various reprogramming factor combinations, resulted in efficient reprogramming as demonstrated by emergence of SSEA4/TRA1-81 positive populations early in the reprogramming process (>0.5% for OCT4/SOX2/SV40LT and >3.5% for OCT4/NANOG/SOX2/SV40LT by day 13; FIG. 5B). Cultures reprogrammed for additional days significantly increased the SSEA4/TRA1-81 positive population (>4.0% for OCT4/SOX2/SV40LT by day 16; FIG. 11B). Surprisingly, the percentage of reprogrammed cells observed was comparable to lentiviral and episomal-induced systems containing the oncogenes KLF4 and MYC (FIGS. 2B, 5B and 11B).

Figures 5C, 5D, 5E:
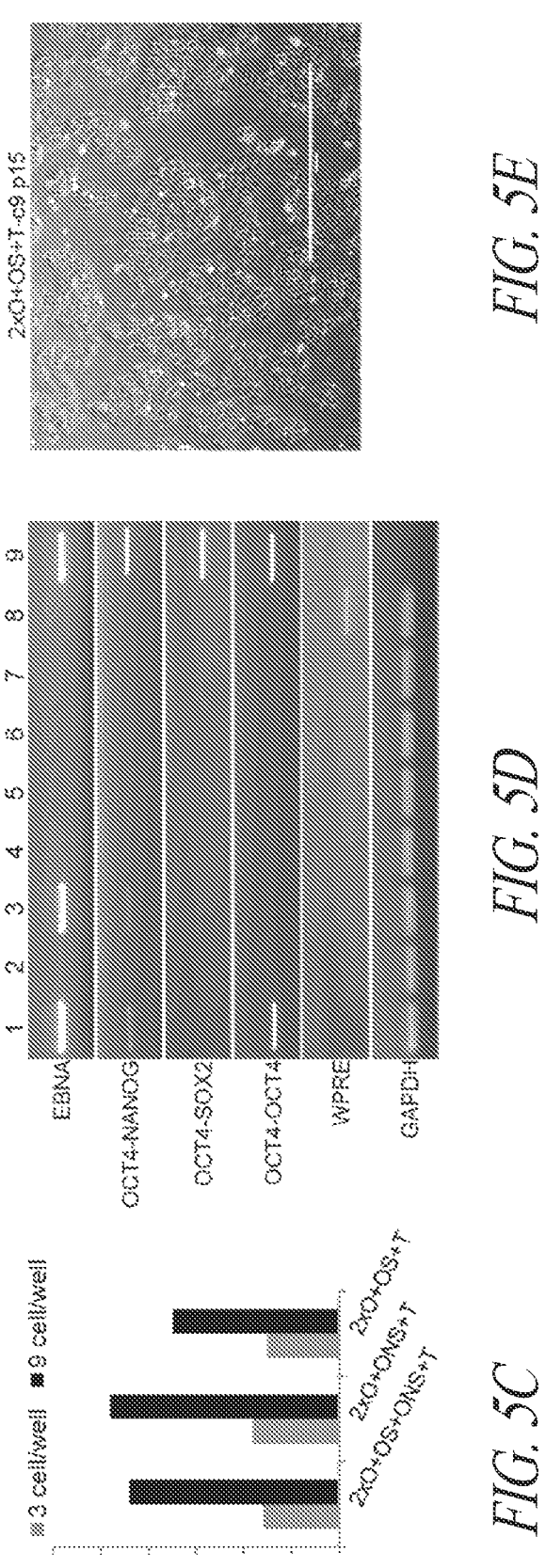
Figure 5F:
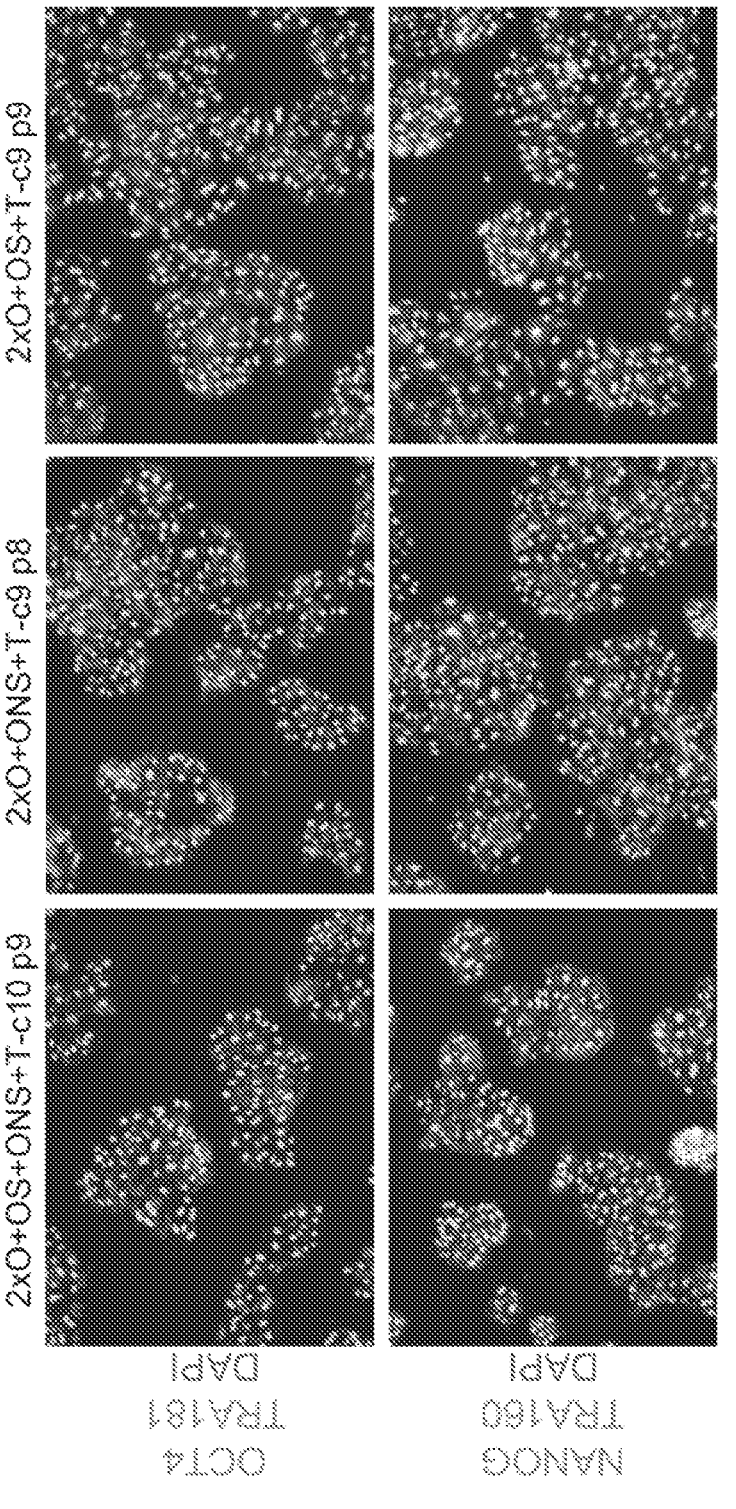
Figure 5G:
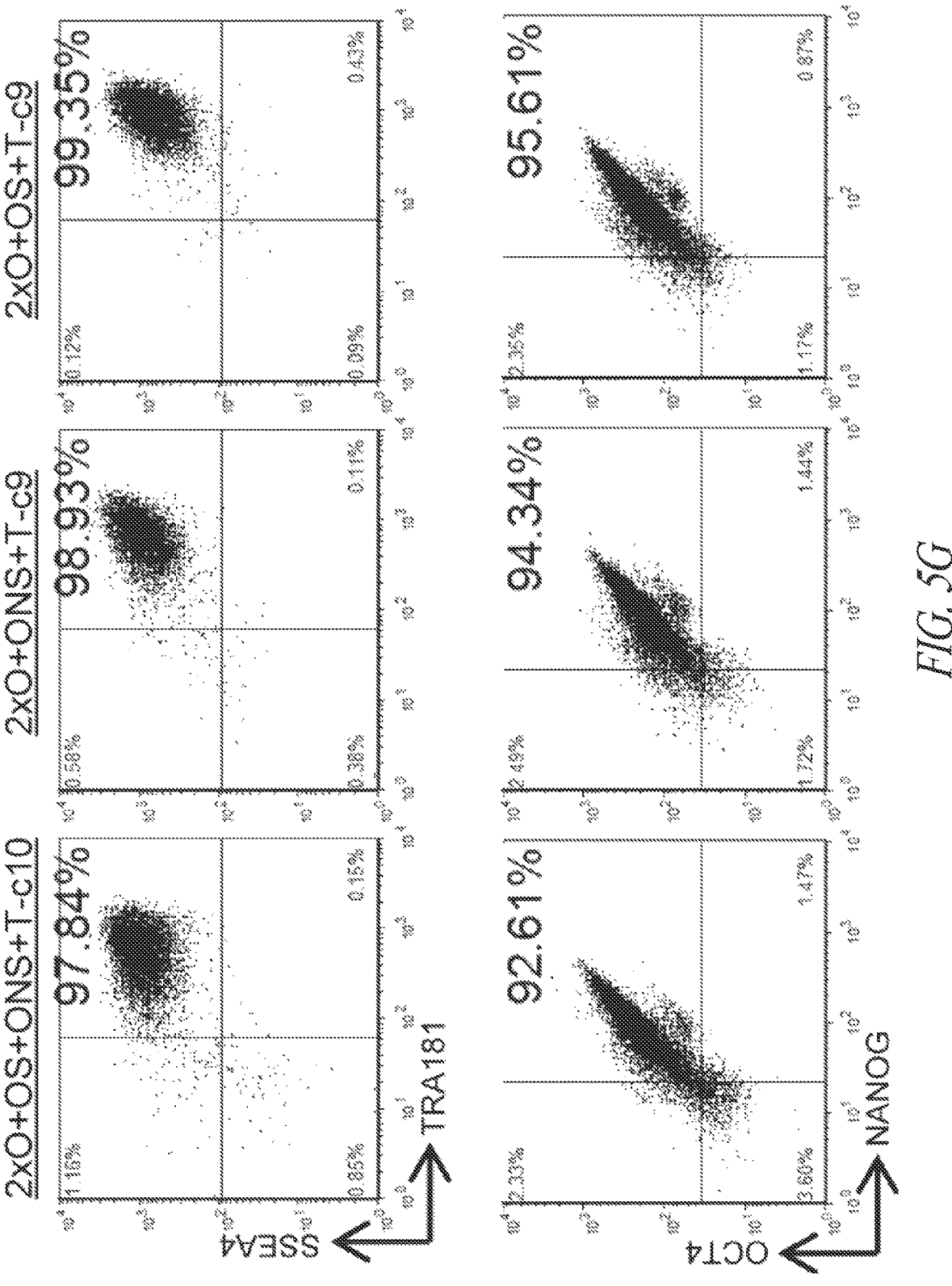
Figure 5H:
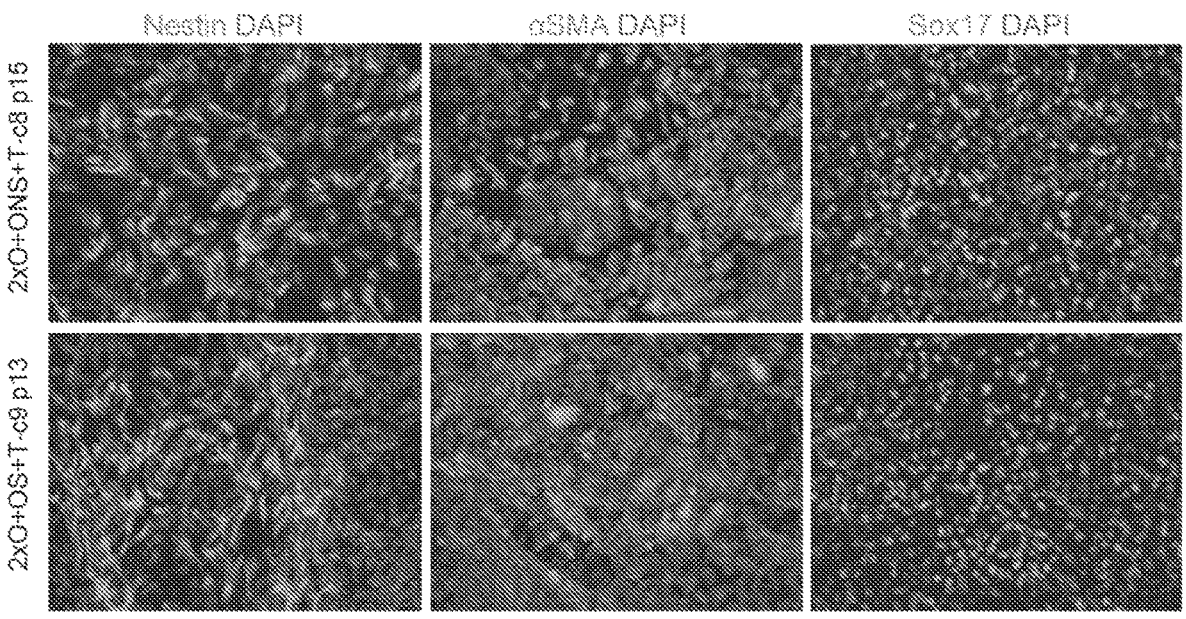
Figure 5I:
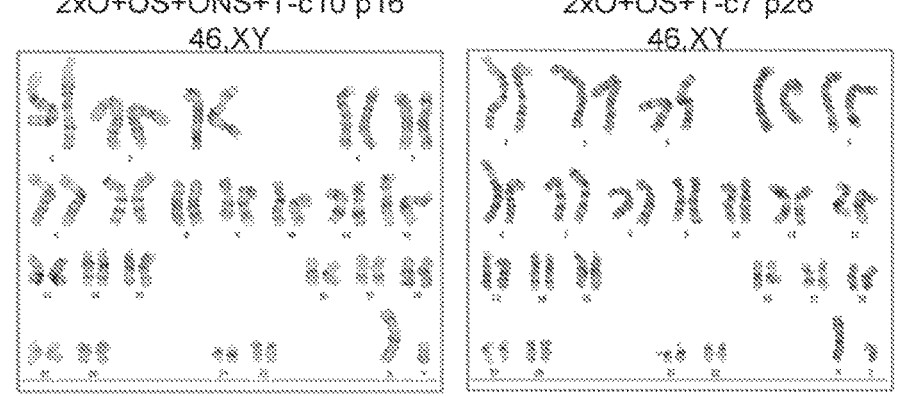
Figure 5J:
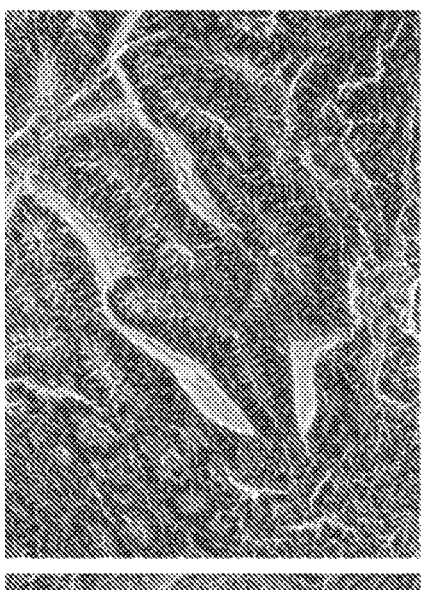
Figure 5J:
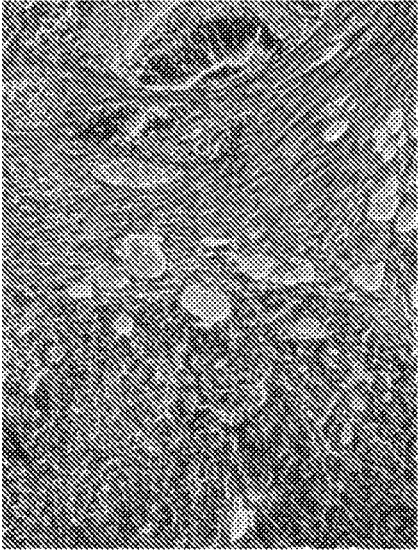
Figure 5J:
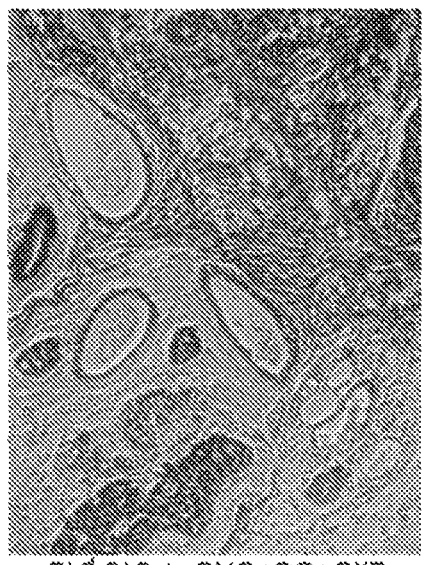

Several reprogramming factor combinations were carried forward and transitioned to FMM medium prior to flow cytometry sorting and selection of individual hiPSC clones. Similar to OSNKLMT episomal reprogramming, clonal hiPSC lines were readily derived from combinations containing minimal genes OCT4, SOX2 and SV40LT (2xO+OS+T) as well as other combinations (FIG. 5C). hiPSC clones that had lost transgenes and episomal vector markers by passages 5-7 were carried forward for further analysis (FIG. 5D). Selected clones were continuously passaged as single cells in a FF environment and maintained a homogeneous population of genomically stable undifferentiated cells and displayed the ability to efficiently differentiate into the three somatic lineages (FIGS. 5E-J).

Collectively, these data indicated that hiPSC were readily generated by transient expression of minimal reprogramming genes in the FRM/FMM, flow cytometry-based reprogramming platform.

Example 5

The FMM Platform Supports Ground State Pluripotency
Overview

Figure 12A:
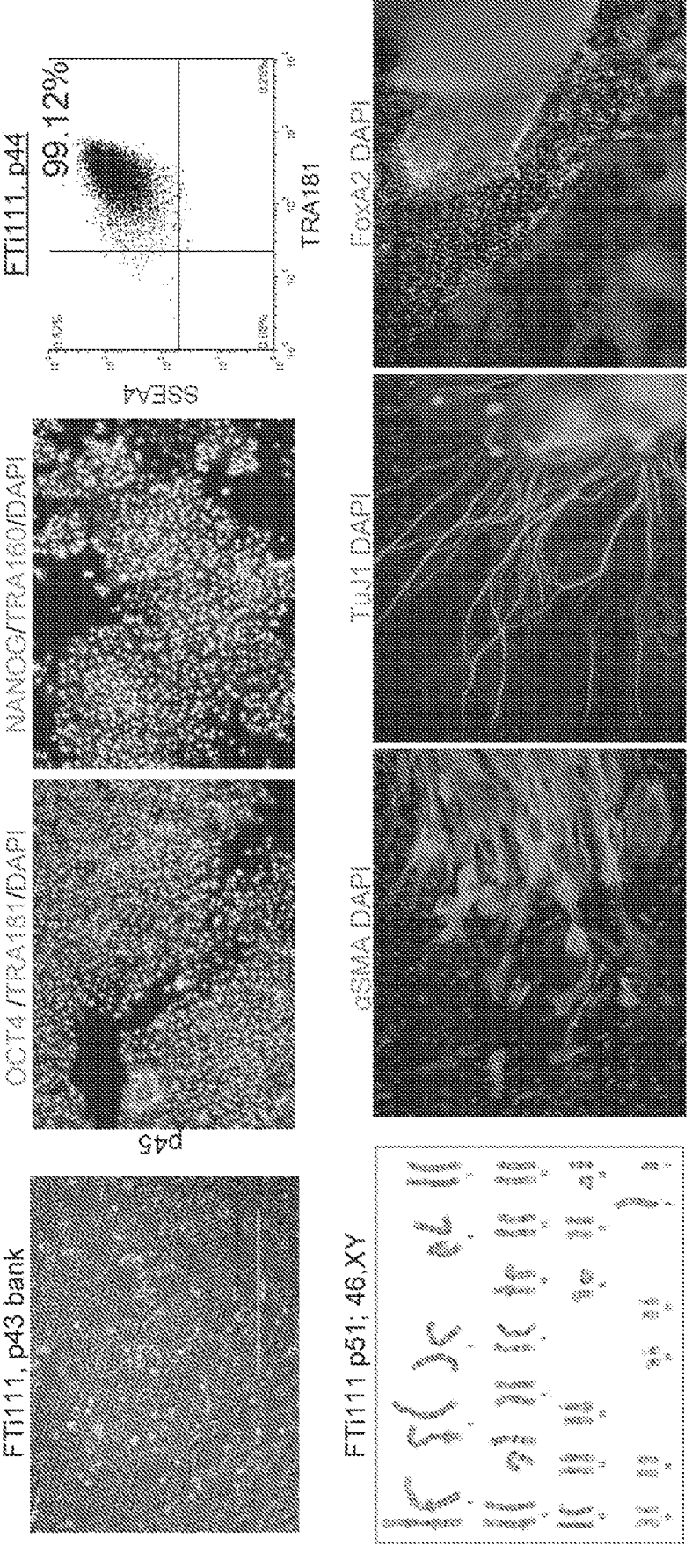
Figure 12B:
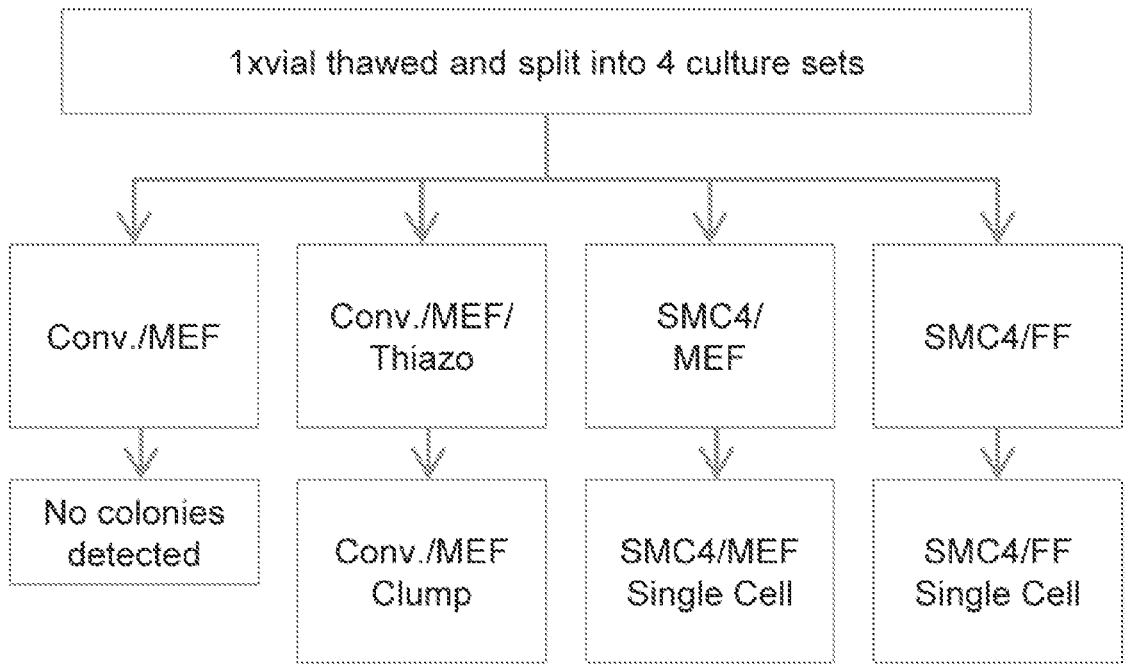
Figure 12C:
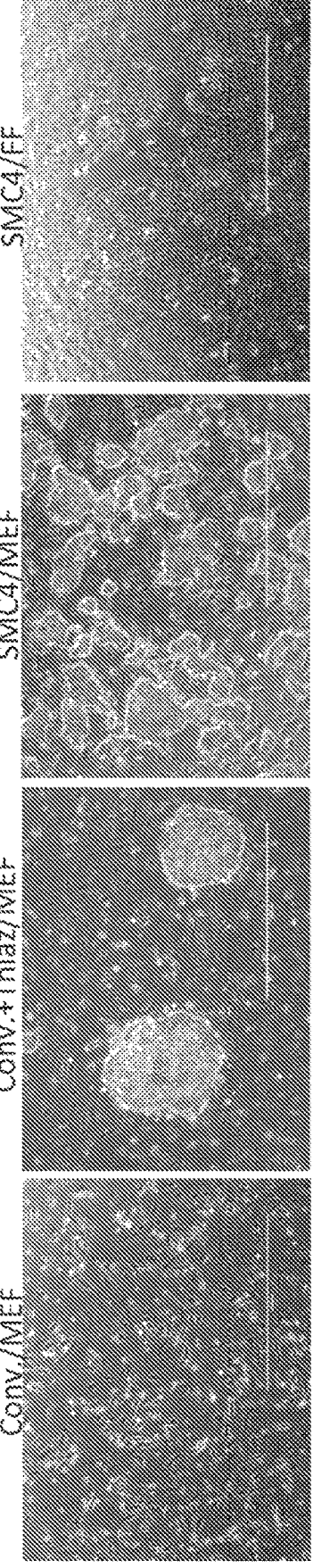
Figure 12D:
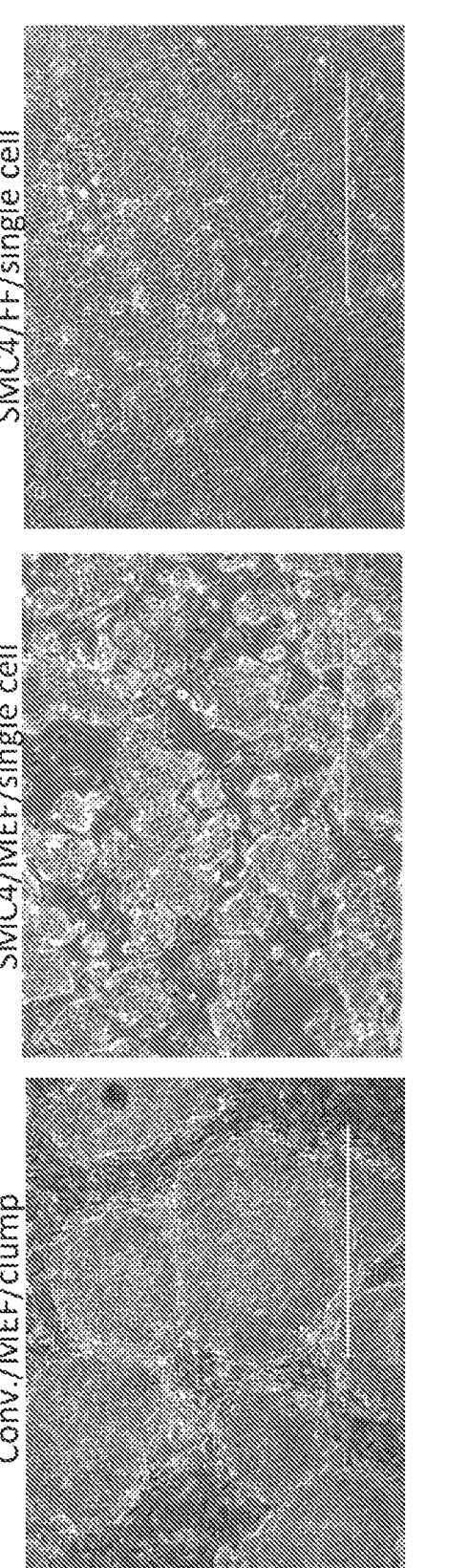
Figure 12E:
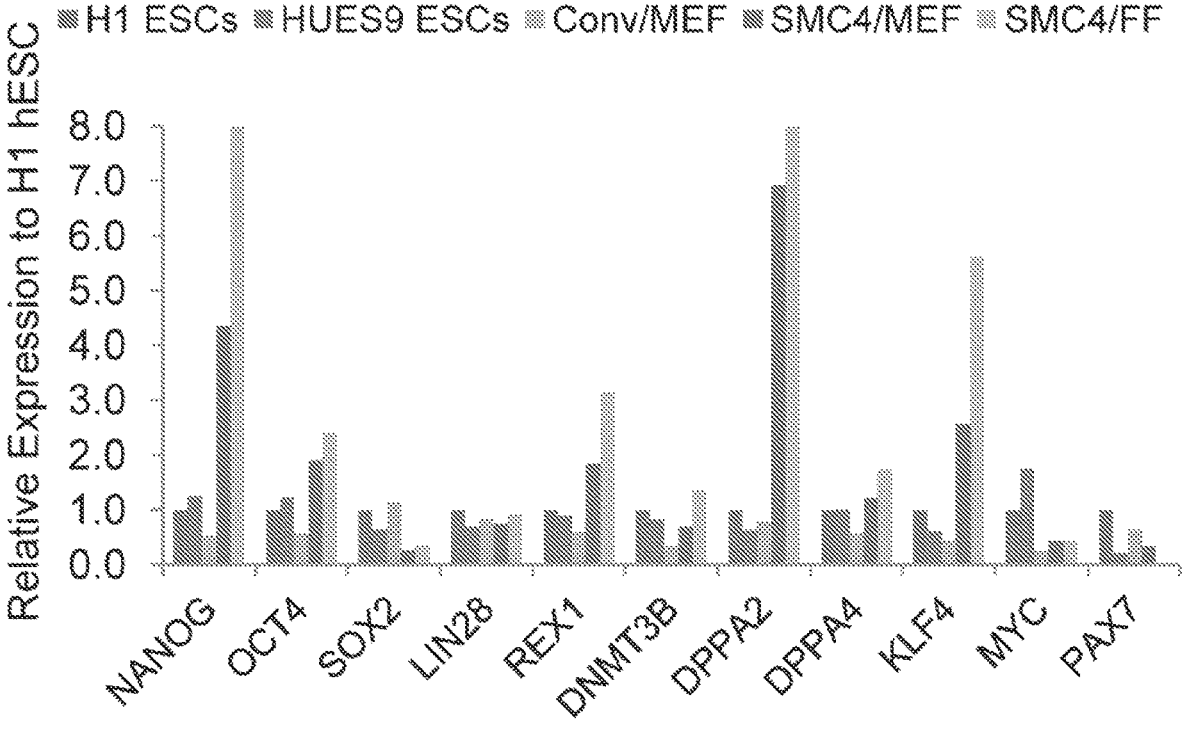

In order to further evaluate the FMM platform, the gene expressions characteristics of somatic cells reprogrammed by existing methods was compared with the gene expressions characteristics of somatic cells reprogrammed using the FMM platform contemplated herein. The gene expression differences between small molecule and conventionally maintained hiPSC cultures (Hanna et al., 2010b; Saha and Jaenisch, 2009) were evaluated.
Results In one set of experiments, the gene expression patterns between small molecule mediated and conventional culture were evaluated. A lentiviral-induced hiPSC clone FTi111 was generated and maintained in small molecule culture and shown to be pluripotent. The clone was thawed directly into various culture environments including: i) conventional medium with feeder cells and ii) small molecule inhibitor-containing medium with feeder cells or on FF surfaces (FIGS. 12A and 12B). hiPSC colonies in conventional culture were only recovered in the presence of Thiazovivin, a ROCK inhibitor and subsequently converting the recovered cells to clump culture (FIGS. 12B and 12C). Each set of culture conditions demonstrated a unique colony morphology (FIG. 12D) and distinct pattern of gene expression for pluripotent markers (FIG. 12E). The conventionally maintained culture on feeder cells more closely resembled hESC controls H1 and HUES9 maintained in conventional culture than its counterpart cultures maintained in small molecules (FIG. 12E). These data showed that distinct gene expression patterns exist between small molecule mediated and conventional culture.

Differences in gene expression were also assessed between hiPSCs derived using lentiviral induction and conventional ESC/feeder culture, and episomal derived lines and further between episomal lines derived with different combinations of reprogramming factors maintained in the FRM/FMM platform. High-content qRT-PCR analysis was used to quantify gene expression associated with pluripotency and differentiation. The majority of the pluripotency genes surveyed displayed comparable expression patterns between hiPSC maintained in FMM culture or conventional cultures containing feeder cells (FIG. 6A). However, differences between cell lines were observed on assessment of genes associated with differentiation (FIG. 6B). FMM maintained hiPSCs displayed lower expression of most genes associated with the three somatic lineages when compared to both hiPSCs and H1 hESCs maintained in conventional medium and on feeder cells. A subset of lines induced by episomal gene set OSNKLMT appeared to show expression of ectoderm lineage, OTX2 and TUJ1, whereas this expression was negligible in the hiPSC episomally-derived without the use of Lin28, KLF4 and c-MYC (FIG. 6B). Surprisingly, the expression of all differentiation genes tested were fully suppressed in all hiPSCs derived from episomal minimal genes sets and maintained in FMM (FIG. 6B). Together, these data indicated that the FRM/FMM platform can robustly reprogram cells with few episomal-based reprogramming factors and can maintain the hiPSCs in a stable ground pluripotent state.

Figure 13B:
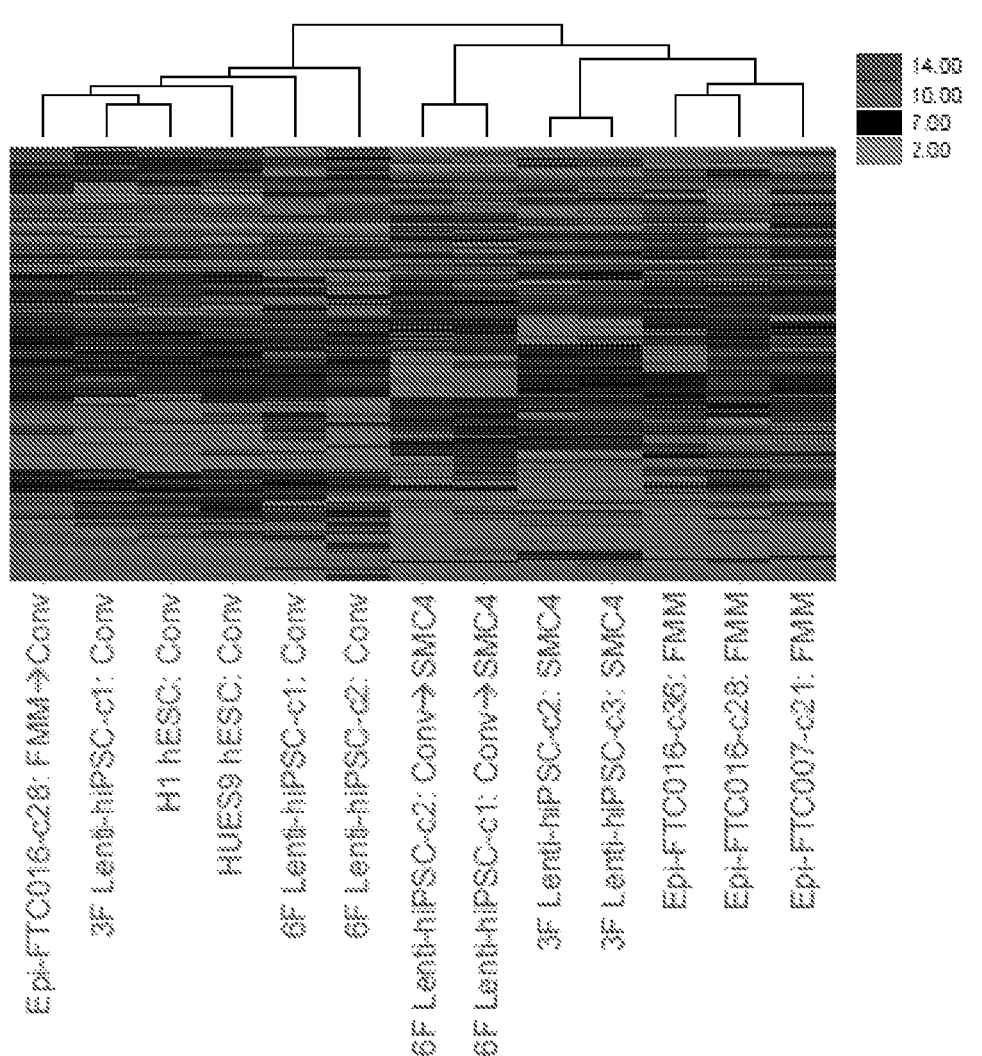

The global gene expression patterns were determined for hiPSCs derived from the following methods: i) episomal induction maintained in FMM, ii) episomal induction maintained in FMM but switched to conventional medium for three passages, iii) lentiviral induction maintained in SMC4; and iv) lentiviral induction maintained in conventional culture (FIG. 13A, 13B). Prior to evaluating the gene expression profiles, all lines were determined to be pluripotent, genomically stable; and able to differentiate to all three somatic lineages. Cluster analysis of differentially genes expressed between small molecule culture and conventional culture revealed that the hiPSC lines grouped based on current culture conditions and not by original derivation method and culture (FIG. 13B). Gene ontology classification of 300 genes displaying 2.5 fold expression differences identified differentiation and development as the main categories highly enriched in the conventional culture group while genes upregulated in small molecule culture group were mostly associated with regulation of cell proliferation and sex development (FIGS. 13C and 13D).

Figure 7A:
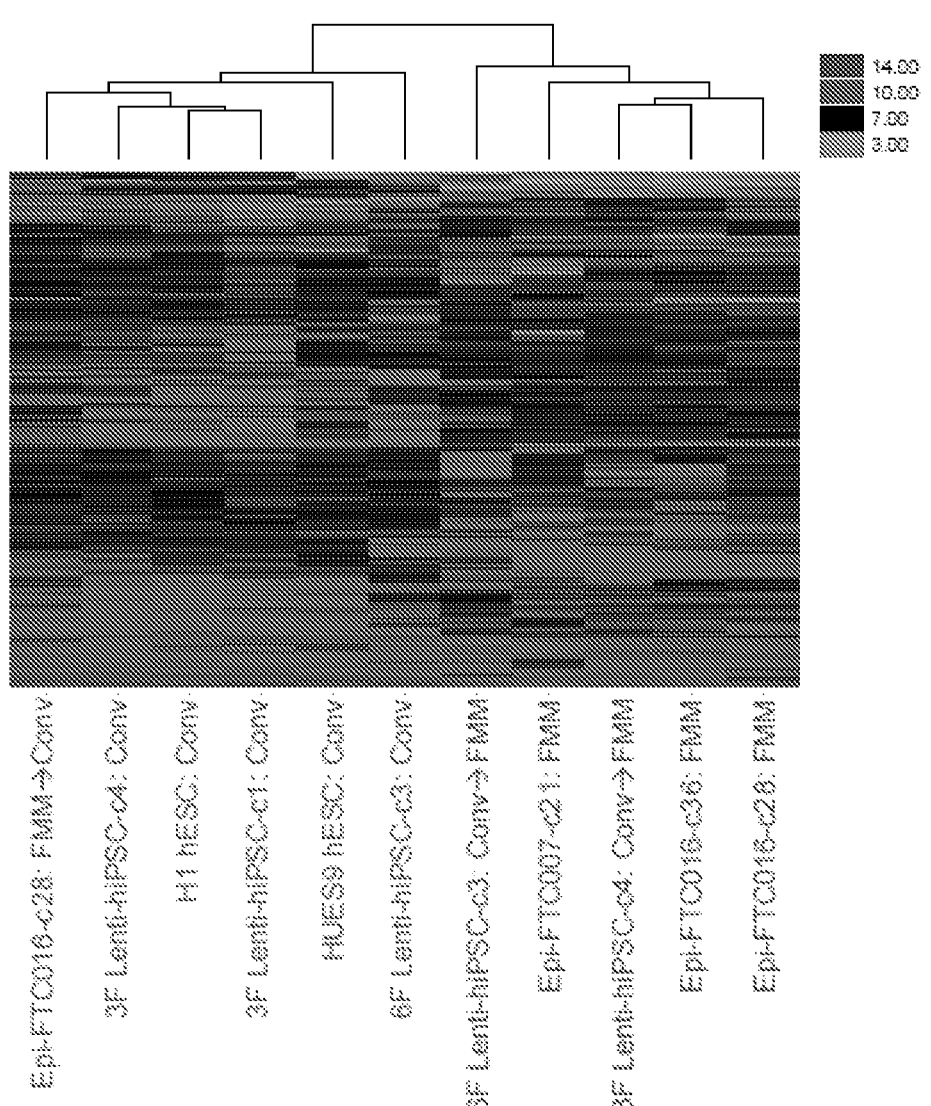

Gene expression analyses were repeated and FMM, conventional, or transition culture systems were directly compared (FMM, Conv, FMM→Conv, Conv→FMM; FIG. 13A). Cluster analysis produced two groups separated based on the current culture system regardless of method of generation or the prior culture system (FIG. 7A). For example, hiPSC cloneFTC016-c28 was generated and maintained under the FRM/FMM platform, prior to transition to conventional culture. This clone grouped with cultures maintained exclusively in conventional culture and not with its parental line maintained in FMM; comparable results were seen with lines such as an OKS lentiviral-induced hiPSC clone which was generated in conventional culture and grouped within the conventional set until transition to FMM, upon which it grouped within the FMM cluster (FIG. 7A). Gene ontology categorized conventional culture to be enriched with genes associated with differentiation and development (i.e., p-value=2.2E-10, pattern specification process; FIGS. 7B and 13E). Collectively, these data showed that genes associated with differentiation propensity are significantly reduced in FMM culture and hiPSCs can be adapted to the FMM culture platform to reduce spontaneous differentiation potential.

Figure 7D:
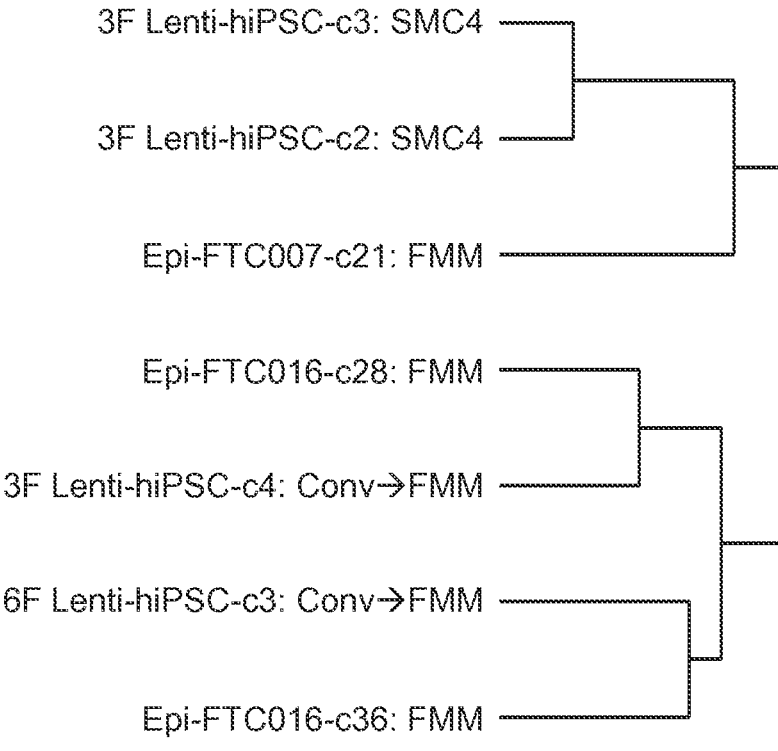
Figure 7E:
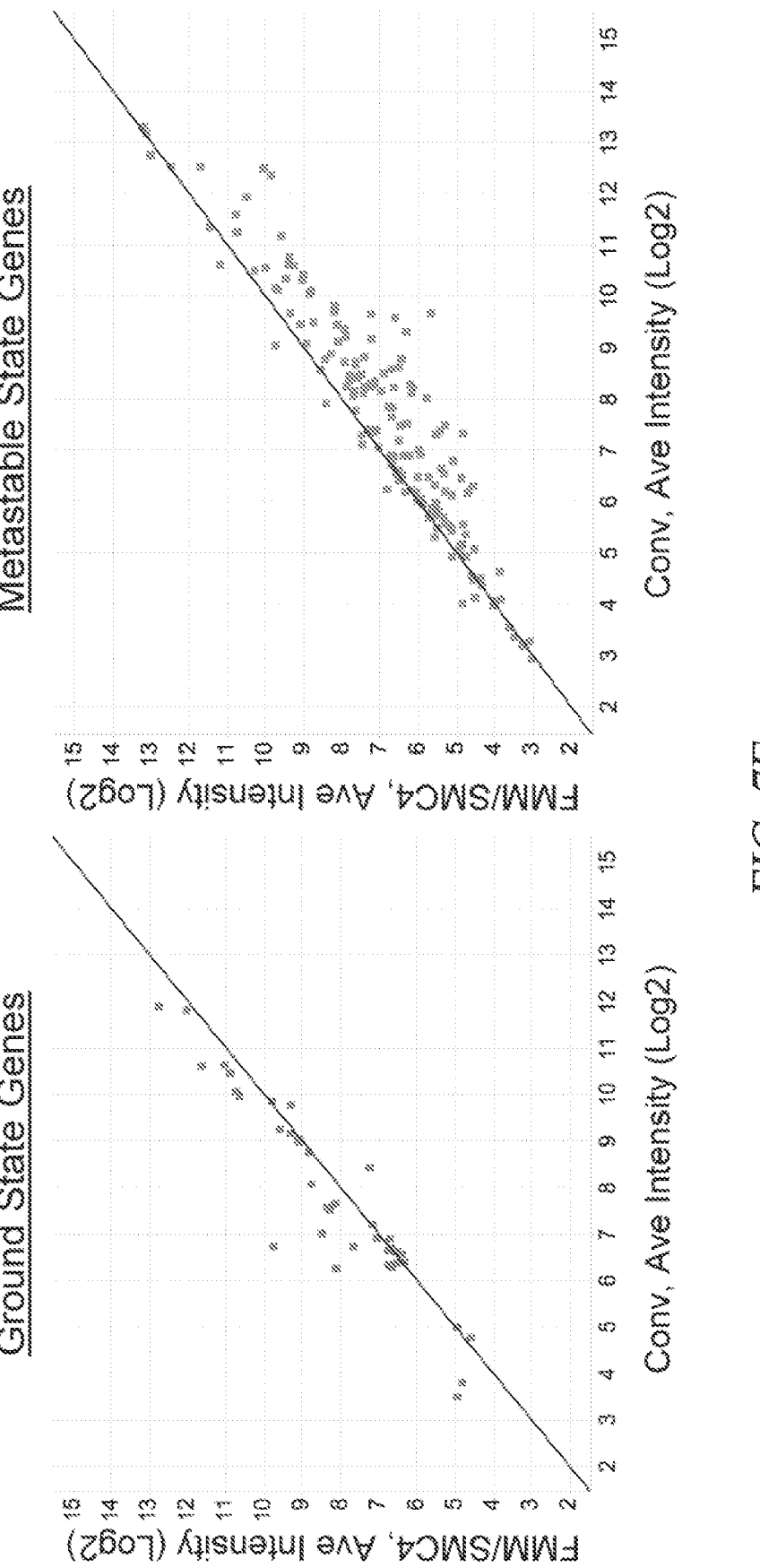

Gene lists were compiled to represent ground state and metastable states of human pluripotent stem cells (De Los Angeles et al., 2012; Han et al., 2011; Hanna et al., 2010a; Hirata et al., 2012; Nichols and Smith, 2012; Valamehr et al., 2012; Zhou et al., 2010) (FIG. 7C). Gene clustering based on these gene lists was performed for hiPSC lines in FMM or conventional culture (FIG. 7D). Similar to global gene expression comparison, the focused gene clustering showed a separation of the cell lines based on their current culture conditions with profiles appearing to be interconvertible. For example, hiPSC clone FTC016-c28 transitioned from FMM to conventional culture grouped with H1 hESC and not with its parental hiPSC line maintained in FMM (FIG. 7D). Similarly, a lentiviral hiPSC clone derived from a fibroblast line maintained in conventional culture grouped with HUES9 hESC and other hiPSC clones in conventional culture; however, when switched to FMM, it grouped with an episomal hiPSC derived from umbilical cord blood as well as other FMM cultured lines (FIG. 7D). The distribution of genes representative of the ground and metastable states within the two clusters was determined by plotting the average intensities for each probe set with respect to small molecule (SMC4/FMM) versus conventional culture (FIG. 7E). Surprisingly, the majority of genes associated with the ground state showed elevated expression in small molecule culture cluster, and increased expression of genes associated with metastable state was detected in the conventional culture cluster (FIG. 7E).

Figure 7F:
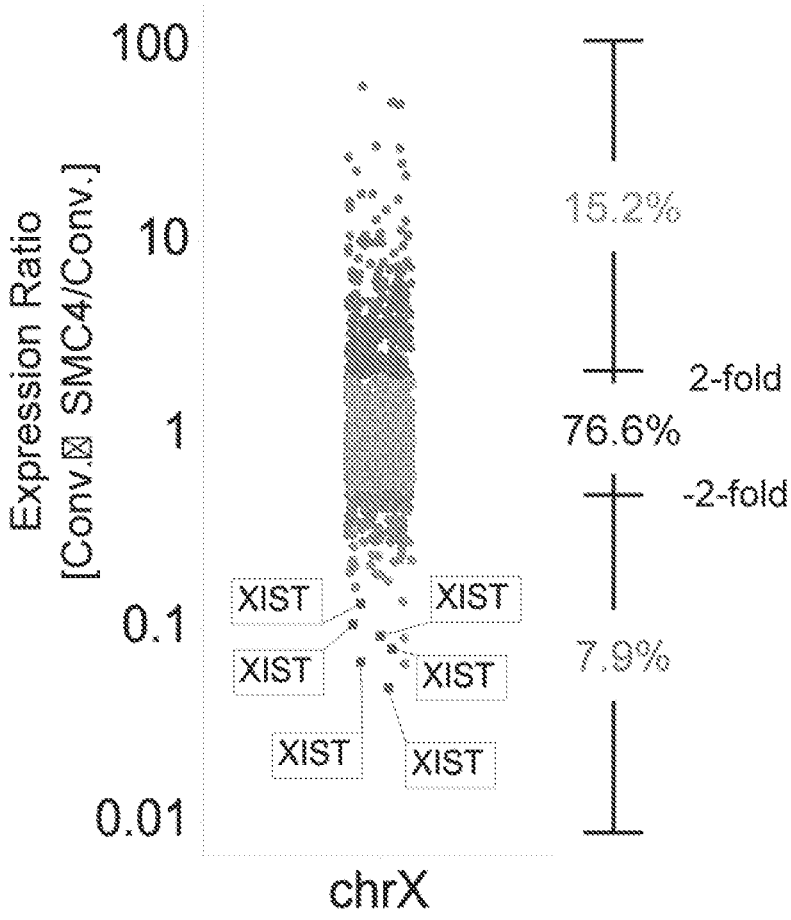
Figure 7G:
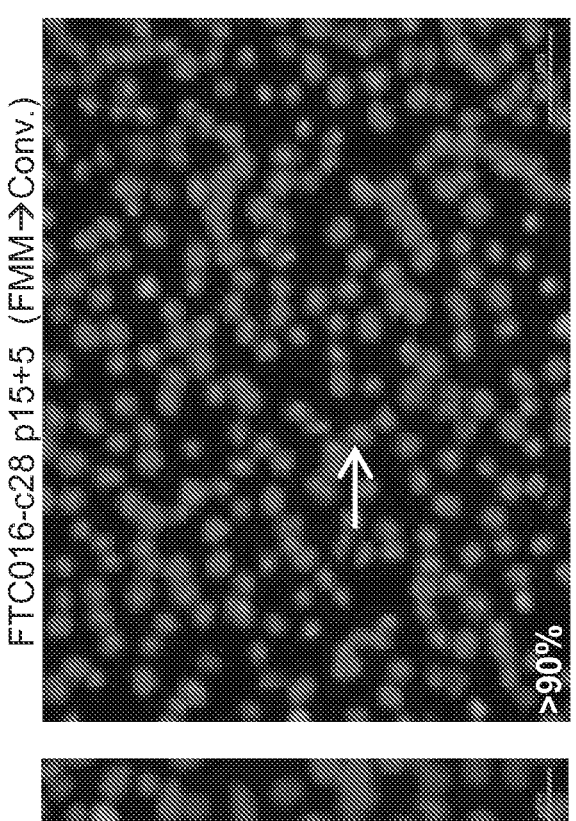
Figure 7G:
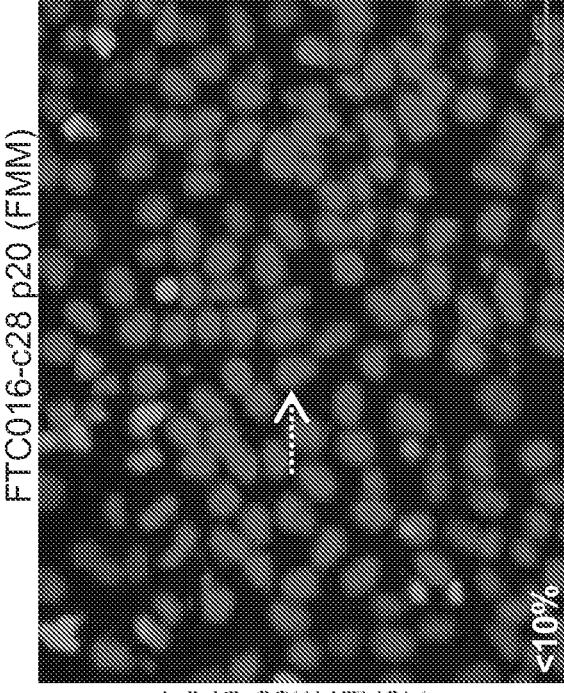

The X-inactivation state of hiPSCs cultured and maintained in conventional culture was compared to its counterpart adapted to small molecule culture and maintained for 10 passages (FIG. 7F). The hiPSC maintained in small molecule culture showed an increase in X chromosome gene expression when compared to conventional culture, which suggested reactivation of the silenced X chromosome (FIG. 7F). The noticeable exception was the X-inactive specific transcript (XIST) which was down-regulated in the switch to small molecule culture (FIG. 7F). Further evidence of X activation was provided by the differential staining of H3K27me3 in hiPSCs cultured in FMM relative to their counterpart culture adapted to conventional medium (FIG. 7G). The majority of hiPSCs in FMM lacked H3K27me3 staining; whereas, the majority of hiPSCs in conventional culture displayed H3K27me3 nuclear foci with the appearance of reduced nuclear size, which suggested X inactivation (<10% H3K27me3 staining in FMM compared to >90% H3K27me3 staining in conventional culture; FIG. 7G).

Example 6 hiPSC Maintenance in Small Molecule Culture

Derived hiPSCs (fibroblasts or blood-cell induced with various combinations of reprogramming factors including OCT4/NANOG/SOX2, OCT4/ECAT1/UTF1, or OCT4/ECAT1/UTF1/ESRRB/NANOG) were routinely passaged as single cells once confluency of the culture reached 75-90%. For single cell dissociation, hiPSCs were washed once with phosphate buffered saline (PBS) (Mediatech) and treated with Accutase (Millipore) for 3 to 5 min at 37° C. followed with pipetting to ensure single cell dissociation. The single cell suspension was then mixed in equal volume with conventional medium, centrifuged at 225 g for 4 min, resuspended in Fate Maintenance Media (FMM) and plated on hESC-qualified Matrigel (Corning) coated surfaces. Matrigel was prepared and used to coat surfaces per manufacturer's instructions. Passages were typically 1:3-1:6, tissue culture plates were previously coated with Matrigel for 1-4 hrs at 37° C., and fed every two to three days with FMM. Cell cultures were maintained in a humidified incubator set at 37° C. and 5% $CO_2$. Conventional medium consists of DMEM/F12 (Mediatech), 20% Knock-Out Serum Replacement (Life Technologies), 1× Glutagro (Mediatech), 1× Non-Essential Amino Acids (NEAA) (Mediatech), 1× Pen/Strep (Mediatech), and 100 µM β-Mercaptoethanol. FMM consists of conventional medium supplemented with 5 µM Thiazovivin (synthesized in-house), 0.4 µM PD0325901 (Biovision), 1 µM CHIR99021 (Biovision), 100 ng/mL bFGF (Life Technologies), and 10 ng/mL hLIF (Millipore). Flow analysis and morphology for cultures expanded in FMM is presented in FIGS. 18A-D and 19A-B. Cells expanded in FMM also demonstrated a normal karyotype over multiple passages as shown in FIGS. 20A-D.

Example 7

Reprogramming with Minimal Genes in Small Molecule Culture

Figure 14A:
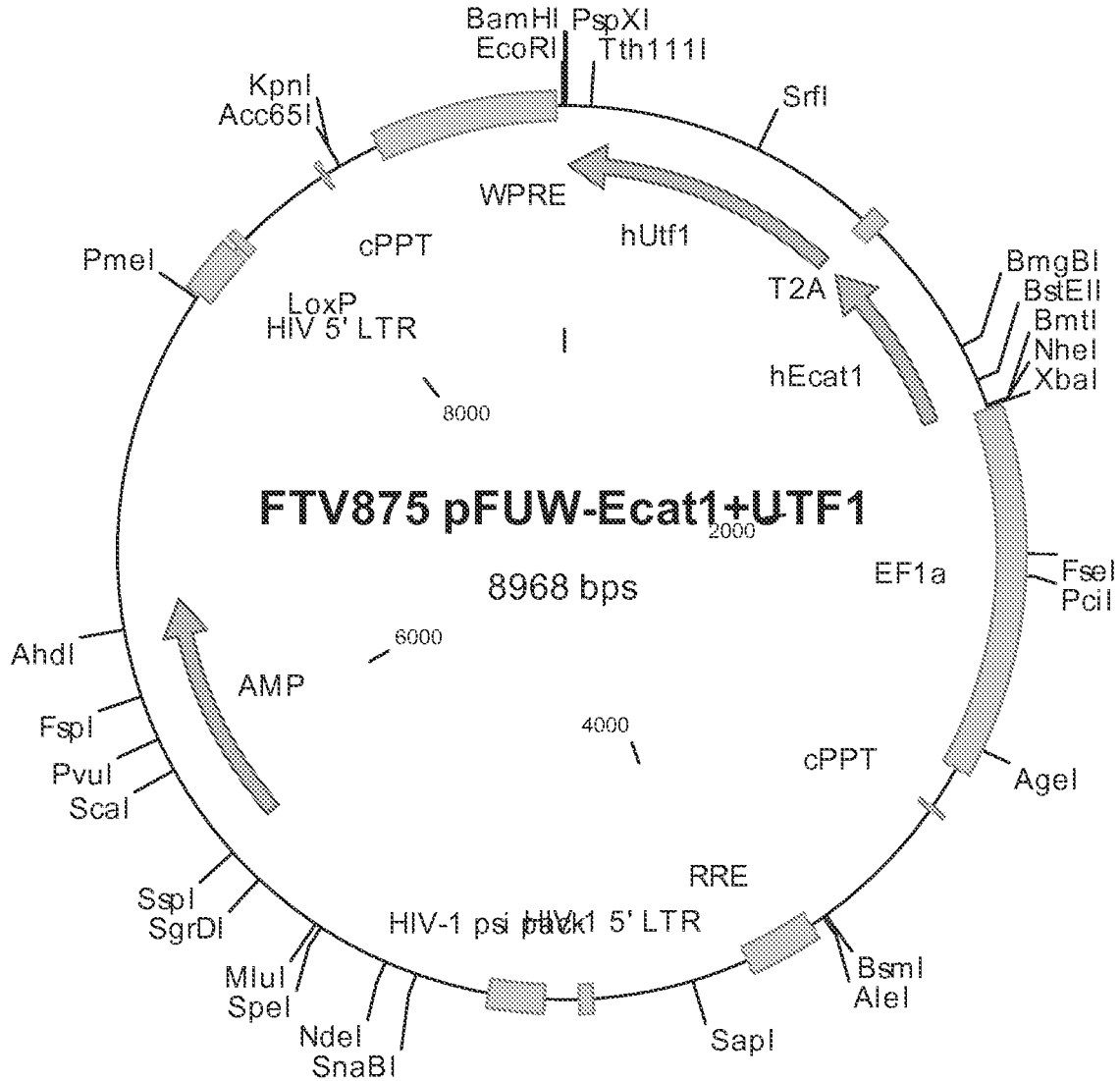
Figure 14B:
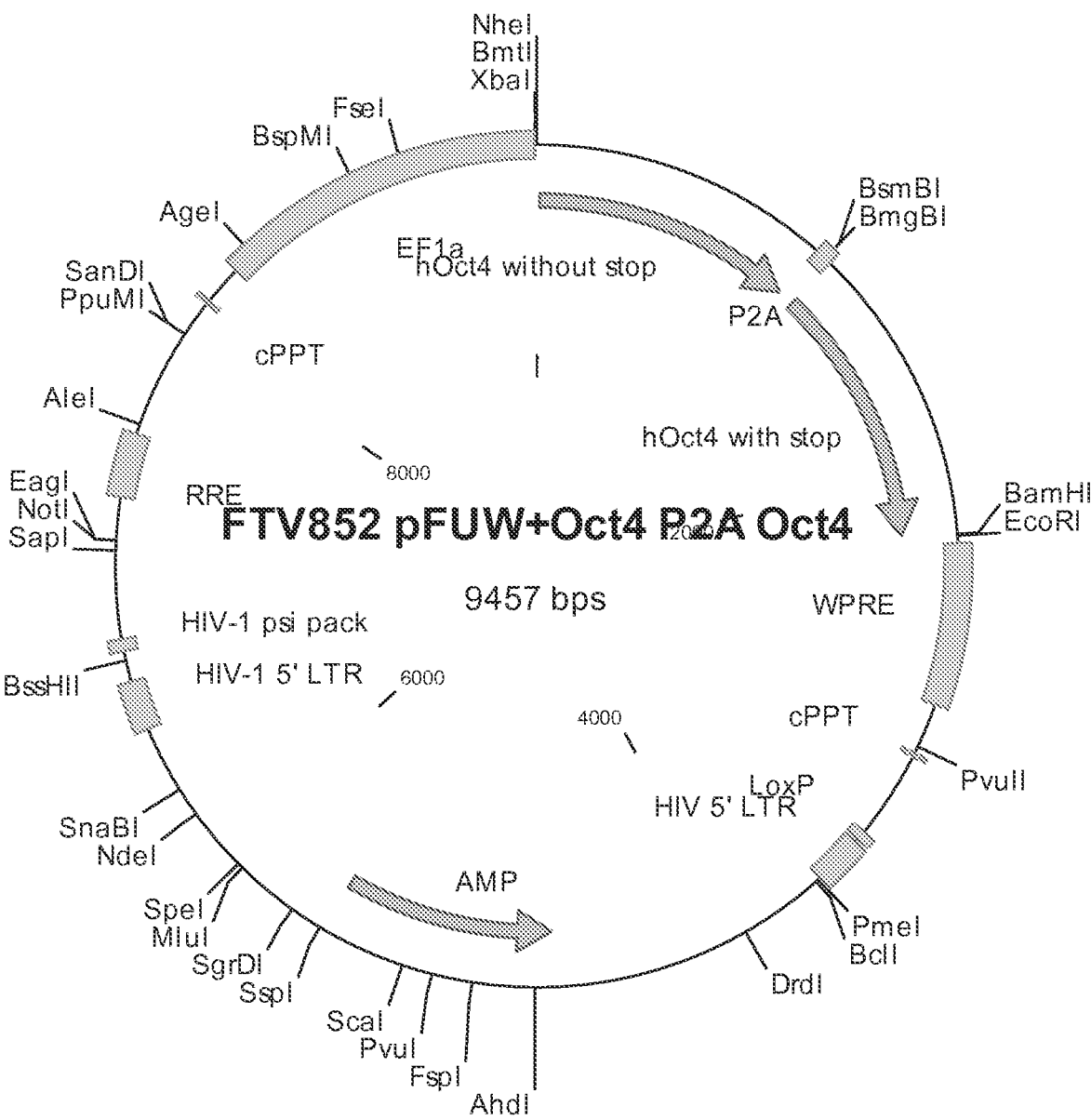
Figure 14C:
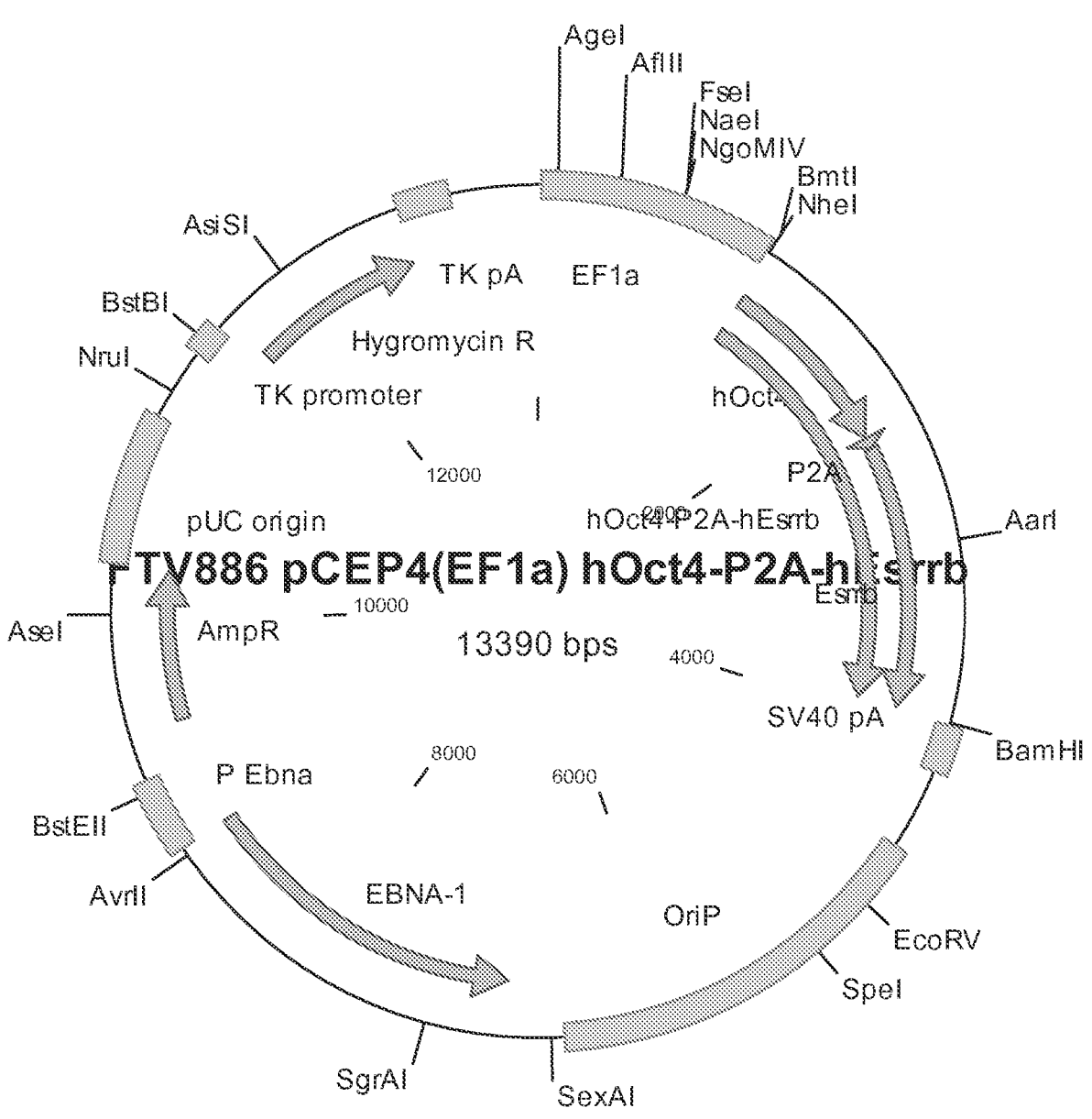
Figure 14D:
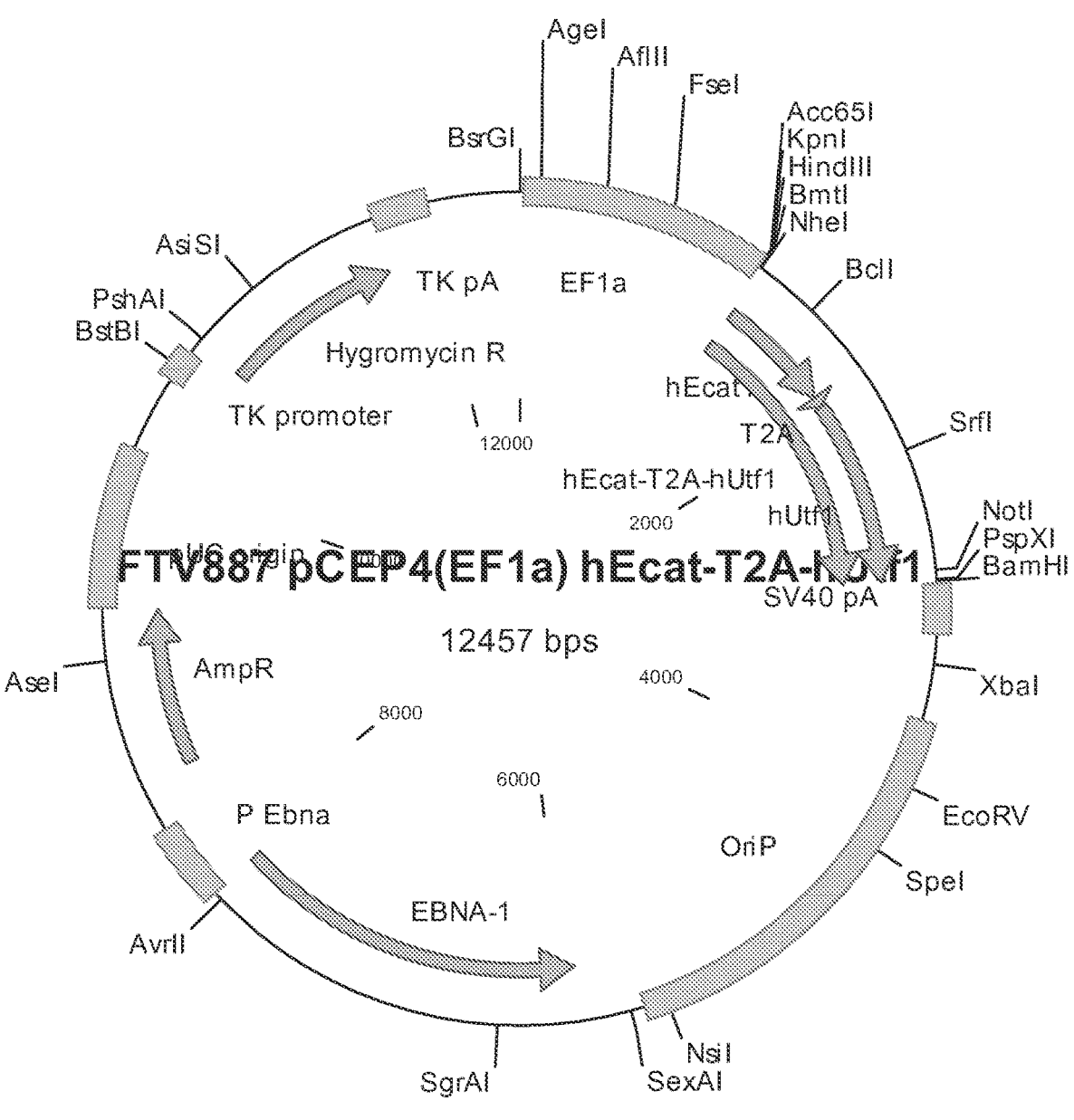
Figure 14E:
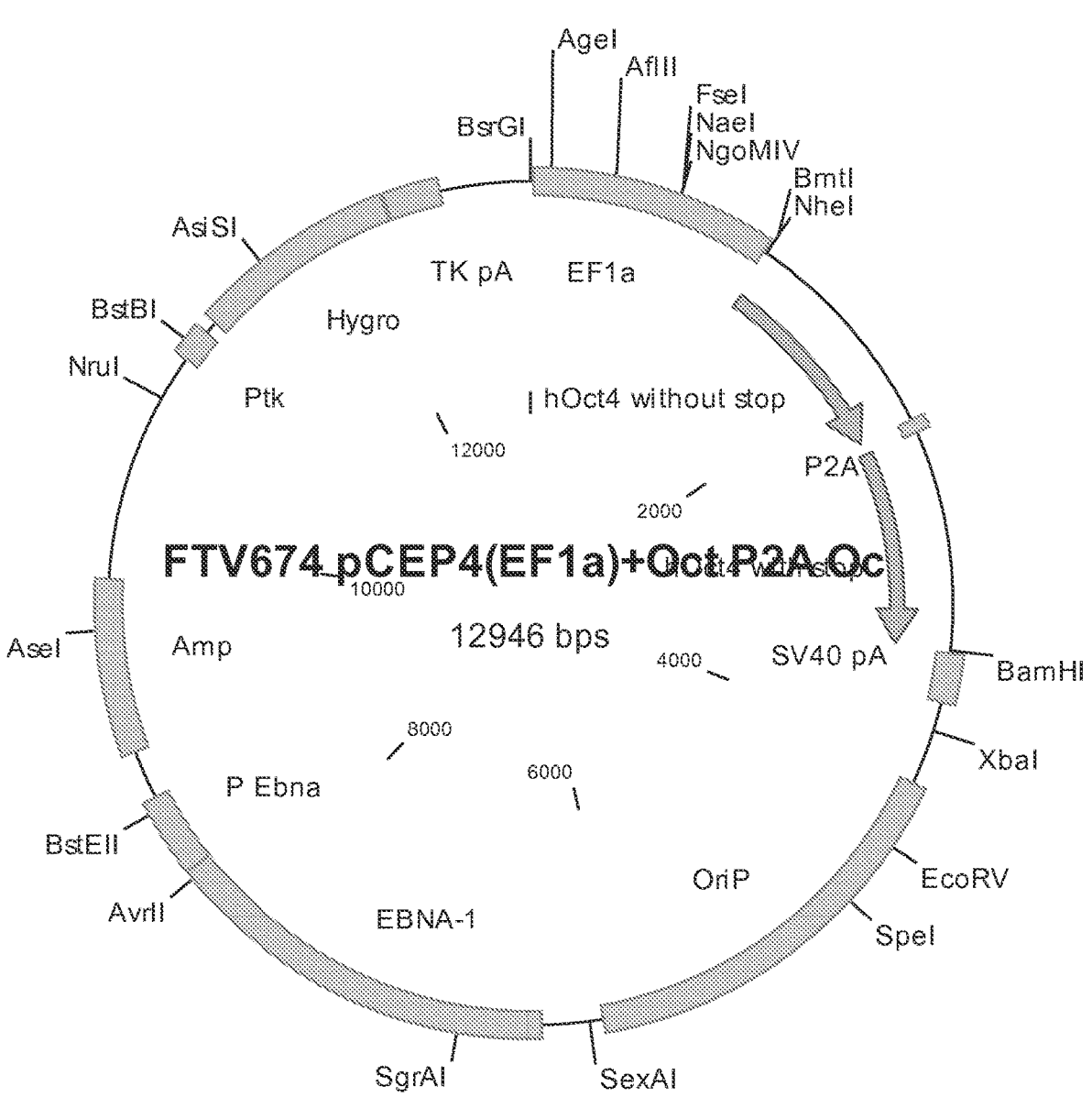
Figure 14F:
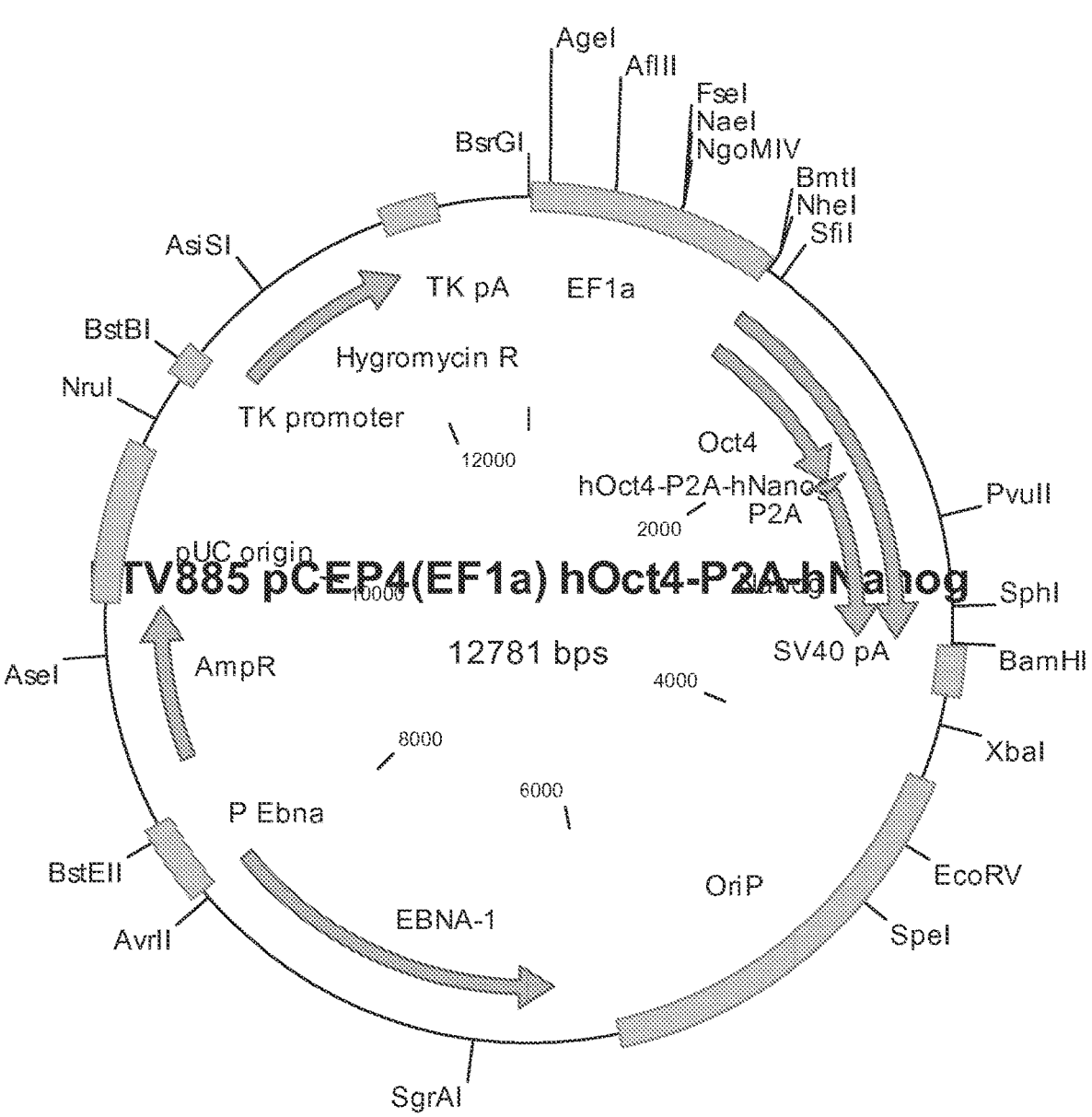

To initiate reprogramming, ectopic expression of reprogramming factors was induced by lentiviral transduction using NIL, traditional integrating lentivirus, or electroporation with episomal vectors. As illustrated in FIGS. 14A-B, the lentiviral expression system consisted of several features including an EF1α promoter, specific gene combinations (Table 3) and a LOXP site at the 3' end to allow for CRE-mediated excision of the integrated transgenes. Upon CRE-excision, the derived hiPSCs genome no longer contained transgenes and were essentially footprint-free. As illustrated in FIGS. 14C-F, the episomal constructs had unique features including an EF1α promoter and unique reprogramming factors. Upon transfection, the episomal constructs resided in the nucleus and acted in a trans-mediated fashion that did not integrate into the genome.

For lentivirus infection, the starting human fibroblast cells were seeded at $7×10^4$-$1×10^5$ cells per well of a 6-well plate coated with Matrigel (Corning) per manufacturer's instructions. Fresh lentiviral supernatant from 293T cells was added to the starting cells at a dilution of 1:2 (one part lentiviral supernatant:one part fibroblast medium). NIL viral supernatant was used at a 1× concentration and not diluted. If previously frozen virus was used, it was not diluted and used at a 1× concentration. Viral supernatants of various factors were combined (Table 3) up to a total of 2 mL of media per 6-well. This was supplemented with 5 µg/mL polybrene (Millipore) and 10 mM Hepes (Meditech) followed by spin infection. Six well plates were sealed with parafilm and centrifuged at 600 g for 90 min at 32° C. Plates were then transferred to 37° C. and 5% $CO_2$ incubators for 12-16 hrs. After incubation with lentivirus, the cells were washed with PBS and the culture medium was switched to 50/50 medium containing one part Fate Reprogramming Medium (FRM) and one part fibroblast medium. The medium was completely switched to FRM between 4 to 6 days post infection. FRM consists of conventional medium (described above) supplemented with 5 µM Thiazovivin (synthesized in-house), 0.4 µM PD0325901 (Biovision), 1 µM CHIR99021 (Biovision), 2 µM SB431542 (Biovision), 100 ng/mL bFGF (Life Technologies), 10 ng/mL hLIF (Millipore), 1× N2 Supplement (Life Technologies), and 1× B27 Supplement (Life Technologies). Once wells became confluent, cells were passaged onto 10 cm dishes previously coated with Matrigel. Passaging consisted of dissociation with Accutase (Millipore) onto Matrigel coated surface (as described above). Between days 14 and 18 or when iPSC colonies became present, the culture media was switched from FRM to FMM. The single cell dissociated cells were expanded onto Matrigel coated plates with FMM and maintained until flow cytometry sorting. Results for expression of hiPSC phenotype are presented in Table 3, FIGS. 15A-C (at 8-15 days), and FIGS. 16A-D, FIGS. 17A-B (Oct-4/Ecat1/UTF1/Esrrb/Nanog at week 4).

58

TABLE 3

| Reprogramming Factor Combinations and Expression of Pluripotent Phenotype | | | |
|---|---|---|---|
| | SSEA4/Tra181 Expression by Flow Cytometry | | |
| Vector System | Day 13-18 Flow (%) | Day 21-27 Flow (%) | iPSC Morphology |
| OCT4-P2A-OCT4 ECAT1-P2A-UTF1 | 0.00 | 0.06 | + |
| OCT4-P2A-OCT4 NANOG-P2A-ESRRB-T2A-LIN28 ECAT1-P2A-UTF1 | 0.02 | 0.19 | ++ |
| OCT4-P2A-ESRRB OCT4-P2A-NANOG ECAT1-P2A-UTF1 | 0.10 | 1.29 | ++ |
| OCT4-P2A-NANOG ECAT1-P2A-UTF1 | 0.05 | 0.14 | ++ |
| OCT4 -P2A-NANOG-T2A-SOX2 SV40LT | 0.14 | 0.90 | ++ |
| OCT4-P2A-OCT4 OCT4-P2A-NANOG-T2A-SOX2 SV40LT | 0.00 | 1.46 | ++ |
| OCT4-P2A-OCT4 ECAT1-P2A-UTF1 SV40LT | 0.03 | 0.90 | + |
| OCT4-P2A-DPPA2 OCT4-P2A-ESRRB ECAT1-P2A-UTF1 | 0.03 | 0.11 | + |
| OCT4-P2A-OCT4 OCT4-P2A-ESRRB ECAT1-P2A-UTF1 | 0.02 | 0.12 | + |

For episomal vector reprogramming, transfection of fibroblast or cord blood cells using the plasmids illustrated in FIG. 13 was conducted using the NEON Transfection System (Life Technologies). Approximately, a total of 3 µg of episomal plasmids containing reprogramming factors was co-transfected with EBNA (either in the form of mRNA or as a cassette in cloning plasmid pCDNA) into $5×10^5$ fibroblast cells or $2.5×10^5$ cord blood cells using settings 1650v/10 ms/3 pulses in appropriate buffers as described by product manual. The transfected cells were seeded directly onto a well of a 6-well plate coated with Matrigel containing either fibroblast medium or cord blood culture medium (depending on the cell type) supplemented with 4 ng/mL bFGF and 5 µg/mL fibronectin (BD Biosciences) without antibiotics. Cord blood culture medium consists of SFMII+ CC110 (Stem Cell Technologies). Twenty-four hours post transfection, FRM was added to the culture in equal volume. For fibroblast cultures, forty-eight hours post transfection 50 µg/mL hygromycin (Corning) was added to the culture. The culture medium was switched entirely to FRM on day 5 with hygromycin removed 7 days post transfection. All reprogramming cultures were switched to FMM 14 days post transfection. For cord blood cultures, twenty-four hours post transfection, FRM was added in equal volume and continuously added every few days until day 14 post transfection where the culture was aspirated and replaced with entirely FMM. In both cases, clusters of adherent rounded cells were seen around 5 to 7 days post transfection. Once in FMM, all reprogramming cultures were maintained and single cell passaged using Accutase on Matrigel coated surfaces (described above). The single cell dissociated cells were expanded onto Matrigel coated plates with FMM and maintained until flow cytometry sorting.

Example 8

Influence of Reprogramming Factors and Their Stoichiometry

Human fibroblast cells were spin infected with lentivirus containing several reprogramming factors. All samples were infected with OCT4, SOX2, NANOG, and SV40LT using a lentiviral plasmid not containing an antibiotic selection factor. Cells were co-infected with a single lentiviral plasmid containing a puromycin selection cassette as well as various reprogramming factors. These factors included either OCT4-P2A-SOX2, OCT4-P2A-NANOG-T2A-SOX2, or OCT4-P2A-OCT4. Two days post infection, 500 ng/mL of Puromycin (Life Technologies) in 50/50 media was added to each to well. On Day 5, after three days of Puromycin selection, media was changed to FRM without Puromycin. On Day 14, media was switched to FMM. Between Days 24 and 27, flow analysis was conducted for SSEA4+/TRA181+ populations. It was observed that increased OCT4 expression significantly improves reprogramming efficiency (FIG. 23A).

Example 9

Experimental Procedures
hiPSC Maintenance in Conventional Culture System Conventionally cultured hiPSCs were maintained on mitomycin C treated MEF (Millipore) feeder cells and cultured with conventional medium (referred to as conventional medium in the text) containing DMEM/F12 (Mediatech), 20% v/v knockout serum replacement (Life Technologies), 1% v/v non-essential amino acids (Mediatech), 2 mM L-glutamine (Mediatech), 100 µM β-mercaptoethanol (Life Technologies) and 10 ng/mL bFGF (Life Technologies). Upon confluency, conventionally cultured hiPSCs were enzymatically dissociated using 1 mg/mL collagenase IV (Life Technologies) for 7 min at 37° C. followed by mechanical dissociation into small pieces (termed as clump passaging), collected and dilute passaged 1:3-1:4 onto freshly seeded feeder cells every 5-7 days with daily addition of conventional medium. In case of excessive spontaneous differentiation, colonies were manually picked and cut into small pieces using the tip of Insulin Syringe (Becton Dickinson) and transferred to freshly seeded feeder cells. Cell cultures were maintained in a humidified incubator set at 37° C. and 5% CO2.
Reprogramming of Somatic Cells To initiate reprogramming, ectopic expression of reprogramming factors were induced by lentiviral transduction or episomal vector transfection. Lentiviral transfection was followed as previously described (Valamehr et al., 2012). Briefly, the starting cells were plated at $1 \times 10^5$ cells per well of a 6-well plate on Matrigel (BD Biosciences) coated surface. Unless specified, all Matrigel coatings consists of adding Matrigel solution (1 aliquot of Matrigel resuspended in 25 mL DMEM/F12) to tissue culture surfaces and allowing for 2-4 hrs incubation at 37° C. Supernatant from 293T cells generating lentivirus expressing transgene OCT4/SOX2/KLF4 was added to the starting cells at a dilution of 1:2 (one part lentiviral supernatant:one part fibroblast medium), supplemented with 4 µg/mL polybrene (Millipore), and transferred to 37° C. and 5% CO2 for 12-16 hrs. Fibroblast medium: DMEM (Mediatech), 10% FBS (Life Technologies), 1× glutamax (Life Technologies), 1× non-essential amino acids (Mediatech). After incubation with lentivirus, the cells were washed three times with PBS and fed with fibroblast medium. 48 hrs post transfection, the culture medium was switched to 50/50 medium containing one part FRM (or SMC4) and one part fibroblast medium. The medium was completely switched to FRM (or SMC4) once the culture was passaged into a larger vessel, usually between days 4 to 6 post infection. Passaging consists of dissociation with Accutase onto Matrigel coated surface (as described below). Cultures were maintained in FRM (or SMC4) until the next application.

For episomal vector reprogramming, transfection of fibroblast or cord blood cells using gene set OCT4/SOX2/NANOG/KLF4/LIN28/MYC/SV40LT (A14703, Life Technologies) was conducted using NEON Transfection System (Life Technologies). Approximately, 4 µg of vector set was transfected into $5 \times 10^5$ fibroblast cells or $2.5 \times 10^5$ cord blood cells using settings 1650v/10 ms/3 pulses in appropriate buffers as described by product manual. The transfected cells were plated directly into a 10 cm dish (fibroblast) or a well of 6-well plate (cord blood) coated with Matrigel and containing either fibroblast culture medium or cord blood culture medium (depending on the cell type) supplemented with 10 ng/mL bFGF and 5 µg/mL fibronectin (BD Biosciences). Cord blood culture medium: SFMII+CC110 (Stem Cell Technologies). Twenty-four hours post transfection, FRM was added to the culture in equal volume. For fibroblast cultures, forty-eight hours post transfection 50 µg/mL hygromycin (Mediatech) was added to the culture. The culture medium was switched to entirely FRM on day 5 with hygromycin removed on day 7 post transfection. All reprogramming cultures were switched to FMM on day 14 post transfection. For cord blood cultures, twenty-four hours post transfection, FRM was added in equal volume and continuously added every few days until day 14 post transfection where the culture was aspirated and replaced with entirely FMM. In both cases, cluster of adherent rounded cells were seen around days 5 to 7 post transfection. Once in FMM all reprogramming cultures were maintained and single cell passaged using Accutase. The single cell dissociated cells were expanded onto Matrigel coated plates with FMM and maintained until flow cytometry sorting. In vitronectin (Life Technologies) surface coating studies, all aspects were kept the same except for the substitution of Matrigel for Vitronectin. For reduced factor episomal reprogramming, pCEP4 (Life Technologies) vector backbone was constructed to contain OCT4-P2A-OCT4, OCT4-P2A-SOX2 or OCT4-P2A-NANOG-T2A-SOX2 under the regulation of EF1α promoter. The transfection of reduced factor episomal vectors followed the same protocol as described above with the exception of few modifications. EBNA was co-transfected as either EBNA mRNA (20 µg) or vector cassette (2 µg) (Howden et al., 2006). Hygromycin selection was maintained for 10 days and FMM was introduced on day 16.
Generation of Lentivirus 293Ts (ATCC) were maintained in fibroblast media without antibiotics and were not allowed to reach over 80% confluency. Fibroblast medium consisted of DMEM (Mediatech), 10% Fetal Bovine Serum (FBS) (Life Technologies), 1× Glutagro (Mediatech), and 1×NEAA (Mediatech). Cells were passaged by first washing with PBS followed by a 4 min incubation at 37° C. with 0.05% Trypsin (Mediatech). Dissociated cells were resuspended in fibroblast media, centrifuged at 225 g for 4 min and seeded onto desired plates. To generate integrating lentivirus, 293Ts were passaged on Day 1 at $3.5 \times 10^6$ cells per 10 cm dish for each viral prep. On Day 2, the media was changed to 10 mL of fresh fibroblast media 1 hour prior to transfection. DNA was transfected using CalPhos Kit (Clontech). The following were combined for the transfection: 5 µg of lentiviral cloning plasmid containing the gene(s) of interest, 3.2 μg of packaging plasmid pPAX, 630 ng of packaging plasmid pMDG, 87 μL Calcium Solution, and water up to 700 μL. 700 μL of HBS Solution was added while creating bubbles using a 1 mL serological pipette. This was incubated at room temperature for 15 min and then added drop-wise to a 10 cm plate of 293Ts. On Day 3, the viral supernatant was removed, discarded, and 15 mL of fresh fibroblast media added to the plate. On Day 4, 48 hrs post transfection, the viral supernatant was collected and stored at 4° C. 15 mL of fibroblast media was added to the plate. On Day 5, 72 hrs post transfection, the viral supernatant was collected and added to the Day 4 supernatant. This viral pool was filtered using a 0.45 μm filter and checked for titer using a Lenti-X GoStix (Clontech). Virus was either used for an infection or frozen in aliquots at –80° C. To generate Non-Integrating Lentivirus (NIL) (Invivogen), the protocol was followed per manufactures instructions using a T75 flask for each viral prep. Viral supernatants were collected 48, 72, and 96 hours post-transfection, pooled, filtered and titered as described above. NIL virus was either used for an infection or frozen in aliquots at –80° C.

hiPSC Maintenance in Small Molecule Culture

Derived hiPSCs were routinely passaged as single cells once confluency of the culture reached 75-90%. Note that over-confluency may result in differentiation. For single cell dissociation, hiPSCs were washed once with phosphate buffered saline (PBS) (Mediatech) and treated with Accutase for 3 to 5 min at 37° C. followed with pipetting to ensure single cell dissociation. The single cell suspension was then mixed in equal volume with conventional medium, centrifuged at 225 g for 4 min, resuspended in FMM and plated on Matrigel coated surface. Passages were typically 1:4-1:8, transferred tissue culture plates previously coated with Matrigel for 2-4 hrs in 37° C. and fed every other day with FMM. Cell cultures were maintained in a humidified incubator set at 37° C. and 5% CO2. Medium formulations for FMM and FRM are described in Table 1. SMC4 culture is discussed previously (Valamehr et al., 2012). Briefly, small molecules 0.4 mM PD0325901 (Biovision), 1 mM CHIR99021 (Biovision), 5 mM Thiazovivin and 2 mM SB431542 (Biovision) are added to conventional culture medium and passaged according to protocol.

Flow Cytometry Analysis and Sorting

Single cell dissociated (described above) reprogramming pools were resuspended in chilled staining buffer containing Hanks' Balanced Salt Solution (MediaTech), 4% fetal bovine serum (Invitrogen), 1× penicillin/streptomycin (Mediatech) and 10 mM Hepes (Mediatech). Conjugated primary antibodies, including SSEA4-FITC, TRA1-81-Alexa Fluor-647 and CD30-PE (BD Biosciences), were added to the cell solution and incubated on ice for 15 min. All antibodies were used at 7-10 μL in 100 μL staining buffer per million cells. The solution was washed once in staining buffer, spun down at 225 g for 4 min and resuspended in staining buffer containing 10 μM Thiazovivin and maintained on ice for flow cytometry sorting. Flow cytometry sorting was performed on FACS Aria II (BD Biosciences) using gating strategy described supra. The sorted cells were directly ejected into 96-well plates using the 100 μM nozzle, at concentrations of 3 and 9 events per well. Sorting 3 cells per well was our preferred concentration as we noticed that events sorted did not necessarily correlate to actual number of cells seen in each well post sort and that 3 cells per well gave us a preferred number of wells containing individual colonies. Each well was prefilled with 200 μL FMM supplemented with 5 μg/mL fibronectin and 1× penicillin/streptomycin (Mediatech) and previously coated overnight with 5× Matrigel. 5× Matrigel precoating includes adding one aliquot of Matrigel into 5 mL of DMEM/F12, then incubated overnight at 4° C. to allow for proper resuspension and finally added to 96-well plates at 50 μL per well followed by overnight incubation at 37° C. The 5× Matrigel is aspirated immediately before the addition of media to each well. Upon completion of the sort, 96-well plates were centrifuged for 1-2 min at 225 g prior to incubation. The plates were left undistributed for seven day. On the seventh day, 150 μL of medium was removed from each well and replaced with 100 μL FMM. Wells were refed with an additional 100 μL FMM on day 10 post sort. Colony formation was detected as early as day 2 and most colonies were expanded between days 7-10 post sort. In the first passage, wells were washed with PBS and dissociated with 30 μL Accutase for approximately 10 min at 37° C. The need for extended Accutase treatment reflects the compactness of colonies that have sat idle in culture for prolonged duration. After cells are seen to be dissociating, 200 μL of FMM is added to each well and pipetted several times to break up the colony. The dissociated colony is transferred to another well of a 96-well plate previously coated with 5× Matrigel and then centrifuged for 2 min at 225 g prior to incubation. This 1:1 passage is conducted to spread out the early colony. Subsequent passages are done routinely with Accutase treatment for 3-5 min and expansion of 1:4 into larger wells previously coated with 1× Matrigel in FMM. Flow cytometry analysis was performed on Guava EasyCyte 8 HT (Millipore) and analyzed using FCS Express 4 (De Novo Software).

Real-Time RT-PCR and Fluidigm Analysis

Total RNA was isolated using Pico Pure RNA Isolation Kit (Life Technologies). Complimentary DNA (cDNA) was reverse transcribed from 100 ng of isolated total RNA using the iScript cDNA Synthesis Kit (Bio-Rad). The cDNA was then used for pre-amplification of 22 specific target genes and two reference control genes using the TaqMan PreAmp Master Mix Kit (Life Technologies) and a 0.2× concentration of pooled TaqMan assays. Specific target amplification (STA) from cDNA was performed using 14 cycles of amplification with the standard cycling conditions stated in the manufacturer's protocol. The pre-amplified cDNA reactions (n=48) were diluted 1:5 (in sterile water) and used as template for the real-time quantitative PCR reactions. 48.48 Dynamic arrays (Fluidigm) were loaded using a NanoFlex IFC Controller MX (Fluidigm) with TaqMan assays loaded in duplicate and real-time reactions were performed using a BioMark Real-Time PCR System (Fluidigm). Results were analyzed using BioMark Real-Time PCR Analysis software (Fluidigm). Samples with cycle thresholds (Cts) above 32 were excluded from the calculations. Average Cts were calculated from the assay duplicates and delta-delta Cts (ΔΔCt) were calculated using the mean of two reference genes (GAPDH and HPRT1) against the median of six control MEF cell lines (OSK hiPSCs on MEF and H1 ESCs). Relative gene expression (RQ) results are displayed in Excel (Microsoft) in heat map format.

TABLE 4

| FAM-labeled TaqMan probes | | | |
|---|---|---|---|
| Assay ID | Catalog Number (Life Tech.) | Gene Symbol | RefSeq |
| Hs00232764_m1 | 4331182 | FOXA2 | NM_021784.4; NM_153675.2 |
| Hs00173490_m1 | 4331182 | AFP | NM_001134.1 |
| Hs00171403_m1 | 4331182 | GATA4 | NM_002052.3 |
| Hs00751752_s1 | 4331182 | SOX17 | NM_022454.3 |
| Hs00610080_m1 | 4331182 | T | NM_003181.2 |
| Hs00607978_s1 | 4331182 | CXCR4 | NM_003467.2; NM_001008540.1 |
| Hs00415443_m1 | 4331182 | NODAL | NM_018055.4 |
| Hs02330075_g1 | 4331182 | MYOD1 | NM_002478.4 |
| Hs00240871_m1 | 4331182 | PAX6 | NM_001127612.1 |
| Hs00801390_s1 | 4331182 | TUBB3 | NM_001197181.1; NM_006086.3 |
| Hs00374280_m1 | 4331182 | STAT3 | NM_139276.2; NM_213662.1; NM_003150.3 |
| Hs04260366_g1 | 4331182 | NANOG | NM_024865.2 |
| Hs00602736_s1 | 4331182 | SOX2 | NM_003106.3 |
| Hs00399279_m1 | 4331182 | ZFP42 | NM_174900.3 |
| Hs01003405_m1 | 4331182 | DNMT3B | NM_001207055.1; NM_001207056.1; NM_006892.3; NM_175848.1; NM_175850.2; NM_175849.1 |
| Hs00702808_s1 | 4331182 | LIN28A | NM_024674.4 |
| Hs99999003_m1 | 4331182 | MYC | NM_002467.4 |
| Hs01081364_m1 | 4331182 | DNMT3L | NM_013369.2; NM_175867.1 |
| Hs00360439_g1 | 4331182 | KLF2 | NM_016270.2 |
| Hs00222238_m1 | 4331182 | OTX2 | NM_172337.1; NM_021728.2 |
| Hs00242962_m1 | 4331182 | PAX7 | NM_001135254.1; NM_002584.2; NM_013945.2 |
| Hs00414521_g1 | 4331182 | DPPA2 | NM_138815.3 |
| Hs00216968_m1 | 4331182 | DPPA4 | NM_018189.3 |
| Hs99999905_m1 | 4331182 | GAPDH | NM_002046.4 |
| Hs01003267_m1 | 4331182 | HPRT1 | NM_000194.2 |

| Custom-made TaqMan Gene Expression Assays | | |
|---|---|---|
| Gene | Forward Primer | Reverse Primer |
| OCT4 | GGGTTTTTGGGATTAAGTTCTTCA (SEQ ID NO: 27) | GCCCCCACCCTTTGTGTT (SEQ ID NO: 11) |
| KLF4 | AGCCTAAATGATGGTGCTTGGT (SEQ ID NO: 28) | TTGAAAACTTTGGCTTCCTTGTT (SEQ ID NO: 12) |

Testing Presence of Transgenes

Genomic DNA was isolated using QIAamp® DNA Mini Kit and Proteinase K digestion (Qiagen). 100 ng of the genomic DNA was amplified using transgene-specific primer sets (Table 5 below) (Yu et al., 2007) using Taq PCR Master Mix Kit (Qiagen). The PCR reactions were run for 35 cycles as follows: 94° C. for 30 sec (denaturation), 60-64° C. for 30 sec (annealing) and 72° C. for 1 min (extension). Genomic DNA from fibroblasts and hiPSCs generated using lentiviral methods were used as negative controls. DNA of the episomal constructs was used as positive control.

TABLE 5

| | Transgene specific primer sets | |
|---|---|---|
| Amplified region | Forward | Reverse |
| Oct4-Oct4 region of episomal transgene | CAGGCCCGAAAGAGAA AGCG (SEQ ID NO: 13) | GGAGGGCCTTGGAAGCTTA G (SEQ ID NO: 14) |
| Oct4-NANOG region of episomal transgene | TATACACAGGCCGATGT GGG (SEQ ID NO: 15) | TTGACCGGGACCTTGTCTTC (SEQ ID NO: 16) |
| OCT4-SOX2 region of episomal transgene | GTGGTCCGAGTGTGGTT CTG (SEQ ID NO: 17) | GTTCTCCTGGGCCATCTTGC (SEQ ID NO: 18) |
| Lin28-SV40pA episomal transgene | AAGCGCAGATCAAAAGG AGA (SEQ ID NO: 19) | CCCCCTGAACCTGAAACAT A (SEQ ID NO: 20) |
| WPRE lentiviral element | TGCTTCCCGTATGGCTTT C (SEQ ID NO: 21) | AAAGGGAGATCCGACTCGT CTG (SEQ ID NO: 22) |
| EBNA1 | ATCGTCAAAGCTGCACA CAG (SEQ ID NO: 23) | CCCAGGAGTCCCAGTAGTC A (SEQ ID NO: 24) |
| Human GAPDH | GTGGACCTGACCTGCCG TCT (SEQ ID NO: 25) | GGAGGAGTGGGTGTCGCTG T (SEQ ID NO: 26) |

Immunocytochemistry Analysis

Cells were fixed using 4% v/v paraformaldehyde (Alfa Aesar), washed three times with PBS containing 0.2% v/v Tween (PBST) (Fisher Scientific) and permeablized using 0.15% v/v TritonX-100 (Sigma-Aldrich) in PBS for 1 hr at 25° C. After permeabilization, cells were blocked with 1% v/v BSA (Invitrogen) in PBST (PBSTB) (Fisher Scientific) for 30 min at 25° C. After gentle removal of PBSTB, cells were incubated with primary antibody in PBSTB overnight at 4° C. Primary antibodies used in this study include OCT4 (Santa Cruz), NANOG (Santa Cruz), TRA160 (Millipore), TRA1-81 (Millipore), SSEA4 (Millipore), β-III Tubulin (TUJ1, R&D Systems), α-Smooth Muscle Actin (Sigma), FoxA2 (R&D Systems), Sox17 (R&D Systems), NESTIN (Abcam) and Alpha-1-Fetoprotein (Dako). After the overnight incubation, cells were washed three times with PBST and stained with secondary antibody (Alexa Fluor 488 or 555; Invitrogen) diluted 1:250 in PBSTB for 1 hr at 37° C. The cells were washed three times in PBST and stained with Hoechst dye (Invitrogen). For H3K27me3 staining analysis, hiPSCs were grown 72 to 96 hrs on cover slips and fixed with 4% paraformaldehyde (Electron Microscopy Science, EMS) in PBS for 15 min at 25° C. Cell permeabilization was performed with 0.1% Triton X-100 in PBS for 1 hour at 25° C., and then cells were incubated with blocking solution (1% BSA in PBS) for 30 min at 25° C. After blocking, cover slips were incubated with 1:1600 dilution of anti-trimethyl-histone H3 (Lys27) antibody (Millipore 07-449, H3K27me3) in blocking solution, overnight at 4° C. Secondary antibodies were Alexa Fluor 555 Goat-anti-Rabbit IgG (Life Technologies, A21429). The nuclei were counterstained with DAPI and viewed with an Axio Observer Inverted Microscope (Carl Zeiss). Images were captured with the AxioVS40 v4.8.1.0 (Carl Zeiss Imaging Solutions Gmbh).

Cells reprogrammed according to Example 7 were fixed using 4% v/v paraformaldehyde (Alfa Aesar), washed with PBS (Mediatech) and permeabilized using 0.15% v/v TritonX-100 (Sigma-Aldrich) in PBS for 1 hr at 25° C. After permeabilization, the cells were blocked with 1% v/v BSA (Sigma) in PBS (PBSB) for 30 min at 25° C. After gentle removal of PBSB, cells were incubated with primary antibody in PBSB overnight at 4° C. Primary antibodies used in this study include OCT4 (Santa Cruz) and TRA181 (Millipore). After the overnight incubation, cells were washed three times with PBS and stained with secondary antibody (Alexa Fluor 488 or 555; Life Technologies) diluted 1:250 in PBSB for 1 hr at 37° C. The cells were washed three times in PBS and stained with Hoechst dye (Invitrogen). Stained cells were viewed with an Axio Observer Inverted Microscope (Carl Zeiss). Images were captured with the AxioVS40 v4.8.1.0 (Carl Zeiss Imaging Solutions Gmbh).

Differentiation Analysis (EB and Directed)

hiPSC were differentiated as EBs in differentiation medium containing DMEM/F12 (Mediatech), 20% fetal bovine serum (Invitrogen), 1% non-essential amino acids (Mediatech), 2 mM L-glutamine (Mediatech) and 100 µM β-mercaptoethanol. Briefly, for EB formation hiPSCs were seeded in FMM and switched to conventional the following day to prime the cells. After 3 to 4 days in conventional medium, cultures were single cell dissociated with Accutase (Millipore) and resuspended in differentiation medium including 10 µM Y27632 to a final concentration of 100,000 cells/mL. Note that ROCK inhibitor Y27632 instead of Thiazovivin is used for EB formation. Cells were seeded at 100 µL/well in V-bottom 96-well non-tissue culture plate (Nunc) and centrifuged at 950 g for 5 min. The following day compact "ball-like clumps" were transfer to ultra-low binding 6-well plate (Corning) using P1000 at approximately 30-40 EBs/well in differentiation medium. After 7 days, EBs were transferred at 1:1 to Matrigel coated 6-well plate and fed with differentiation medium every three days. After 3 weeks in culture, cells were fixed and stained. For directed monolayer differentiation, hiPSCs were seeded on Matrigel coated wells in FMM to deliver 50% and 90% confluency the following day. Both densities were induced to differentiate. For neural induction, FMM media was replaced with hESC media supplemented with 10 µM SB431542 and 100 nM LDN-193189 (both SMAD inhibitors, Biovision). Following 2 days, differentiation media with supplemented with 3 µM CHIR99021 (Biovision) in addition to the dual SMAD inhibitors. Cells were fixed two days later and stained for Nestin (Abcam). For mesoderm differentiation, media was replaced with RPMI (Mediatech) supplemented with 1x B27 media additive (Life Technologies), 3 µM CHIR99021, 4 ng/ml bFGF and 10 ng/ml BMP4. Media was changed every other day and cells were fixed on the 4th day and stained for aSMA (Sigma). Endoderm differentiation was performed using the Human Pluripotent Stem Cell Functional Identification Kit (R&D Systems). hiPSCs were incubated with endoderm differentiation media for 3 days, fixed and stained for SOX17 (R&D Systems).

Gene Expression Analysis

RNA was extracted using the PicoPure RNA Isolation kit (Life Technologies) using the manufacturers recommended protocol. Total RNA was quantified using the Nanodrop 2000 Spectrophotometer (Thermo Scientific). In brief, biotinylated aRNA was prepared from roughly 100 ng of total RNA using the standard protocol for MessageAmp II aRNA Amplification Kit (Applied Biosystems/Ambion, Austin, TX) utilizing the optional Second Round Amplification and then transcribed into biotin labeled aRNA using MessageAmp II Biotin Enhanced Kit (Applied Biosystems/ Ambion, Austin, TX) using the standard protocol. Biotin labeled aRNA was purified and fragmented according to Affymetrix recommendations. 20 μg of fragmented aRNA were used to hybridize to the Human Genome U133-plus-2.0 chips (Affymetrix Inc. Santa Clara, CA) for 16 hours at 45° C. The arrays were washed and stained in the Affymetrix Fluidics Station 450 and scanned using the Affymetrix GeneChip Scanner 3000 7G. Raw expression data files are available on Gene Expression Omnibus (GSE50868). The image data were analyzed using Affymetrix Expression Console software using default analysis settings. Arrays were normalized by log scale robust multi-array analysis (RMA, Affymetrix) and visualized in Spotfire for Genomics 4.5 (Tibco Spotfire, Palo Alto, CA). Biological pathway enrichment analysis of the differentially expressed probes was performed against the Gene Ontology (GO) database (Singular Enrichment to GO Biological Process and p-value<0.01) using Database for Annotation, Visualization and Integrated Discovery (DAVID v6.7). Hierarchical clustering was performed to compare the gene expression profiles between samples based on Log 2 expression levels using a complete linkage clustering method with Euclidean distance measurements (Spotfire for Genomics 4.5). Probe sets for clustering were selected by either an overall differential in expression levels (><2.5-fold) or presence on targeted gene lists defining a ground or metastable state. For X Chromosome gene expression comparison, RMA normalized Affymetrix gene chip intensities were converted to linear expression values by taking the $2^\wedge$[RMA log 2 intensity]. Linear expression ratios were calculated as the naïve expression set divided by the primed expression set. The expression ratios for all probe sets mapped to the X chromosome were visualized in Spotfire 4.5 with the probe sets greater or less than 2 fold enrichment ratio highlighted.

Karyotype Analysis

Cytogenetic analysis was performed on twenty to forty G-banded metaphase cells by WiCell Research Institute (Madison, WI).

Teratoma Formation

Single cell dissociated hiPSCs, at concentrations of 0.5 and 3 million cells per 200 μL solution (100 μL FMM and 100 μL Matrigel) were injected subcutaneously into NOD/SCID/γ null mice. After 5-6 weeks (3 million cells injection) and 7-8 weeks (0.5 million cells injection), teratomas were harvested in PBS, fixed overnight at room temperature in 4% paraformaldehyde and maintained thereafter in 70% ethanol at room temperature for processing. Samples were submitted to UCSD Histology Core Facility for sectioning and hematoxylin and eosin staining. Sections were examined, interpreted and photographed using a Nikon Eclipse TS100 microscope equipped with a Nikon DS-Fi1 camera.

Statistical Analysis

Student's t test was used for statistical evaluations pertaining to standard deviation. StepOne Software v2.2 (Life Technologies) was used to determine RQ minimum and maximum values (error bars) pertaining to qRTPCR data.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

The invention claimed is:

1. A culture system comprising a cell culture platform for manufacturing induced pluripotent stem cells (iPSCs), the cell culture platform comprising a first composition and a second composition, wherein:
- (i) the first composition comprises non-pluripotent cells in a first culture medium comprising a Wnt pathway agonist, a MEK inhibitor, a ROCK inhibitor, and a TGFβR inhibitor;
- (ii) the second composition comprises iPSCs in a second culture medium comprising:
  - (a) a Wnt pathway agonist;
  - (b) a MEK inhibitor; and
  - (c) a ROCK inhibitor; and
- (iii) the second composition does not comprise a TGFβR inhibitor.

2. The culture system of claim 1, wherein
- (i) the Wnt pathway agonist of the second composition is a GSK3 inhibitor;
- (ii) the Wnt pathway agonist of the second composition is CHIR99021 or BIO;
- (iii) the MEK inhibitor of the second composition is PD98059 or PD032901;
- 1v) the ROCK inhibitor of the second composition is thiazovivin or Y27632; or
- (v) the Wnt pathway agonist of the second composition is CHIR99021; the MEK inhibitor of the second composition is PD032901; and the ROCK inhibitor of the second composition is thiazovivin.

3. The culture system of claim 1, wherein the second composition further comprises (i) bFGF or LIF; or (ii) bFGF and LIF.

4. The culture system of claim 1, wherein the iPSCs are reprogrammed from non-pluripotent cells comprising (i) one or more exogenous polynucleotides that encode at least one, two or three polypeptides selected from the group consisting of an OCT4 polypeptide, an ECAT1 polypeptide, a UTF1 polypeptide, a NANOG polypeptide, and an ESRRB polypeptide, or (ii) at least one, two or three exogenous polypeptides selected from an OCT4 polypeptide, an ECAT1 polypeptide, a UTF1 polypeptide, a NANOG polypeptide, and an ESRRB polypeptide.

5. The culture system of claim 4, wherein the non-pluripotent cells from which the iPSCs are reprogrammed comprise: (i) one or more exogenous polynucleotides that encode an OCT4 polypeptide, an ECAT1 polypeptide, a UTF1 polypeptide, a NANOG polypeptide, and an ESRRB polypeptide, or (ii) one or more exogenous polynucleotides that encode an OCT4 polypeptide, an ECAT1 polypeptide, and a UTF1 polypeptide.

6. The culture system of claim 4, wherein the one or more exogenous polynucleotides were introduced to the non-pluripotent cells from which the iPSCs are reprogrammed by a retrovirus, a lentivirus, a Sendai virus, an adenovirus, an episome, mini-circle, vector system with expression cassette, or mRNA.

7. The culture system of claim 4, wherein the one or more exogenous polynucleotides are removable by CRE-mediated excision.

8. The culture system of claim 4, wherein the one or more exogenous polynucleotides comprise a polycistronic vector comprising a plurality of polynucleotides that are separated by at least one 2A peptide.

9. The culture system of claim 8, wherein the polycistronic vector comprises a plurality of polynucleotides each encoding an OCT4 polypeptide.

10. The culture system of claim 4, wherein the exogenous polynucleotide encoding an OCT4 polypeptide is linked to a selectable marker.

11. The culture system of claim 4, wherein the one or more exogenous polynucleotides comprise:
- (a) at least one OCT4 encoding polynucleotide, at least one ECAT1 encoding polynucleotide, at least one UTF1 encoding polynucleotide;
- (b) at least one OCT4 encoding polynucleotide, at least one ECAT1 encoding polynucleotide, at least one UTF1 encoding polynucleotide, and at least one NANOG encoding polynucleotide;
- (c) at least two OCT4 encoding polynucleotides, and at least one NANOG encoding polynucleotide; or
- (d) at least one OCT4 encoding polynucleotide, at least one DPPA2 encoding polynucleotide, and at least one ESRRB encoding polynucleotide.

12. The culture system of claim 1, wherein the iPSCs comprise ground state pluripotency.

13. The culture system of claim 12, wherein the iPSCs do not comprise an exogenously introduced polynucleotide encoding a reprogramming factor polypeptide.

14. The culture system of claim 1, wherein the iPSCs comprise single cell dissociated iPSCs.

15. The culture system of claim 1, wherein at least 70% of the iPSCs are positive for both SSEA4 and TRA1-81.

* * * * *